US009618506B2

(12) United States Patent
Lowe et al.

(10) Patent No.: US 9,618,506 B2
(45) Date of Patent: Apr. 11, 2017

(54) ASSAY DEVICE AND METHOD

(75) Inventors: Phillip Lowe, Tullibody (GB); Steven Alexander Keatch, Stirling (GB); Steven Howell, Crieff (GB); Claus Marquordt, Edinburgh (GB); Ruth Polwart, Clackmannanshire (GB); Alan Kenneth Thomson, Fife (GB)

(73) Assignee: INVERNESS MEDICAL SWITZERLAND GMBH, Zug (CH)

( * ) Notice: Subject to any disclaimer, the term of this patent is extended or adjusted under 35 U.S.C. 154(b) by 2145 days.

(21) Appl. No.: 12/294,818

(22) PCT Filed: Mar. 29, 2007

(86) PCT No.: PCT/IB2007/001756
§ 371 (c)(1),
(2), (4) Date: Sep. 10, 2010

(87) PCT Pub. No.: WO2007/110779
PCT Pub. Date: Oct. 4, 2007

(65) Prior Publication Data
US 2011/0053289 A1 Mar. 3, 2011

Related U.S. Application Data

(60) Provisional application No. 60/868,480, filed on Dec. 4, 2006, provisional application No. 60/908,729, filed on Mar. 29, 2007.

(30) Foreign Application Priority Data

Mar. 29, 2006 (GB) .................................. 0606263.2

(51) Int. Cl.
*G01N 33/553* (2006.01)
*G01N 33/558* (2006.01)
(Continued)

(52) U.S. Cl.
CPC .......... *G01N 33/558* (2013.01); *B01L 3/5027* (2013.01); *B01L 3/502761* (2013.01);
(Continued)

(58) Field of Classification Search
CPC ......... G01N 33/54326; G01N 2333/58; G01N 33/558; G01N 33/54366; G01N 35/0098;
(Continued)

(56) References Cited

U.S. PATENT DOCUMENTS 5,279,936 A * 1/1994 Vorpahl ....................... 435/6.16
5,348,876 A    9/1994 Michaelsen et al.
(Continued)

FOREIGN PATENT DOCUMENTS

EP            215419        5/1991
EP       1 882 941 A2       1/2008
(Continued)

OTHER PUBLICATIONS

Ullman et al., *Proc. Natl. Acad. Sci.* 91:5426-5430 1994.
(Continued)

*Primary Examiner* — Erik B Crawford
(74) *Attorney, Agent, or Firm* — Steptoe & Johnson LLP

(57) ABSTRACT

An assay method and device can perform at least one (e.g., at least two) assays on a single aliquot of a sample liquid. The device can mix a sample liquid with assay reagents including magnetically susceptible particles. The device is configured to create a sample liquid-air interface with the sample liquid. The magnetically susceptible particles can be located (via an applied magnetic field) at the liquid-air interface when a second liquid contacts the interface to form a liquid-liquid interface. The magnetic particles travel across the liquid-liquid interface to the second liquid. The magnetically susceptible particles are configured to transport an analyte across the interface into the second liquid. An assay
(Continued)

for the analyte is performed in the second liquid. An assay for another analyte can also be performed in the sample liquid.

25 Claims, 69 Drawing Sheets

(51) Int. Cl.
  *B01L 3/00* (2006.01)
  *G01N 33/543* (2006.01)
  *B01L 9/00* (2006.01)
  *G01N 35/00* (2006.01)

(52) U.S. Cl.
  CPC .. *B01L 3/502769* (2013.01); *G01N 33/54326* (2013.01); *G01N 33/54366* (2013.01); *B01L 3/502715* (2013.01); *B01L 9/527* (2013.01); *B01L 2200/0621* (2013.01); *B01L 2200/0668* (2013.01); *B01L 2300/0636* (2013.01); *B01L 2300/0645* (2013.01); *B01L 2300/0672* (2013.01); *B01L 2300/0816* (2013.01); *B01L 2300/0867* (2013.01); *B01L 2300/0887* (2013.01); *B01L 2400/0406* (2013.01); *B01L 2400/0683* (2013.01); *B01L 2400/0688* (2013.01); *B01L 2400/086* (2013.01); *G01N 35/0098* (2013.01)

(58) Field of Classification Search
  CPC ............ B01L 3/502769; B01L 3/5027; B01L 3/502761; B01L 2300/0636; B01L 2200/0668; B01L 2300/0645; B01L 9/527; B01L 2300/0887; B01L 2400/04
  USPC .................................................. 436/518, 526
  See application file for complete search history.

(56) References Cited

U.S. PATENT DOCUMENTS

| | | | |
|---|---|---|---|
| 5,647,994 A | 7/1997 | Tuunanen et al. | |
| 5,708,247 A | 1/1998 | McAleer et al. | |
| 6,143,514 A | 11/2000 | Ullman et al. | |
| 6,241,862 B1 | 6/2001 | McAleer et al. | |
| 6,306,659 B1* | 10/2001 | Parce et al. | 436/47 |
| 6,773,655 B1 | 8/2004 | Tunis, III et al. | |
| 7,314,763 B2 | 1/2008 | Song et al. | |
| 7,435,381 B2 | 10/2008 | Pugia et al. | |
| 2002/0166764 A1 | 11/2002 | MacPhee et al. | |
| 2002/0166800 A1 | 11/2002 | Prentiss et al. | |
| 2004/0043507 A1 | 3/2004 | Song et al. | |
| 2005/0054078 A1 | 3/2005 | Miller et al. | |
| 2005/0074748 A1 | 4/2005 | Rothschild et al. | |
| 2005/0100930 A1 | 5/2005 | Wang et al. | |
| 2005/0106652 A1 | 5/2005 | Massey et al. | |
| 2005/0142549 A1 | 6/2005 | Ginot et al. | |
| 2005/0147963 A1 | 7/2005 | Su et al. | |
| 2005/0148096 A1 | 7/2005 | Cole et al. | |
| 2005/0149169 A1 | 7/2005 | Wang et al. | |
| 2006/0023039 A1 | 2/2006 | Padmanabhan et al. | |
| 2007/0031283 A1* | 2/2007 | Davis et al. | 422/58 |
| 2007/0099289 A1* | 5/2007 | Irimia et al. | 435/287.2 |
| 2008/0257754 A1 | 10/2008 | Pugia et al. | |

FOREIGN PATENT DOCUMENTS

| | | |
|---|---|---|
| WO | WO 03/007227 A1 | 9/2003 |
| WO | WO2006/053588 | 5/2006 |
| WO | WO2007/002579 | 1/2007 |
| WO | 2007/093902 | 8/2007 |

OTHER PUBLICATIONS

Khanna, P.L. and Coty, W.A. (1993) In: *Methods of Immunological Analysis, volume 1* (Masseyeff, R.F., Albert, W.H., and Staines, N.A., eds.) Weinheim, FRG: VCH Verlagsgesellschaft MbH, 1993: 416-426.

Coty, W.A., Loor, R., Powell, M., and Khanna, P.L. (1994) *J. Clin. Immunoassay* 17(3): 144-150.

Coty, W.A., Shindelman, J., Rouhani, R. and Powell, M.J. (1999) *Genetic Engineering News* 19(7).

U.S. Appl. No. 60/736,302, Nov. 15, 2005, Satwinder et al.

U.S. Appl. No. 11/013,353, Dec. 12, 2004, Sheard et al.

* cited by examiner

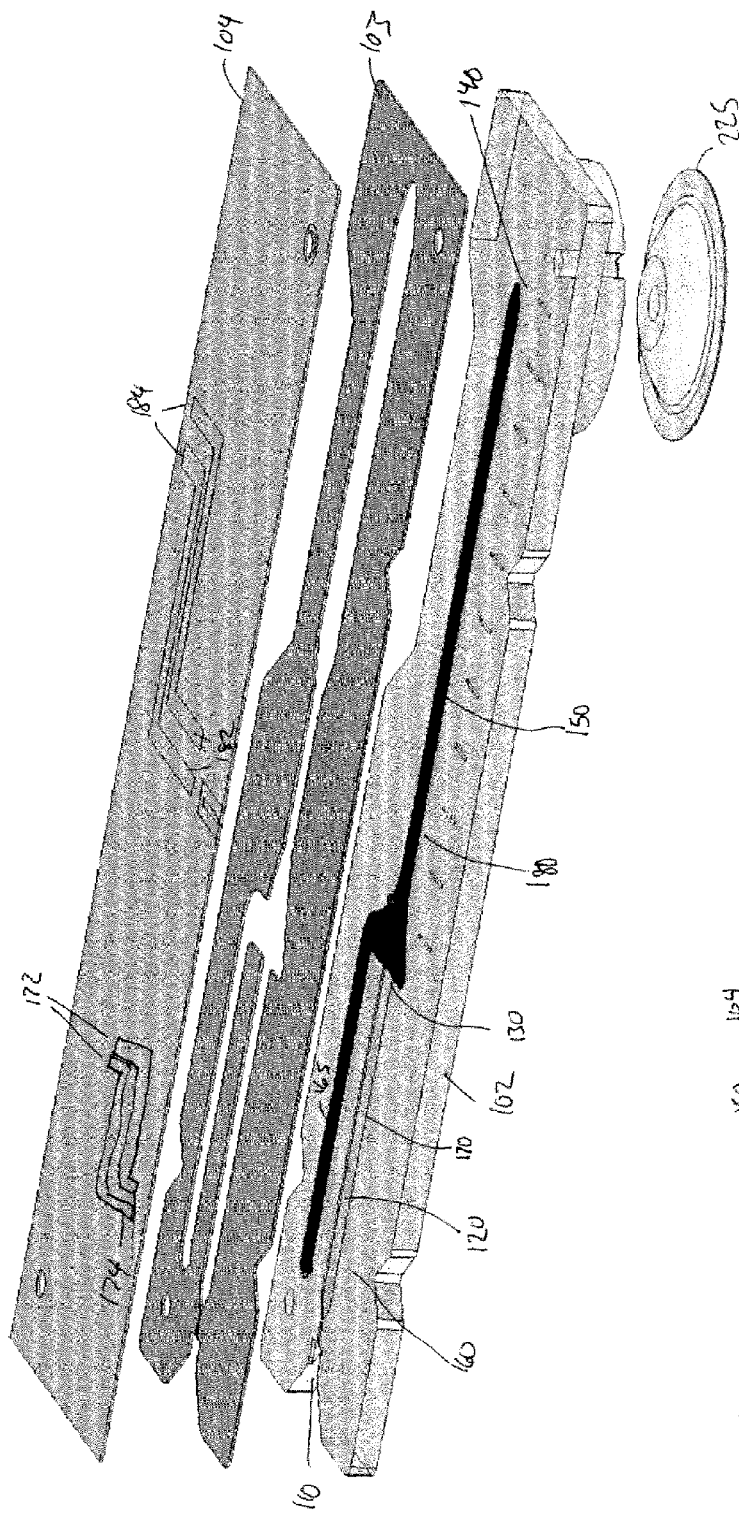
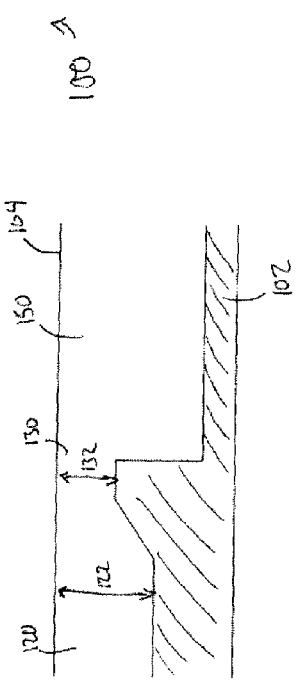
Figure 11A
Figure 11B

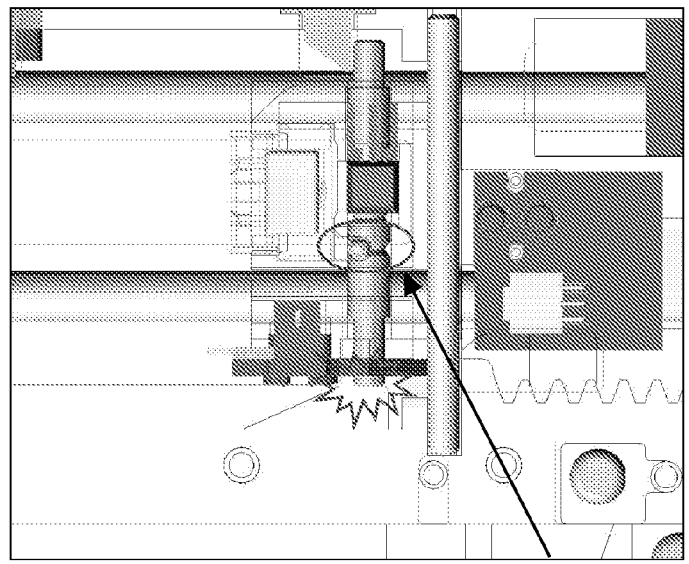
Figure 24F
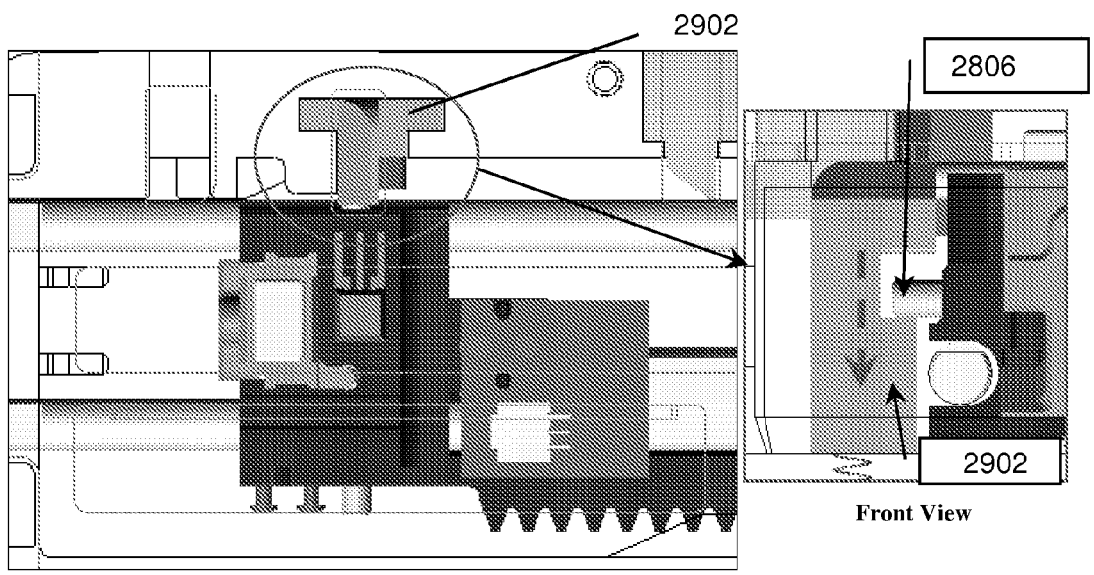
Figure 24G
Figure 24H

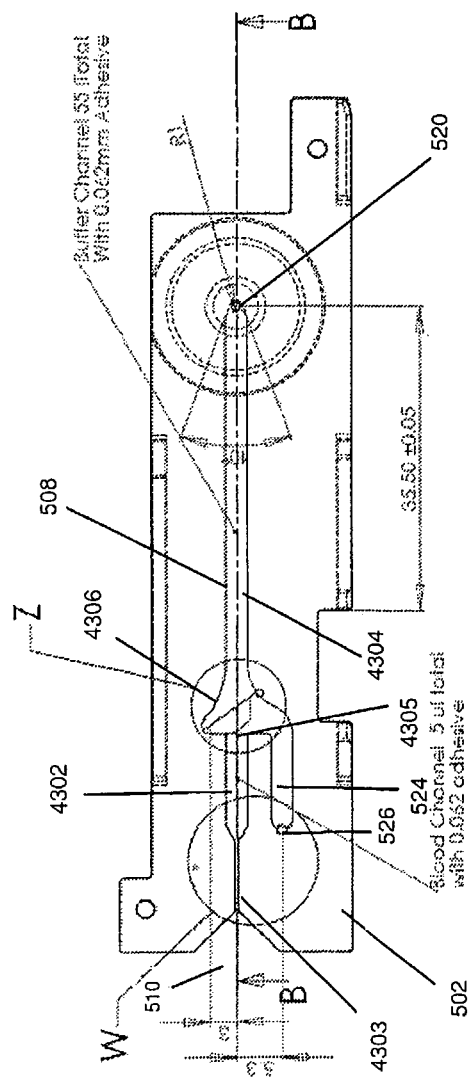
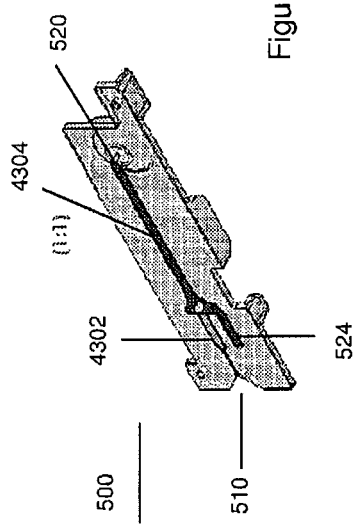
Figure 38I
Figure 38J

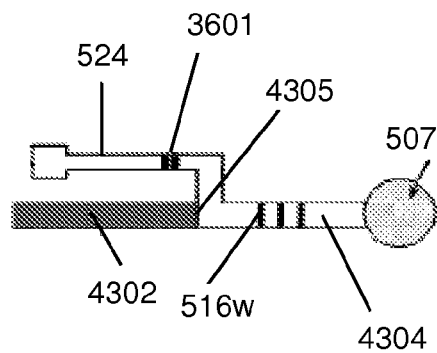
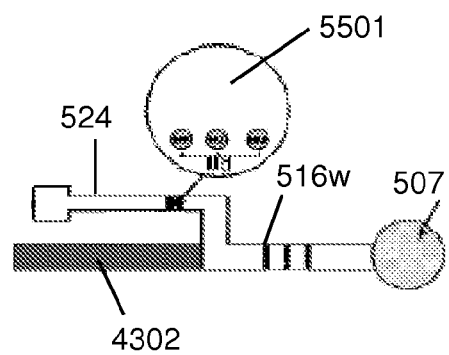
Figure 50A        Figure 50B
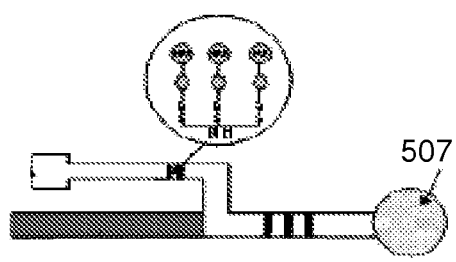
Figure 50C
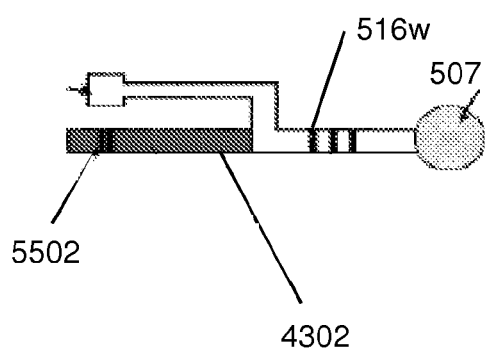
Figure 50D

ASSAY DEVICE AND METHOD

CLAIM OF PRIORITY

This application claims priority under 35 USC 371 to International Application No. PCT/IB2007/001756, filed on Mar. 29, 2007, which claims priority to Great Britain Application Serial No. 0606263.2, filed on Mar. 29, 2006, U.S. Provisional Application Ser. No. 60/868,480, filed on Dec. 4, 2006, and U.S. Provisional Application Ser. No. 60/908,729, filed on Mar. 29, 2007, each of which is incorporated by reference in its entirety.

TECHNICAL FIELD

The present invention relates to assays.

BACKGROUND

Heart failure is a chronic, progressive disease that affects a substantial portion of the world's population. The prevalence and incidence of heart failure is growing due to an aging population and a greater number patients who survive a myocardial infarction.

Clinically, heart failure can be characterized by a syndrome of breathlessness and fatigue, often accompanied by fluid retention, as indicated by an elevated jugular venous pressure and edema. The progression of heart failure is defined in four stages. The term heart failure refers to all of these. Stage A-at risk: patients at high-risk of developing heart failure (patients with coronary heart disease, diabetes, hypertension, and/or valvular heart disease). Stage B-pre-heart failure: patients with structural heart disease but without clinical heart failure symptoms, many of whom have decreased systolic function. Stage C-heart failure: patients who have prior or current symptomatic heart failure due to systolic or diastolic dysfunction and who are responding to therapy. Stage D-advanced heart failure: patients in end-stage or refractory-to-therapy.

Many of the tests and procedures for accurately and successfully diagnosing, managing and treating heart failure are complex, expensive and available only at a hospital or other health-care setting.

SUMMARY

The present invention relates to assays.

In one aspect, a method includes transporting a magnetic or magnetically susceptible particle across and interface between a sample reagent mixture and another medium (e.g., a fluid such as a gas or liquid). The particle includes a binder for an analyte or analyte complex. The analyte is determined after transporting the particle and bound analyte across the interface. At least the step of transporting can be performed in a microfluidic device.

The assay method and device can be used in home testing kits for analyzing species present in the blood. In particular, the device and method facilitate the performance of more than one assay on a small sample volume, and are suitable for use with home testing kits that use the "finger stick" or "finger prick" procedure.

The assay device and method can accept small fluid samples in a simple step, and is able to present small fluid samples for immediate testing in a reliable and reproducible fashion. The present invention provides an efficient way to utilise obtained blood samples in a home testing kit by allowing the performance of a series of tests on the same sample.

Finally, the device and method of the present invention facilitate the execution of more than one assay on the same blood sample by separating and isolating analytes of interest, within a complex mixture. This enables the visualisation of the analytes by a detection procedure. In particular, the present invention affords the use a specific reagent for visualising a marker related to an analyte and the reliable quantification of its presence to inform on a disease state in a subject.

Embodiments permit determination of several analytes, such as analytes indicative of disease states in a subject, to be detected.

In one aspect, the invention relates to a device. In some embodiments, the device comprises an inlet in fluid connection with a first portion of a channel, the inlet configured to receive a liquid; a second portion of the channel connected to the first portion at a junction; magnetically susceptible particles disposed in the first channel portion; wherein the device is configured to form, with a liquid received by the inlet, a liquid interface proximal the junction.

The liquid may be a first liquid and the device further comprise a reservoir containing a quantity of second liquid, the reservoir configured to deliver second liquid released from the reservoir into the second channel portion such that the second liquid flows towards the junction.

In some embodiments, the device comprises an inlet in fluid connection with a first portion of a channel, the inlet configured to receive a liquid; a second portion of the channel connected to the first portion at a junction and containing flowable media between the junction and a detection zone in the second channel portion; magnetically susceptible particles disposed in the first channel portion; wherein the device is configured to form, with a liquid received by the inlet, a liquid:second medium interface proximal the junction.

The second medium may be a liquid (e.g., a buffer) or a gel.

The device may further comprise at least one sensor disposed within the second channel portion and configured to detect an analyte within the second liquid.

The first channel portion may have a maximum lateral dimension, that is substantially perpendicular to its longitudinal axis, of 2.5 mm or less. The first channel portion may be a capillary.

The device may include a capillary stop at, or adjacent, the junction.

At the junction, the cross sectional area of the first channel portion is typically less than the cross sectional area of the second channel portion.

The device may include one or more reagents disposed within the first channel portion (e.g., the reagents may be disposed in dry form on an internal surface of the first channel portion). For example, the reagents may be disposed as deposits of dry reagent.

A first reagent may be disposed at a first position on an internal surface of the first channel portion and a second reagent disposed at a second position on an internal surface of the first channel portion. A third reagent may be disposed at a third position on an internal surface of the first channel portion. A forth reagent may be disposed at a forth position on an internal surface of the first channel portion The positions at which at least two of the reagents are disposed may be physically distinct. For example, the positions of the at least two reagents may be spaced apart along the length of the first channel portion. The reagents may be deposited in a predetermined order along the first channel portion. Magnetically susceptible particles may be deposited proximal to the inlet with first and second binding agents deposited closer to the junction. Reagent deposits of the same type may be grouped together or different reagents may be deposited in alternate sequence along the first channel portion. Magnetically susceptible particle deposits may be grouped together and first and second binding agent deposits positioned in alternating sequence.

The first reagent may comprise magnetically susceptible particles comprising a binding agent adapted to bind to an analyte in the first liquid. For example, the first reagent may comprise magnetically susceptible particles bound to an anti-NTproBNP antibody or an anti-BNP antibody. The antibody may be selected from the group consisting of monoclonal mouse anti-human NT-proBNP antibodies 5B6, 7B5, 13G12, 11D1, 16E6, 15D7, 24E11, 28F8, 18H5, 16F3, or combination thereof. In some embodiments, the antibody is monoclonal mouse anti-human NT-proBNP antibody 15C4 (HyTest Ltd.; Catalogue #:4NT1).

The second reagent may comprise a binding agent capable of binding to an analyte in the first liquid. The binding agent of the second reagent may be capable of binding to a different epitope of the analyte than the binding agent of the first reagent. The binding agent of the second reagent may be a second anti-NTproBNP antibody or a second anti-BNP antibody. The second anti-NTproBNP antibody or second anti-BNP antibody may bind to NTproBNP (or BNP) at a different epitope to the first anti-NTproBNP antibody (or to the first anti-BNP antibody). The second anti-NTproBNP antibody may be selected from the group consisting of monoclonal mouse anti-human NT-proBNP antibodies 5B6, 7B5, 13G12, 11D1, 16E6, 15D7, 24E11, 28F8, 18H5, 16F3 (HyTest Ltd.; Catalogue #:4NT1), or combination thereof. The second anti-NTproBNP antibody may be 15F11 (HyTest Ltd.; Catalogue #:4NT1). The second anti-NT-proBNP antibody may be 29D12 (HyTest Ltd.; Catalogue #:4NT1).

The second reagent may be conjugated to a second particle (e.g., a non-magnetically susceptible particle such as a sol particle (e.g., a gold sol)). The second particle may comprise at least one (e.g., multiple) label(s). The label may be an enzyme label (e.g., horse-radish peroxidise). In embodiments, a gold sol includes multiple enzyme labels conjugated thereto.

The junction of the first and second channel parts may be substantially orthogonal to a longitudinal axis of the first channel portion. The junction may be substantially orthogonal to a longitudinal axis of the second channel portion. The first and second channel parts may have a common longitudinal axis.

At the junction, the first channel portion may have a height h1 and the second channel portion a height h2, wherein h2>h1. The ratio h1:h2 may be at least 1:2.

At the junction, the first channel portion may have a cross-sectional area A1, and the second channel portion has a cross-sectional area A2, wherein A1<A2. The ratio of A1:A2 may be at least 1:3.

At the junction the first channel portion may have a width w2, and the second channel portion has a width w5, wherein w5>w2. The ratio w2:w5 may be at least 1:3.

Adjacent the junction of the first and second channel portions, a base of the second channel portion may be sloped between a region of the second channel portion distal of the junction and having height h3 and a region of the second channel portion adjacent the junction and having height h2, wherein h2>h3. The slope may extend obliquely with respect to a longitudinal axis of the second channel portion.

Height h2 may be less than about 0.6 mm. Height h3 may be less than about 0.4 mm.

The second channel portion may include a bend portion, the inside wall of the bend formed by a first wall of the second channel and the outside wall of the bend formed by a second wall of the second channel, wherein the first or second wall also comprises, at least partially, the junction of the first and second channels. In embodiments, the second wall comprises, at least partially, the junction of the first and second channels.

The inside wall of the bend may comprises means (e.g., a capillary stop, a notch) to retard the flow of liquid along the inside wall.

The bend portion may include a capillary stop on a first wall of the second channel and a sloped base having an upper edge extending obliquely across the channel from the first wall in the region of the capillary stop and towards a region of the second channel at which the second channel portion has a greater width.

The slope may have an angle of inclination θ with respect to a base of the second channel, wherein θ is in the range 5 to 25°.

A wall of the second channel portion may have a capillary stop, an upper edge of the slope extending across the second channel portion from a region at, or adjacent, the capillary stop towards the opposing wall of the second channel portion. The upper edge of the slope may extend obliquely across the channel and towards the junction.

The second channel portion may have a first region distal to the junction wherein the channel has a width w6 and height h3, the second channel portion having a tapered neck region formed between the first region and the junction in which the channel width and height increases to height h2 and width w5 at the junction.

The device may further include means to release second liquid from the reservoir. The means may include a sharp projection, which may be hollow to allow released second liquid to pass through the projection.

At least one of the reservoir and projection may be toward the other such that the sharpened projection punctures a wall of the reservoir.

In embodiments, the junction has a cross sectional area of about 1 mm$^2$ or less (e.g., about 0.8 mm$^2$ or less, about 0.75 mm$^2$ or less, about 0.6 mm$^2$ or less, about 0.4 mm$^2$ or less, about 0.2 mm$^2$ or less). The junction may have a cross-sectional area of at least about 0.15 mm$^2$. In embodiments, the junction has a cross-sectional area in the range about 0.15 mm$^2$ to about 1 mm$^2$.

The first channel portion may have a volume V μl and the junction a cross sectional area A mm$^2$. The ratio V:A may be about 1.0 or less (e.g., about 0.5 or less, about 0.3 or less). The ratio V:A may be at least about 0.2. In embodiments, the ratio of V:A is in the range of about 0.2 to about 1.0.

The device may include a first liquid (e.g., human blood) is disposed in the first portion of the channel, the first liquid forming a liquid:gas interface at the junction. Magnetically susceptible particles may be disposed (e.g., clustered) in the first liquid proximal the interface. A second, different, liquid (e.g., a buffer solution) may be disposed in the second portion of the channel. At least a portion of the second liquid may be in contact with and flowing relative to the first liquid, the flow of the second liquid decreasing an area of the first liquid-gas interface. A main direction of flow of the second liquid at the interface may be transverse with respect to the liquid-gas interface of the first liquid. The buffer solution may be free of analyte.

The device may include a first liquid (e.g., human blood) disposed in the first portion of the channel, the first liquid forming a liquid:liquid interface at the junction with a second, different, liquid (e.g., a buffer solution) disposed in the second channel portion and in fluid contact with the first liquid. Magnetically susceptible particles may be disposed (e.g., clustered) in the first liquid proximal the interface. The buffer solution may be free of analyte.

The device may be configured to direct the flow of the second liquid across the face of the first liquid in a direction substantially orthogonal to the direction of flow of the first liquid in the first channel portion immediately before the junction.

The device may be configured to direct the flow of the second liquid across the face of the first liquid in a direction substantially orthogonal to the direction of flow of first liquid occurring in the first channel portion at distance D before the junction, wherein D is less than 10 mm. The first channel portion may have a volume of less than 20 µl (e.g., a volume of about 10 µl, a volume of about 5 µl or less). In embodiments, the first channel portion has a volume of about 5 µl.

In embodiments, the first channel portion is rectangular in cross section and has height h1 and width w2, wherein h1 is at least about 0.06 mm and w2 is at least about 1.0 mm.

In embodiments, at the junction of the first and second channel portions, the second channel portion is generally rectangular in cross section and has a height h2, and width w5, wherein h2 is at least about 0.35 mm and w5 is at least about 9 mm. The second channel portion may have a height h3 and a width w6 at distance d2 from the junction, wherein d2 is at least about 3.5 mm, and wherein the second channel portion has height h2 and width w5 at the junction of the first and second channel portions, wherein h2>h3 and w5>w6.

The device may be free of a membrane or filter in the first or second channel portion (e.g., at the junction thereof) and/or at the inlet.

The device may be an assay device for use with liquid samples which may contain an analyte, the device comprising a support in which the channel is formed.

The sensor of the device may be disposed within the second channel portion in order to determine an analyte within the second liquid.

The second channel portion may comprise first and second sensors, wherein the first sensor is located at a first portion of the second channel portion and the second sensor is located at a second portion of the second channel portion, wherein the junction is between the first and second portions.

The device may include at least one sensor disposed within the first channel portion to determine an analyte within or a property of the first liquid.

The device may include an overflow channel configured to receive an overflow amount of second liquid when the liquid sample-second liquid interface is formed. The overflow channel may include a sensor configured to determine the presence of the second liquid within the overflow channel.

Any sensor of the device may include at least one electrode (e.g., at least two electrodes).

The sensor may include electrodes configured on the device to detect an electrochemical signal from liquid in the second channel portion, wherein the signal is indicative of the presence of analyte.

At least one wall, base or lid of the first and/or second channel portion may be transparent to light.

The device may be a microfluidic device.

In some embodiments, the device is positioned within a meter. The meter may include a housing configured to receive the device, a magnet configured to localize a magnetic field at a first position and at least one second position of the received device, an actuator moveable between a first position and second position, wherein in the second position the actuator contacts the reservoir.

In some embodiments, the device is a microfluidic device comprising an inlet configured to receive a human blood sample, the inlet in fluid connection with a first portion of a channel containing a quantity of human blood; reagents disposed in the first channel portion, the reagents comprising magnetically susceptible particles conjugated to a first anti-NTproBNP antibody, and a second anti-NTproBNP antibody conjugated to an enzyme label, human blood contained in the first channel portion comprising NTproBNP bound to the first and second anti-NTproBNP antibodies, a second portion of the channel connected to the first portion at a junction; wherein the device comprises a blood:gas interface proximal the junction. The device may further comprise a reservoir containing a quantity of second liquid and configured to deliver second liquid released from the reservoir into the second channel portion such that the second liquid flows towards the junction, the second liquid comprising a substrate of the enzyme label, and at least one electrode configured on the second channel portion to detect an electrochemical signal from the second liquid.

In embodiments, the device comprises an inlet in fluid connection with a first portion of a channel, the inlet configured to receive a liquid; a second portion of the channel connected to the first portion at a junction; magnetically susceptible particles disposed in the first channel portion; wherein the device is configured to form, with a liquid received by the inlet, a liquid interface proximal the junction. The device may further comprise a reservoir containing a quantity of second liquid and configured to deliver second liquid released from the reservoir into the second channel portion such that the second liquid flows towards the junction, and at least one sensor configured on the second channel portion to detect a signal from the second liquid.

In embodiments, the device comprises an inlet connected to a first portion of a channel, magnetically susceptible particles disposed in the first portion of the channel, a second portion of the channel connected to the first portion of the channel at a junction of the channel, a first liquid disposed in the first portion of the channel, the first liquid forming a liquid:gas interface proximal the junction, a second, different, liquid disposed in the second portion of the channel, the second liquid in contact with and flowing relative to the first liquid, the flow of the second liquid decreasing an area of the first liquid:gas interface and forming a liquid:liquid interface.

The first liquid may be a quantity of human blood. The magnetically susceptible particles may be clustered in the first liquid proximal the interface.

The second liquid may be a buffer solution.

The device may be configured to direct the flow of the second liquid across the face of the first liquid at the interface in a direction substantially orthogonal to the direction of flow of the first liquid in the first channel portion immediately before the interface.

The device may be configured to direct the flow of the second liquid across the face of the first liquid at the interface in a direction substantially orthogonal to the direction of flow of first liquid occurring in the first channel portion at distance D before the interface, wherein D is less than 10 mm.

In some embodiments, the device is a portable assay device for use with liquid samples which may contain an analyte, the device comprising a support configured to provide a shallow liquid flow channel adapted to receive liquid from an inlet, a first portion of the channel adapted to control liquid flow from the inlet to an intermediate position within the length of the channel; wherein at least one surface accessible to the liquid flow in the first portion of the channel has a dry reagent deposited thereon the reagent comprising a plurality of magnetically susceptible particles adapted to bind an analyte in the liquid sample, and wherein the device has a second channel portion connected to the first channel portion at the intermediate position wherein the second channel portion is provided with a sensor configured upon the device and juxtaposed with respect to the channel such that, in use of the device with a liquid sample, a characteristic of the liquid sample may be sensed.

In some embodiments, the device comprises a channel having first and second channel portions, the device having an inlet configured to receive a first liquid, the inlet being in fluid connection with the first channel portion such that first liquid from the inlet may flow into the first channel portion, wherein the first and second channel portions are connected at a junction, the device configured to form a first liquid:gas interface at the junction, wherein the second channel portion is configured to receive a second liquid and direct the second liquid to the junction such that the second liquid contacts the first liquid and displaces gas to form an interface of the first and second liquids.

In another aspect, the invention relates to a method.

In some embodiments, the method includes introducing a liquid sample to a first portion of a channel of a microfluidic device; contacting, within the microfluidic device, magnetically susceptible particles with the liquid sample, the magnetically susceptible particles comprising a binding agent configured to bind an analyte; forming, proximal to a junction between the first portion of the channel and a second portion of the channel, a liquid sample:gas interface; forming a liquid sample:second liquid interface by displacing gas of the liquid sample:gas interface with a second liquid, and magnetically moving the magnetically susceptible particles across the liquid sample:second liquid interface into the second liquid.

The method may be a method for detecting an analyte in the liquid sample, the magnetically susceptible particles adapted to bind the analyte wherein the method further comprises the step of detecting analyte in the second liquid.

The method may be for detecting an analyte and comprise the step of determining an amount of the analyte.

The method may include separating an analyte from the liquid sample and transporting the analyte into the second liquid.

The method may be an in vitro method.

The first and second liquids are typically different. The first liquid may be a bodily fluid from a human or mammal (e.g., blood, serum, or plasma). The second liquid may be a buffer solution.

In some embodiments, the method is an in vitro method for detecting an analyte in a liquid sample of blood, plasma or serum from a human comprising introducing the liquid sample to a first portion of a channel of a microfluidic device; contacting, within the microfluidic device, magnetically susceptible particles with the liquid sample, the magnetically susceptible particles comprising a binding agent configured to bind an analyte; forming, proximal to a junction between the first portion of the channel and a second portion of the channel, a liquid sample:gas interface; forming a liquid sample:second liquid interface by displacing gas of the liquid sample:gas interface with a second liquid, and magnetically moving the magnetically susceptible particles across the liquid sample:second liquid interface into the second liquid.

The method may include determining an assay result. The method may include determining an amount of the analyte. The method may include comparing the amount of analyte determined against a reference amount to produce an assay result. The method may include displaying the determined amount of analyte. The method may include displaying information based on an assay result. The information may be indicative of the assay result (e.g., may be indicative of the amount of analyte in the second liquid). The assay result displayed may be proportional to the amount of analyte in the second liquid.

The method may include determining analyte in liquid contained in the second channel portion.

The step of contacting magnetically susceptible particles with the liquid sample typically includes forming a mixture of the liquid sample and magnetic particles.

The method may include allowing a binding reagent of the magnetically susceptible particles to bind analyte.

The step of contacting magnetically susceptible particles with the liquid sample may include contacting the liquid sample with a second binding agent configured to bind the analyte. The method may include forming complexes of magnetically susceptible particle, analyte and second binding agent.

In embodiments, the binding agent is conjugated to a detectable label (e.g., an enzyme label such as horse radish peroxidise). The second liquid may contain an enzyme label substrate.

In embodiments, the magnetically susceptible particles are conjugated to a first antibody configured to bind the analyte. In embodiments, the second binding agent is a second antibody configured to bind the analyte at a different epitope to the first antibody.

The detectable label (e.g., enzyme label) and second binding reagent (e.g., second antibody) may be attached to non-magnetically susceptible particles (e.g., sol particles such as gold sol particles).

The second liquid is typically different to the first liquid. The second liquid may be substantially miscible with the liquid sample. The second liquid may be a buffer solution.

The step of forming the liquid sample:gas interface may include forming the interface substantially parallel to the orientation of a local gravitational field of the earth.

The step of forming the liquid sample:second liquid interface may include forming the interface substantially parallel to the orientation of a local gravitational field of the earth.

The step of forming the liquid sample:gas interface may include forming the interface in a substantially vertical plane.

The step of forming the liquid sample:second liquid interface may include forming the interface in a substantially vertical plane.

The step of magnetically moving the magnetically susceptible particles across the liquid sample:second liquid interface into the second liquid may comprise applying a magnetic field to a first position in the first channel portion, and moving the applied magnetic field along the channel through the junction to a second position in the second channel portion.

The magnetic field may be moved continuously, without pause, between the first and second positions.

The method may include pausing the movement of the magnetic field in the region of the junction and positioning magnetically susceptible particles in the liquid sample adjacent the interface.

The method may include pausing the movement of the magnetic field in the region of the junction and positioning magnetically susceptible particles in the second liquid adjacent the interface.

The method may include moving the magnetic field from the first position towards the junction at a first speed S1, and moving the magnetic field from a region of the first and/or second channel portion adjacent the junction towards the second position at a second speed S2, wherein S2>S1.

The speed of movement of the magnetic field can be increased as the magnetic field is moved through the junction.

The method may comprise determining a characteristic of the second liquid at the second position.

The method may comprise, after the step of contacting multiple magnetically susceptible particles with the liquid sample and before the step of magnetically moving the magnetically susceptible particles across the liquid sample:second liquid interface into the second liquid, magnetically positioning magnetically susceptible particles in the first liquid adjacent the liquid sample:gas interface.

The method may comprise, after the step of contacting multiple magnetically susceptible particles with the liquid sample and before the step of magnetically moving the magnetically susceptible particles across the liquid sample:second liquid interface into the second liquid, magnetically positioning magnetically susceptible particles in the first liquid adjacent the liquid sample:second liquid interface.

Positioning the magnetically susceptible particles can be performed using a magnet located external of the channel. In some embodiments, the particles are not contacted with the magnet.

The magnetically susceptible particles can be magnetically positioned in the first liquid adjacent the liquid sample:gas interface and/or liquid sample:second liquid interface for a predetermined period of time DK, wherein DK may be at least 1 second (e.g., at least 5 seconds, at least 10 seconds). DK may be about 120 seconds or less (e.g., about 60 seconds or less).

The time between the formation of a liquid sample:gas interface and the formation of a liquid sample:second liquid interface may be less than time TK, wherein TK may be about 120 seconds or less (e.g., about 60 seconds or less, about 30 seconds or less). Time TK may be at least about 1 second (e.g., at least about 5 seconds, at least about 10 seconds, at least about 20 seconds).

The time between magnetically positioning the magnetically susceptible particles in the liquid sample adjacent the liquid sample:gas or liquid sample:second liquid interface and magnetically moving the magnetically susceptible particles across the liquid sample:second liquid interface may be less than TJ, wherein TJ may be about 300 seconds or less (e.g., about 200 seconds or less, about 100 seconds or less, about 60 seconds or less).

The magnetically susceptible particles may be moved across the liquid sample:second liquid interface into the second liquid within a time TP after forming the liquid sample:second liquid interface, wherein TP may be about 120 seconds or less (e.g., about 60 seconds or less, about 30 seconds or less, about 15 seconds or less, about 10 seconds or less).

Magnetically positioning magnetically susceptible particles in the first liquid adjacent the liquid sample:gas and/or liquid sample:second liquid interface may comprise positioning the particles to within a distance D mm of the respective interface, wherein D may be about 10 mm or less (e.g., about 5 mm or less).

Forming a liquid sample:second liquid interface by displacing gas of the liquid sample:gas interface with a second liquid may comprise directing the second liquid across the face of the liquid sample at the liquid sample:gas interface.

Forming a liquid sample:second liquid interface by displacing gas of the liquid sample:gas interface with a second liquid may comprise directing a flow of second liquid across the face of the liquid sample at the liquid sample:gas interface to decrease an area of the liquid sample:gas interface. During flow of the second liquid across the face of the liquid sample the first liquid may be held essentially static.

The method may comprise the step of forming a liquid sample:second liquid interface in which substantially no bulk movement of liquid (other than diffusion) occurs across the interface.

The method may comprise the step of magnetically positioning magnetically susceptible particles at a predetermined detection zone in the second channel portion.

The method may comprise magnetically moving the magnetically susceptible particles adjacent or upon a sensor located in, or juxtaposed to, the second channel portion of the device. The particles may be magnetically retained adjacent or upon the sensor for an amount of time sufficient for the sensor to detect a characteristic of the second liquid.

The method may include magnetically positioning the magnetically susceptible particles adjacent one or more electrodes configured in the second channel portion to contact the second liquid. The method may include detecting a characteristic of the second liquid at the electrode(s). The step of detecting a characteristic may comprise detecting an electrochemical signal in the second liquid. The magnetically susceptible particles may be held adjacent or upon the one or more electrodes for an amount of time sufficient for the electrodes to detect an electrochemical signal in the second liquid. The detection may comprise detecting the presence of analyte in the second liquid. The detection may comprise detecting an amount of analyte in the second liquid.

The detection of analyte in the second liquid may comprise measuring at time T1 the electrochemical signal Q1 at the working electrode, comparing Q1 against a T1 calibration dataset and, where Q1 is within the T1 dataset, using the T1 dataset to determine an amount of analyte in the buffer liquid, where Q1 does not exist in the T1 calibration dataset, measuring at time T2 the electrochemical signal Q2 at the working electrode, wherein T2>T1, comparing Q2 against a T2 calibration dataset and where a valid comparison of Q2 and T2 is made, and determining an amount of analyte in the buffer liquid. The method may include repeating one or more of these steps for one or more subsequent times Tx and electrochemical signals Qx.

The step of introducing the liquid sample may comprise depositing a quantity of the liquid sample at an inlet of the device, wherein the inlet is in fluid connection with the first channel portion.

The liquid sample:gas interface may have a cross sectional area of about 1 mm2 or less. The liquid sample:gas interface may have a cross sectional area of about 0.15 mm2 or more. The liquid sample:gas interface may have a first dimension H and a second dimension W and a ratio of W to H may be at least 2 (e.g., at least 3.5, at least 5). The ratio W to H may be about 30 or less (e.g., about 20 or less, about 10 or less).

The liquid sample:second liquid interface may have a cross sectional area of about the same as the liquid sample: gas interface or less.

A time TI between forming the liquid sample:gas interface and forming the liquid sample:second liquid interface may be at least 5 seconds (e.g., at least 15 seconds, at least 30 seconds). Time TI may be about 600 seconds or less (e.g., about 300 seconds or less, about 150 seconds or less, about 60 seconds or less). The method may include inducing essentially no movement of the particles for a time TD after forming the liquid sample:gas interface, wherein TD may be at least 5% (e.g., at least 10%, at least 25%) of time TI.

In some embodiments, upon forming the liquid sample: gas interface, the liquid may occupy a volume V of the channel upstream from the liquid sample:gas interface and the method may comprise magnetically oscillating the particles within the volume V after forming the first liquid:gas interface and prior to forming the liquid sample:second liquid interface.

In some embodiments, upon forming the liquid sample: gas interface, the liquid occupies a volume V of the channel upstream from the liquid sample:gas interface and the method comprises magnetically oscillating the particles within the volume V after forming the liquid air interface and prior to forming the liquid sample:second liquid interface for a total time TO, wherein TO may be at least 30% of time TI. TO may be 90% or less of time TI.

In some embodiments, upon forming the liquid sample: gas interface, the liquid may occupy a total volume V of the channel upstream of the first liquid sample:gas interface and the method may comprise mixing the sample liquid by magnetically moving the particles within the volume V after forming the liquid sample:gas interface.

In some embodiments, upon forming the liquid sample: gas interface, the liquid may occupy a total volume V of the channel upstream of the first liquid sample:gas interface and the method may comprise mixing the sample liquid by magnetically moving the particles within the volume V after forming the liquid sample:gas interface and prior to forming the sample liquid:second liquid interface.

The method may comprise moving the liquid sample:gas interface by a distance DC or less along the channel between forming the liquid sample:gas interface and forming the liquid sample:second liquid interface, wherein DC may be about 3 mm or less (e.g., about 2 mm or less, about 1 mm or less). DC may be essentially zero.

The liquid sample:gas interface may be essentially static with respect to movement along the channel between forming the liquid sample:gas interface and forming the liquid sample:second liquid interface.

In some embodiments, upon forming the liquid sample: second liquid interface, sample liquid and second liquid adjacent the interface may be essentially static for a time TM, wherein TM may be at least 1 second (e.g., at least 5 seconds, at least 10 seconds, at least 30 seconds). Time TM may be sufficiently long to permit the particles to be transported across the sample liquid:second liquid interface and the detection of analyte associated with the transported particles.

The step of magnetically moving the magnetically susceptible particles across the liquid sample:second liquid interface into the second liquid may comprise moving substantially all of the magnetic or magnetically susceptible particles across the liquid sample:second liquid interface.

The step of magnetically moving the magnetically susceptible particles across the liquid sample:second liquid interface into the second liquid may comprise moving at least about 70% (e.g., at least about 80%, at least about 90%) of a total number N magnetic or magnetically susceptible particles across the liquid sample:second liquid interface.

The step of magnetically moving the magnetically susceptible particles across the liquid sample:second liquid interface into the second liquid may comprise moving a total number N particles across the liquid sample:second liquid interface and substantially all of the N particles are moved across the liquid sample:second liquid interface within a time TN of one another, where TN is about 10 seconds or less (e.g., about 5 seconds or less, about 3 seconds or less).

In some embodiments, upon forming the liquid sample: gas interface, the sample liquid may occupy a volume V of the channel upstream from the liquid-air interface, wherein V may be 0.5 µl or more (e.g., at least about 1 µl). V may be about 10 µl or less (e.g., about 7.5 µl or less, about 5 µl or less).

In some embodiments, upon forming the liquid sample: gas interface, the sample liquid may occupy a volume V of the channel upstream from the liquid-air interface, wherein V may be chosen from one of: about 2 µl, about 3 µl, about 5 µl, 5 µl, about 6 µl, about 7 µl, about 8 µl, about 9 µl, about 10 µl, about 15 µl, about 20 µl.

The method may include detecting the presence of the second liquid (e.g., detecting flow of the second liquid) in the second channel portion. The presence of the second liquid in the second channel portion may be detected prior to the second liquid contacting the sample liquid. Detecting the presence of the second liquid in the second channel portion and/or in an overflow channel portion may be performed additionally (or alternatively) after the second liquid has contacted the sample liquid.

The method may be a diagnostic method.

The method may be performed outside of the presence of a medical practitioner.

In some embodiments, the method is a method for detecting NTproBNP in a liquid sample of blood, plasma or serum from a human and the method includes introducing the liquid sample to a first portion of a channel of a microfluidic device; contacting, within the microfluidic device, the liquid sample with reagents comprising magnetically susceptible particles conjugated to a first anti-NTproBNP antibody, and a second anti-NTproBNP antibody conjugated to an enzyme label, to form complexes comprising magnetically susceptible particle, NTproBNP and enzyme label; forming, proximal to a junction between the first portion of the channel and a second portion of the channel, a liquid sample:gas interface; forming a liquid sample:second liquid interface by displacing gas of the liquid sample:gas interface with a second liquid; magnetically moving the magnetically susceptible particles across the liquid sample:second liquid interface into the second liquid; and detecting NTproBNP in the second liquid.

Another aspect of the invention relates to an interface of a liquid sample and a second, different, liquid in a channel of a microfluidic device. The interface includes the second liquid in contact with and flowing across a liquid sample:gas interface, the flow of the second liquid decreasing the area of the liquid sample:gas interface and forming a liquid:liquid interface, wherein the liquid sample is chosen from human blood, plasma or serum and contains magnetic particles adjacent the interface. The particles may be conjugated to a binding agent which is bound to an analyte in the liquid sample. The interface may be disposed within a microfluidic device.

Another aspect of the invention relates to assay system comprising a microfluidic assay device and a meter, the assay device comprising an inlet in fluid connection with a first portion of a channel, the inlet configured to receive a liquid; a second portion of the channel connected to the first portion at a junction; magnetically susceptible particles disposed in the first channel portion; wherein the device is configured to form, with a liquid received by the inlet, a liquid interface proximal the junction. The assay device may further comprise a reservoir containing a quantity of second liquid and configured to deliver second liquid released from the reservoir into the second channel portion such that the second liquid flows towards the junction, and at least one sensor configured on the second channel portion to detect a signal from the second liquid. The meter may comprise a housing configured to receive the assay device, a magnet configured to localize a magnetic field at a first position and at least one second position of the received assay device.

In some embodiments, the meter comprises a magnet mounted on a carriage, wherein the carriage is moveable to position the magnet at the first and second positions. The assay device comprises a sharp projection, and one of the reservoir and projection are moveable toward the other such that the sharpened projection punctures a wall of the reservoir, and wherein the meter comprises an actuator operable to move the reservoir toward the projection.

Another aspect of the invention relates to a meter for use in determining an assay result, comprising: a housing configured to receive a microfluidic assay device, a magnet configured to localize a magnetic field at a first position and at least one second position of the received assay device, an actuator moveable between a first position and second position, wherein in the second position the actuator contacts a reservoir of an assay device received in the meter. In some embodiments, the magnet is mounted on a carriage, wherein the carriage is moveable to position the magnet at the first or second position. The meter may include, received in the meter, an assay device as described above.

Another aspect of the invention relates to a method comprising forming a liquid-gas interface, magnetically positioning magnetic or magnetically susceptible particles adjacent the interface, and forming a liquid-second liquid interface by displacing gas at the liquid-gas interface, whereupon the magnetically susceptible particles cross the liquid-liquid interface.

Another aspect of the invention relates to a method comprising: forming a liquid-gas interface within a channel of a microfluidic device, magnetically moving magnetically susceptible particles to within a distance D mm of the interface, forming a liquid-second liquid interface by displacing gas at the liquid-gas interface, and magnetically moving the magnetically susceptible particles across the liquid-second liquid interface within a time T seconds after moving the particles to within the distance D mm of the liquid-gas interface. The distance D may be 10 mm or less (e.g., 5 mm or less). The time T may be 20 seconds or less (e.g., 10 seconds or less).

The steps of moving the magnetically susceptible particles may be performed without directly contacting the particles.

In embodiments, the junction has a cross sectional area of about 5 mm2 or less (e.g., about 2.5 mm or less, 1.5 mm2 or less, 1 mm2 or less, about 0.8 mm$^2$ or less, about 0.75 mm$^2$ or less, about 0.6 mm$^2$ or less, about 0.4 mm$^2$ or less, about 0.2 mm$^2$ or less). The junction may have a cross-sectional area of at least about 0.15 mm$^2$ (e.g., about 0.5 mm2 or more). In embodiments, the junction has a cross-sectional area in the range about 0.15 mm$^2$ to about 1 mm$^2$.

The liquid sample:gas interface may have a first dimension H and a second dimension W and a ratio of W to H may be at least 2 (e.g., at least 3.5, at least 5). The ratio W to H may be about 30 or less (e.g., about 20 or less, about 10 or less).

The liquid-second liquid interface may have a cross sectional area of about the same as the liquid-gas interface or less.

In some embodiments, upon forming the liquid sample:gas interface, the liquid may occupy a volume V of the channel upstream from the liquid sample:gas interface and the method may comprise magnetically oscillating the particles within the volume V after forming the first liquid:gas interface and prior to forming the liquid sample:second liquid interface.

A time TI between forming the liquid sample:gas interface and forming the liquid sample:second liquid interface may be at least 5 seconds (e.g., at least 15 seconds, at least 30 seconds). Time TI may be about 600 seconds or less (e.g., about 300 seconds or less, about 150 seconds or less, about 60 seconds or less). The method may include inducing essentially no movement of the particles for a time TD after forming the liquid sample:gas interface, wherein TD may be at least 5% (e.g., at least 10%, at least 25%) of time TI.

In some embodiments, upon forming the liquid sample:gas interface, the liquid occupies a volume V of the channel upstream from the liquid sample:gas interface and the method comprises magnetically oscillating the particles within the volume V after forming the liquid air interface and prior to forming the liquid sample:second liquid interface for a total time TO, wherein TO may be at least 30% of time TI. TO may be 90% or less (e.g., 75% or less) of time TI.

The method may comprise moving the liquid sample:gas interface by a distance DC or less along the channel between forming the liquid sample:gas interface and forming the liquid sample:second liquid interface, wherein DC may be about 3 mm or less (e.g., about 2 mm or less, about 1 mm or less). DC may be essentially zero.

The liquid sample:gas interface may be essentially static with respect to movement along the channel between forming the liquid sample:gas interface and forming the liquid sample:second liquid interface.

The step of magnetically moving the magnetically susceptible particles across the liquid sample:second liquid interface into the second liquid may comprise moving at least about 70% (e.g., at least about 80%, at least about 90%) of a total number N magnetic or magnetically susceptible particles across the liquid sample:second liquid interface.

The step of magnetically moving the magnetically susceptible particles across the liquid sample:second liquid interface into the second liquid may comprise moving a total number N particles across the liquid sample:second liquid interface and substantially all of the N particles are moved across the liquid sample:second liquid interface within a time TN of one another, where TN is about 10 seconds or less (e.g., about 5 seconds or less, about 3 seconds or less).

In some embodiments, upon forming the liquid sample:gas interface, the sample liquid may occupy a volume V of the channel upstream from the liquid-air interface, wherein V may be 0.5 μl or more (e.g., at least about 1 μl). V may be about 10 μl or less (e.g., about 7.5 μl or less, about 5 μl or less).

In some embodiments, upon forming the liquid sample: gas interface, the sample liquid may occupy a volume V of the channel upstream from the liquid-air interface, wherein V may be chosen from one of: about 2 µl, about 3 µl, about 5 µl about 6 µl, about 7 µl, about 8 µl, about 9 µl, about 10 µl, about 15 µl about 20 µl.

The liquid of the liquid-gas interface may be blood.

In some embodiments, a method comprises forming a liquid-gas interface between a mixture and a gas, the mixture comprising a first liquid and magnetically susceptible particles, subjecting the particles to a magnetic force directed, at least in portion, toward the liquid-gas interface, and with the particles being subjected to the force, displacing at least some of the gas with a second liquid to form a liquid-liquid interface between the first and second liquids, whereupon the particles cross the liquid-liquid interface into the second liquid. The method may be performed without directly contacting the particles after forming the liquid-gas interface and prior to the particles crossing the liquid-liquid interface.

In some embodiments, essentially none of the particles cross the liquid-gas interface.

A ratio of a number of particles that cross the liquid-gas interface to a number of particles that cross the liquid-liquid interface may be less than 0.1 (e.g., less than 0.05, less than 0.01, less than 0.001).

The first liquid may be blood and the second liquid may be a buffer solution.

In some embodiments, the method comprises forming the liquid-gas and liquid-liquid interfaces within a microfluidic network of a microfluidic device. The microfluidic device may have a sensor disposed adjacent the liquid-liquid interface (e.g., within about 10 mm or less of the interface, within about 7.5 mm or less, within about 5 mm or less). The sensor may be an electrochemical sensor. The particles that cross the liquid-liquid interface may move directly to the sensor. For example, the particles that cross the liquid-liquid interface may move to a surface of the sensor without first contacting another surface of the microfluidic device after crossing the interface. For example, the surface of the sensor may be a surface of an electrode of the sensor in embodiments in which the sensor is an electrochemical sensor.

The total volume of the liquid for the mixture may be about 10 µl or less (e.g., about 7.5 µl or less, about 5 µl or less).

In embodiments, the cross sectional area of each of the liquid-gas and liquid-liquid interfaces is about 5 mm2 or less (e.g., about 2.5 mm or less, 1.5 mm2 or less, 1 mm2 or less, about 0.8 mm$^2$ or less, about 0.75 mm$^2$ or less, about 0.6 mm$^2$ or less, about 0.4 mm$^2$ or less, about 0.2 mm$^2$ or less). The cross sectional area of each of the liquid-gas and liquid-liquid interfaces may be at least about 0.15 mm$^2$ (e.g., about 0.5 mm2 or more). In embodiments, the cross sectional area of each of the liquid-gas and liquid-liquid interfaces may be in the range about 0.15 mm$^2$ to about 1 mm$^2$.

In some embodiments, a method comprises forming a first mixture within a microfluidic device, the first mixture comprising a first reagent and a liquid sample, the first reagent comprising a particle that is magnetic or magnetically susceptible and a binder for an analyte, transporting the first reagent across an interface between the mixture and a fluid, an determining the presence of analyte transported across the interface by the particles. The fluid may be a gas (e.g., air).

The method may include contacting the particles with a liquid reagent after the step of transporting and wherein determining comprises determining the presence of the analyte in the liquid reagent.

The fluid may be a liquid reagent (e.g., a buffer solution).

The determining may comprise determining the presence of the analyte in the liquid reagent.

In some embodiments, the method includes forming a liquid-liquid interface between first and second different liquids, the first liquid comprising first and second analytes, determining the first analyte within the first liquid, moving the second analyte across the liquid-liquid interface into the second liquid, and determining the second analyte within the second liquid.

Determining the first analyte comprises indirectly determining the first analyte. The first liquid may further comprise a first reagent capable of forming a complex with the first analyte and indirectly determining the first analyte comprises determining the first reagent within the first liquid. Determining the first reagent may comprise electrochemically determining the first reagent. The first reagent may be a metal or ion thereof. The first reagent may be cobalt and the first analyte albumin.

Prior to forming the liquid-liquid interface, the method may include introducing sample material to a microfluidic device comprising a microfluidic network and wherein the sample material comprises the first and second analytes, the first liquid comprises at least some of the sample material, and the forming the liquid-liquid interface comprises forming the interface within the microfluidic network.

The sample material may comprise blood or a liquid derived from blood. The sample material may comprise blood, the introducing the sample material to the microfluidic device may comprise introducing blood to the microfluidic device and the method may further comprise obtaining the blood (e.g., all of the blood) from a finger stick.

After the introducing the sample material, the method may further comprise combining the sample material with the first reagent and a second reagent, the second reagent having an affinity for the second analyte.

The second reagent may be a particulate reagent comprising a first portion having the affinity for the second analyte and a particle. Prior to the combining, the first and second reagents may be present in a dried state within the microfluidic network and the method comprise wetting the dried first and second reagents with the first liquid.

Moving the second analyte across the liquid-liquid interface may comprise applying a force to the second reagent, the second analyte having associated with the second reagent.

The particle of the second reagent may be magnetically susceptible and the moving the second analyte comprise subjecting the second reagent to a magnetic field sufficient to move the second reagent across the liquid-liquid interface.

Determining the second analyte may comprise electrochemically determining the second analyte.

Combining the sample material with the first reagent and a second reagent may further comprise combining the sample material with a third reagent, the second analyte, the second reagent, and the third reagent are capable of forming a complex, and the third reagent participates in the electrochemical determination of the second analyte.

The third reagent may be an enzyme and electrochemically determining the second analyte may comprise contacting the enzyme with a substrate for the enzyme.

The enzyme may be a glucose oxidase and the substrate may be glucose.

Determining the first analyte may be performed before the moving the second analyte across the liquid-liquid interface.

Forming the liquid-liquid interface may comprise introducing the first liquid at a first location of a channel within a substrate and introducing the second liquid at a second location of the channel, the second channel being spaced apart from the first location and the liquid-liquid interface is formed between the first and second locations.

A maximum cross-sectional area of the channel between the first and second locations may be about 5 mm2 or less (e.g., about 1 mm2 or less).

Forming a liquid interface may comprise moving at least one of the first and second liquids along the channel by capillary action.

In embodiments, the method includes forming a mixture comprising sample material, a metal ion, and an enzymatic reagent, the sample material comprising a protein and a second biological analyte, the metal ion being capable of forming a complex with the protein, the enzymatic reagent being capable of forming a complex with the biological analyte, detecting an amount of the metal ion not complexed with the protein, determining an amount of the protein based on the amount of metal ion not complexed with the protein, separating enzymatic reagent complexed with the biological analyte and enzymatic reagent not complexed with the biological analyte, contacting enzymatic reagent complexed with the biological analyte with a second reagent capable of participating in an enzymatic reaction with the enzymatic reagent, detecting an amount of a product of the enzymatic reaction, and determining an amount the biological reagent based on the amount of product. The protein may be albumin. The metal ion may be cobalt ion. The sample material may be blood or a liquid derived from blood. The biological analyte may be a natriuretic peptide. The enzymatic reagent may be an enzyme and the second reagent may be a substrate for the enzyme. Detecting an amount of the product of the enzymatic reaction may comprise indirectly detecting the product. The enzymatic reagent may be a glucose oxidase, the second reagent a substrate for the glucose oxidase, and the product an oxidized form of the substrate.

The mixture may further comprise a magnetic particulate reagent capable of forming a complex with the enzymatic reagent and the biological analyte, and the separating comprises subjecting the mixture to a magnetic field. Subjecting the mixture to a magnetic field may move the complex with the enzymatic reagent, the biological analyte, and the magnetic particulate reagent from a first location to a second location spaced apart from the first location. The separating comprises moving enzymatic reagent complexed with the biological analyte across a liquid-liquid interface between first and second liquids, the first liquid comprising the mixture, and the second liquid being different from the first liquid.

In another aspect, the invention relates to an assay for selectively determining a plurality of characteristics of an aqueous liquid sample containing at least one chemical moiety of interest amongst other sample components, the assay comprising, providing a lateral flow device for use in performing the assay, the flow device comprising at least one lateral flow channel, a sample collection site, at least one reagent deposit zone proximate to the lateral flow channel and sensor means functionally juxtaposed with respect to the lateral flow channel; providing particles adapted to exhibit a selective affinity towards a target chemical moiety to be determined in an assay, said particles further being susceptible to manipulation by means of a magnetic field; applying a liquid sample to the sample collection site in a sufficient amount to permit flow thereof into the lateral flow channel and said at least one reagent deposit zone, and for a period sufficient to permit adequate interaction of the particles with chemical moiety present in the sample to capture same; applying a magnetic field in a controlled manner to localise the particles and captured chemical moiety; transferring the particles and captured chemical moiety by manipulation with the applied magnetic field through a surface of the liquid sample whereby the particles and captured chemical moiety are separated from other sample components remaining in the liquid sample; and using the sensor means to detect at least one of the following characteristics selected from the group consisting of an optical characteristic, an electrochemical characteristic, a radiation characteristic and an immunological characteristic.

A further liquid may be introduced to the lateral flow device after the sample is applied to the sample collection site and permitted to flow into the lateral flow channel, the further liquid being introduced to the lateral flow channel at a point remote from the sample collection site to permit flow towards the latter such that an interface is formed between the liquid sample and the further liquid at a predictable position in the lateral flow channel.

The step following applying of the sample may comprise conducting an electrochemical measurement using sensor means comprising an electrode.

The step of applying of the sample may include a mixing of sample with said particles.

The step of providing said particles may comprise deposition of same at the sample collection site.

The sample may be treated with at least one reagent selected from the group consisting of an optically detectable label, an immuno-responsive label, a radioactive label, and conjugates of the aforesaid labels.

The label may be selected from the group consisting of enzymes, carrier-hapten conjugates, aptamers, antibodies, radioisotopes, fluorescent compounds, colloidal metals, chemiluminescent compounds, phosphorescent compounds and bioluminescent compounds.

The label may be bound to an insoluble solid support particle (e.g., a resin bead).

Another aspect of the invention relates to an assay for selectively determining a plurality of characteristics of a liquid sample containing several differing components, the assay comprising the steps of introducing to a liquid sample, a quantity of particles exhibiting a preferential affinity towards a component of the liquid sample, said particles further being susceptible to manipulation by means of a magnetic field; causing the liquid sample to flow in a lateral flow channel to a predetermined point at which a liquid meniscus is formed; manipulating the particles by means of an applied magnetic field to localise the particles at the liquid meniscus; introducing a further liquid by lateral flow up to the liquid meniscus of the sample liquid to form a liquid/liquid interface; and manipulating the localised particles by means of an applied magnetic field to transfer the localised particles through the liquid/liquid interface.

An electrochemical measurement may be carried out on the liquid sample before the particles are introduced to the liquid sample.

An electrochemical measurement is carried out on the liquid sample after the particles are introduced to the liquid sample.

The particles may present a surface which is functionalised to interact with a biomolecular species in the liquid sample. The functionalised surface may comprise an antibody or functional binding fragment thereof, capable of binding with the biomolecular species. The functionalised surface may comprise at least one species selected from the group consisting of a protein, an oligopeptide, a peptide, a lipoprotein, a polysaccharide, a sugar residue, a vitamin, an enzyme, enzyme conjugate, and a ligand. The functionalised surface may comprise a protein selected from the group consisting of a cell-surface associated protein, an immunoglobulin-binding protein, streptavidin and biotin.

The particles may present a surface which is functionalised to interact with a chemical moiety in the liquid sample. The surface may be functionalised with a functionality selected from the group consisting of carboxyl, amine, aldehyde, epoxide, N hydroxy-succinimide, chloromethyl, polyglutaraldehyde, thiol, cyanuric, tosyl, hydrazide, and hydroxide.

The lateral flow channel may comprise at least a portion adapted to facilitate capillary flow of an aqueous liquid.

Another aspect of the invention relates to an assay for selectively determining a plurality of characteristics of an aqueous liquid sample containing at least one chemical moiety of interest amongst other sample components, the assay comprising, providing a lateral flow device for use in performing the assay, the flow device comprising at least one capillary flow channel, a sample collection site, at least one reagent deposit zone proximate to the capillary flow channel and an electrode functionally juxtaposed with respect to the capillary flow channel; providing particles adapted to exhibit a selective affinity towards a target chemical moiety to be determined in an assay, said particles further being susceptible to manipulation by means of a magnetic field; applying a liquid sample to the sample collection site in a sufficient amount to permit flow thereof into the capillary flow channel and said at least one reagent deposit zone, and for a period sufficient to permit adequate interaction of the particles with chemical moiety present in the sample to capture same; applying a magnetic field in a controlled manner to localise the particles and captured chemical moiety; transferring the particles and captured chemical moiety by manipulation with the applied magnetic field through a surface of the liquid sample whereby the particles and captured chemical moiety are separated from other sample components remaining in the liquid sample; and using the electrode to perform an electrochemical analysis step.

A redox mediator may be introduced to the sample liquid to facilitate determination of a characteristic of the sample.

The liquid sample is a fresh physiological fluid (e.g., blood) applied directly to a sample collection site in the lateral flow device, and the sample collection site is provided with a deposit of reagents which include said particles, and labelling means adapted to selectively discriminate one component of the sample from another.

Mixing of the sample and reagents may be promoted by applying a magnetic field and manipulating the particles with the applied field to move the particles in the sample.

Another aspect of the invention relates to a portable lateral flow assay device for use with liquid samples which may contain an analyte, the device comprising a support configured to provide a shallow liquid flow channel adapted to receive liquid from more than one point, wherein at least a substantial part of said channel is covered, and at least one further part of said channel is adapted to control liquid flow up to at least one intermediate position within the length of said channel; wherein at least one surface accessible to the liquid flow channel has a dry reagent deposited thereon, and wherein said device is provided with sensor means configured upon the device and juxtaposed with respect to said channel such that, in use of the device with a liquid sample, a characteristic of the liquid sample may be sensed.

The sensor means may include an electrode positioned within (e.g., at one end) of the flow channel.

The surface where dry reagent is deposited may be remote from the sensor means.

The surface where dry reagent is deposited may be adjacent the sensor means.

The channel may be adapted to control capillary flow by the presence of at least one air vent to provide a stop at an intermediate position within the length of the channel.

The channel may be adapted to control capillary flow by the presence of a plurality of fusible vents whereby capillary flow may be selectively inhibited or extended.

A step change in configuration of the channel may be provided to control lateral flow within the channel.

The channel may have wide and narrow portions, a narrow portion being provided between wide portions.

The channel may follow a substantially straight linear path throughout.

The device may be a rectilinear planar device configured such that a sample application site is provided at a proximal end of the channel and a port is provided at a distal end of the channel. The port may be adapted to receive a liquid to be introduced into the channel.

The channel may follow a path which is configured to provide a plurality of straight sections, the path overall lying within a single plane of the device. The channel may be bifurcated.

The channel may consist of a plurality of successive sections separable by capillary flow control means selected from the group consisting of air vents, and step changes in a dimension of the channel.

Each section of the channel may be adapted to a different analytical step purpose by one or more adaptations selected from the group consisting of, the presence of a selected reagent deposited on a surface in the section, the presence of sensor means, and the presence of ports for admitting or venting fluids. The channel may follow a curved linear path (e.g., a helical path).

The device may comprise a hydrophobic base part and a hydrophilic cover part configured to define therebetween said flow channel, wherein said sensor means configured upon the device comprises a screen-printed electrode positioned on a surface of the base part at one end of the flow channel, said one end of the flow channel being adapted to serve as a site for application of a sample liquid, said one end of the flow channel also being exposed to a first surface upon which assay reagents are dry-deposited, said reagents comprising the particles, and a label for identifying presence of an analyte in a sample liquid, the flow channel having a second surface upon which assay reagents are dry-deposited, said second surface being laterally spaced from said first surface and wherein said further assay reagents comprising at least a REDOX mediator, and the flow channel further being provided with a port close to said second surface for introduction of a reaction buffer.

The second surface may be adjacent a further sensor means for sensing a characteristic of the sample after exposure to said further assay reagents.

The pouch may be provided in fluid communication with the channel for application of a liquid into the channel.

The sensor means may be positioned within a recess.

The sensor means may comprise an electrode.

At least a portion of the cover over the channel is sufficiently transparent to permit observation of the channel.

The channel may be covered by an antifog material.

Another aspect of the invention relates to an assay for determining the presence in a physiological fluid of biomarkers indicative of a potential cardiovascular dysfunction in a patient, comprising the steps of providing a lateral flow device in which a shallow well is available for receipt of a liquid and in which at least one dry reagent is deposited, said reagent being one capable of interacting with a first biomarker in a predictable way to serve as an aid to detection of the biomarker; introducing to the well a sample of the physiological fluid, and particles susceptible to manipulation under magnetic influence, wherein said particles have a selective affinity towards a biomarker to the extent that any biomarker present in the sample is liable to become associated with the particles, subsequently applying a magnetic field to the device to localise the particles in a selected position, and using sensor means sensitive to the reagent-biomarker combination to detect presence of biomarker; and further introducing a liquid to the well to flow fill up to the sample and form a liquid-sample interface; applying a magnetic field to the device to manipulate the particles and transfer the particles from the sample across the liquid-sample interface into the liquid, and conducting a further test for another biomarker in that liquid.

The first biomarker may be ischemia modified albumen (IMA), and the first assay step may be an electrochemical test using an electrode to indirectly determine IMA.

A further biomarker may be NTprohormone-brain natriuretic peptide (NTproBNP), and the further test may comprise introducing a reagent to permit formation of a reagent-modified NTproBNP species the presence of which presents a distinctive characteristic which is selected from the group consisting of an optical characteristic, an electromagnetic characteristic, an electrochemical characteristic, a radiation characteristic and an immunological characteristic.

A further biomarker may be NTprohormone-brain natriuretic peptide (NTproBNP), and the further test comprises introducing a reagent to permit formation of a reagent-modified NTproBNP species the formation of which suppresses a distinctive characteristic of the reagent which characteristic is selected from the group consisting of an optical characteristic, an electromagnetic characteristic, an electrochemical characteristic, a radiation characteristic and an immunological characteristic. The modified NTproBNP species may be formed using a reagent which comprises a labelled binding partner for NTproBNP.

The modified NTproBNP species may be formed using a reagent which is selected from the group consisting of a labelled molecular probe capable of covalently bonding to NTproBNP, a labelled NTproBNP antibody, a labelled binding fragment of an NTproBNP antibody, and an insoluble resin capture bead functionalised to adsorb NTproBNP.

Another aspect of the invention relates to a method for conducting a plurality of determinations of characteristics selected from the group consisting of biological, biochemical, chemical and physical characteristics, upon a sample in a liquid form, comprising providing a portable lateral flow device in which at least one shallow covered channel is available for receipt of a liquid, the channel being configured to provide for bidirectional lateral flow of liquid therethrough and having a plurality of reagent treatment zones spaced at intervals in the channel, each such zone having a dry reagent deposited thereon for the purpose of promoting or visualising at least one of the characteristics to be determined, the device further comprising means for controlling flow of liquid to said zones by selectively inhibiting or extending lateral flow of liquid therein, and sensor means configured upon the device and juxtaposed with respect to said channel such that, in use of the device with a liquid sample, flowing of said liquid to said zones permits a characteristic of the liquid sample to be sensed selectively at more than one of said reagent treatment zones.

Another aspect of the invention relates to a microanalysis system comprising a planar device comprising a base part and a cover part which in combination provide walls defining a lateral flow path for a liquid, and at least one of said parts comprises fusible vent means for selectively controlling the flow of liquid within the device by excluding or admitting air to the flow path.

A reservoir of liquid may be associated with the flow path and provided with means operable to control liquid flow in the flow path by transfer of liquid between the reservoir and the flow path.

The reservoir may comprise a compressible surface to effect transfer of liquid.

At least one dry reagent may be deposited upon a surface of at least part of one of the walls defining the lateral flow path to define a reagent treatment zone; and further comprising a magnetic field source juxtaposed with the device and operable to apply a magnetic field to the device in a localised selected position.

The sensor means may comprise an electrode recessed into a well in the base part and juxtaposed with respect to said channel such that, in use of the device with a liquid, an electrochemical characteristic of the liquid may be determined.

Another aspect of the invention relates to an electrochemical lateral flow device comprising a base part and a cover part, at least one of said parts having configured thereon a first electrode set including an electrode adapted to detect an analyte in a liquid, and a counter electrode, the base part and cover part being configured to provide at least one well therebetween and ports for introducing a liquid to the well and for venting liquid therefrom, the well having deposited therein at least one dry reagent and being positioned with respect to the first electrode set such that when liquid is introduced to the well it reaches the electrode set, and dry reagent is taken up into the liquid, such that presence of the analyte in the liquid can be detected, said parts of the device further having formed therebetween a covered channel having a proximal end opening at the well whereby said channel is adapted to be filled with a liquid by lateral flow, and at least one of said parts has a further electrode set spaced from the first and positioned at a distal end of the channel for the purposes of conducting a further electrochemical test.

Another aspect of the invention relates to a method of determining the presence of analytes in a liquid medium which contains at least one analyte (AOI), the method comprising the steps of providing magnetic particles adapted to capture said at least one AOI to form a detectable capture particle species, introducing the liquid medium including said at least one AOI, with said magnetic particles to a capillary and allowing the capillary to flow fill to a predetermined lateral flow limit point, applying a magnetic field to the capillary to gradually localise the magnetic particles at a selected point within the capillary, thereby isolating said detectable capture particle species at the selected point, and conducting an analytical test on the capture particle species at the selected point.

Another aspect of the invention relates to a method of separating analyte(s) from a liquid medium which contains at least one analyte (AOI), the method comprising the steps of providing magnetic particles adapted to capture said at least one AOI to form a detectable capture particle species, introducing the liquid medium including said at least one AOI, with said magnetic particles to a capillary and allowing the capillary to flow fill to a predetermined lateral flow limit point, applying a magnetic field to the capillary to gradually localise the magnetic particles and detectable capture particle species at a selected point proximate to said lateral flow limit point, introducing a second liquid to said capillary to form a liquid-liquid interface at said lateral flow limit point, applying a magnetic field to the capillary to transfer the localised magnetic particles and detectable capture particle species through the liquid-liquid interface into the second liquid.

Another aspect of the invention relates to a test device for conducting a plurality of determinations of characteristics selected from the group consisting of biological, biochemical, chemical and physical characteristics, upon a liquid sample, said device comprising a generally planar base part and a corresponding cover part superposed upon the base part, and configured to define at least one shallow well therebetween for receiving a liquid sample at a first zone, said well being dimensioned to facilitate lateral flow of liquid between said first zone and a plurality of discrete distal zones spaced apart from each other, wherein at least some of said discrete distal zones each have a dry reagent deposited therein, and sensor means configured upon the device and juxtaposed with respect to said distal zones such that, in use of the device with a liquid sample, a characteristic of the liquid sample may be sensed selectively at more than one of said distal zones.

A disposable single use test device for detecting an analyte in a candidate liquid sample, said device comprising a planar substrate having a sample deposition zone defined at a first location, a reagent dry-deposited proximate to said first location, said reagent containing releasable magnetic particles adapted to capture the analyte when contacted by the candidate liquid sample, a liquid impermeable membrane positionable so as to overly the planar substrate to form a lateral flow region for liquid, and a detection zone remote from the sample deposition zone and juxtaposed with an edge of said membrane to receive in use liquid flowed from the lateral flow region which may contain captured analyte for detection thereof.

Another aspect of the invention relates to a method, comprising: forming a liquid-liquid interface between first and second different liquids, the first liquid comprising first and second analytes, determining the first analyte within the first liquid, moving the second analyte across the liquid-liquid interface into the second liquid, and determining the second analyte within the second liquid. The determining the first analyte comprises indirectly determining the first analyte.

The first liquid may further comprise a first reagent capable of forming a complex with the first analyte and indirectly determining the first analyte comprises determining the first reagent within the first liquid.

Determining the first reagent may comprise electrochemically determining the first reagent. The first reagent may be a metal or ion thereof. The first reagent may be cobalt and the first analyte is albumin.

Prior to forming the liquid-liquid interface, the method may include introducing sample material to a microfluidic device comprising a microfluidic network and wherein the sample material comprises the first and second analytes, the first liquid comprises at least some of the sample material, and the forming the liquid-liquid interface comprises forming the interface within the microfluidic network. The sample material may comprise blood or a liquid derived from blood. The sample material may comprise blood, and the introducing the sample material to the microfluidic device comprises introducing blood to the microfluidic device and the method further may comprise obtaining the blood from a finger stick.

After the introducing the samples material, the method may include combining the sample material with the first reagent and a second reagent, the second reagent having an affinity for the second analyte.

The second reagent may be a particulate reagent comprising a first portion having the affinity for the second analyte and a particle.

Prior to the combining, the first and second reagents may be present in a dried state within the microfluidic network and the method comprises wetting the dried first and second reagents with the first liquid.

Moving the second analyte across the liquid-liquid interface may comprise applying a force to the second reagent, the second analyte having associated with the second reagent.

The particle of the second reagent may be magnetically susceptible and the moving the second analyte may comprise subjecting the second reagent to a magnetic field sufficient to move the second reagent across the liquid-liquid interface.

Determining the second analyte comprises electrochemically determining the second analyte.

Combining the sample material with the first reagent and a second reagent may further comprise combining the sample material with a third reagent, the second analyte, the second reagent, and the third reagent are capable of forming a complex, and the third reagent participates in the electrochemical determination of the second analyte.

The third reagent may be an enzyme and electrochemically determining the second analyte may comprise contacting the enzyme with a substrate for the enzyme.

The enzyme may be a glucose oxidase and the substrate glucose.

Determining the first analyte may be performed before the moving the second analyte across the liquid-liquid interface.

Forming the liquid-liquid interface may comprise introducing the first liquid at a first location of a channel within a substrate and introducing the second liquid at a second location of the channel, the second channel being spaced apart from the first location and the liquid-liquid interface is formed between the first and second locations.

A maximum cross-sectional area of the channel between the first and second locations may be about 5 mm2 or less (e.g., about 1 mm2 or less).

Forming a liquid interface may comprise moving at least one of the first and second liquids along the channel by capillary action.

In another aspect of the invention, a method comprises forming a mixture comprising sample material, a metal ion, and an enzymatic reagent, the sample material comprising a protein and a second biological analyte, the metal ion being capable of forming a complex with the protein, the enzymatic reagent being capable of forming a complex with the biological analyte, detecting an amount of the metal ion not complexed with the protein, determining an amount of the protein based on the amount of metal ion not complexed with the protein, separating enzymatic reagent complexed with the biological analyte and enzymatic reagent not complexed with the biological analyte, contacting enzymatic reagent complexed with the biological analyte with a second reagent capable of participating in an enzymatic reaction with the enzymatic reagent, detecting an amount of a product of the enzymatic reaction, and determining an amount the biological reagent based on the amount of product.

The protein may be albumin. The metal ion may be cobalt ion. The sample material may be blood or a liquid derived from blood. The biological analyte may be a natriuretic peptide.

The enzymatic reagent may be an enzyme and the second reagent a substrate for the enzyme.

Detecting an amount of the product of the enzymatic reaction may comprise indirectly detecting the product. The enzymatic reagent may be a glucose oxidase, the second reagent a substrate for the glucose oxidase, and the product an oxidized form of the substrate.

The mixture may further comprise a magnetic particulate reagent capable of forming a complex with the enzymatic reagent and the biological analyte, and the separating comprises subjecting the mixture to a magnetic field.

Subjecting the mixture to a magnetic field may move the complex with the enzymatic reagent, the biological analyte, and the magnetic particulate reagent from a first location to a second location spaced apart from the first location.

Separating may comprise moving enzymatic reagent complexed with the biological analyte across a liquid-liquid interface between first and second liquids, the first liquid comprising the mixture, and the second liquid being different from the first liquid.

Another aspect of the invention relates to a method, comprising: forming a liquid-gas interface, magnetically positioning magnetic or magnetically susceptible particles adjacent the interface, forming a liquid-second liquid interface by displacing gas at the liquid-gas interface, whereupon the magnetically susceptible particles cross the liquid-liquid interface.

Another aspect of the invention relates to method, comprising: forming a liquid-gas interface within a channel of a microfluidic device, magnetically moving magnetically susceptible particles to within a distance D mm of the interface, forming a liquid-second liquid interface by displacing gas at the liquid-gas interface, and magnetically moving the magnetically susceptible particles across the liquid-second liquid interface within a time T seconds after moving the particles to within the distance D mm of the liquid-gas interface; wherein: the distance D is about 10 mm or less (e.g., about 5 mm or less, about 3 mm or less, about 2.5 mm or less). The time T may be about 15 seconds or less (e.g., about 10 seconds or less, about 7.5 seconds or less, about 5 seconds or less, about 3 seconds or less).

The steps of moving the magnetically susceptible particles may be performed without directly contacting the particles.

In embodiments, the junction has a cross sectional area of about 5 mm2 or less (e.g., about 2.5 mm or less, 1.5 mm2 or less, 1 mm2 or less, about 0.8 $mm^2$ or less, about 0.75 $mm^2$ or less, about 0.6 $mm^2$ or less, about 0.4 $mm^2$ or less, about 0.2 $mm^2$ or less). The junction may have a cross-sectional area of at least about 0.15 $mm^2$ (e.g., about 0.5 mm2 or more). In embodiments, the junction has a cross-sectional area in the range about 0.15 $mm^2$ to about 1 $mm^2$.

The liquid sample:gas interface may have a first dimension H and a second dimension W and a ratio of W to H may be at least 2 (e.g., at least 3.5, at least 5). The ratio W to H may be about 30 or less (e.g., about 20 or less, about 10 or less).

The liquid sample:second liquid interface may have a cross sectional area of about the same as the liquid sample:gas interface or less.

A time TI between forming the liquid sample:gas interface and forming the liquid sample:second liquid interface may be at least 5 seconds (e.g., at least 15 seconds, at least 30 seconds). Time TI may be about 600 seconds or less (e.g., about 300 seconds or less, about 150 seconds or less, about 60 seconds or less). The method may include inducing essentially no movement of the particles for a time TD after forming the liquid sample:gas interface, wherein TD may be at least 5% (e.g., at least 10%, at least 25%) of time TI.

In some embodiments, upon forming the liquid sample: gas interface, the liquid may occupy a volume V of the channel upstream from the liquid sample:gas interface and the method may comprise magnetically oscillating the particles within the volume V after forming the first liquid:gas interface and prior to forming the liquid sample:second liquid interface.

In some embodiments, upon forming the liquid sample: gas interface, the liquid occupies a volume V of the channel upstream from the liquid sample:gas interface and the method comprises magnetically oscillating the particles within the volume V after forming the liquid air interface and prior to forming the liquid sample:second liquid interface for a total time TO, wherein TO may be at least 30% of time TI. TO may be 90% or less of time TI.

In some embodiments, upon forming the liquid sample: gas interface, the liquid may occupy a total volume V of the channel upstream of the first liquid sample:gas interface and the method may comprise mixing the sample liquid by magnetically moving the particles within the volume V after forming the liquid sample:gas interface.

In some embodiments, upon forming the liquid sample: gas interface, the liquid may occupy a total volume V of the channel upstream of the first liquid sample:gas interface and the method may comprise mixing the sample liquid by magnetically moving the particles within the volume V after forming the liquid sample:gas interface and prior to forming the sample liquid:second liquid interface.

The method may comprise moving the liquid sample:gas interface by a distance DC or less along the channel between forming the liquid sample:gas interface and forming the liquid sample:second liquid interface, wherein DC may be about 3 mm or less (e.g., about 2 mm or less, about 1 mm or less). DC may be essentially zero.

The liquid sample:gas interface may be essentially static with respect to movement along the channel between forming the liquid sample:gas interface and forming the liquid sample:second liquid interface.

In some embodiments, upon forming the liquid sample: second liquid interface, sample liquid and second liquid adjacent the interface may be essentially static for a time TM, wherein TM may be at least 1 second (e.g., at least 5 seconds, at least 10 seconds, at least 30 seconds). Time TM may be sufficiently long to permit the particles to be transported across the sample liquid:second liquid interface and the detection of analyte associated with the transported particles.

The step of magnetically moving the magnetically susceptible particles across the liquid sample:second liquid interface into the second liquid may comprise moving substantially all of the magnetic or magnetically susceptible particles across the liquid sample:second liquid interface.

The step of magnetically moving the magnetically susceptible particles across the liquid sample:second liquid interface into the second liquid may comprise moving at least about 70% (e.g., at least about 80%, at least about 90%) of a total number N magnetic or magnetically susceptible particles across the liquid sample:second liquid interface.

The step of magnetically moving the magnetically susceptible particles across the liquid sample:second liquid interface into the second liquid may comprise moving a total number N particles across the liquid sample:second liquid interface and substantially all of the N particles are moved across the liquid sample:second liquid interface within a time TN of one another, where TN is about 10 seconds or less (e.g., about 5 seconds or less, about 3 seconds or less).

In some embodiments, upon forming the liquid sample:gas interface, the sample liquid may occupy a volume V of the channel upstream from the liquid-air interface, wherein V may be 0.5 µl or more (e.g., at least about 1 µl). V may be about 10 µl or less (e.g., about 7.5 µl or less, about 5 µl or less).

In some embodiments, upon forming the liquid sample:gas interface, the sample liquid may occupy a volume V of the channel upstream from the liquid-air interface, wherein V may be chosen from one of: about 2 µl, about 3 µl, about 5 µl, about 6 µl, about 7 µl, about 8 µl, about 9 µl, about 10 µl, about 15 µl, about 20 µl.

The liquid of the liquid-gas interface may be blood.

Another aspect of the invention relates to a method, comprising: forming a liquid-gas interface between a mixture and a gas, the mixture comprising a first liquid and magnetically susceptible particles, subjecting the particles to a magnetic force directed, at least in part, toward the liquid-gas interface, and with the particles being subjected to the force, displacing at least some of the gas with a second liquid to form a liquid-liquid interface between the first and second liquids, whereupon the particles cross the liquid-liquid interface into the second liquid.

The method may be performed without directly contacting the particles after forming the liquid-gas interface and prior to the particles crossing the liquid-liquid interface.

In some embodiments, essentially none of the particles cross the liquid-gas interface.

A ratio of a number of particles that cross the liquid-gas interface to a number of particles that cross the liquid-liquid interface may be less than 0.1 (e.g., less than 0.05, less than 0.01, less than 0.001).

The first liquid may be blood and the second liquid may be a buffer solution.

The method may comprise forming the liquid-gas and liquid-liquid interfaces within a microfluidic network of a microfluidic device. A total volume of the liquid of the mixture may be about 10 µl or less (e.g., about 7.5 µl or less, about 5 µl or less).

In embodiments, the cross sectional area of each of the liquid-gas and liquid-liquid interfaces is about 5 mm2 or less (e.g., about 2.5 mm or less, 1.5 mm2 or less, 1 mm2 or less, about 0.8 $mm^2$ or less, about 0.75 $mm^2$ or less, about 0.6 $mm^2$ or less, about 0.4 $mm^2$ or less, about 0.2 $mm^2$ or less). The cross sectional area of each of the liquid-gas and liquid-liquid interfaces may be at least about 0.15 $mm^2$ (e.g., about 0.5 mm2 or more). In embodiments, the cross sectional area of each of the liquid-gas and liquid-liquid interfaces may be in the range about 0.15 $mm^2$ to about 1 $mm^2$.

Another aspect of the invention relates to a method, comprising: forming a first mixture within a microfluidic device, the first mixture comprising a first reagent and a liquid sample, the first reagent comprising a particle that is magnetic or magnetically susceptible and a binder for an analyte, transporting the first reagent across an interface between the mixture and a fluid, and determining the presence of analyte transported across the interface by the particles.

The fluid may be a gas (e.g., air).

The method may further comprise contacting the particles with a liquid reagent after the step of transporting and wherein determining comprises determining the presence of the analyte in the liquid reagent. The fluid may be a liquid reagent.

The following exemplary embodiments concern the measurement of analytes in complex mixtures (e.g., blood). The amount of analyte present can be detected indirectly and accurately, and in turn can be used to signal the occurrence or non-occurrence of a medical event in a subject. The invention enables efficient use of small sample volumes for analysis of differing analytes of interest upon a single small device by a variety of techniques. Particularly the invention enables capture of analytes in physiological fluids, manipulation of the captured analytes for treatment with assay reagents in simultaneous or successive assay procedures in a manner intended to obviate or mitigate problems normally associated with other components of the physiological fluid.

According to one aspect of the invention there is provided an assay for selectively determining a plurality of characteristics of an aqueous liquid sample containing at least one chemical moiety of interest amongst other sample components. A lateral flow device suitable for use in performing the assay comprises at least one lateral flow channel, a sample collection site, at least one reagent deposit zone proximate to the lateral flow channel and sensor means functionally juxtaposed with respect to the lateral flow channel. One reagent used in the assay comprises particles adapted to exhibit a selective affinity towards a target chemical moiety to be determined in the assay, said particles further being susceptible to manipulation by means of a magnetic field.

Typically, a liquid sample is applied to the sample collection site in a sufficient amount to permit flow thereof into the lateral flow channel and the reagent deposit zone, for a period sufficient to permit adequate interaction of the particles with chemical moiety present in the sample to capture same.

A magnetic field is applied in a controlled manner to localise the particles and captured chemical moiety e.g. to allow transferring of the particles and captured chemical moiety through a surface of the liquid sample so that the particles and captured chemical moiety are separated from other sample components remaining in the liquid sample.

One way of achieving the separation is to transfer the particles and captured chemical moiety into another medium e.g. another liquid. This would be achievable if a further liquid is introduced to the lateral flow device after the sample is applied to the sample collection site and permitted to flow into the lateral flow channel, the further liquid being introduced to the lateral flow channel at a point remote from the sample collection site to permit flow towards the latter such that an interface is formed between the liquid sample and the further liquid at a predictable position in the lateral flow channel.

During the above procedure, it is possible to select a suitable sensor means to detect at least one of the following characteristics of a component of the sample, namely an optical characteristic, an electrochemical characteristic, a radiation characteristic and an immunological characteristic. An electrochemical characteristic may be measured initially or later, whereas another characteristic may be better measured after the particles are separated from the sample.

Broadly, an assay method of the following exemplary embodiments comprises the steps of introducing to a liquid sample, a quantity of particles exhibiting a preferential affinity towards a component of the liquid sample, said particles further being susceptible to manipulation by means of a magnetic field; causing the liquid sample to flow in a lateral flow channel to a predetermined point at which a liquid meniscus is formed; manipulating the particles by means of an applied magnetic field to localise the particles at the liquid meniscus; and optionally introducing a further liquid by lateral flow up to the liquid meniscus of the sample liquid to form a liquid/liquid interface; and manipulating the localised particles by means of an applied magnetic field to transfer the localised particles through the liquid/liquid interface.

Accordingly the following exemplary embodiments permit an assay to be designed for determining the presence in a physiological fluid of biomarkers indicative of a potential cardiovascular dysfunction in a patient. Such an assay comprises the steps of providing a lateral flow device in which a shallow well is available for receipt of a liquid and in which at least one dry reagent is deposited, said reagent being one capable of interacting with a first biomarker in a predictable way to serve as an aid to detection of the biomarker; introducing to the well a sample of the physiological fluid, and particles susceptible to manipulation under magnetic influence, wherein said particles have a selective affinity towards a biomarker to the extent that any biomarker present in the sample is liable to become associated with the particles, subsequently applying a magnetic field to the device to localise the particles in a selected position, and using sensor means sensitive to the reagent-biomarker combination to detect presence of biomarker; and further introducing a liquid to the well to flow fill up to the sample and form a liquid-sample interface; applying a magnetic field to the device to manipulate the particles and transfer the particles from the sample across the liquid-sample interface into the liquid, and conducting a further test for another biomarker in that liquid.

In such an assay, the first biomarker may be ischemia modified albumen (IMA), and the first assay step may be an electrochemical test using an electrode to indirectly determine IMA.

Furthermore, in such an assay a further biomarker may be NTprohormone-brain natriuretic peptide (NTproBNP), and the further test would comprise introducing a reagent to permit formation of a reagent-modified NTproBNP species the presence of which presents a distinctive detectable characteristic such as an optical characteristic, an electromagnetic characteristic, an electrochemical characteristic, a radiation characteristic and an immunological characteristic.

According to a further aspect of the invention, there is provided a method for conducting a plurality of determinations of characteristics selected from the group consisting of biological, biochemical, chemical and physical characteristics, upon a sample in a liquid form, comprising providing a portable lateral flow device in which at least one shallow covered channel is available for receipt of a liquid, the channel being configured to provide for bidirectional lateral flow of liquid therethrough and having a plurality of reagent treatment zones spaced at intervals in the channel, each such zone having a dry reagent deposited thereon for the purpose of promoting or visualising at least one of the characteristics to be determined, the device further comprising means for controlling flow of liquid to said zones by selectively inhibiting or extending lateral flow of liquid therein, and sensor means configured upon the device and juxtaposed with respect to said channel such that, in use of the device with a liquid sample, flowing of said liquid to said zones permits a characteristic of the liquid sample to be sensed selectively at more than one of said reagent treatment zones.

According to a further aspect of the invention there is provided a method comprising forming a liquid-liquid interface between first and second different liquids, the first liquid comprising first and second analytes, determining the first analyte within the first liquid, moving the second analyte across the liquid-liquid interface into the second liquid, and determining the second analyte within the second liquid.

Determining the first analyte can comprise indirectly determining the first analyte. Also, the first liquid can further comprise a first reagent capable of forming a complex with the first analyte and the first analyte can be indirectly determined by determining the first reagent within the first liquid. Furthermore, determining the first reagent can comprise electrochemically determining the first reagent.

The first reagent may be, although is not limited to, a metal or ion thereof. In some embodiments the first reagent may be cobalt and the first analyte may be albumin.

Prior to forming the liquid-liquid interface, the method can further comprise introducing sample material to a microfluidic device which comprises a microfluidic network, wherein the sample material comprises the first and second analytes. The first liquid can comprise at least some of the sample material, and forming the liquid-liquid interface can comprise forming said interface within the microfluidic network.

The sample material may comprise blood or a liquid derived from blood. When the sample material comprises blood, introducing the sample material to the microfluidic device can comprise introducing blood to the microfluidic device. Furthermore, when the sample material comprises blood, the method can further comprise a plasma separation step.

After the introducing the sample material, the method can further comprise combining the sample material with the first reagent and a second reagent, the second reagent having an affinity for the second analyte. The second reagent can be a particulate reagent comprising a first portion having an affinity for the second analyte, and a particle.

Prior to combining, the first and second reagents can be present in a dried state within the microfluidic network, and the method can comprise wetting the dried first and second reagents with the first liquid.

Moving the second analyte across the liquid-liquid interface can comprise applying a force to the second reagent, the second analyte having associated with the second reagent. The particle of the second reagent may be magnetic and the moving the second analyte can comprise subjecting the second reagent to a magnetic field sufficient to move the second reagent across the liquid-liquid interface.

Determining the second analyte may comprise electrochemically determining the second analyte.

Combining the sample material with the first reagent and a second reagent can further comprise combining the sample material with a third reagent. The second analyte, the second reagent, and the third reagent are capable of forming a complex, and the third reagent participates in the electrochemical determination of the second analyte.

The third reagent may be an enzyme. Electrochemically determining the second analyte can comprise contacting the enzyme with a substrate for the enzyme. The enzyme may be, although is not limited to, glucose oxidase and the substrate may be, although is not limited to, glucose.

Determining the first analyte can be performed before the moving the second analyte across the liquid-liquid interface. Also, forming the liquid-liquid interface can comprise introducing the first liquid at a first location of a channel within a substrate and introducing the second liquid at a second location of the channel, the second channel being spaced apart from the first location, and the liquid-liquid interface being formed between the first and second locations.

The maximum cross-sectional area of the channel between the first and second locations may be about 5 mm² or less. In some embodiments the maximum cross-sectional area may be about 1 mm² or less.

Forming a liquid interface can comprise moving at least one of the first and second liquids along the channel by capillary action.

According to a further aspect of the invention there is provided a method comprising contacting a first reagent and a second reagent with a liquid sample material comprising first and second analytes, the second reagent comprising a magnetic particle, and mixing the liquid sample material, the first reagent, and the second reagent by subjecting the second reagent to a magnetic field.

According to a still further aspect of the invention there is provided a method comprising forming a mixture comprising sample material, a metal ion, and an enzymatic reagent, the sample material comprising a protein and a second biological analyte, the metal ion being capable of forming a complex with the protein, the enzymatic reagent being capable of forming a complex with the biological analyte; detecting an amount of the metal ion not complexed with the protein; determining an amount of the protein based on the amount of metal ion not complexed with the protein; separating enzymatic reagent complexed with the biological analyte and enzymatic reagent not complexed with the biological analyte; contacting enzymatic reagent complexed with the biological analyte with a second reagent capable of participating in an enzymatic reaction with the enzymatic reagent; detecting an amount of a product of the enzymatic reaction; and determining an amount of the biological reagent based on the amount of product.

The protein may be, although is not limited to, albumin and the metal ion may be, although is not limited to, cobalt ion. The sample material may comprise blood or a liquid derived from blood, and the biological analyte may be, although is not limited to, a natriuretic peptide. The enzymatic reagent may be, although is not limited to, an enzyme and the second reagent may be a substrate for the enzyme.

Detecting an amount of the product of the enzymatic reaction can comprise indirectly detecting the product.

In one embodiment, the enzymatic reagent may be a glucose oxidase, the second reagent may be a substrate for the glucose oxidase, and the product may be an oxidized form of the substrate.

The mixture can further comprise a magnetic particulate reagent capable of forming a complex with the enzymatic reagent and the biological analyte, and the separating can comprise subjecting the mixture to a magnetic field.

Subjecting the mixture to a magnetic field can move the complex with the enzymatic reagent, the biological analyte, and the magnetic particulate reagent from a first location to a second location spaced apart from the first location.

Separating can comprise moving enzymatic reagent complexed with the biological analyte across a liquid-liquid interface between first and second liquids, the first liquid comprising the mixture, and the second liquid being different from the first liquid.

According to a general embodiment of the invention there is provided an assay device for performing more than one assay. The assay device comprises a test strip that has at least two detection zones, and at least one linear channel therebetween. The channel has at least one application zone at which a sample (such as blood), or a buffer, can be added to the device. The detection zones are equipped with electrodes (or other apparatus) suitable for detecting a component of the sample. At a point substantially equidistant from the two detection areas there is provided a fusable vent. The vent acts to prevent or promote flow of the sample in the channel.

In the channel there is provided dried reagents that are resuspended on the addition of a fluid such as blood or buffer. At least one of the dried reagents contains magnetic particles attached to an antibody, which will bind with an antigen in the blood sample.

The assay device can be further provided with a magnet, which acts on the magnetic particles in the channel. The magnet is used to move the magnetic particles, and anything bound to them, from one area of the test strip to another. The test strip is suitable for insertion into a reader, which presents to the user the results of the two assays.

The assay device is suitable for performing a first assay which detects a first analyte present in a sample, and a second assay which detects a second analyte present in the sample. The first and second analytes can be different species and the first and second assays can be carried out using the same or different techniques (e.g., electrochemistry and photochemistry).

In a general embodiment of the method, a sample of blood is added to a first application zone on the test strip of the assay device. A first reagent dried onto a first channel in the test strip is resuspended on addition of the blood sample. The first reagent interacts with a first analyte in the sample and the first analyte is indirectly detected by way of, for example, electrochemistry. A first enzyme linked to an antibody and a magnetic particle linked to an antibody, both which are dried onto the first channel in the test strip, are also resuspended on addition of the blood sample. The antibodies recognise antigens on a second analyte and act to form a ternary complex of the second analyte with antibody bound magnetic particle and antibody bound enzyme.

The magnetic particles, and all that is bound to them, are moved along the first channel, using the magnet, to the vent where flow of the sample constituents ceases. The magnet is moved past the vent, but the magnetic particles and all that is bound to them remains at the meniscus formed at the vent.

A second fluid, which may be a buffer, is introduced at a second application zone connected to a second channel. The second fluid acts to resuspend further reagents, such as a redox mediator and a substrate for the first enzyme, that are dried onto the second channel. The second fluid flows along the second channel to the vent at which point the first and second fluids form a fluid-fluid interface.

The formation of the fluid-fluid interface facilitates the movement of the magnetic particles selectively from the first fluid (blood) to the second fluid (buffer), leaving interferents and analytes that are not of interest in the first fluid. That is, only the magnetic particles and all that is bound to them, such as the second analyte (in the form of a ternary complex of the second analyte with antibody bound magnetic particle and antibody bound enzyme) are transferred to the second fluid in the second capillary channel. The magnetic particles are moved to a second detection zone where the second analyte is indirectly detected by way of, for example, electrochemistry.

The assay device can be a home testing kit and the assays can provide information relating to the absence or presence of a medical condition such as heart disease.

In more detail, the assay device (e.g., a cartridge or test strip) generally includes a base and a lid. A void between the base and the lid defines at least a first capillary flow channel of specific volume, through which a fluid can flow. Alternatively, a third component between the base and lid can provide walls to define the void. The configuration of the device is such that introduction of a fluid at selected points results in inevitable fluid flow to or from points connected by fluid pathways. Thus the capillary flow channel is fluidly connected to at least one application zone and at least one detection zone, to facilitate the flow of applied fluid. There may also be at least one reagent zone fluidly connected to the capillary flow channel. The application zone includes an inlet for accepting fluids. The application zone is fluidly connected to the capillary flow channel, and to the detection zone, to facilitate the flow of the applied sample. Optionally, the assay device can also include at least one reference zone. The reagent zone, application zone, detection zone and reference zone may be combined in different ways such that at least two of said zones are incorporated into the same zone. The base and lid also define at least one vent adapted to selectively inhibit or extend capillary flow within the capillary flow channel. The vent can be a fusable vent, and can take the form of a weir.

Optionally the assay device can include, on a surface of the base, lid, or both, the at least one reagent zone, reference zone, detection zone, application zone or a combination of these. Alternatively, on at least a third component between the base and lid there is located at least one of the reagent zone, reference zone, detection zone and application zone. In some embodiments, the assay device includes a plurality of reagent zones, a reference zone, application zone and a detection zone. The reagent zones can overlap with one another or with the reference, detection or application zones; or the reagent zones can be separated from each other or from the reference, detection or application zones. Also, the flow channel can be configured such that it is unsuitable for supporting capillary flow. The flow in the channel can be induced by, for example, a pump or a combination of magnet and magnetic particles.

Typically the reference and detection zones will be separated from each other. The detection zone and reference zone can be located such that a sample in the capillary flow channel contacts the detection zone and reference zone. A reagent zone can be located such that a sample will contact the reagent zone after the sample is applied to the sample inlet. For example, the reagent zone can be in the application zone, the detection zone, the reference zone or the capillary channel.

The assay device may comprise a second reagent zone, a second detection zone for performing a second assay. Optionally, the assay device further comprises a second application zone and a second reference zone. These zones can be fluidly connected as described above. The second application zone can be used to add a second fluid to the assay device. Optionally the second fluid is a solution such as a salt solution. The salt solution can be a buffer. Alternatively the second fluid is a physiological fluid. The physiological fluid can be blood or a fluid derived at least in part therefrom.

The assay device may comprise a second capillary flow channel fluidly connected to a vent. The vent can provide a demarcation between the first and second capillary channels. The second capillary flow channel can be fluidly connected to the first capillary flow channel. The second capillary flow channel can also be fluidly connected to the second reagent zone, the second detection zone, the second application zone and the second reference zone.

At least one reagent zone includes a first reagent capable of recognizing a desired analyte. Recognition can include binding the analyte. For example, recognition includes selectively binding the analyte; that is, binding the analyte with a higher affinity than other components in the sample. This recognition reagent can be, for example, a protein, a peptide, an antibody, a nucleic acid, a small molecule, a modified antibody, a chimeric antibody, a soluble receptor, an aptamer, or other species capable of binding the analyte.

The recognition reagent can optionally produce a detectable change. For example, the recognition reagent can be an element, or one of its corresponding ions, that binds to at least one epitope of the analyte. Alternatively, or in addition, the recognition reagent is linked (e.g., by covalent bond, electrostatic interaction, adsorption, or other chemical or physical linkage) to a further reagent that can produce a detectable change. The detectable change can be, for example, a change in electrical properties (e.g., redox potential, a voltage, a current, or the like), or optical properties (e.g., a change in absorption, reflectance, refraction, transmittance, or emission of light).

A reagent zone can also include a second reagent capable of recognizing a desired analyte. The second reagent can recognize the same or a different analyte. The first and second recognition reagents can be selected to recognize the same analyte simultaneously. For example the first and second recognition reagents can each be an antibody that recognizes distinct epitopes of the analyte. In this way, a ternary (i.e., three-component) complex of analyte, first recognition reagent and second recognition reagent can be formed. In general, the first and second recognition reagents do not associate with one another in the absence of analyte. The presence of analyte, however, can associate the first and second recognition reagents together, in a ternary complex. The reagent zones can include further reagents such as redox mediators, substrates for particular enzymes and salts suitable for forming buffer solutions.

The second recognition reagent can be linked to a particle that can induce mobility on the so-formed ternary complex. The particle can be, for example, a polymer microsphere, a metal nanoparticle, or a magnetic particle. A magnetic particle is a particle that is influenced by a magnetic field. The magnetic particle can be, for example, a magnetic particle described, in U.S. Patent Application Publication Nos. 20050147963 or 20050100930, or U.S. Pat. No. 5,348,876, each of which is incorporated by reference in its entirety, or commercially available beads, for example, those produced by Dynal AS under the trade name DYNABEADS™. In particular, antibodies linked to magnetic particles are described in, for example, United States Patent Application Nos. 20050149169, 20050148096, 20050142549, 20050074748, 20050148096, 20050106652, and 20050100930, and U.S. Pat. No. 5,348,876, the teachings of each of which is incorporated by reference in its entirety.

Generally, the detection zones collect the analytes and are the sites of detectable changes. The extent of the detectable changes can be measured at the detection zones. Usually, greater amounts of analytes will result in greater detectable changes; however, the assays can also be configured to produce smaller changes when the analytes are present in greater quantities. The detection zones can collect the analytes by immobilizing them (for example, with a reagent immobilized in the detection zone, where the immobilized reagent binds to the analyte). Alternatively, the detection zone can attract or immobilize a component associated with the analyte. For example, a recognition reagent that binds an analyte and is linked to a magnetic particle can be attracted to a particular detection zone by a magnetic field provided in one or more detection zones.

In some embodiments, one or more of the detection zones include one or more electrodes. The electrodes can be formed of a material selected for electrical conductivity and low reactivity with sample components, for example, silver, gold, aluminum, palladium, platinum, iridium, a conductive carbon, a doped tin oxide, stainless steel, or a conductive polymer. The electrodes in the detection zones (the working electrodes), in conjunction with second electrodes in the reference zones (the reference electrodes) can measure an electrical property of the sample, such as a voltage or a current. Alternatively, the detection zones and the reference zones can each have at least one working electrode and counter electrode. That is, the detection and reference zones can make independent measurements. Optionally, counter electrodes are also included in the assay device. Assay devices including electrodes for measuring electrical properties of a sample are described in, for example, U.S. Pat. Nos. 5,708,247, 6,241,862, and 6,733,655, each of which is incorporated by reference in its entirety.

In some embodiments, the assay device base, assay device lid, or both have a translucent or transparent window aligned with the detection zone. An optical change that occurs in the detection zone can be detected through the window. Detection can be done visually (i.e., the change is measured by the user's eye) or measured by an instrument (e.g., a photodiode, photomultiplier, or the like). In general, the reference zone is similar in nature to the detection zone. In other words, when the detection zone includes an electrode, the reference can likewise include an electrode. When the detection zone is aligned with a window for optical measurement, the reference zone can similarly be aligned with a window for optical measurement. In some embodiments, the reference zone is not adapted to collect analyte. Alternatively, the reference zone is adapted to collect analyte, but performs a different analysis on said analyte. Thus, the detectable change measured in the reference zone can be considered a background measurement to be accounted for when determining the amount of analyte present in the sample.

The sample can be any biological fluid, such as, for example, blood, blood plasma, serum, urine, saliva, mucous, tears, or other bodily fluid. The analyte can be any component that is found (or may potentially be found) in the sample, such as, for example, a protein, a peptide, a nucleic acid, a metabolite, a saccharide or polysaccharide, a lipid, a drug or drug metabolite, or other component. The assay device can optionally be supplied with a blood separation membrane arranged between a sample inlet and the detection zone, such that when whole blood is available as a sample, only blood plasma reaches the detection zone.

The assay device and included reagents are typically provided in a dry state. Addition of a liquid sample to the assay device (i.e., to the capillary channel) can resuspend dry reagents.

In any of the foregoing, the analyte may be selected from the group consisting of a natriuretic peptide (e.g., NTproBNP, BNP, combination thereof) potassium ion, cystatin C, troponin T, troponin I, myeloperoxidase, creatine kinase MB, or combination thereof. In some embodiments, the analyte includes a natriuretic peptide (e.g., NTproBNP, BNP, combination thereof) and the method includes determining the analyte in human blood. For example, the analyte may be NTproBNP and the method may include determining the analyte in human blood.

The invention includes the combination of the described aspects and features except where such a combination is clearly impermissible or expressly excluded.

All documents mentioned in this text are incorporated herein by reference.

BRIEF DESCRIPTION OF THE DRAWINGS

FIG. 11A is a perspective view of the separated layers of the assay device;

FIG. 11B is a side view of the interface zone;

FIG. 23A shows a perspective view of magnet transmission system; FIG. 23B shows the locking bar.

FIGS. 24A-J show the internal configuration of the meter during operation;

FIG. 25A-I show the internal configuration of the meter during operation;

FIG. 38I shows a plan view from above of an assay device; FIG. 38J shows a perspective view of the underside of an assay device containing a blood sample, buffer liquid and blood:buffer interface;

FIGS. 50A-D show on-board control configurations;

DETAILED DESCRIPTION

Figure 1:
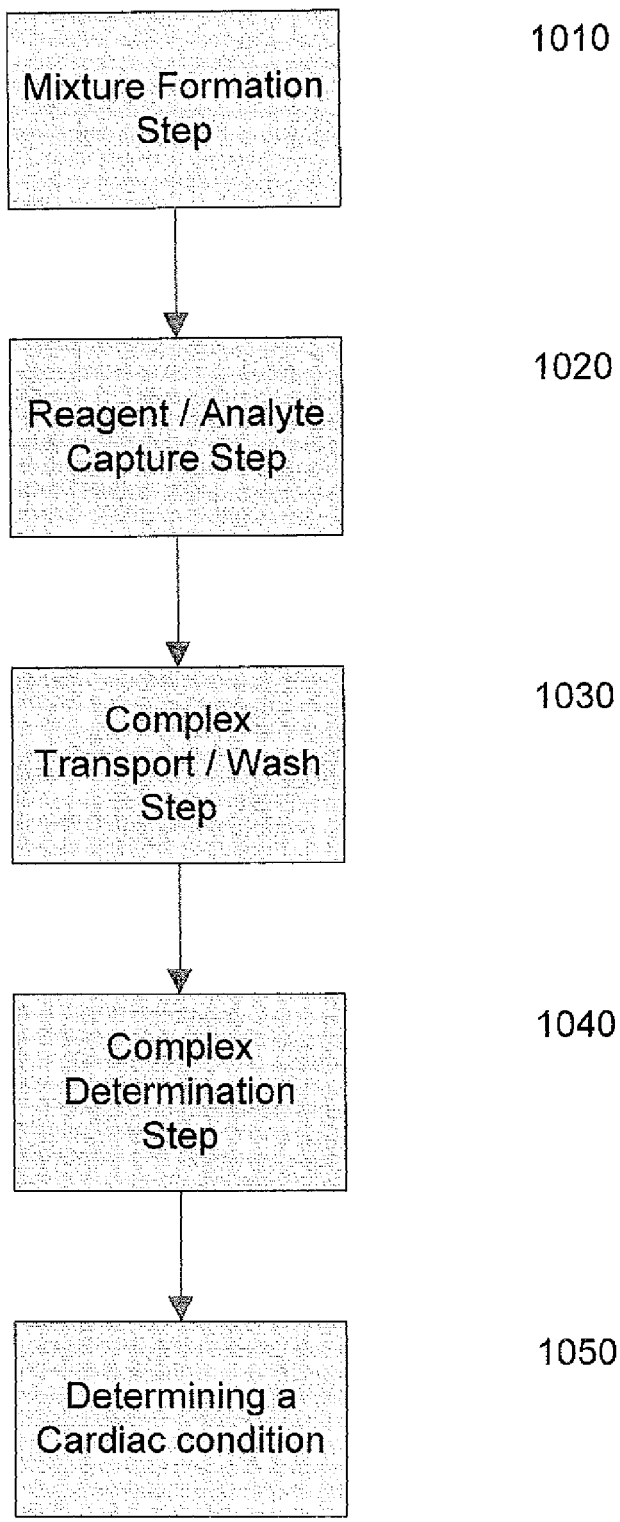
FIG. 1 is a flow chart of an assay method.

Assays for determining (e.g. quantitatively or qualitatively) one or more analytes or indicators in sample material (e.g., a biological sample) are described. Typical analytes are biomarkers related to (e.g., indicative of) the presence of a physiological condition in a mammalian subject. The presence of the physiological condition can be determined based at least in part on the result of the determination of the biomarker (e.g., by comparing the result to a reference value).

The assays can be for use in reaching a diagnosis or prognosis. Assay methods can comprise methods of diagnosis or prognosis of a pathological condition or disease state in a user or susceptibility of the user to a pathological condition or disease state. The assay device can be provided for use in a method of diagnosis or prognosis of a pathological condition or disease state in a user or susceptibility of a user to a pathological condition or disease state. In exemplary embodiments the assay method is an in vitro method not practised on the human or animal body. In exemplary embodiments the assay method is practised on a liquid sample which may be a sample collected from the human or animal body, e.g. a bodily fluid sample such as a human blood sample. In exemplary embodiments the sample is used to conduct the assay and is then discarded, and is not returned to the human or animal from which it was collected.

In exemplary embodiments, magnetically susceptible particles are used in the capture of an analyte, the separation of an analyte from a liquid sample, and in the positioning of the analyte proximal a detection zone.

In some embodiments, an analyte is separated from a liquid sample. After being separated, the analyte is detected in a second medium (e.g., another fluid (e.g., a gas such as air, a different liquid such as a buffer) or flowable medium (e.g., a gel, such as an electrophoresis gel). An exemplary method includes combining magnetically susceptible particles adapted to bind the analyte with the liquid sample to form complexes of magnetically susceptible particle bound analyte. In exemplary embodiments, the combining is facilitated by application of a time varying magnetic field to the liquid sample. The complexes are magnetically separated from the liquid sample into the second medium.

Separation of the complexes from the liquid sample into the second medium (e.g., another fluid (e.g., a gas such as air, a different liquid such as a buffer) or flowable medium (e.g., a gel, such as an electrophoresis gel)) is typically achieved by a method that includes forming an interface between the liquid sample and second medium. In embodiments, the interface is stable, and essentially static (i.e. diffusion may occur with respect to the interface but the position of the interface is essentially constant). For example, in embodiments in which the interface is performed within a microfluidic device, the position of the interface relative to the microfluidic device may be essentially constant (e.g., the relative position may change by about 5 mm or less, about 2.5 mm or less, about 1 mm or less) at least prior to the transport of the magnetically susceptible particles across the interface as described below. Typically, bulk movement of at least one (e.g., both) of the liquid sample and second medium does not occur with respect to the interface at least prior to the transport of the particles across the interface. In an exemplary embodiment, the position of the interface is essentially constant at least prior to determination of the analyte.

The interface is typically substantially free of gas bubbles. For example, it can be free of gas bubbles or may contain a small number of gas bubbles that do not prevent transfer across the interface of substantially all of the magnetically susceptible particles clustered in the liquid sample adjacent the interface, wherein substantially all of the magnetically susceptible particles is at least about 70% (e.g. at least about 80%, at least about 85%, at least about 90%, at least about 95%, at least about 98%) of the clustered magnetically susceptible particles.

In exemplary embodiments, the interface is formed between the liquid sample and the second medium (e.g., another fluid (e.g., a gas such as air, a different liquid such as a buffer) or flowable medium (e.g., a gel, such as an electrophoresis gel)). In exemplary embodiments the interface is defined by the contacting parts of the liquid sample and the second medium.

A magnetic field is applied to the magnetically susceptible particle:analyte complexes in the liquid sample and the complexes are magnetically moved towards the liquid sample:second medium interface. The magnetic field moves the complexes across the interface and into the second medium. The transport across the interface separates the complexes from the liquid sample.

In exemplary embodiments movement of substantially all of the magnetically susceptible particle:analyte complexes across the liquid sample:liquid interface is optimized by controlling the speed of movement of the magnetic field towards the interface, and across the interface. The timing of movement of the magnetically susceptible particle:analyte complexes across the interface can be controlled to be coincident with, or very shortly after, formation of the liquid sample:second liquid interface.

Having separated the complexes from the liquid sample, the complexes can be further magnetically moved to a sensor (e.g., an electrochemical sensor including one or more electrodes), where the presence of analyte can be detected directly or indirectly.

In exemplary embodiments an indirect detection is performed wherein the complexes include an enzyme label capable of producing a detectable reaction in the presence of one or more enzyme substrates and/or cofactors. For example, the enzyme may produce a product such as an oxidized or reduced enzyme substrate, cofactor or byproduct. The product can be detected electrochemically using the electrochemical sensor. For example, the electrochemical sensor may include one or more electrodes in contact with the second medium.

In exemplary embodiments, the separation of analyte from the liquid sample is desirable as the presence of analyte can then be detected without interference from contaminants (e.g., molecular components such as biological compounds) of the liquid sample. For example, some liquid samples (e.g. blood) produce a non-negligible background electrochemical signal which can interfere with electrochemical determination of certain analytes. Hence separation of analyte from blood may be desirable in order to accurately determine the presence of the analyte.

A device is provided to perform the method of detecting an analyte. The method of detection is an assay for the presence of analyte in the liquid sample and the device an assay device for that method.

The assay device is a microfluidic device having a channel network. The network comprises an inlet connected to a first channel portion, which is connected to a second channel portion at a junction (e.g., a capillary stop) at an intermediate position in the channel network. At the junction the second channel portion can have a cross-sectional area that is larger than the first channel portion creating a capillary stop pressure ($p_{capstop}$) and forming the capillary stop. The capillary stop can alternatively be formed by other means, such as the use of a hydrophobic patch disposed on one or more interior surfaces of the channel.

Liquid sample deposited at the inlet can flow into the first channel portion and fill the first channel portion up to the junction. Liquid sample forms an interface (e.g., a liquid sample:second medium interface) proximal to the junction of the first and second channel portions. The second medium is typically another fluid (e.g., a gas such as air, a different liquid such as a buffer) or flowable medium (e.g., a gel, such as an electrophoresis gel). In embodiments, the second medium is a gas and the interface is a liquid sample-gas interface (e.g., a meniscus).

In some embodiments, the interface is formed by contacting a first interface between (a) one of the liquid sample and the second medium and (b) third medium with the other of the liquid sample and the second medium such that the other of the liquid sample and the second medium displaces the third medium from the first interface. In some embodiments, the third medium is a second liquid (e.g., a buffer) and the device further includes, or is configured to cooperate with, a reservoir of second liquid from which second liquid can be released into the second channel portion to flow towards the junction (e.g., towards the interface). For example, in embodiments where the interface is a liquid sample-gas interface, the second channel portion directs released second liquid to the liquid sample:gas interface to displace the gas (e.g., air) and form a liquid sample:second liquid interface.

In exemplary embodiments the region of the second channel portion adjacent the junction is configured to direct second liquid transversely across a face of the liquid sample: air interface to progressively decrease the area of the liquid sample:air interface as the second liquid flows across the face of the liquid sample:air interface. Subsequent to forming the liquid sample:second liquid interface, the interface may be essentially static and/or bulk movement of liquid relative to the interface may be absent at least until transport across the interface as described above.

The configuration of the second channel portion adjacent the interface can include a change in height and/or width of the second channel portion. In exemplary embodiments the configuration of the second channel portion adjacent the interface includes a tapering of the width and height of the second channel portion to increase the second channel portion width and height at the junction. The second channel portion can further include a change of direction proximal to the junction provided by a bend portion in the second channel portion adjacent the junction. An inside wall of the bend portion can further comprise a capillary stop (e.g. a notch or vent in the inside wall and/or a hydrophobic patch), whilst an outside wall of the bend does not have a corresponding capillary stop. Second liquid advancing towards the junction is retarded at the capillary stop on the inside wall of the bend such that the second liquid advances more rapidly around the outside wall of the bend, in which the junction of the first and second channel portions can be located (at least partially). Typically, the portion of second liquid adjacent the outside wall pivots with respect to the capillary stop. This directs the flow of second liquid transversely across the face of the liquid sample:air interface formed at the junction and facilitates formation of a liquid sample:second liquid interface that is substantially free of air bubbles.

Reagents in the first channel portion form magnetically susceptible particle:analyte complexes with analyte in the liquid sample. These complexes can now be magnetically moved across the liquid sample:second liquid interface and towards a sensor, e.g. one or more electrodes, in the second channel portion where the presence of the analyte can be detected.

The device is configured for operation in conjunction with a meter or reader into which the device is inserted. The meter includes a magnet, which may be an electromagnet, for magnetically moving the magnetically susceptible particles and complexes. The meter also includes components configured to receive signals from the assay device, and a processor and display for determining and displaying an assay result.

The device can be configured to detect more than one analyte.

Assays for determining (e.g. quantitatively or qualitatively) one or more analytes or indicators in sample material (e.g., a biological sample) are described. Typical analytes are biomarkers related to (e.g., indicative of) the presence of a physiological condition in a mammalian subject. The presence of the physiological condition is determined based at least in part on the result of the determination of the biomarker (e.g., by comparing the result to a reference value). Determination of an analyte can be direct or indirect. For example, the presence of an analyte can be indirectly determined by detecting a signal (e.g., an electrochemical or optical signal) resulting from a detectable label (e.g., an enzyme label) conjugated to the analyte. An analyte can be directly determined by, for example, detecting a signal (e.g., an electrochemical or optical signal) resulting from the analyte itself.

Any of the devices or methods described herein can be further configured or implemented to perform at least one action at least in part based on and/or using a result of the determination. For example, the at least one action can be selected from the group consisting of storing the result, making the result available for further processing, displaying the at least one result, recording the result, transmitting the result to a remote location, comparing the result to a reference value, displaying information related to the result, choosing from among multiple actions based on the result, or combination thereof. Here, the term "result" includes values or indicia indicative of the result.

For example, an assay may result in the determination of a characteristic or the detection of an analyte. The result of the determination or detection may be further stored, and/or processed and/or recorded and/or transmitted to a remote location and/or compared to a reference value (e.g. a standard subject population reference value or an individual subject reference value (e.g., a baseline determined from one or more prior determinations of the analyte from the patient)) and/or displayed as an assay result (e.g. to a user of the apparatus) and/or acted on (e.g. through the alteration of a therapeutic programme or strategy). Transmission of a determination or detection to a remote location can be carried out by a communications network, e.g. LAN, WAN, and may be via the internet. Transmission can be wireless transmission to a server, host or proxy. Wireless transmission can be implemented using the Bluetooth® transmission protocol.

The analyte may be any analyte, and more particularly any analyte to which a binding agent, such as an antibody, may be raised and coupled to a magnetically susceptible particle.

In exemplary embodiments an analyte is a natriuretic peptide such as at least one of BNP or NT-proBNP. NT-proBNP (N-terminal truncated pro-brain natriuretic peptide) is the amino-terminal fragment of BNP (brain natriuretic peptide or B-type natriuretic peptide). BNP is the 32 amino acid (aa) peptide cardiac hormone synthesized by ventricular cells and stored as a 108aa pro-peptide. It is secreted in response to ventricular expansion or pressure overload. The pro-peptide is cleaved to release the 32aa active BNP and a 76aa N-terminal fragment (NT-proBNP). BNP and NT-proBNP are markers of ventricular distension and overload. NT-proBNP is correlated with ambulatory cardiac filling pressures in outpatients with chronic heart failure (Braunschweig et al., European Journal of Heart Failure 8 (2006) 797-803) and is indicated as a biomarker of myocardial stretch and chronic heart failure (Murdoch et al., Am Heart J 138(6):1126-1132, 1999) and as a predictor of mortality in acute heart failure (Sakhuja et al., Clincal Chemistry 53:3 412-420 (2007).

Exemplary assays for determining a concentration or amount (qualitative or quantitative) of NT-proBNP in a human blood sample can therefore be used in the monitoring, diagnosis, prognosis, assessment of risk of, and/or assessment of susceptibility to a pathological condition or disease wherein, for example, the pathological condition or disease is chosen from a cardiac condition or disease; heart failure; chronic heart failure; congestive heart failure; myocardial infarction; hypertension.

In other exemplary embodiments the analyte can be chosen from potassium ion, cystatin C, troponin T, troponin I, myeloperoxidase, creatine kinase MB.

The analyte can be a biomarker for a condition that afflicts the mammalian body. The term "biomarker" refers to a biochemical in the body that has a particular molecular trait to make it useful for diagnosing a condition, disorder, or disease and for measuring or indicating the effects or progress of a condition, disorder, or disease. For example, common biomarkers found in a person's bodily fluids (i.e., breath or blood), and the respective diagnostic conditions of the person providing such biomarkers include, but are not limited to, ischemia modified albumin "IMA" (source: lack of oxygen to the blood; diagnosis: coronary artery disease), N-terminal truncated pro-brain natriuretic peptide "NT proBNP" (source: stretching of myocytes; exemplary diagnosis related to congestive heart failure), acetaldehyde (source: ethanol; diagnosis: intoxication), acetone (source: acetoacetate; diagnosis: diet; ketogenic/diabetes), ammonia (source: deamination of amino acids; diagnosis: uremia and liver disease), CO (carbon monoxide) (source: $CH_2Cl_2$, elevated % COH; diagnosis: indoor air pollution), chloroform (source: halogenated compounds), dichlorobenzene (source: halogenated compounds), diethylamine (source: choline; diagnosis: intestinal bacterial overgrowth), H (hydrogen) (source: intestines; diagnosis: lactose intolerance), isoprene (source: fatty acid; diagnosis: metabolic stress), methanethiol (source: methionine; diagnosis: intestinal bacterial overgrowth), methylethylketone (source: fatty acid; diagnosis: indoor air pollution/diet), O-toluidine (source: carcinoma metabolite; diagnosis: bronchogenic carcinoma), pentane sulfides and sulfides (source: lipid peroxidation; diagnosis: myocardial infarction), $H_2S$ (source: metabolism; diagnosis: periodontal disease/ovulation), MeS (source: metabolism; diagnosis: cirrhosis), and $Me_2S$ (source: infection; diagnosis: trench mouth). The biomarker can be a marker of heart failure (e.g. chronic heart failure, heart disease or susceptibility to myocardial infarction (MI), e.g. a marker of MI risk) or a renal marker, e.g. a marker of glomerular filtration rate, which may provide information on blood volume.

In exemplary embodiments the sample material is a liquid such as a biological liquid (e.g., blood, blood plasma, serum, urine, saliva, mucous, tears, semen, cerebrospinal fluid (CSF), lymph or other bodily fluid). In exemplary embodiments the sample material is a bodily fluid from a mammal (e.g. a human who may be male or female). In exemplary embodiments the sample material is whole blood from a human. The analyte can be any component that is found (or may potentially be found) in the sample, such as, for example, a protein, a peptide, a nucleic acid, a metabolite, a saccharide or polysaccharide, a lipid, a drug or drug metabolite, or other component. The assay device can optionally be supplied with a blood separation membrane arranged between a sample inlet and the detection zone, such that when whole blood is available as a sample, only blood plasma reaches the detection zone.

Magnetically susceptible particles can include magnetic particles or particles that can be manipulated (e.g., moved) and/or positioned by a magnetic field. The magnetically susceptible particles can be non-magnetic but susceptible to manipulation or positioning by a magnetic field or be magnetic (e.g. a source of a magnetic field lines). The magnetically susceptible particles can be spherical beads and can have a diameter of at least about 0.05 microns, at least about 1 micron, at least about 2.5 microns, and typically less than about 20 µm. A magnetically susceptible particle can be, for example, a magnetic particle described, in U.S. Patent Application Publication Nos. 20050147963 or 20050100930, or U.S. Pat. No. 5,348,876, each of which is incorporated by reference in its entirety, or commercially available beads, for example, those produced by Dynal AS (Invitrogen Corporation, Carlsbad, Calif. USA) under the trade name DYNABEADS™ and/or MYONE™. In particular, antibodies linked to magnetic particles are described in, for example, United States Patent Application Nos. 20050149169, 20050148096, 20050142549, 20050074748, 20050148096, 20050106652, and 20050100930, and U.S. Pat. No. 5,348,876, each of which is incorporated by reference in its entirety. The magnetically susceptible particles may be ferrous particles.

The magnetic field to which the particles are susceptible can be applied by a magnet, which can be any kind of magnet including a permanent magnet, temporary magnet, or electromagnet. The magnet can be used as a magnetic source for application of a magnetic field towards magnetically susceptible particles.

In exemplary embodiments components or liquid:gas or liquid:liquid interfaces can be positioned proximal to a physical structure. Proximal positioning refers to positioning close to the physical structure. The positioning can be at, or adjacent, the physical structure.

Exemplary embodiments include a microfluidic device. A microfluidic device can comprise a support in which one or more channels are formed to provide a channel network capable of directing flow, and optionally controlling flow, of liquid through part or all of the network. Typically the channel network will have multiple channel portions. In exemplary embodiments the microfluidic device is configured to perform a desired assay, and can be configured to interact with a meter in order to provide an assay result. The microfluidic device is generally small enough to fit on a laboratory bench, and in exemplary embodiments is small enough to be carried by an individual human user in one or two hands.

In exemplary embodiments, channels and channel portions are generally enclosed spaces defined by surrounding walls. The channel can have any cross-sectional shape (e.g. rectangular, trapezoidal, or circular). Channels can be in fluid communication with the atmosphere external to the microfluidic device by means of apertures (e.g., inlets, outlets or vents) formed in the channel network. Channels or channel portions can be open to the atmosphere for part or all of their length, e.g. by not having an enclosing lid. Channels or channel portions can comprise a capillary, i.e. a channel of small internal diameter capable of holding or transporting liquid by capillary action, wherein capillary action is (at least in part) the effect of surface tension that draws a liquid into or along the channel.

Devices according to embodiments can be for use in performing an assay, e.g. on a blood sample. The user can be a human (male or female). In exemplary embodiments the user can perform the assay in the absence of the presence, or in-person assistance, (verbal or otherwise) of a medical practitioner (e.g. nurse, physician, medical doctor, general practitioner, surgeon or phlebotomist). Accordingly, the assay devices can be configured for use away from the hospital, doctor's office, surgery or other medical establishment and can be used in a domestic environment, such as the home or office, or in any convenient location.

A method and/or device and/or meter can be configured for conduct of an assay and production of an assay result to a user in a total test time of less than about 30 minutes (e.g. less than about 20 minutes, less than about 15 minutes, less than about 10 minutes) and in one embodiment in about 10, 11 or 12 minutes.

In exemplary embodiments one or more sensors can be used to determine a characteristic of a liquid and/or to detect a signal. The signal can be the presence or absence of a component, e.g. analyte or oxidized compound. In preferred exemplary embodiments the sensor is an electrochemical sensor including one or more electrodes and the signal is an electrochemical signal (e.g., a signal formed by the reduction of an oxidized compound at an electrode, or the oxidation of a reduced compound at an electrode), which can be detected and/or measured amperometrically and/or voltametrically at the electrode(s). Other sensors include detectors of radiation (e.g. light, X-ray, γ-ray radiation) and/or optical (e.g., fluorescence, reflectance, or absorbance).

In exemplary embodiments components can be bound or conjugated to one another to form complexes (e.g. a magnetically susceptible particle can be conjugated to a binding agent). Binding or conjugation of components can be direct (e.g. binding of an analyte to an anti-analyte antibody) or indirect (e.g. binding of a magnetically susceptible particle to a binding agent through linkers such as streptavidin and biotin).

In exemplary embodiments binding agents are molecules capable of specifically binding to a selected target with high affinity, having a $K_d$ for the target of about 100 µM or less (e.g. less than about 50 µM, less than about 10 µM, less than about 1 µM, less than about 100 nM, less than about 10 nM, less than about 1 nM, less than about 100 pM, less than about 10 pM). The first and second binding agents can be respectively chosen from an antibody (monoclonal or polyclonal), antibody fragment (e.g. scFV fragment), antibody binding domain, aptamer or other recognition reagent. The first and second binding agents can be different, e.g. an antibody and an aptamer.

In exemplary embodiments reagents are provided in an assay device (e.g., in dry form). The reagents can be configured to participate in an assay, e.g. to detect presence of analyte, and can be configured to form conjugates and/or bind the analyte. In exemplary embodiments, the reagents include conjugates of magnetically susceptible particle and at least one reagent (e.g., an antibody labeled enzyme) configured to bind the analyte and form a ternary complex with the magnetically susceptible particle. In exemplary embodiments conjugates of magnetically susceptible particle and reagents are configured to participate in a sandwich assay involving first and second binding agents to form a ternary complex.

Exemplary embodiments provide a device and method for performing an assay on a single small volume blood sample, or other biological materials or complex mixtures.

Exemplary embodiments will now be described in detail, with reference to the accompanying figures. The invention includes the combination of the features described in the exemplary embodiments except where such a combination is clearly impermissible or expressly avoided.

Figure 18:
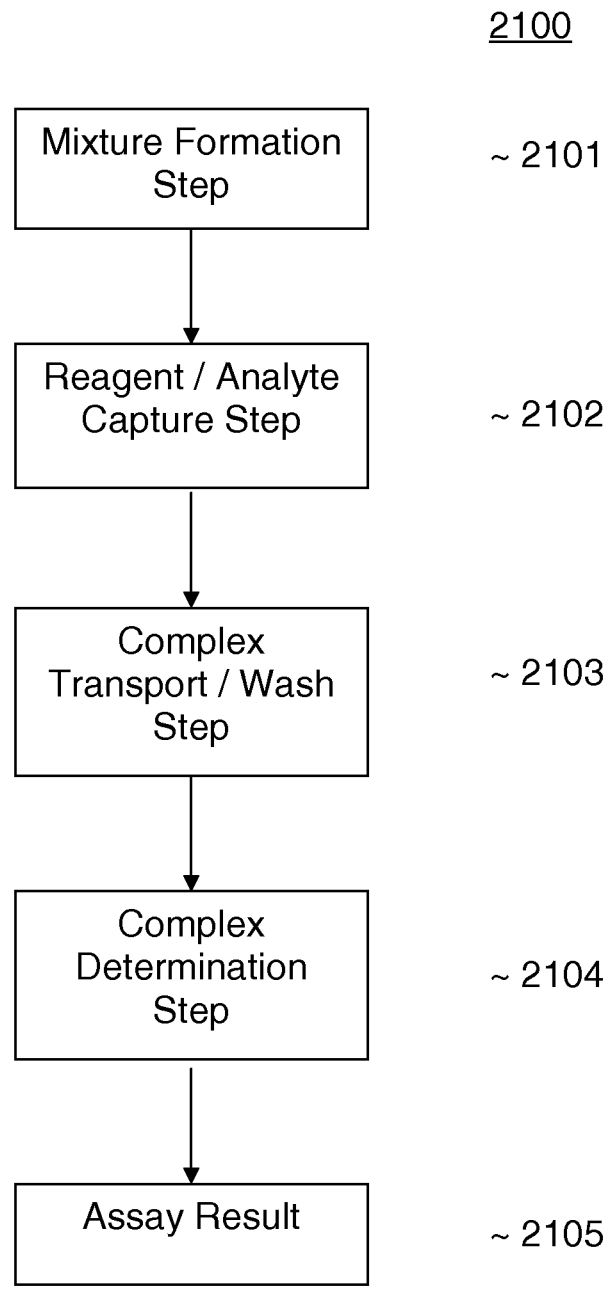
FIG. 18 is a flow chart of an assay method

Referring to FIG. 18 an assay method 2100 includes a mixture formation step 2101, a reagent/analyte capture step 2102, a complex transport step 2103, a complex determination step 2104 and a formation of an assay result step 2105. Typically, method 2100 is performed using an assay device including a reagent zone, in which the sample reacts with the reagents, a detection zone in which determination of the analyte is performed (either qualitatively or quantitatively), and an interface zone, which provides an interface between the reagent zone and the detection zone.

In mixture formation step 2101 a mixture including a quantity of sample material (e.g. a sample liquid such as blood from a human) and reagents capable of binding to an analyte is formed. In an exemplary embodiment the reagent capable of binding to the analyte may be an antibody or antibody domain or fragment (e.g. scFv) capable of binding to the analyte. In reagent/analyte capture step 2102 the reagents capable of binding the analyte form complexes with analyte that is present in the sample. In complex transport step 2103 reagent:analyte complexes formed during the previous step may be washed to remove non-complex material and are transported to a detection zone. In complex determination step 2104, the presence of reagent: analyte complexes that have been transported to the detection zone is determined (e.g. qualitatively or quantitatively). The assay result is formed in step 2105 as a result of the extent of detection of reagent:analyte complexes in the preceding step. For example, detection of reagent:analyte complexes may be indicative of the diagnosis or prognosis (new or continued) of a disease state or pathological condition of a user or patient. Therefore, the detection of reagent:analyte complexes may be used or processed (e.g. by comparison with a reference value), to provide an assay result, which may be displayed to the user.

Assay method 2100 will now be discussed in greater detail.

In mixture formation step 2101 a mixture is formed between reagent materials that are disposed within a reagent zone of an assay device and a quantity of sample material sufficient to fill the reagent zone of the assay device. A sample of blood can be obtained from a finger stick or a venous puncture.

In some embodiments a volume of blood required to fill the reagent zone can be obtained from a small number of (e.g. three or less, two or less, one) finger sticks. For example in some embodiments the volume of blood required to fill reagent zone can be obtained from a single finger stick. The volume of blood is typically about 10 µl or about 5 µl (e.g. at least about 0.5 µl, at least about 1 µl, at least about 5 µl, at least about 15 µl, at least about 25 µl, at least about 50 µl). In some embodiments the volume of blood required to fill the reagent zone is about 50 µl or less (e.g. about 40 µl or less, about 25 µl or less, about 15 µl or less, about 10 µl or less, about 5 µl or less). In one exemplary embodiment the volume of sample required to fill the device is 10. In another exemplary embodiment the volume of sample required to fill the device is 5 µl.

Several reagents are present within the reagent zone of the assay device. The reagents typically include the following species; magnetically susceptible particles, a first reagent capable of binding to the analyte, a second reagent capable of binding to the analyte concurrently with the first reagent (e.g., as in a sandwich). Typically, the reagent binds to a first unique region of the analyte and the second reagent binds to a second unique region of the analyte. The first reagent is configured to bind to the magnetically susceptible particles even in the absence of analyte (e.g., in a non-specific binding reaction). For example, the first reagent may include a biotin portion and the particle may be coated with streptavidin, which captures the biotin modified first reagent. The second reagent includes a detectable label (e.g., an enzymatic label such as an enzyme). In an exemplary embodiment, the second reagent is a labeled particle (e.g., a non-magnetically susceptible particle such as a colloidal gold sol particle) that is conjugated with a binding reagent for the analyte (e.g., an antibody for the analyte) and with an enzymatic label. Typically, the particle includes multiple enzymatic labels thus increasing the number of enzyme labels that become part of the reagent:analyte complex. The second antibody-enzyme conjugate is typically provided pre-associated with the labeled particles.

In general, the first and second recognition reagents do not associate with one another in the absence of analyte. The presence of analyte, however, can associate the first and second recognition reagents together, in a ternary complex The second reagent can recognize the same or a different analyte and can be a binding agent that specifically binds the same or a different analyte. The reagent zones can include further reagents such as redox mediators, substrates for particular enzymes and salts suitable for forming buffer solutions. The second binding agent can be linked to a particle that can induce mobility on the so-formed ternary complex. The particle can be, for example, a polymer microsphere, a metal nanoparticle, or a magnetically susceptible particle.

When the reagents are mobilized by a sample liquid including the analyte, the reagents interact with the analyte to form a complex including the magnetically susceptible particle, the first reagent, the analyte, and the second reagent. The streptavidin coated magnetically susceptible particle can accommodate a number of biotin modified reagents capable of binding to the analyte. Accordingly, each complex may include multiple analyte molecules and multiple second reagents.

The reagent zone may include one or more additional reagents such as, for example, an anti-coagulant to inhibit clotting of blood within the reagent zone and/or buffer salts. Buffer salts present in the reagent zone control the pH of the mixture to give a pH value that favours the formation of complexes. The pH value is maintained at a desired pH, for example the pH may be maintained within a range of between about pH 7.2 and about pH 7.6 (e.g. about 6.9 or more, about 7.0 or more, about 7.1 or more, about 7.2 or more, about 7.3 or more, about 7.4 or more, about 7.5 or more) (e.g. about 8.0 or less, about 7.9 or less, about 7.8 or less, about 7.7 or less, about 7.6 or less, about 7.5 or less, about 7.4 or less).

When the sample material is blood, an anticoagulant that does not interfere with the formation of reagent-analyte complexes is typically included to prevent the sample of blood from coagulating within the reagent zone and therefore reducing the likelihood that complexes could be transported from the reagent zone to the detection zone.

Reagent/analyte capture step 2102 includes forming complexes between the reagents and analyte contained within the sample. When a sample is applied to the assay device, the dried reagents initially form an inhomogeneous mixture with the sample. Within a short interval of time (within about 1 second, about 5 seconds, about 20 seconds, about 60 seconds), the reagents become sufficiently hydrated that they begin to interact with the sample. Where present, the anticoagulant disperses through the sample to inhibit clot formation and therefore maintain the sample in a fluid state. The buffer salts disperse through the sample to maintain the pH of the sample to a desirable value that favours formation of reagent:analyte complexes. The first and second antibodies bind to analyte and form complexes. The biotin labelled first reagent binds to the streptavidin coated magnetically susceptible particle(s). The second reagent (e.g., a non-magnetically susceptible particle conjugated to an enzyme label and a binding agent for the analyte) binds the analyte.

The sample and reagents remain in contact for a period of time that is sufficient to ensure that adequate complex formation occurs to permit detection of analyte within a desired concentration range. The period of time during which the sample and reagents remain in contact during reagent/analyte capture step 2102 may be at least about 30 seconds (e.g. at least about 60 seconds, at least about 120 seconds, at least about 240 seconds, at least about 420 seconds, at least about 600 seconds, at least about 900 seconds, at least about 1800 seconds). The period of time during which the sample and reagents remain in contact during reagent:analyte capture step 2102 may be about 2000 seconds or less (e.g. at about 1500 seconds or less, about 1000 seconds or less, about 800 seconds or less). In an exemplary embodiment the period of time is about 600 seconds.

In some embodiments a time varying magnetic field is applied to reagent zone during the period of time in which the sample and reagents are in contact. The magnetic field moves the magnetically susceptible particle(s) within the reagent zone facilitating the combination (e.g., mixing) of the sample and reagents increasing the likelihood that the target analyte forms complexes with the first and second antibodies. For example, the magnetically susceptible particle(s) can be oscillated/moved within the reagent zone to cause agitation of the blood sample.

Complex transport/wash step 2103 includes moving the reagent:antibody complexes from the reagent zone to the detection zone. The detection zone is filled (e.g., actively) with a buffer solution during the course of a sample assay. Buffer is released from a reservoir at a predefined time after sample has been applied to the assay device. Buffer solution fills the detection zone and the reagent zone. When buffer solution is delivered into the interface zone, the buffer forms a sample liquid:second liquid interface with the sample in the reagent zone (as will be described in more detail below). Excess buffer solution moves in to an overflow channel. When buffer has made contact with and formed an interface with the sample there is a continuous liquid path through the microfluidic network of the assay device. The reagent:analyte complex can thus be moved along the length of the assay device supported in a continuous liquid stream.

A magnetic field can be used to manipulate the reagent:analyte complex within the assay device. The reagent:analyte complex can be drawn along the reagent zone, through the interface zone to the detection zone by a magnetic field. In some embodiments the magnetic field can be a permanent magnet on a drive mechanism that tracks a path parallel to and beneath the microfluidic network in the assay device. The path of the magnet moves in a direction that transfers magnetically susceptible particle complexes from the reagent zone to the detection zone. In other embodiments the magnetic field can be an electromagnetic field, which can produce a magnetic field gradient that will cause the magnetically susceptible complexes to move within the assay device from the reagent zone to the detection zone.

When reagent:analyte complexes form within reagent zone during reagent:analyte capture step 2102 it is possible for other sample components to become trapped or associated with the so formed complexes. Such extraneous material could interfere with the detection of target analyte and it is therefore desirable to minimise the amount of extraneous material associated with complexes prior to complex determination step 2104. At this stage enzyme labelled second reagent that is not associated with analyte and first reagent:magnetically susceptible particle(s) is considered extraneous material. It is desirable to reduce to a minimum any extraneous material prior to complex determination step 2104. When reagent:analyte complexes are transported across the liquid sample:buffer interface into the interface zone under the influence of a magnetic field, buffer may be flowing in a direction opposite or across the direction of movement of the reagent:analyte complexes. Buffer can be continually delivered through detection zone, across interface zone, and into an overflow while complexes are transferred from reagent zone into detection zone. The counter-flow of buffer over the reagent:analyte complexes effectively separates extraneous material from the magnetically susceptible complexes. Extraneous material is thus transported away from the detection zone towards the overflow. Magnetically susceptible complexes can thus be transported to detection zone with minimal extraneous material associated therewith.

Generally, the detection zones collect the analytes and are the sites of detectable changes. The extent of the detectable changes can be measured at the detection zones. Usually, greater amounts of analytes will result in greater detectable changes; however, the assays can also be configured to produce smaller changes when the analytes are present in greater quantities. The detection zones can collect the analytes by immobilizing them (for example, with a reagent immobilized in the detection zone, where the immobilized reagent binds to the analyte). Alternatively, the detection zone can attract or immobilize a component associated with the analyte. For example, a recognition reagent that binds an analyte and is linked, directly or indirectly, to a magnetically susceptible particle can be attracted to a particular detection zone by a magnetic field provided in one or more detection zones.

In some embodiments, one or more of the detection zones include one or more electrodes. The electrodes can be formed of a material selected for electrical conductivity and low reactivity with sample components, for example, silver, gold, aluminum, palladium, platinum, iridium, a conductive carbon, a doped tin oxide, stainless steel, or a conductive polymer. The electrodes in the detection zones (the working electrodes), in conjunction with second electrodes in the reference zones (the reference electrodes) can measure an electrical property of the sample, such as a voltage or a current. Alternatively, the detection zones and the reference zones can each have at least one working electrode and counter electrode. That is, the detection and reference zones can make independent measurements. Optionally, counter electrodes are also included in the assay device. Assay devices including electrodes for measuring electrical properties of a sample are described in, for example, U.S. Pat. Nos. 5,708,247, 6,241,862, and 6,733,655, each of which is incorporated by reference in its entirety.

In some embodiments, the assay device base, assay device lid, or both have a translucent or transparent window aligned with the detection zone. An optical change that occurs in the detection zone can be detected through the window. Detection can be done visually (i.e., the change is measured by the user's eye) or measured by an instrument (e.g., a photodiode, photomultiplier, or the like). In general, the reference zone is similar in nature to the detection zone. In other words, when the detection zone includes an electrode, the reference zone can likewise include an electrode. When the detection zone is aligned with a window for optical measurement, the reference zone can similarly be aligned with a window for optical measurement. In some embodiments, the reference zone is not adapted to collect analyte. Alternatively, the reference zone is adapted to collect analyte, but performs a different analysis on said analyte. Thus, the detectable change measured in the reference zone can be considered a background measurement to be accounted for when determining the amount or concentration of analyte present in the sample.

During complex determination step 2104 magnetically susceptible reagent:analyte complexes that have been transferred to the detection zone can be measured. In an exemplary embodiment the detection zone includes electrodes that can be used to perform an electrochemical analysis of the sample. The enzyme labelled second reagent that is part of reagent:analyte complex can convert a substrate present in the buffer used to fill the detection zone. The substrate can be converted from a first form that is not detectable to a second form that is detectable. A measurement electrode within the detection zone can be used to measure the detectable form of the substrate. For example, an amperometric measurement can be made, in which a working electrode is polarised at a certain potential versus a reference electrode e.g. a silver/silver chloride (Ag/AgCl) reference electrode. For example, potassium ferricyanide can be converted (reduced) to potassium ferrocyanide by glucose oxidase during the conversion of glucose to gluconic acid. Any potassium ferrocyanide formed can be measured at about +400 mV vs Ag/AgCl as a positive current. The ferrocyanide is re-oxidised back to ferricyanide by the working electrode. An electroactive species can be oxidised, in which case it loses electrons to the electrode, or reduced, in which case it receives electrons from the electrode. The transfer of electrons between the electrode and the electroactive substance results in a measurable current, which may be a positive or negative current.

An amperometric measurement of an electroactive substance can be used to construct a calibration line. A known amount of substance yields a unique current, which can be described by the equation (Eq. 1) y=mx+c, where y represents the measured current, x represents the concentration of substance, m is the gradient of the line and c is the intercept of the line on the y-axis. Thus the measured current can be used to determine the concentration of an unknown amount of substance in solution following rearrangement of Eq. 1 to give (Eq. 2) x=(y−c)/m.

The buffer contained within the reservoir of the assay device includes a buffer salt and a substrate for the enzyme. The buffer salt buffers the pH to provide an environment suitable for the enzyme to convert the substrate to a product which can be detected. For example, the buffer salt may be an acetate buffer (e.g., sodium acetate). In some embodiments, the buffer can include at least about 100 mM sodium acetate (e.g., at least about 110 mM sodium acetate). In some embodiments, the buffer can include about 150 mM sodium acetate (e.g., about 135 mM sodium acetate). In an exemplary embodiment, the buffer salt includes about 125 mM sodium acetate (e.g., made to pH4.0 by addition of 125 mM sodium acetate with 125 mM acetic acid). The buffer solution can also contain a chloride salt to stabilise the electrochemistry of the reference electrode during analysis (e.g. potassium chloride (KCl)). In some embodiments the chloride salt can include at least about 100 mM KCl (e.g. at least about 125 mM KCl). In some embodiments the chloride salt can be at least about 200 mM KCl (e.g. at least about 175 mM KCl). In an exemplary embodiment the chloride salt includes 150 mM KCl. The buffer solution can also include a detergent to reduce the likelihood of antibody complexes from adhering to the internal surfaces of microfluidic network 508. In some embodiments the buffer can contain at least about 0.05% (v/v) Tween-20™, (e.g. at least about 0.075% (v/v) Tween-20™). In some embodiments the buffer can contain at least about 0.25% (v/v) Tween-20™, (e.g. at least about 0.15% (v/v) Tween-20™). In an exemplary embodiment the buffer solution includes 0.1% (v/v) Tween-20™. The buffer also includes substrate(s) for the enzyme label, which in the case of horse radish peroxidase is 2,2'-azino-bis(3-ethylbenzthiazoline-6-sulphonic acid) (ABTS) and hydrogen peroxide ($H_2O_2$). In some embodiments the buffer contains at least about 5 mM ABTS and at least about 5 mM $H_2O_2$ (e.g. at least about 7.5 mM ABTS and at least about 7.5 mM $H_2O_2$). In some embodiments the buffer contains at least about 15 mM ABTS and at least about 15 mM $H_2O_2$ (e.g. at least about 12.5 mM ABTS and at least about 12.5 mM $H_2O_2$). In other exemplary embodiments the buffer can contain about 5 mM ABTS or less (e.g. less than about 4 mM ABTS, less than about 3 mM ABTS, less than about 2 mM ABTS, less than about 1 mM ABTS) and about 5 mM $H_2O_2$ or less (e.g. less than about 4 mM $H_2O_2$, less than about 3 mM $H_2O_2$, less than about 2 mM $H_2O_2$, less than about 1 mM $H_2O_2$). In an exemplary embodiment the buffer includes 10 mM ABTS and 10 mM $H_2O_2$. The buffer solution has a final pH equal 4.2 (e.g. a pH at least about 3.8, a pH at least about 4.0) (e.g. a pH of 4.6 or less, a pH of 4.4 or less).

Figure 57:
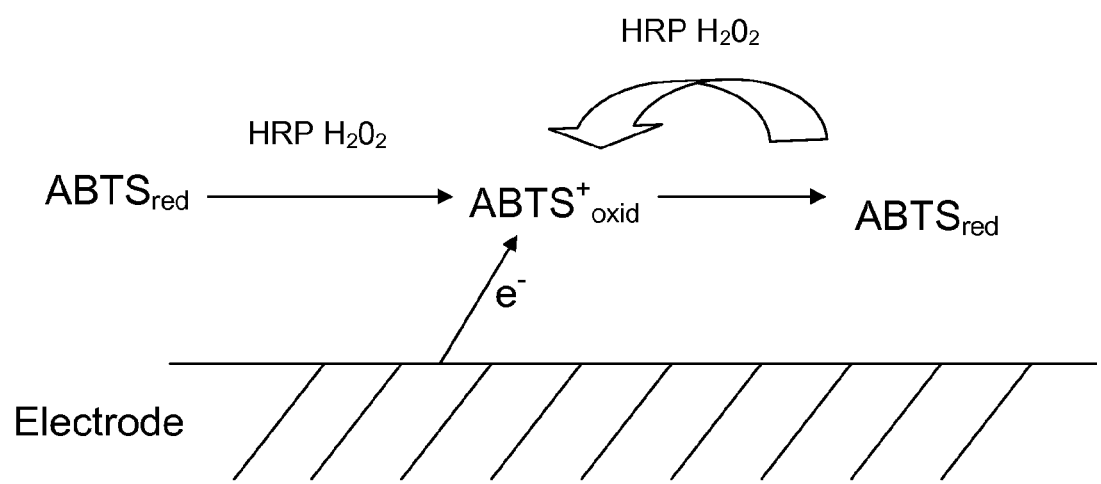
FIG. 57 illustrates electrochemical measurement of ABTS.

The enzyme label that is conjugated to second binding agent can be horse radish peroxidase (HRP), for example. HRP catalyses the conversion of hydrogen peroxide and ABTS to water and oxidised-ABTS (see FIG. 57). Any oxidised-ABTS that is produced can be measured electrochemically at a working electrode. Therefore during complex determination step 2104 any reagent:antibody complexes that have been transported through the microfluidic network of assay device can be measured according to the amount of oxidised-ABTS that is produced in the proximity of a measurement electrode. The measured current is proportional to the amount of oxidised-ABTS according to Eq. 2 and hence the measured current is proportional to the amount of analyte in the complexes that have been transported to the electrode.

In forming an assay result step 2105, the measurement result obtained during complex determination step 2104 is used to determine an assay result. In exemplary embodiments the assay result comprises displaying or communicating a value or signal indicative of the amount or concentration (quantitative or qualitative) of analyte detected in the assay. In exemplary embodiments the assay result comprises determining the status of the user, as regards the analyte. Depending on the analyte under investigation an elevated measurement result can indicate a diagnosis or prognosis for a disease state or pathological condition associated with the analyte. An elevated result may be one that is greater than a level that would be measured in a cross section of a population known not to have a particular condition (e.g. not be experiencing heart failure) (inter-population variation). Alternatively, an elevated result may be one that is greater than a baseline level previously determined for the individual user (intra-user variation).

In forming an assay result step 2105 a user of the assay device can be presented with information. If the user is qualified to make a clinical judgment (such as a medical doctor) the information might be different compared with a non qualified person, such as a user performing a self-test measurement. The information produced following a test can be classified into groups according to the qualification of the user. In a first group information might be a positive or negative indicator, e.g. the measurement result is or is not indicative of heart failure. In a second group information might be a numerical value indicative of the amount or concentration of analyte present in the sample. In a third group information might be presented as one or more "textual prompts", for example "contact your health care professional", "take an additional tablet", "take a nap". Thus in forming an assay result step 2105 the application of measurement data obtained during complex determination step 2104 will differ according to the end user of the information. A health care professional will typically want numerical data that will facilitate a prognosis or provide a diagnosis. An end user will typically want reassurance that "the way they feel" is a consequence of (i) an unrelated issue, e.g. indigestion or (ii) occurrence or re-occurrence of heart failure, in which case they will be prompted to dial 911, for example.

Assay Device

Figure 3:
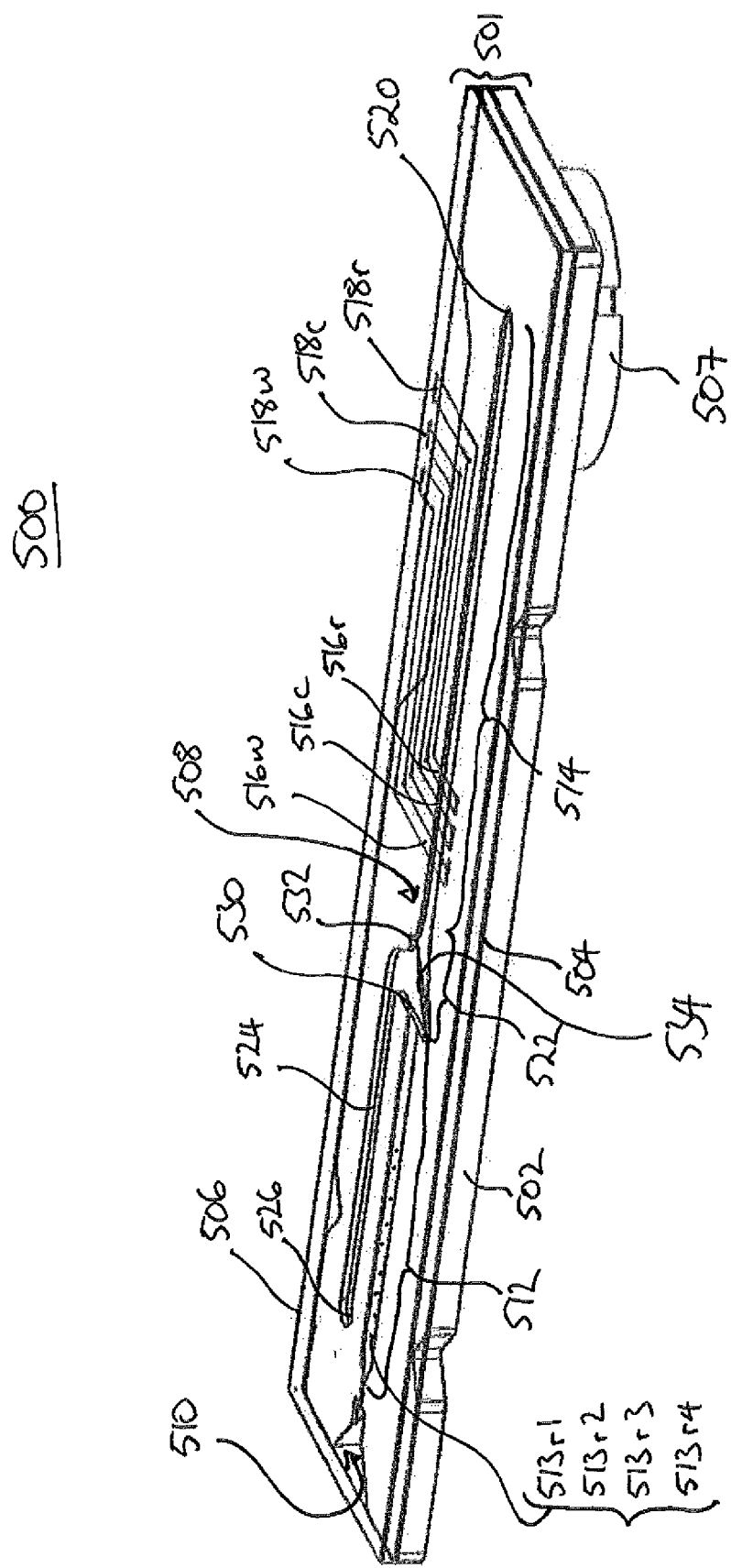
FIG. 3 is a perspective view of an exemplary assay device.
Figure 4:
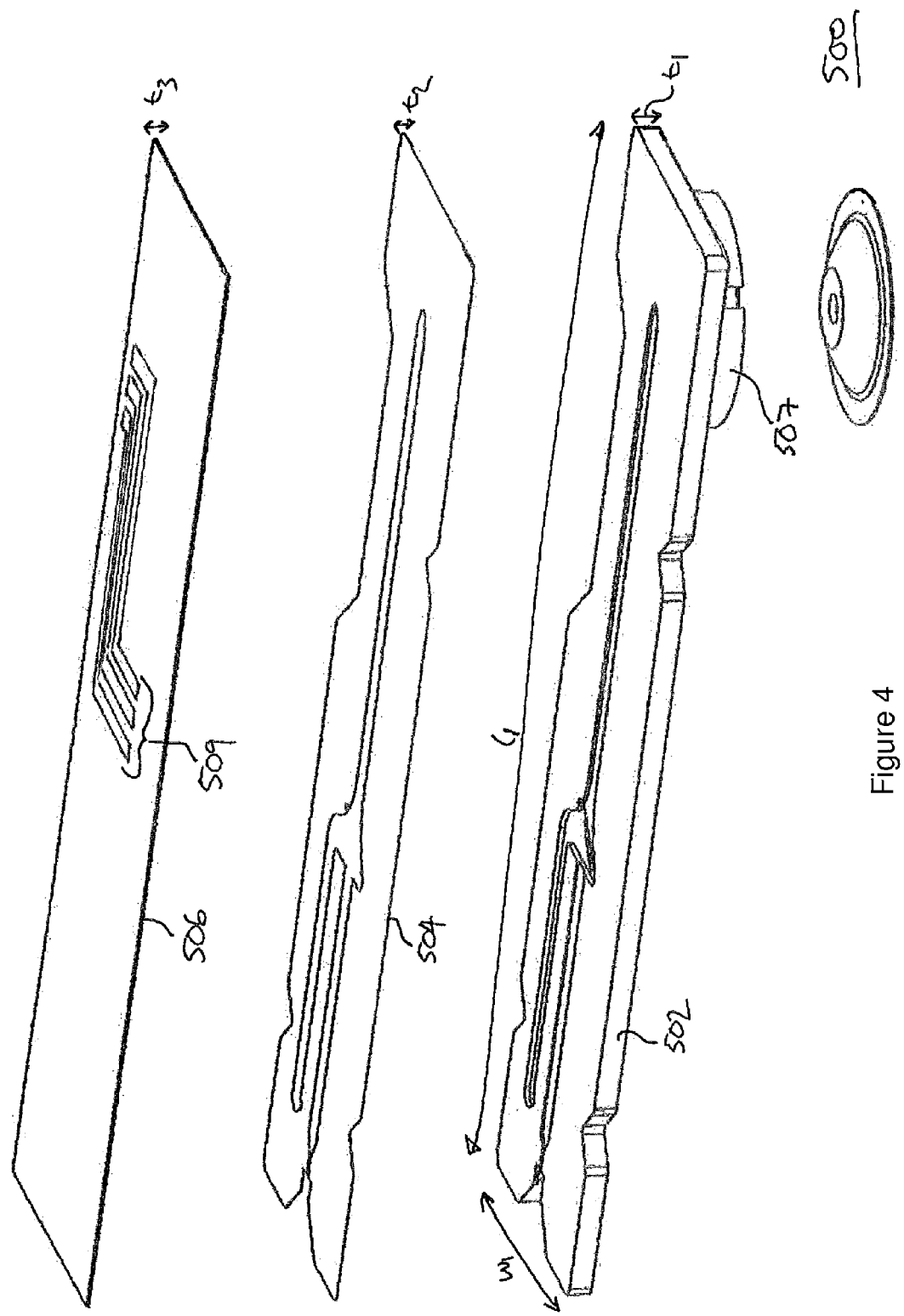
FIG. 4 is an exploded perspective view of an assay device.

Referring now to FIGS. 3 and 4, assay device 500 includes composite 501 that defines a microfluidic network 508. In exemplary embodiments, composite 501 includes first, second and third substrates 502, 504, 506 respectively. Microfluidic network 508 includes one or more zones, including reagent zone 512 which is in communication with detection zone 514 at interface zone 522. Microfluidic network 508 also includes sample inlet 510 in communication with a reagent zone 512 and a buffer inlet 520 in communication with a detection zone 514. Detection zone 514 is in communication with a reservoir 507 via buffer inlet 520. Interface zone 522 contains a capillary stop 530, which acts to contain a sample within reagent zone 512. Microfluidic network 508 has an overflow channel 524 in communication with interface zone 522. Overflow channel 524 has a vent 526 through first substrate 502. Overflow channel 524 receives buffer from reservoir 507 that has moved through detection zone 514 and interface zone 522.

Sample inlet 510 defines a region that receives a sample, for example a blood sample, and transfers the sample into reagent zone 512.

Reagent zone 512 has a width w2 of at least about 0.5 mm (e.g. at least about 1 mm; at least about 1.5 mm; at least about 2 mm; at least about 2.5 mm; at least about 3 mm; at least about 4 mm; at least about 5 mm; at least about 8 mm) (e.g., less than about 3 mm; less than about 3.5 mm; less than about 4 mm) In one exemplary embodiment w2 is about 2.5 mm.

Reagent zone 512 has a height h1 of at least about 0.04 mm (e.g. at least about 0.06 mm; at least about 0.08 mm; at least about 0.1 mm; at least about 0.15 mm; at least about 0.2 mm; at least about 0.4 mm; at least about 0.50 mm; less than about 1 mm) In one exemplary embodiment h1 is about 0.09 mm. In another exemplary embodiment h1 is about 0.15 mm.

Reagent zone 512 has a length l2 of at least about 25 mm, (e.g. at least about 5 mm; at least about 7 mm; at least about 10 mm; at least about 15 mm; at least about 20 mm; at least about 26.7 mm; at least about 30 mm; at least about 50 mm) (e.g., less than about 30 mm; less than about 20 mm; less than about 15 mm) In one exemplary embodiment 12 is about 10 mm. In another exemplary embodiment 12 is about 25 mm.

Reagent zone 512 has, therefore, a volume of at least about 2 µl (e.g. at least about 5 µl; at least about 7.5 µl; at least about 7.5 µl; at least about 10 µl; at least about 20 µl). A sample is drawn into reagent zone 512 by capillary forces and the sample moves into reagent zone 512 until the sample reaches capillary stop 530.

Once a sample has reached capillary stop 530, the changes in capillary force between the sample zone and the buffer zone are sufficient that no further sample is drawn into reagent zone 512. Typically a pressure difference of at least about 4 millibars (e.g. at least about 2 millibars; at least about 6 millibars) will cause the sample to stop flowing when it reaches the capillary stop. A capillary stop can be achieved by introducing a change in channel dimensions, or by introducing a hydrophobic patch (e.g. altering the contact angle of the surface), for example, such that flow of fluid along the channel is impeded. The pressure difference required to stop flow at the junction can be defined as the pressure that would need to be applied to the advancing liquid front to cause it to stop advancing.

Reagent zone 512 contains reagents (e.g., as described with respect to mixture formation step 2101 of method 2100). Typically, reagent zone 512 includes first, second, third, and fourth reagents 513$r$1, 513$r$2, 513$r$3, 513$r$4. Reagent 513$r$1 comprises a magnetically susceptible particle; reagent 513$r$2 comprises the first binding agent; reagent 513$r$3 comprises a second binding reagent (e.g., as described with respect to mixture formation step 2101 of method 2100). Reagent 513$r$4 is optional and can comprise a further reagent such as an anticoagulant.

As the sample is drawn into reagent zone 512 (e.g. by capillary forces), reagents 513$r$1, 513$r$2, 513$r$3, 513$r$4 initially combine with the sample to form an inhomogeneous mixture. A magnetic field can be used to agitate reagent 513$r$1 and cause reagent 513$r$1 to move within the sample as described with respect to a reagent/analyte capture step 2102 of method 2100. For example, reagent 513$r$1 may be used to disperse and mix the reagents 513$r$1, 513$r$2, 513$r$3, 513$r$4 within the reagent zone to enhance the distribution of each reagent throughout the sample and thereby increase the likelihood that a specific component of the sample is contacted by one or more of reagents 513$r$1, 513$r$2, 513$r$3, 513r4. Reagents 513r1, 513r2, 513r3, 513r4 will interact with the sample for a period of time (e.g., as described with respect to reagent/analyte capture step 2102 of method 2100).

FIG. 4 depicts the respective layers used to form composite 501. First substrate 502 has a first major surface and a second major surface with a width w1, length l1 and thickness t1. One major surface of first substrate 502 includes microfluidic network 508. Another major surface of first substrate 502 includes reservoir 507 and buffer inlet 520. First substrate 502 can be formed from a hydrophobic material such as polystyrene or polycarbonate. First substrate 502 can also be formed from a hydrophilic material such as polyester. First substrate 502 can be formed by injection moulding, hot embossing, laser ablation, etching, milling. The width w1 can be at least about 25 mm (e.g. at least about 15 mm; at least about 20 mm; at least about 30 mm; at least about 50 mm) The length l1 can be at least about 100 mm (e.g. at least about 50 mm; at least about 75 mm; at least about 125 mm; at least about 150 mm; at least about 200 mm) The thickness t1 can be at least about 1.5 mm (e.g. at least about 0.5 mm; at least about 0.75 mm; at least about 1.5 mm; at least about 2.0 mm at least about 2.5 mm; at least about 5 mm). In one exemplary embodiment t1 is about 1.5 mm.

Reagent zone 512 includes reagents 513r1, 513r2, 513r3, 513r4, which can be applied to the major surface of first substrate 502 that includes microfluidic network 508. Each respective reagent 513r1, 513r2, 513r3, 513r4 can be applied to the surface of first substrate 502 within the confines of the region that represents reagent zone 512. When substrate 502 has hydrophobic characteristics the likelihood that reagents will migrate away from the location to which they were applied is negligible. When substrate 502 has hydrophilic characteristics there is increased likelihood that reagents might migrate from the location to which they were applied. Reagents can be applied by a process of microspotting, inkjet printing, pipetting, slot dye printing, or the like, which methods of deposition allow accurate and controlled dosing of each respective reagent. Reagents 513r1, 513r2, 513r3, 513r4 can be applied in discrete areas such that they are physically distant or they can be applied as a laminate or as interspersed dots. Reagents can be formulated to facilitate rapid solubilisation upon contact with a sample.

The reagents can be deposited into the reagent zone using a number of known techniques, including for example, dispensing or aspirating from a nozzle, using an electromagnetic valve and servo- or stepper-driven syringe. These methods can deposit droplets or lines of reagents in a contact or non-contact mode. Other methods for depositing reagents include pad printing, screen printing, piezoelectric print head (e.g., ink-jet printing), or depositing from a pouch which is compressed to release reagent (a "cake icer"). Deposition can preferably be performed in a humidity- and temperature-controlled environment. Different reagents can be dispensed at the same or at a different station.

Fluorescent or coloured additives can optionally be added to the reagents to allow detection of cross contamination or overspill of the reagents outside the desired deposition zone. Product performance can be impaired by cross-contamination. Deposition zones can be in close proximity or a distance apart. The fluorescent or coloured additives are selected so as not to interfere with the operation of the assay device, particularly with detection of the analyte.

After deposition, the reagents are dried. Drying can be achieved by ambient air drying, infrared drying, infrared drying assisted by forced air, ultraviolet light drying, forced warm air, controlled relative humidity drying, or a combination of these.

Second substrate 504 has a first major surface and a second major surface which includes an opening within the profile of microfluidic network 508. Substrate 504 has a width w1, a length l1 and a thickness t2. Thickness t2 can be about 0.062 mm (e.g. at least about 50 µm, at least about 20 µm; at least about 40 µm; at least about 60 µm; at least about 100 µm). Second substrate 504 has adhesive characteristics and can be used to physically attach first substrate 502 to third substrate 506. Second substrate 504 can be a single material or a composite material. For example second substrate can be a double sided adhesive layer which includes a carrier layer onto which is disposed one each major surface an adhesive layer. An adhesive layer can be a pressure sensitive adhesive, which will adhere to another substrate when pressure is applied to compress the adhesive layer against the substrate. Adhesive layer can be a heat sensitive adhesive, in which case elevated temperature and pressure bond the adhesive to a substrate. Second substrate 504 can have a hydrophobic or a hydrophilic characteristic. When second substrate 504 is a composite material on a carrier layer one major surface can be a pressure sensitive adhesive and the other major surface can be a heat sensitive adhesive. When second substrate 504 is a composite with an inner carrier layer each major surface can be a pressure sensitive adhesive or heat sensitive adhesive as required. The profile of microfluidic network 508 is provided in second substrate 504. When second substrate 504 is applied to first substrate 502 the profile of microfluidic network 508 is registered over first substrate 502.

In some embodiments first substrate 502 does not include microfluidic network 508. In which case second substrate 504, which includes features of microfluidic network 508, defines the outline of microfluidic network 508 when it is bonded between first substrate 502 and third substrate 506.

Third substrate 506 has a first major surface and a second major surface, with a width w1, a length l1 and a thickness t3. On one major surface is disposed a conductive network 509 that defines a series of one or more electrodes and terminals. Conductive network 509 can be formed by a process of screen printing of a conductive paste, for example a carbon paste, a gold paste, a silver paste, a platinised carbon paste. Conductive network 509 can also be formed by a process of photolithography, photogravure, laser ablation, laser etching to define a pattern in a metallic or metallised film. Metallic or metallised films can be formed by sputtering, electroplating, or rolling.

Conductive network 509 can include one or more independent conductive traces that connect an electrode that is intended to make contact with a fluid in microfluidic network 508 with a detector and/or processor in meter 400. An electrode might be used to measure a substance or parameter of interest within a sample applied to assay device 500. A substance of interest can include a biomarker indicative of a cardiac condition, such as for example NT-proBNP. A parameter of interest could be a haematocrit value, the percentage of red blood cells within the sample.

Figure 5:
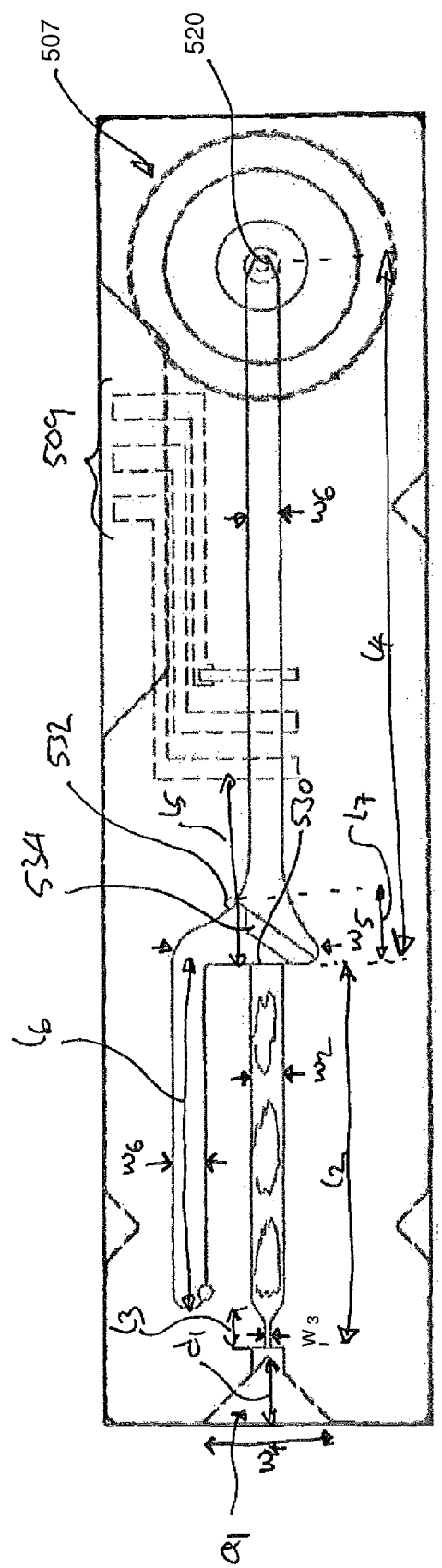
FIG. 5 is a plan view from above of an assay device.

Lamination of first, second and third substrates 502, 504, 506, to yield composite 501 involves registration of each respective layer with respect to the other. For example, first substrate 502 and second substrate 504 are placed together such that the profile of microfluidic network 508 formed in first substrate 502 is aligned with the profile of microfluidic network 508 in second substrate 504. Third substrate 506 is then placed onto second substrate 504 such that conductive network 509 and in particular first, second and third electrodes 516w, 516r, 516c are correctly aligned over detection zone 516. FIG. 5 represents a plan view from above of assay device 500 and indicates the spatial location of the various features of the device. Microfluidic network 508 is defined by a series of dimensional parameters; length l2, length l3, length l4, length l5, length l6, width w2, width w3, width w4, width w5, width w6, area a1, distance d1.

Sample inlet 510 has an area a1 of at least about 1.57 mm$^2$ (e.g. at least about 1 mm$^2$, at least about 1.25 mm$^2$, at least about 1.75 mm$^2$, at least about 2 mm$^2$), which is defined by distance d1 and width w4. Width w4 is at least about 2.5 mm (e.g. at least about 1 mm, at least about 1.5 mm, at least about 2 mm, at least about 3 mm, at least about 5 mm) and distance d1 is at least about 1.24 mm (e.g. at least about 1 mm; at least about 1.15 mm, at least about 1.5 mm, at least about 2 mm; at least about 5 mm; at least about 7.50 mm; at least about 7.65 mm, less than about 8.0 mm, less than about 7.90 mm, less than about 7.80 mm) In one exemplary embodiment d1 is about 7.75 mm.

Reagent zone 512 has a minor portion with a length l3 and width w3, and a major portion with a length l2 and a width w2 that terminates at capillary stop 530. Length l3 is at least about 2 mm (e.g. at least about 1 mm, at least about 1.5 mm, at least about 2 mm, at least about 3 mm, at least about 5 mm) and width w3 is at least about 0.45 mm (e.g. at least about 0.1 mm; at least about 0.2 mm; at least about 0.3 mm; at least about 0.40 mm; at least about 0.5 mm; at least about 0.6 mm)(e.g., less than about 0.60 mm; less than about 0.55 mm; less than about 0.50 mm).

Interface zone 522 has a length l7 and a width w5, and includes chamfer 534 and capillary stop 532. Length l7 is at least about 4.9 mm (e.g. at least about 2.5 mm, at least about 4 mm, at least about 6 mm) and width w5 is at least about 11 mm (e.g. at least about 6 mm, at least about 8 mm, at least about 9 mm, at least about 10 mm, at least about 12 mm, at least about 15 mm, less than about 20 mm) In one exemplary embodiment w5 is about 10.37 mm. Interface zone 522 will be described in more detail with reference to FIG. 6. Detection zone 514 has a length l4, length l5 and width w6. Length l4 is at least about 53 mm (e.g. at least about 35 mm, at least about 40 mm, at least about 45 mm, at least about 55 mm, at least about 65 mm), length l5 is at least about 14.6 mm (e.g. at least about 10 mm, at least about 20 mm, at least about 25 mm, at least about 30 mm) and width w6 is at least about 2.5 mm (e.g. at least about 1 mm, at least about 1.5 mm, at least about 2 mm, at least about 3 mm, at least about 5 mm)(e.g., less than about 3.50 mm, less than about 4 mm, less than about 6 mm).

Length l5 represents the distance from capillary stop 530 to measurement electrode 516w. Length l6 represents the distance between buffer inlet 520 and capillary stop 530.

Prior to addition of a sample to assay device 500, microfluidic network 508 is filled with a gas, for example air. When a sample is applied to application zone 510, the sample is drawn in to reagent zone 512, e.g. by capillary forces. The gas within reagent zone 512 is expelled via interface zone 522 as liquid moves into and through reagent zone 512. The back pressure experienced by the advancing liquid front is negligible compared with the capillary force that causes the sample liquid:gas interface to advance along the capillary channel. Thus as the sample liquid:gas interface moves further along the reagent zone, driving the gas ahead of it, additional fluid is drawn in from sample zone 510. As the fluid within reagent zone 512 reaches capillary stop 530, the difference in pressure on either side of the capillary stop is sufficient to halt the flow of liquid.

Capillary stop 530 is configured such that the effective back pressure applied to the liquid front is greater on the detection zone 514 side of the capillary stop than reagent zone 512 side. The driving force on the reagent zone 512 side of the capillary stop is lower than the back pressure exerted by the detection zone 514 side of the capillary stop. When fluid approaches capillary stop from detection zone 514, capillary stop 530 would not impede the flow of fluid into reagent zone 512, since the capillary pressure is greatest on the side of the capillary stop from which the fluid is approaching. Whereas when fluid approaches capillary stop 530 from the reagent zone 512, a sample:gas interface forms at the capillary stop.

Detection zone 514 includes first, second and third electrodes 516w, 516r, 516c respectively. First, second and third electrodes 516w, 516c, 516r are in communication with terminals 518w, 518c, 518r. Terminals 518w, 518c, 518r interface with meter 400 as described herein with reference to FIG. 2. When a sample has been applied to assay device 500, a buffer solution is introduced into detection zone 514 from reservoir 507. In some embodiments, buffer solution is introduced only after a period of time sufficient to allow reagents 513r1, 513r2, 513r3, 513r4 to interact with the sample and form a complex between the reagents and the analyte (e.g. NT-proBNP) as described in capture step 2102 of method 2100.

Reservoir 507 is pressurised by reservoir actuator 408 under control of a processor (as will be described in greater detail with reference to FIG. 8). Buffer is driven from reservoir 507 at a rate that reduces the likelihood of air bubbles being trapped within microfluidic network 508 (e.g. at a flow rate of at least 1 µl/s; at least 5 µl/s; at least 10 µl/s). In an exemplary embodiment buffer initially fills detection zone 514 from the opposite end of assay device 500 to which sample is applied. An advancing buffer:gas (e.g. air) interface moves uniformly along the edge walls of detection zone 514 towards capillary stop 530. The gas contained within detection zone 514 is expelled from assay device 500 through vent 526 within overflow channel 524.

Interface zone 522 includes capillary stop 530, chamfer 534, and capillary stop 532. Chamfer 534 and capillary stop 532 permit controlled movement of buffer through interface zone 522. When the advancing buffer:gas interface reaches interface zone 522, capillary stop 532 retards the movement of the advancing buffer front along one edge wall of microfluidic network 508. Buffer opposite stop 532 continues to advance and pivots about stop 532. Capillary stop 532 thus acts to steer the buffer:gas interface around the corner in which capillary stop 532 is located. The advancing buffer gas interface thus moves down chamfer 534 and along the edge of microfluidic network 508 in which capillary stop 530 is formed. Buffer moves transversely across the sample: gas interface held at capillary stop 530 to form a sample: buffer (e.g. liquid:liquid) interface. The sample:buffer interface is formed in such a way that retention of air bubbles at the interface is minimised. Once a sample:buffer interface has been formed, excess buffer moves into overflow 524 until it reaches vent 526.

Figure 6:
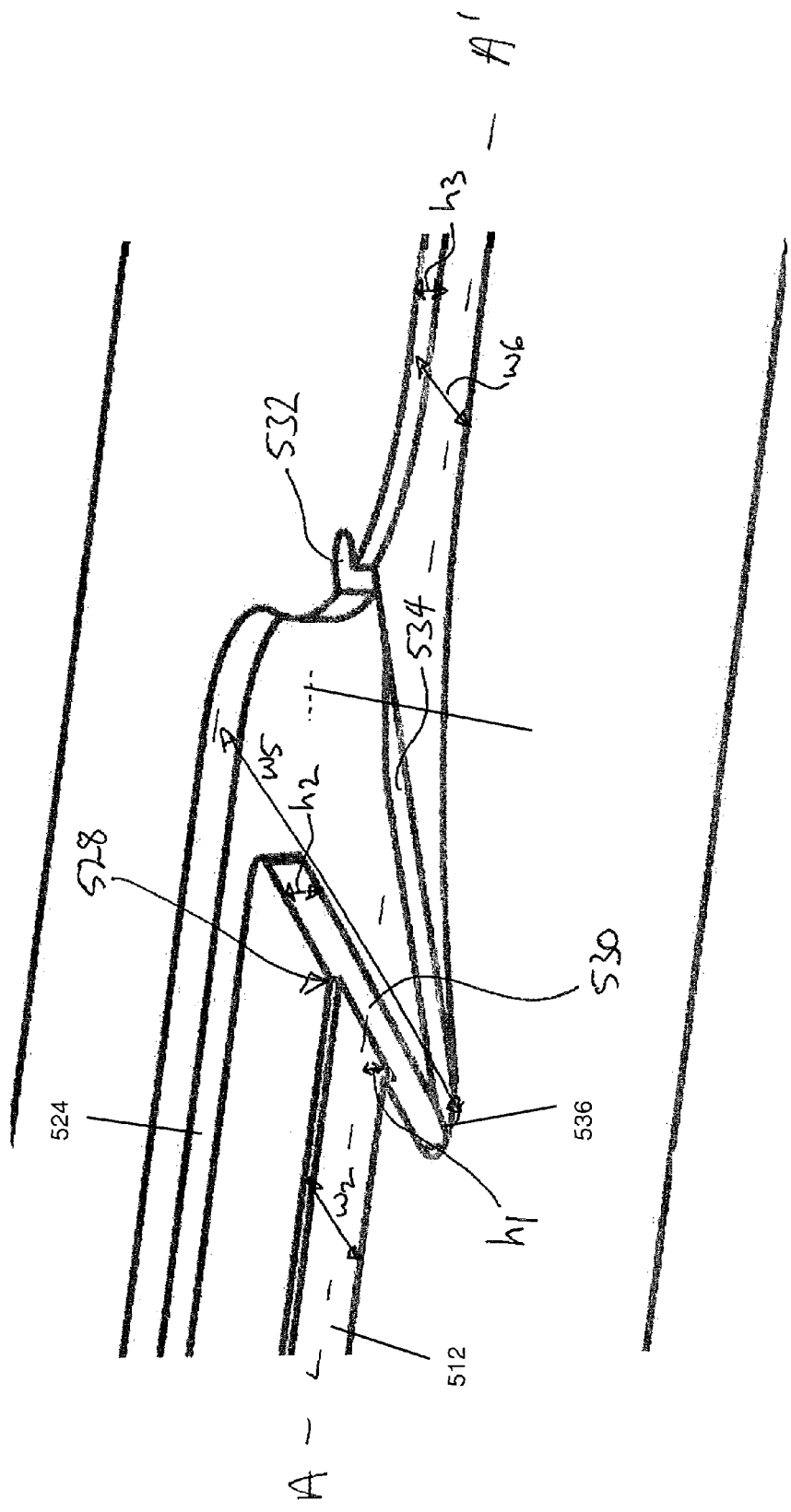
FIG. 6 is an exploded view of an interface formation feature of an assay device.

The formation of a bubble free liquid:liquid interface between the sample in reagent zone 512 and the buffer in interface zone 522 is achieved by the design of the interface as will be described with reference to FIG. 6, which shows an expanded perspective view of interface zone 522. FIG. 6 depicts the various aspects of interface zone 522 that enable formation of a stable interface between liquid sample and buffer.

Referring to FIG. 6, on the left hand side as drawn, reagent zone 512 has a width w2 and a height h1 and terminates at capillary stop 530. Reagent zone 512 has an edge 528 that represents an opening that forms the transition from reagent zone 512 into interface zone 522. Edge 528 has a square profile with a negligible radius of curvature (e.g. the angle between the two edges is typically close to 90 degrees). Edge 528 is sufficiently well defined that the likelihood of liquid sample breaching capillary stop 530 is negligible. Liquid sample is thus prevented from crossing the interface and entering the gas filled interface zone 522.

Interface zone 522 has a height h2 of at least about 0.45 mm (e.g. at least about 0.2 mm, at least about 0.3 mm, at least about 0.35 mm, at least about 0.40 mm, at least about 0.5 mm, at least about 0.75 mm) In one exemplary embodiment h2 is about 0.45 mm. Interface zone 522 has a width w5. Corner 536 is at least about 3 mm (e.g. at least about 1.5 mm, at least about 4.5 mm) from the longitudinal centre line of reagent zone 512, such that there is a clear and distinct separation between heights h1 and h2 to reduce the likelihood of liquid in reagent zone 512 breaching edge 528 to enter interface zone 522. Chamfer 534 provides a smooth transition between height h3 of detection zone 514 and h2 of interface zone 522 which leads into overflow channel 524. Detection zone 514 has a height h3 of at least about 0.25 mm (e.g. at least about 0.1 mm, at least about 0.15 mm, at least about 0.2 mm, at least about 0.4 mm, at least about 0.5 mm) (e.g., less than about 0.30 mm, less than about 0.35 mm, less than about 0.40 mm) In one exemplary embodiment h3 is about 0.25 mm. When buffer approaches interface zone 522 from detection zone 514 (flowing right to left as drawn) the buffer:gas interface contacts capillary stop 532.

Figure 7:
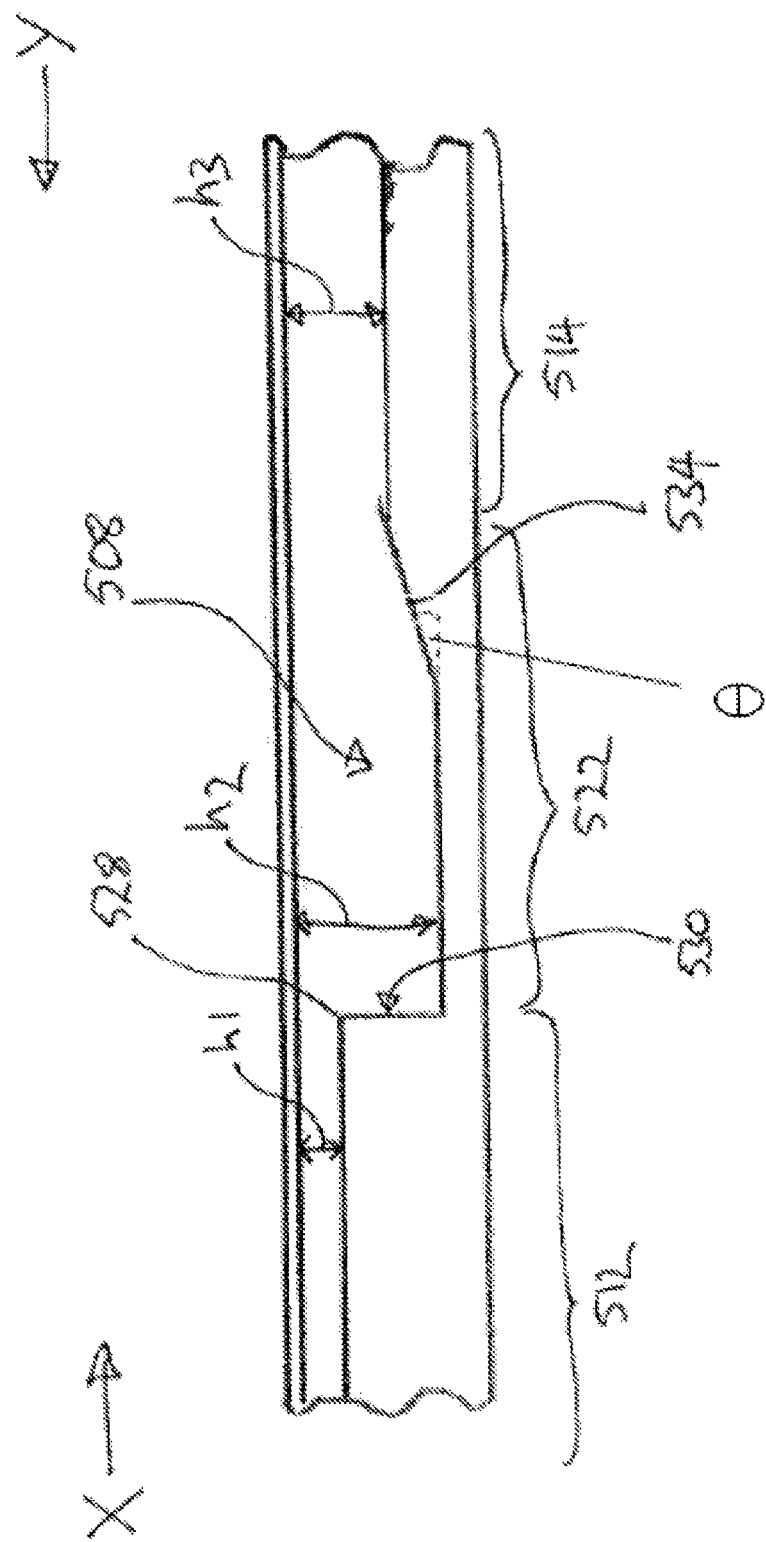
FIG. 7 is a cross sectional view of FIG. 6.

Referring now to FIG. 7, which shows a cross sectional view through line A-A' of FIG. 6 and represents the profile of interface zone 522. FIG. 7 shows the respective heights h1, h2, h3 of microfluidic network 508 through the transition from reagent zone 512, interface zone 522 and detection zone 514. When liquid moves into microfluidic network 508 in direction X along reagent zone 512, it approaches edge 528 of capillary stop 530. The difference in height h1 compared with height h2 is such that the capillary force in reagent zone 512 is different to the capillary force in interface zone 522. The capillary pressure exerted by interface zone 522 in direction Y is greater than the capillary force exerted by reagent zone 512 in direction X. Therefore when sample liquid approaches and reaches edge 528 of capillary stop 530 sample flow stops and a liquid:gas interface forms. The liquid:gas meniscus thus defines one end wall of the volume of liquid that is contained within reagent zone 512. The effect of capillary stop 530 is thus to contain liquid sample within reagent zone 512. As has been described herein above, other means of controlling the flow of liquid within a channel also exist. One such example is the use of a hydrophobic patch, which may be provided as a ring around the walls of the capillary channel. The characteristics of the hydrophobic material are such that when a liquid approaches the ring of hydrophobic patch it is retarded in much the same way as capillary stop 530. The hydrophobic ring exerts a force in direction Y equivalent to that exerted by capillary stop 530.

Figure 8:
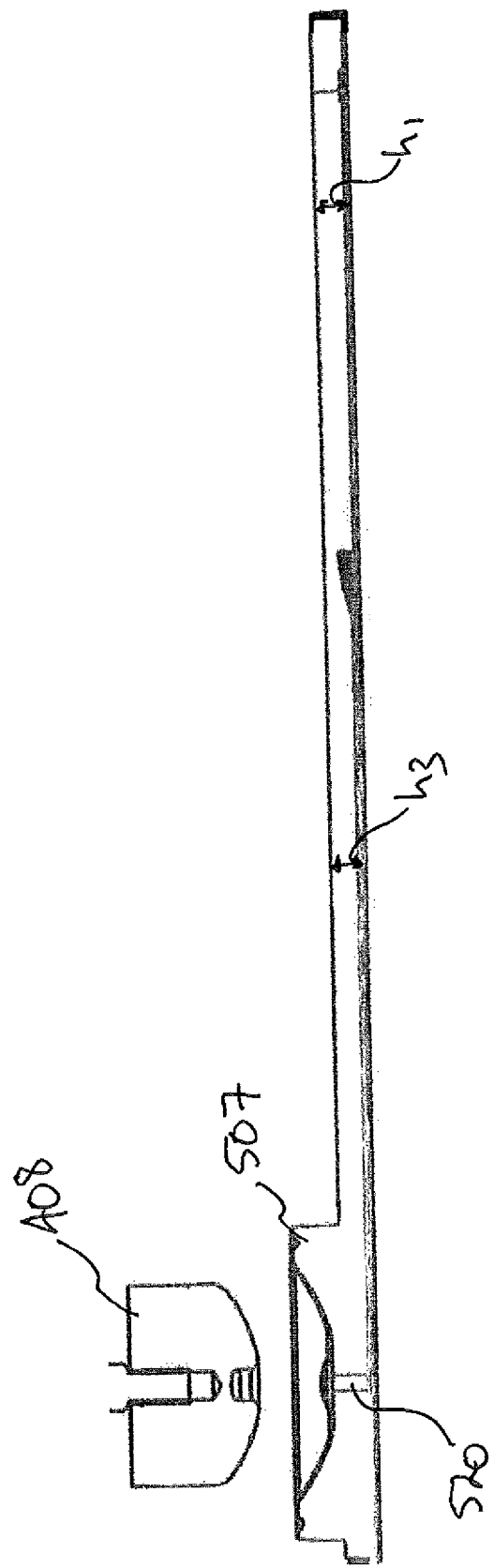
FIG. 8 is a longitudinal cross sectional view through an assay device.

Referring now to FIG. 8 which shows a longitudinal cross section through assay device 500, and includes the cross sectional view of FIG. 7. FIG. 8 includes fluid reservoir 507, buffer inlet 520, detection zone 514, interface zone 522, reagent zone 512 and sample inlet 510. FIG. 8 also shows reservoir activator 408. Reservoir activator 408 is urged towards fluid reservoir 507 under control of a processor of meter 400 at a defined rate which causes fluid to be released from fluid reservoir 507 via buffer inlet 520, wherein the buffer enters detection zone 514.

When a user correctly inserts assay device 500 into meter 400, a processor is actuated to conduct a measurement cycle. The processor causes information relevant to the measurement to be made to be displayed on interface 406. The information includes prompts to apply a sample to assay device 500. When a sample has been applied to assay device 500, detector senses the presence of sample in reagent zone 512 and provides feedback to the processor. The processor then actuates reservoir actuator 408. After a predefined interval of time from the presence of sample being detected in reagent zone 512, reservoir activator 408 is urged towards and makes contact with reservoir 507. After initial contact is made with reservoir 507, reservoir activator 408 continues to be urged into reservoir 507. Reservoir activator 408 applies pressure to reservoir 507, which is in turn pressed against buffer inlet 520. Buffer inlet 520 has a sharpened element that protrudes towards reservoir 507. Prior to insertion into meter 400, reservoir 507 can be protected by a removable cover that prevents premature rupture and therefore accidental release of fluid from the reservoir. In which case a user would first remove the protective cover before inserting assay device 500 into meter 400. In some instances protective cover may not be provided with assay device 500, and in other instances the protective cover may not require removal prior to insertion of assay device 500 into meter 400.

The movement of reservoir activator 408 towards reservoir 507 under control of processor 414 occurs at such a rate that following initial rupture of reservoir 507 and therefore release of fluid contained therein that fluid is delivered through buffer inlet 520 into detection zone at a controlled and defined flow rate. In an exemplary embodiment buffer is moved through microfluidic network at a flow rate of about 0.5 mL/min (e.g. at least about 0.1 mL/min, a1 least about 0.3 mL/min, about 0.7 ml/min or less, about 0.9 mL/min or less). Fluid is pumped towards interface zone 522 until the meniscus reaches capillary stop 532. The fluid front is then caused to turn about capillary stop 532. The meniscus continues to be pushed around the opposite edge wall of interface zone 522 to capillary stop 532 as reservoir activator is further urged into reservoir 507 under control of a processor. Once the progressing fluid front has moved across the end of reagent zone 512, thereby forming an interface between the liquid in reagent zone 512 and the fluid that has been pushed from reservoir 507, the fluid is further driven into overflow channel 524 towards vent 526.

Referring to FIGS. 30-39, an exemplary embodiment of the assay device is shown. The assembled device is shown in FIG. 38J. The assay device is in the form of a elongate thin strip having a thickness t1, as described above. Referring to FIG. 38I, the assay device is a microfluidic device in which a channel network 508 is formed. The device has a base 502 that can be formed from a plastics substrate, such as polycarbonate. The channel network 508 can be formed by techniques well known to persons skilled in the art such as moulding, laser ablation or milling of the substrate (as described above).

The device has a laminate structure (as shown in FIGS. 4, 30-34, 36 and 39) being made up of multiple layers. The microfluidic network 508 is defined by a three layer laminate in which a first substrate layer 502 is joined to a third substrate layer 506 by a second substrate layer 504 comprising an adhesive strip, as described above. Referring to FIGS. 30-34, 36 and 39, in an exemplary embodiment a further adhesive strip 3501 joins the third substrate layer 506 with a packing piece 3502 to form a device having five laminate layers. The packing piece has a U-shaped cut-out section 3511 configured to permit a magnet 2803 in meter 400 to be positioned in close proximity with the external surface of the third substrate layer 506.

The first substrate 502 layer further comprises a raised annulus 3510 having a liquid inlet 520 proximal its centre and a sharp projection 3506 positioned at or adjacent the inlet. An O-ring seal 3504 is seated on the annulus and a liquid containing reservoir 507 (as described above) is received in the annulus, a wall of which is positioned adjacent the sharp element or projection 3506 (as described above).

Figure 44:
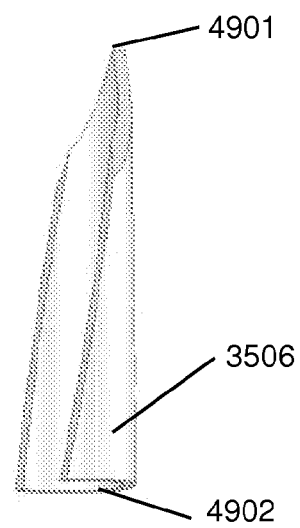
FIG. 44 shows the sharp projection.

Referring to FIG. 44, the sharp projection 3506 can be made of metal (e.g. steel) or plastics material. The projection 3506 can have a single curved wall extending from a base section where the wall has a C-shaped cross section 4902 towards a tip forming the sharp part of the projection. The wall can be chamfered to provided bevel edges meeting at tip 4901 to provide cutting edges which facilitate puncture of reservoir 507. In assembly of the device 500, the projection 3506 is inserted through the liquid inlet 520 so as to project into the centre of the space defined by the raised annulus 3510 and towards a base wall of the reservoir 507 when received in the annulus. The curved wall of the projection 3506 defines a partial tube structure forming a flow path for liquid from the punctured reservoir 507 through the liquid inlet 520 into the second channel portion 4304.

Figure 43:
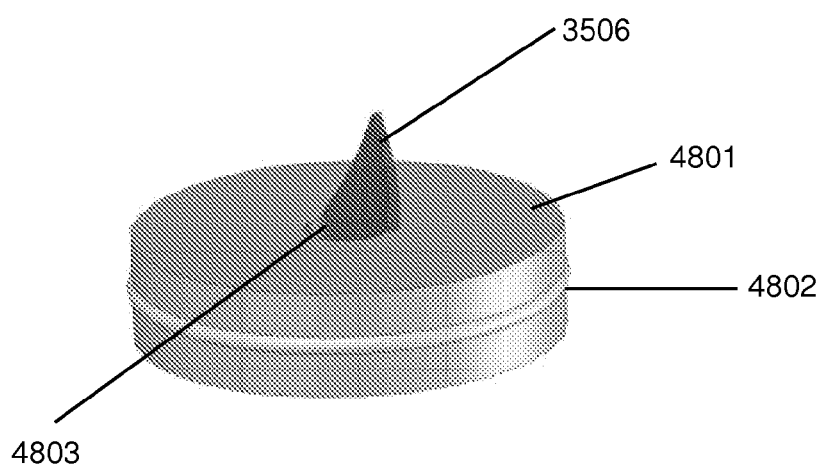
FIG. 43 shows an annular insert and sharp projection.

Referring to FIG. 43, in one exemplary embodiment the sharpened projection forms part of an annular insert 4801. The insert 4801 has a shallow cylindrical body having an O-ring seal or gasket extending around a circumference of the body. Projection 3506 is formed on one of the planar surfaces of the insert 4801 and is positioned adjacent an aperture 4803. Aperture 4803 extends through the insert from one planar surface to the opposing planar surface, e.g. approximately through the centre of the insert, and defines a flow path for liquid from reservoir 507 through liquid inlet 520 into the second channel portion 4304. The curved wall of the projection 3506 follows an arc-line of the circumference of the aperture such that the position of the tip 4901 of the projection 3506 is offset from the centre of the aperture, the curved wall of the projection forming a guide to direct flow of liquid into the aperture.

Insert 4801 can be positioned in an aperture of corresponding size formed in the first substrate layer 502 within the annulus 3510 of the first substrate layer 502. The O-ring seal 4802 provides an air tight seal with the first substrate layer 502 to prevent loss of liquid or gas from the second channel portion 4304.

In exemplary embodiments the reservoir 507 is a pouch having a wall, e.g. a base wall, that may be ruptured by a sharp projection 3506, e.g. a needle, on the assay device 500. In one exemplary embodiment the wall of the reservoir 507 can have a concave portion forming a dimple extending in a direction towards the internal volume of the pouch and configured to align with the sharp projection. In another exemplary embodiment the base wall has a generally smooth outer surface which may be generally planar or convex.

A seal or gasket (e.g. an O-ring seal), e.g. of about 400-600 μm thickness, having an internal diameter corresponding to the diameter of the sharp projection 3506 at its base (e.g. about 1 mm) can be placed around the sharp projection 3506 such that when the reservoir 507 is compressed against the assay device and toward the sharp projection 3506 a gas-tight seal is formed between the reservoir and the assay device preventing air from entering the assay device via the inlet 520 such that liquid in the second channel portion 4304 is substantially free of air or other gas bubbles. In some exemplary embodiments the reservoir 507 is made from plastics material and sealed to form a pouch, bag or sachet containing liquid, e.g. buffer liquid. The reservoir 507 can be made from first and second plastics materials, wherein one of the plastics materials is softer than the other, the softer plastics material forming at least part of the wall that is configured for rupture by the sharp projection 3506 on the assay device 500. The softer plastics material can have a shore hardness of about 30 (e.g. about 28, about 29, about 31, about 32). The reservoir 507 can have a volume of at least about 150 μl (e.g. at least about 160 μl, at least about 170 μl, at least about 180 μl) and less than about 300 μl (e.g. less than about 290 μl, less than about 280 μl, less than about 270 μl, less than about 260 μl, less than about 250 μl). In one exemplary embodiment the reservoir 507 has a volume of about 180 μl. In another exemplary embodiment the reservoir 507 has a volume of about 250 μl.

Figure 31:
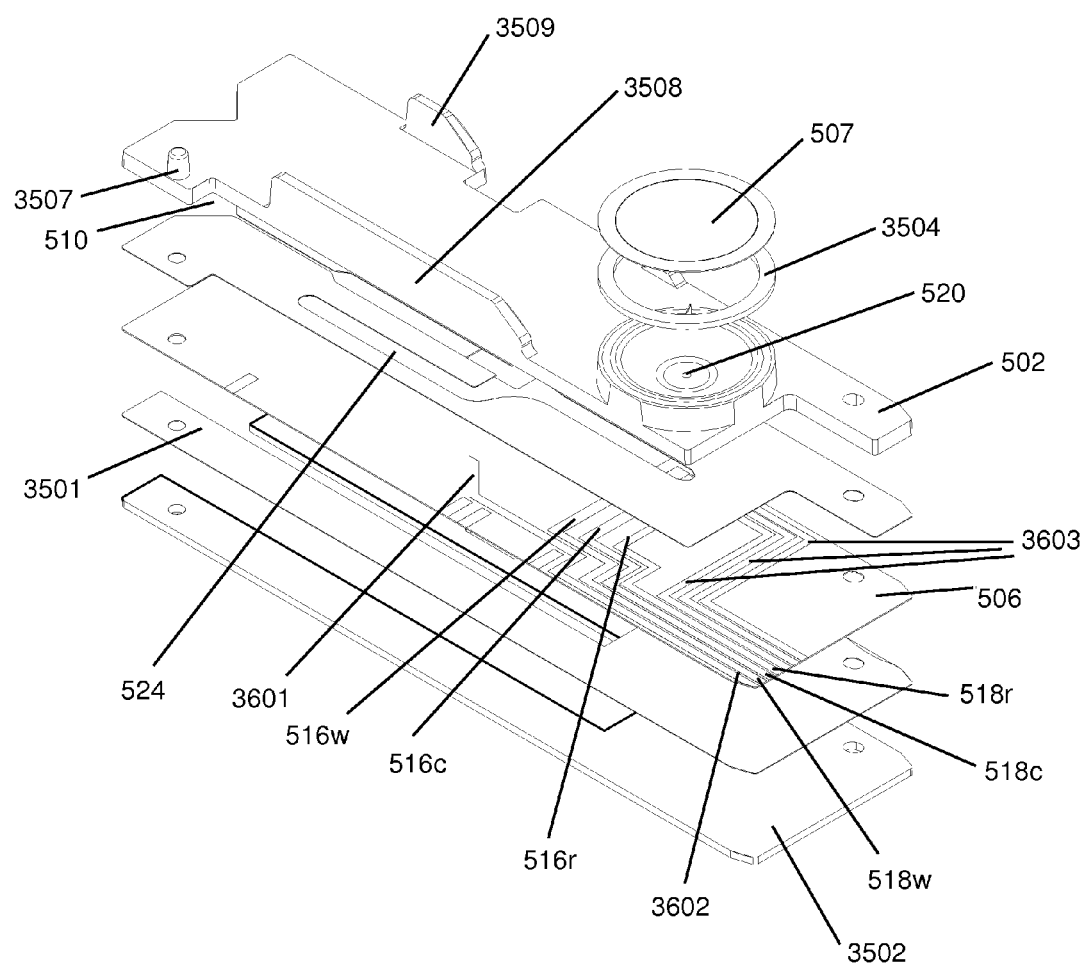
FIG. 31 shows a perspective view from above of the components of an assay device.
Figure 32:
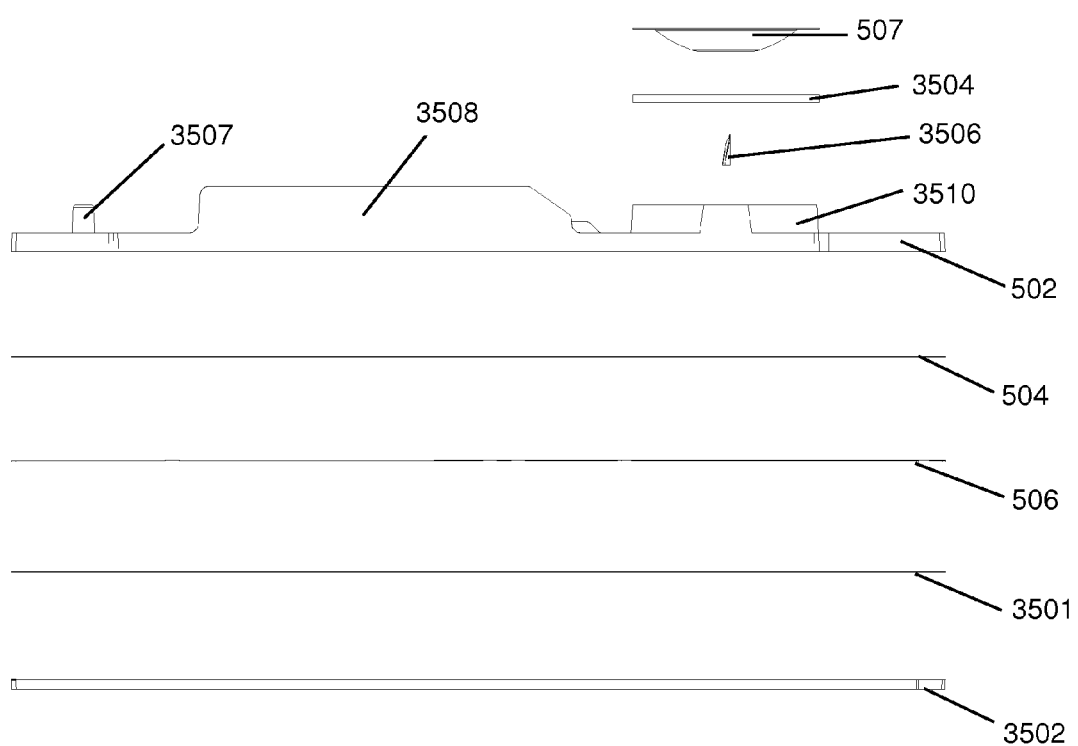
FIG. 32 shows a side view of the components of an assay device.
Figure 33:
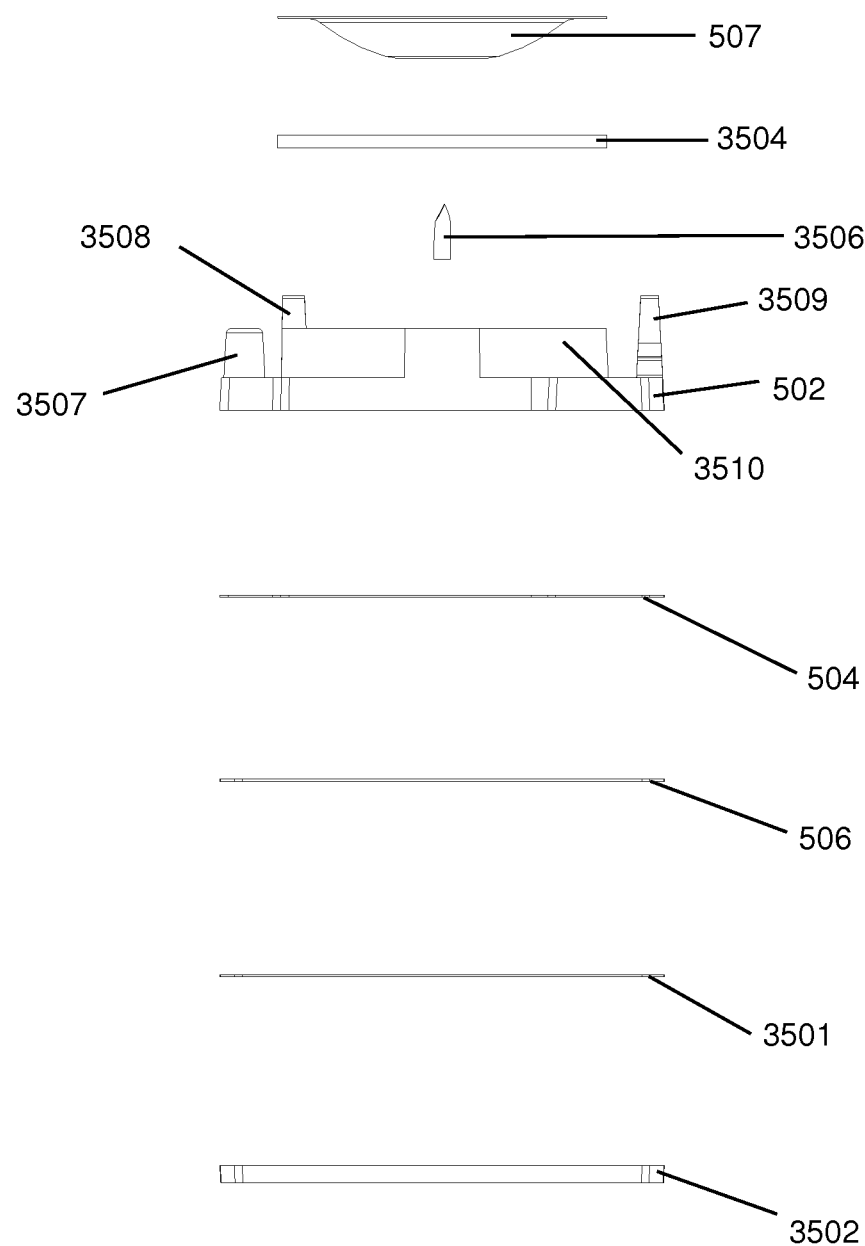
FIG. 33 shows a rear view of the components of an assay device.
Figure 34:
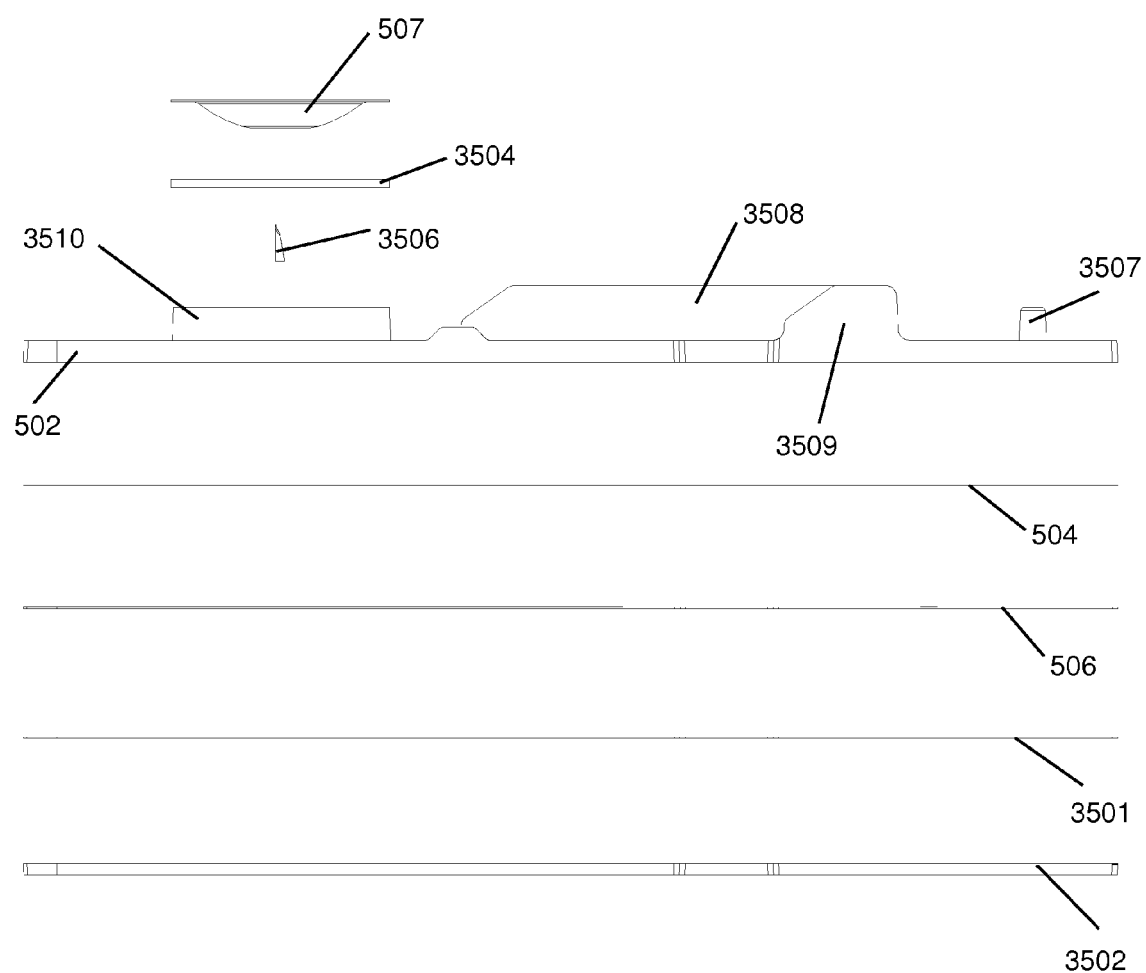
FIG. 34 shows an alternate side view of the components of an assay device.

Referring to FIG. 31, the first substrate layer 502 is shaped to provide a pin 3507 and raised fins 3508 and 3509. Fins 3508 and 3509 provide for positioning and locking of the device 500 in meter 400 (as will be described below).

Figure 35:
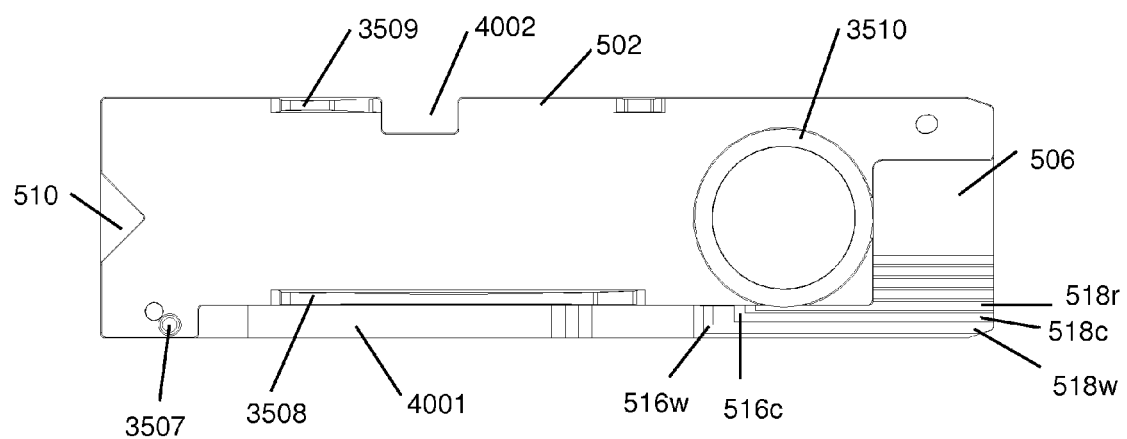
FIG. 35 shows a plan view of an assay device above.
Figure 36:
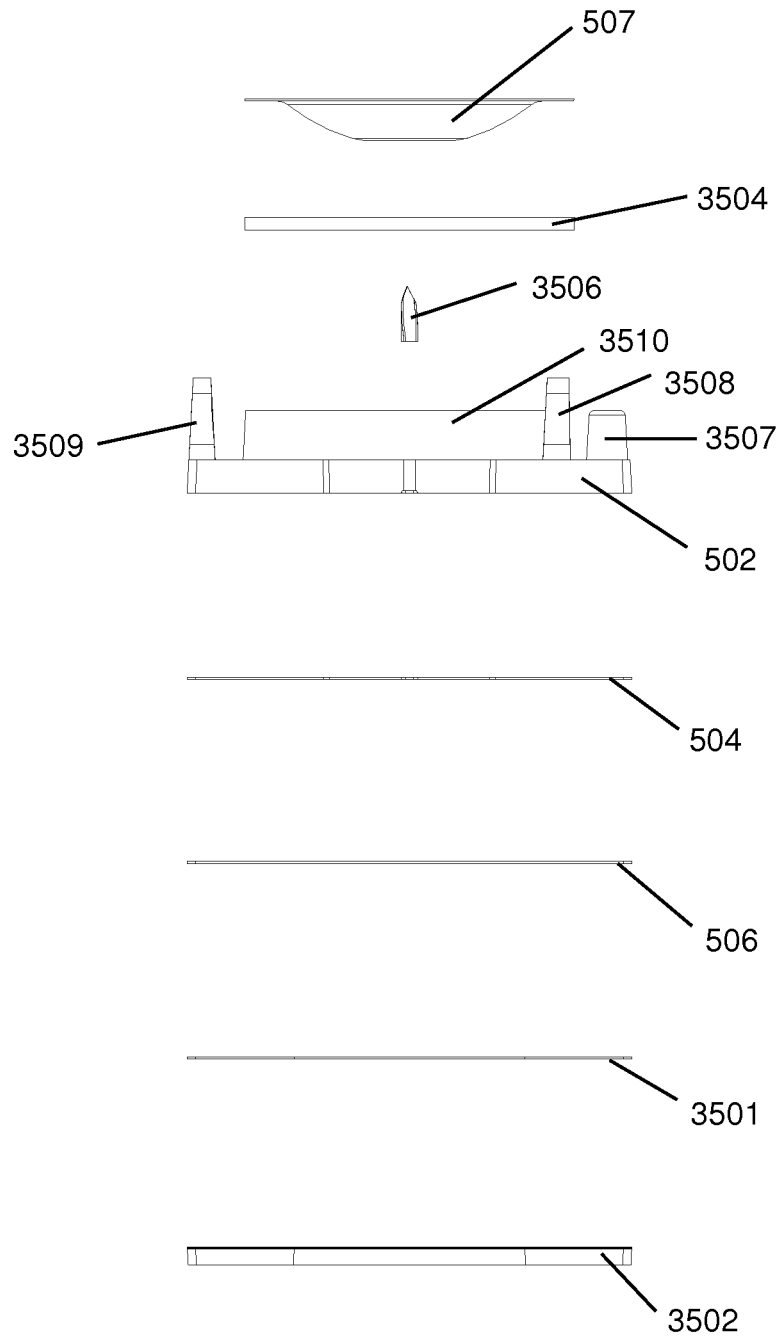
FIG. 36 shows a front view of the components of an assay device.
Figure 37:
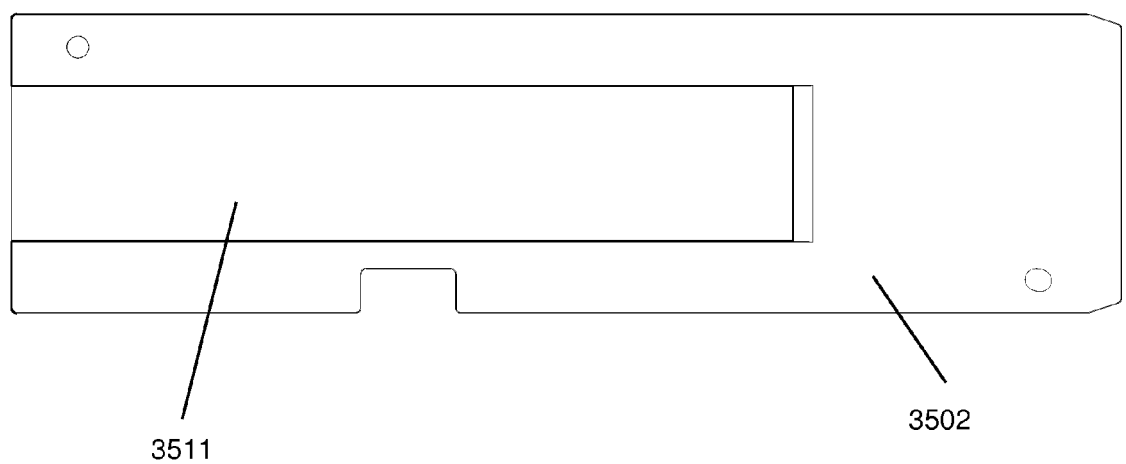
FIG. 37 shows a plan view of an assay device from underneath.

Referring to FIG. 35, a plan view of the first substrate layer 502 forming an upper main side of the device 500 is illustrated showing the raised annulus 3510, raised fins 3508, 3509 and locating pin 3507. The first substrate layer 502 is shaped to expose terminals 518$w$, 518$c$, 518$r$ at one short end of the device. Exposure of these terminals provides for their interaction with corresponding electrical contacts in the meter 400. The third substrate layer 506 is also exposed beyond the first substrate layer 502 at inlet 510. Inlet 510 is formed by a triangular cut-out portion in the first substrate layer 502. The third substrate layer 506 does not have a corresponding cut-out portion and overlaps to form a supporting surface at inlet 510 on which a liquid sample can be deposited and from which the liquid sample can enter the first channel portion (not shown in FIG. 35). In exemplary embodiments where the assay device is for use with a blood sample, the overlapping part of the third substrate layer forming the inlet 510 can be coated in an anti-coagulant reagent, e.g. heparin, to prevent or reduce coagulation of the blood sample at the inlet 510.

One of the long sides 4001 of the device can be marked (e.g. by printing) with a code (e.g. a bar code) to be read by a corresponding sensor (e.g. a photosensor, bar code reader) in meter 400. This code can carry information describing the device, which can include one or more of: the device batch number; types and amounts of reagents contained in the device; assay type; calibration characteristics. This information can be read by the meter 400 and used to assess the detected signal to produce an assay result which can be displayed to the user.

Referring to FIG. 35, the substrate layers can further be configured to form cut-out portions in one or more sides of the device configured to engage with the meter 400, e.g. with locking member 2902 in the meter 400.

Figure 38A:
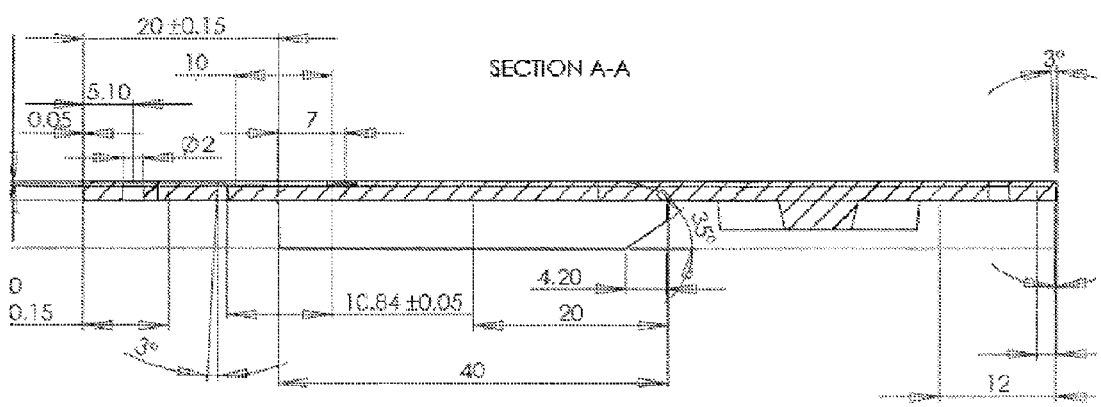
FIG. 38A shows a cross-section through line A-A of FIG. 38C.
Figure 38B:
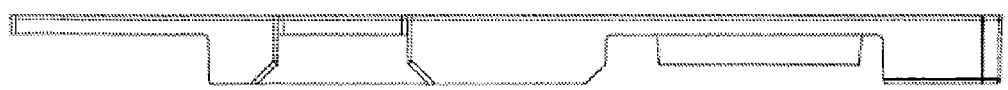
FIG. 38B shows a side view of an assay device.
Figure 38C:
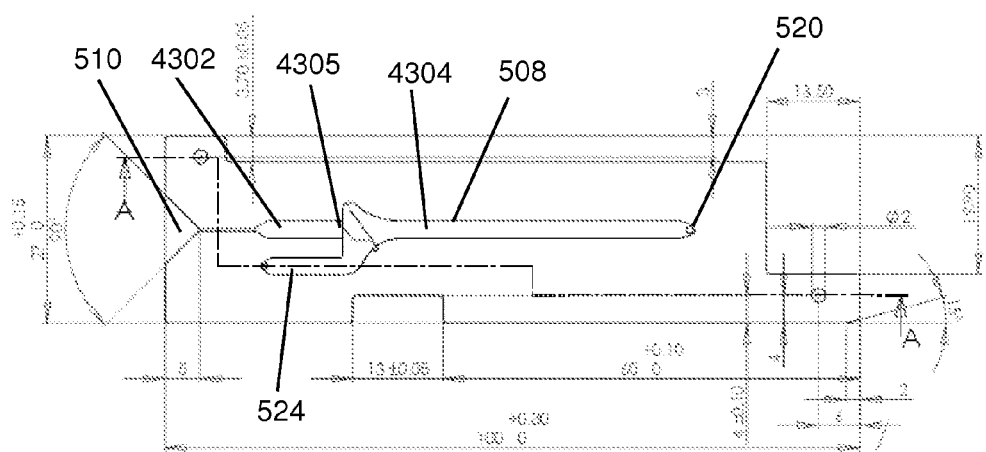
FIG. 38C shows a plan view of an assay device from above.
Figure 38D:
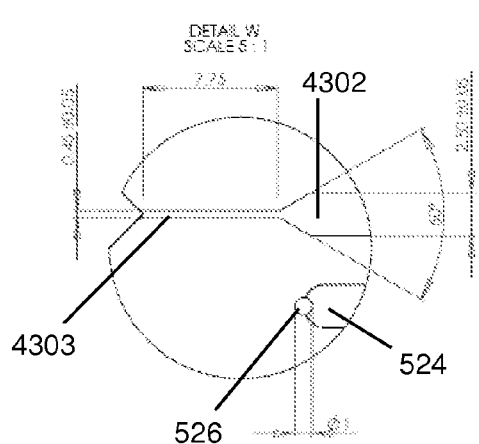
FIG. 38D shows the inlet channel and first channel portion.

Referring to FIG. 38I, the device has an inlet 510 at one end of the strip, the inlet 510 is connected to the channel network 508 such that sample liquid received at the inlet can enter the channel network. The channel network 508 has a first channel portion 4302 forming a reagent zone 512. In an exemplary embodiment the first channel portion 4302 is connected directly to the inlet 510. In other exemplary embodiments, an inlet channel 4303 connects the inlet 510 and first channel portion 4302.

The inlet channel 4303 has a smaller cross-sectional area than the first channel portion 4302 owing to a smaller width and/or height of the inlet channel 4303. The inlet channel has a width w3 and length d1 (as described above). The inlet channel can be configured to facilitate draw through of liquid sample from inlet 510 into first channel portion 4302, e.g. by capillary action. The inlet channel 4303 facilitates complete filling of the first channel portion 4303, e.g. when a low volume of liquid sample is deposited at inlet 510.

The first channel portion 4302 is connected to a second channel portion 4304 at a junction 4305. In an exemplary embodiment the plane of the junction is substantially orthogonal to the main longitudinal axis of the second channel portion. The first and second channel portions can have a common longitudinal axis.

The inlet channel 4303 can have an amount of coagulant deposited in the channel, or coating one or more of the channel walls. The coagulant does not react with an introduced blood sample immediately allowing through flow of blood into the first channel portion 4302 but reacts with stationary blood in the inlet channel 4303 after a period of time (e.g. at least about 5 seconds, at least about 10 seconds, at least about 20 seconds, at least about 30 seconds, at least about 1 minute) to coagulate blood in the inlet channel 4303, but not affecting substantially all of the blood in the first channel portion 4302. The coagulated blood in the inlet channel 4303 serves to resist any back-pressure that may be applied to the blood sample at junction 4305, e.g. when being contacted by the second liquid during formation of the blood:liquid interface, which may act to push blood from the first channel portion 4302 back towards inlet 510.

The first channel portion 4302 is generally rectangular in cross-section, although it may have a different cross-sectional shape, e.g. circular. At the junction 4305 the first channel portion 4302 has a cross-sectional area $A^1$ which is less than the cross-sectional area $A^2$ of the second channel portion 4304 at the junction 4305. The difference in cross-sectional area of the first and second channel portions at the junction 4305 provides a capillary stop 530, as described above. A liquid sample deposited at inlet 510 flows into first channel portion 4302 (e.g. by capillary action) and on reaching the capillary stop 530 the liquid sample meniscus forms a liquid sample:air interface with air contained in the second channel portion. The interface is positioned proximal the junction 4305.

The capillary stop is formed by the difference in capillary pressure between the first and second channel portions at the junction 4305. This difference can be provided by a change in channel dimensions. In this exemplary embodiment, the height of the first channel portion h1 is increased at the junction to height h2 of the second channel portion, and the width w2 of the first channel portion is increased to width w5 of the second channel portion at the junction.

Cross-sectional area $A^1$ is at least about 0.375 mm$^2$ (e.g. at least about 0.1 mm$^2$, at least about 0.2 mm$^2$, at least about 0.3 mm$^2$, less than about 0.4 mm$^2$, less than about 0.6 mm$^2$, less than about 0.8 mm$^2$, less than about 1.0 mm$^2$) and $A^2$ is about 4.67 mm$^2$ (e.g. at least about 4 mm$^2$, at least about 3.5 mm$^2$, at least about 3 mm$^2$, at least about 2 mm$^2$, less than about 6 mm$^2$, less than about 5 mm$^2$, less than about 4.5 mm$^2$) The ratio of $A^1$:$A^2$ is about 1:12 (e.g. at least about 1:2, at least about 1:3, at least about 1:4, at least about 1:5, at least about 1:7, at least about 1:9, at least about 1:10, at least about 1:12, at least about 1:15, at least about 1:20). The liquid sample:gas and/or liquid sample:liquid interface will have a cross-sectional area $A^3$ that is substantially the same as area $A^1$ but may be slightly smaller or slightly larger, e.g. $A^3$ can be chosen from one of at least about 0.1 mm$^2$, at least about 0.2 mm$^2$, at least about 0.3 mm$^2$, less than about 0.4 mm$^2$, less than about 0.6 mm$^2$, less than about 0.8 mm$^2$, less than about 1.0 mm$^2$.

A capillary stop can also be provided at, or adjacent, the junction 4305 by providing the second channel portion 4304 at the junction 4305 with an increase in height only, or width only, as compared to the first channel portion which also provides an increase in cross-sectional area at the junction 4305 when moving from the first channel portion to the second channel portion.

The ratio of w2:w5 is about 1:4 (e.g. at least about 1:2, at least about 1:3, at least about 1:5, less than about 1:6). The ratio h1:h2 is about 1:3 (e.g. at least about 1:2, at least about 1:4, at least about 1:5, less than about 1:6).

Figures 45, 46:
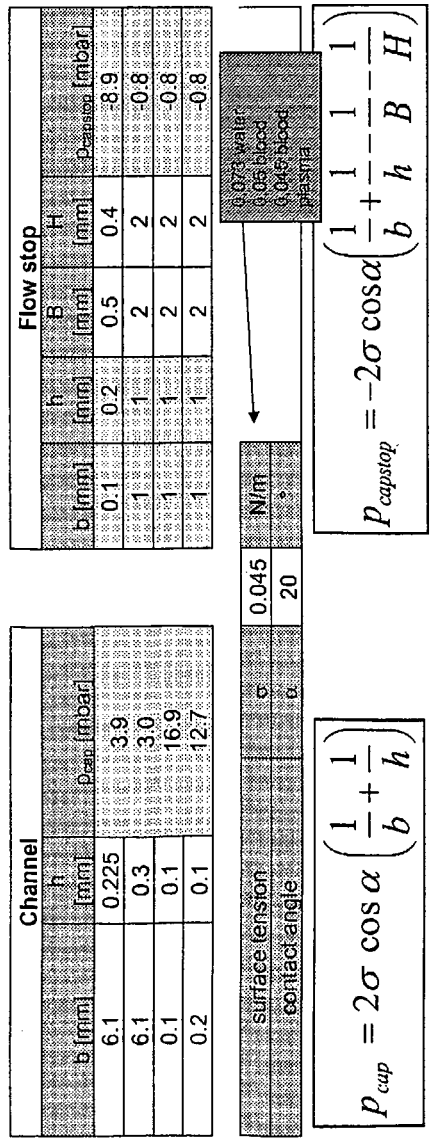
FIG. 45 and FIG. 46 are Tables illustrating calculation of capillary pressure and capillary stop pressure.

Referring to FIGS. 45 and 46, for a channel of rectangular cross-section and having height h (mm) and width b (mm) capillary pressure $p_{cap}$ (mbar) is calculated by the equation:

$$p_{cap} = 2\sigma\cos\alpha\left(\frac{1}{b} + \frac{1}{h}\right) \qquad \text{Equation 3}$$

A capillary stop can be achieved by introducing a change in channel dimensions. Referring to FIG. 46, the "flow stop" calculation indicates the capillary stop pressure $P_{capstop}$ (mbar) when a channel of first height and width is changed to become a channel of second height and width, and is calculated by the equation:

$$p_{capstop} = -2\sigma\cos\alpha\left(\frac{1}{b} + \frac{1}{h} - \frac{1}{B} - \frac{1}{H}\right) \qquad \text{Equation 4}$$

where σ=surface tension (N/m) and α=contact angle (deg.).

Referring to FIG. 46, a ratio of first channel height h to second channel height H (where H>h), h:H, of about 1:2 to about 1:3 (e.g. about 1:1.7, about 1:1.8, about 1:1.9, about 1:2, about 1:2.5, about 1:3, about 1:4) is sufficient to achieve capillary stop at the junction of the channels. Similarly a ratio of first channel width b to second channel width B (where B>b), b:B, of about 1:2 to about 1:3 (e.g. about 1:1.7, about 1:1.8, about 1:1.9, about 1:2, about 1:2.5, about 1:3, about 1:4) is sufficient to achieve capillary stop at the junction of the channels. Capillary stop can be achieved by increasing both channel height and width at the junction of the channels, i.e. increasing the cross-sectional area from $A^1$ in the first channel to $A^2$ in the second channel (i.e. $A^1<A^2$). A ratio of $A^1$:$A^2$ sufficient to achieve a capillary stop at the junction of the channels is at least about 1:2 (e.g. about 1:2, about 1:2.5, about 1:3, about 1:4, at least about to 1:3, at least about 1:4, at least about 1:5).

In other exemplary embodiments, the capillary stop is provided by a hydrophobic patch or hydrophobic ring applied to the first channel part proximal to the junction, as described above.

The first channel portion 4302 has a generally rectangular cross-section and has a width w2. The first channel portion has a length l2 and height h1. The first channel portion has a volume of about 5 μl (e.g. at least about 1 μl, at least about 2 μl, at least about 3 μl, at least about 4 μl, less than about 20 μl, less than about 15 μl, less than about 10 μl, about 10 μl, about 20 μl).

The ratio of the cross-sectional area of the liquid sample: liquid interface (mm²), or the junction 4305 (mm²), to the volume of the first channel portion (µl), is about 1:13 (e.g. at least about 1:1, at least about 1:3, at least about 1:5, at least about 1:7, at least about 1:9, at least about 1:11, less than about 1:19, less than about 1:17, less than about 1:15).

The first channel portion 4302 can be an "open" channel, i.e. the channel is bounded by walls defining a central channel space which can contain reagents and is otherwise open for fluid flow throughout such that the volume of liquid in the first channel portion when full of liquid is substantially the same as the volume space defined by the width, height and length of the first channel portion 4302 (taking account of its cross-sectional shape—e.g. rectangular or circular).

Figure 42:
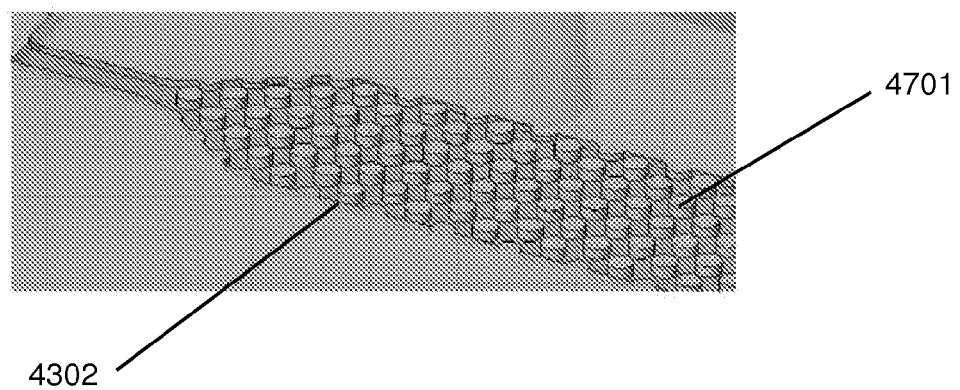
FIG. 42 shows columns formed in a first channel portion.

Referring to FIG. 42, in one exemplary embodiment the first channel portion can be partially obstructed by multiple columns 4701 formed in the first channel portion 4302. The columns 4701 can be formed from the first substrate material 502, e.g. by laser ablation or molding parts of the substrate to form a first channel portion 4302 having a liquid flow path connecting the inlet 510 and junction 4305 whilst retaining intact substrate column parts within the first channel portion 4302. The obstructions can be in the form of walls or columns and can extend the full height or width of the first channel portion 4302, or can extend a partial height or width of the first channel portion 4302, provided a liquid flow path between inlet 510 and junction 4305 is maintained. The walls or columns can be any shape or design. Referring to FIG. 42 columns 4701 act to disrupt the flow of liquid sample entering the first channel portion 4302 and facilitate mixing of the liquid sample with reagents contained in the first channel portion 4302.

The second channel portion 4304 has a generally rectangular cross-section. Distal to the junction 4305 the second channel portion has a width w6 and a height h3, as described above. The second channel portion extends from the junction 4305 towards a liquid inlet 520 over a length (l4) of about 50 mm (e.g. at least about 20 mm, at least about 30 mm, at least about 40 mm, less than about 60 mm, less than about 70 mm, less than about 80 mm) and has a volume of about 55 µl (e.g. at least about 40 µl, at least about 45 µl, at least about 50 µl, less than about 60 µl, less than about 65 µl, less than about 70 µl).

Figure 38E:
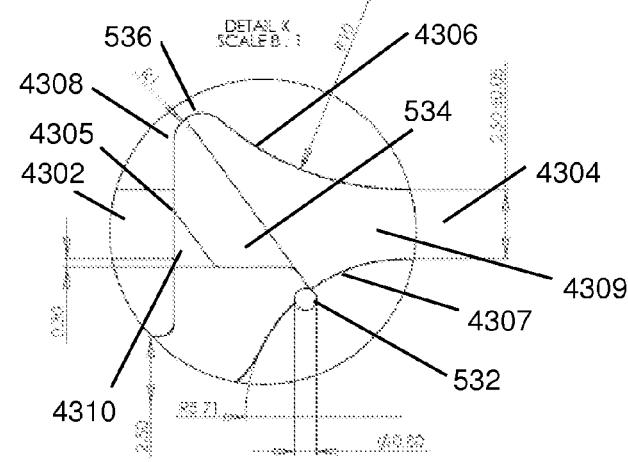
FIG. 38E shows the interface zone.
Figure 38F:
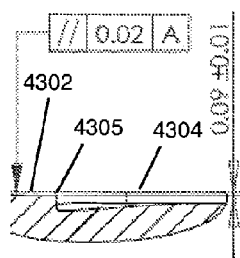
FIG. 38F shows a cross section through the interface zone.
Figure 38G:
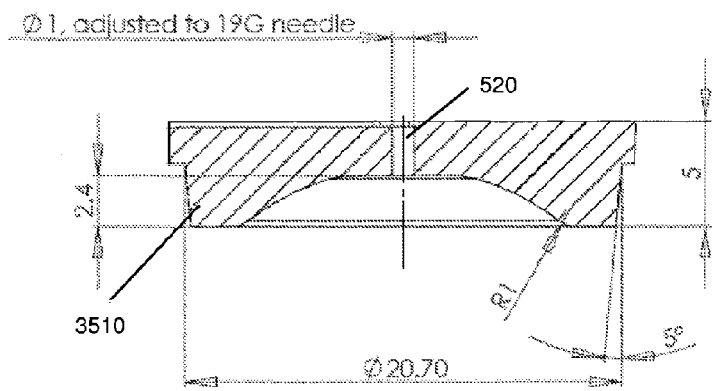
FIG. 38G shows a cross-section through the raised annulus and inlet 520.
Figure 38H:
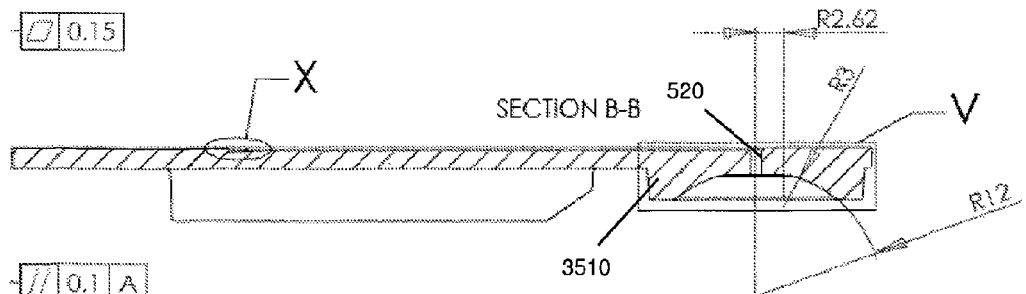
FIG. 38H shows a cross-section through the line B-B of FIG. 38I.
Figure 39:
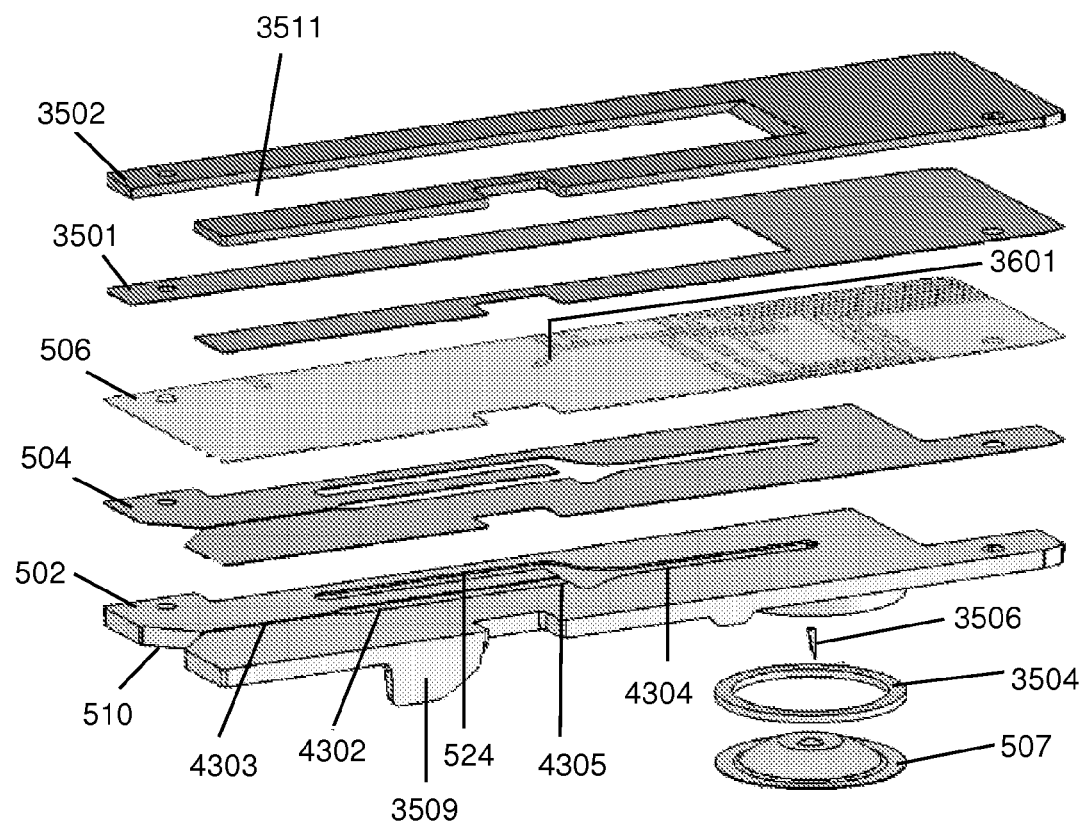
FIG. 39 shows a perspective view of the components layers of an assay device
Figure 40:
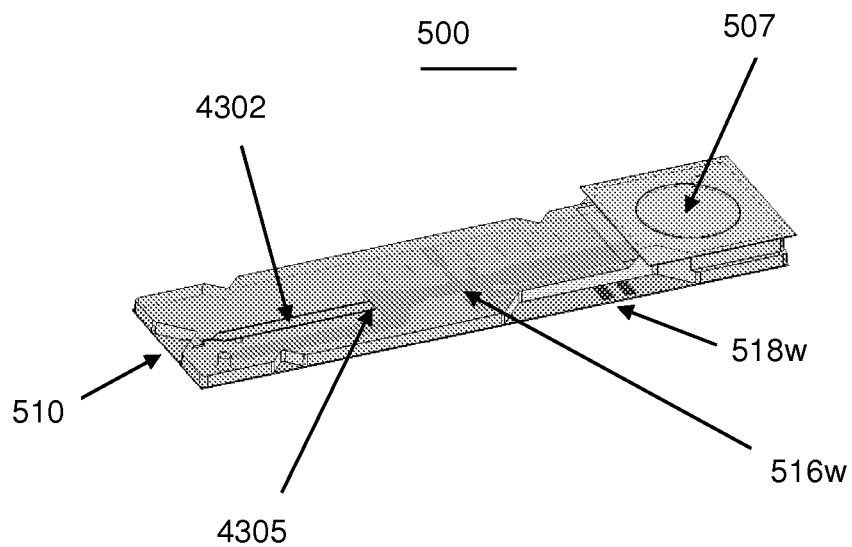
FIG. 40 shows a perspective view of the assay device of FIG. 5.

Referring to FIG. 38E, adjacent the junction 4305, the second channel portion has a tapered neck region 4306 in which the width and height of the second channel portion 4304 increases when moving along the second channel portion from the liquid inlet 520 towards the junction 4305. The tapered neck region 4306 provides an increase in the width of the second channel portion from width w6 distal to junction 4305 to width w5 at the junction 4305 and an increase in the height of the second channel portion from height h3 distal to the junction 4305 to height h2 at the junction 4305.

Referring to FIG. 38E, the tapered neck region 4306 of the second channel portion further comprises a bend portion in which the flow path defined by the second channel portion 4304 is changed from a direction that is substantially toward the junction 4305 to one that is substantially across the junction 4305. The bend portion is formed by an inside wall 4307 and an outside wall 4308 of the second channel portion 4304. The outside wall 4308 contains a corner 536 and the inside wall 4307 has a means 532 to retard the flow of liquid towards the junction 4305. The means 532 can be a capillary stop. The outside wall 4308 also comprises, at least partially, the junction 4305 of the first and second channel portions.

Between the corner 536 and the capillary stop 532 the base of the second channel portion has a slope or chamfer 534 which connects a region 4309 of the second channel portion 4304 that is distal to the junction 4305 and has height h3 with a region 4310 of the second channel portion 4304 that is proximal the junction 4305 and has height h2, wherein h2>h3. The slope 534 extends obliquely across the second channel portion from a region proximal the capillary stop 532 towards the opposing channel wall and corner 536. The upper edge of slope 534 extends from a region proximal the capillary stop 532 at the inside wall 4307 of the bend portion across the second channel portion 4304 slanting forwards towards the junction 4305. The upper edge of slope 534 extends from the region near the capillary stop 532 obliquely forwards towards the junction 4305 and towards a region of the second channel portion having a greater width. The lower edge of slope 534 contacting the region 4310 of second channel portion 4304 having height h2 makes an angle of about 36° (e.g. at least about 25°, at least about 30°, at least about 35°, less than about 45°, less than about 40°) with the plane of junction 4305. The oblique direction of the slope across the second channel portion towards the junction can thus also be described as an oblique slant of about 54° (e.g. at least about 65°, at least about 60°, at least about 55°, less than about 45°, less than about 50°) from a main width w2 of the second channel portion 4304, wherein the main width w2 is perpendicular to the main longitudinal axis of the second channel portion 4304 extending towards the junction 4305.

The upper edge of slope 534 (distal to junction 4305) at its most distal from the junction, and in the region of capillary stop 532, is about 4.5 mm from the wall of the second channel portion 4304 in which the junction 4305 is formed in a direction along a line parallel to the main longitudinal axis of the second channel portion. This distance d2 is about 4.5 mm (e.g. at least about 3.5 mm, at least about 4.0 mm, less than about 5.5 mm, less than about 5.0 mm) The distance between lower edge of slope 534 (proximal to junction 4305) at its most distal from the wall of the second channel portion 4302 in which the junction 4305 is formed, and in a direction along a line parallel to the main longitudinal axis of the second channel portion 4304, is called d3 and is about 1.6 mm (e.g. at least about 1.2 mm, at least about 1.4 mm, less than about 2.0 mm, less than about 1.8 mm) The shortest distance from the upper edge of slope 534 to the lower edge of slope 534 is d4, which is about 2.9 mm (e.g. at least about 2.0 mm, at least about 2.5 mm, less than about 3.0 mm, less than about 3.5 mm, less than about 4.0 mm).

The slope 534 has an angle of inclination θ (indicated on FIG. 7) of about 8° (e.g. at least about 5°, less than about 15°, less than about 25°), being the angle of inclination of the slope 534 from the base of the second channel portion 4304 adjacent the junction 4305 and having height h3.

Slope 534 and capillary stop 532 control movement of liquid through the second channel portion 4304 from liquid inlet 520 towards junction 4305. Liquid moving through the second channel portion 4304 from liquid inlet 520 towards junction 4305 has an advancing liquid meniscus forming a liquid:gas interface that is advancing towards junction 4305. Prior to reaching junction 4305 the advancing meniscus encounters capillary stop 532 which retards the movement of the advancing liquid meniscus along the inside wall 4307 of the bend portion. Capillary stop 532 thus acts to steer the liquid:gas interface around the corner in which capillary stop 532 is located, as described above. The advancing liquid:gas interface thus moves down chamfer 534 and across the face of the junction 4305 of the first and second channel portions.

When a liquid sample is contained in the first channel portion 4302 forming a liquid sample:air interface at the junction, movement of liquid through the second channel portion towards the junction 4305 and across the face of the junction 4305 acts to displace the air from the liquid sample:air interface and form an interface of the liquid sample and liquid contained in the second channel portion, e.g. buffer liquid.

The bend portion, capillary stop 532 and slope 534 act together to advance the flow of liquid in the second channel portion 4304 towards the junction 4305 initially around the outside wall 4308 of the bend portion and past corner 536, thereby directing liquid flow across the wall in which the junction 4305 is formed. This acts to displace air from the liquid sample:air interface and form the liquid sample:liquid interface with minimum retention of air bubbles at the interface. Excess liquid flowing in the second channel moves into overflow channel 524 until it reaches vent 526.

A liquid sample:liquid interface is thereby formed at the junction 4305 by flowing liquid in the second channel portion 4304 across a face of the liquid sample:air interface so as to displace the air from that interface and progressively decrease the area of the liquid sample:air interface until the air is displaced and the liquid sample:air interface is replaced by a liquid sample:liquid interface.

During flow of liquid in the second channel portion 4304 across the liquid sample:air interface, liquid sample in the first channel portion is held substantially static. Once the liquid sample:liquid interface is formed and flow of liquid in the second channel part 4304 and overflow 524 has stopped the liquid sample:liquid interface is also substantially static with no bulk movement of liquid occurring across the interface, in either direction.

In an exemplary embodiment the use of a second liquid introduced to the second channel portion of assay device 500 to form the liquid sample:liquid interface is replaced by inclusion of a flowable media in the second channel portion. On introduction of the liquid sample to the first channel portion 4302 a liquid sample:flowable media interface is formed proximal the junction 4305. Magnetic transfer of magnetically susceptible particles across the interface into the flowable media and to the working electrode is then performed as described herein with respect to the other embodiments described. In such embodiments the assay device 500 does not require integration of reservoir 507.

The flowable media can be a liquid. However, in exemplary embodiments, the flowable media is a viscous liquid or gel. For example, the gel can be a matrix or electrophoresis gel such as an agarose or polyacrylamide gel, or other crosslinked polymer. The gel should provide a continuous flowable media path between the interface and sensor (e.g. working electrode 516w) allowing for movement of magnetically susceptible particle:first binding agent:analyte complexes from the interface through the gel to the sensor. The gel can also contain substrates (e.g. ABTS and $H_2O_2$) required to detect analyte at the sensor.

The first channel portion 4302 contains reagents. The reagents include multiple magnetically susceptible particles (e.g. at least about 50, at least about 100, at least about 150 magnetically susceptible particles) and a first binding agent configured to bind an analyte. The first binding agent is configured to also bind to the magnetically susceptible particles such that complexes of analyte:first binding agent: magnetically susceptible particle can be formed when the reagents are contacted with a liquid sample containing the analyte. These complexes can be magnetically moved through the liquid sample:liquid interface.

In one exemplary embodiment the reagents include a second binding agent configured to bind the analyte at a different spatial location (epitope) on the analyte to the first binding agent. The first and second binding agents can both be bound to an analyte molecule at the same time to form a "sandwich" complex. The sandwich complex can comprise first and second binding agents bound to the analyte and magnetically susceptible particle bound to the first binding agent. These complexes can be magnetically moved through the liquid sample:liquid interface.

The first or second binding agent can be conjugated to a detectable marker. The detectable marker can be any detectable label, e.g. enzyme label, fluorescent marker, radiolabel. An enzyme label can provide or cause a detectable signal, e.g. an electrochemical signal—oxidation or reduction at an electrode—following interaction with a substrate of the enzyme. A fluorescent marker can provide an optical signal—fluorescence—which can be detected by an optical sensor or scintillation counter. A radiolabel can provide an electromagnetic signal which can be detected by a sensor that can detect the electromagnetic radiation.

In an exemplary embodiment, the second binding agent is conjugated to an enzyme label, e.g. horse radish peroxidise. Second binding agent:enzyme label conjugates are further absorbed onto a colloidal sol particle, e.g. colloidal gold sol particles. The colloidal sol particles can have a diameter of about 20 nm or about 40 nm.

The magnetically susceptible particles and first binding agent are modified to incorporate complementary linkers, e.g. one of biotin and streptavidin, in order to provide conjugates of the magnetically susceptible particles and first binding agent. The magnetically susceptible particles and first binding agent can be deposited in the first channel portion in pre-conjugated form, or can be deposited separately such that the conjugates form on mixing of the reagents in the liquid sample.

Figure 41:
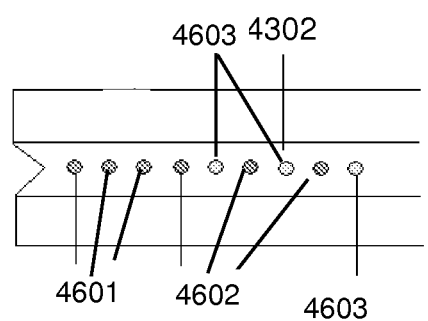
FIG. 41 shows the arrangement of dry reagent deposits in a first channel portion.

FIG. 41 illustrates an exemplary embodiment of deposited reagents in the first channel portion 4302. The reagent deposits include first reagent deposits 4601, second reagent deposits 4602, and third reagent deposits 4603. The reagents are dry deposited, as described above. The individual reagent deposits are spaced apart. In an exemplary embodiment the first reagent deposits 4601 are streptavidin coated magnetically susceptible particles; the second reagent deposits 4602 are colloidal gol sol:second binding agent: enzyme label conjugates; and the third reagent deposits 4603 are biotinylated first binding agent.

First channel portion 4302 has multiple separate reagent deposits and in an exemplary embodiment the reagents are deposited in a predetermined order, e.g. with first reagents deposited nearest the inlet 510 and second and third reagents deposited towards the junction 4305. The first and/or second and/or third reagent deposits can be made in alternate sequence. Additional fourth and fifth reagents can be deposited.

In an exemplary embodiment the first and second binding agents are molecules capable of specifically binding to a selected target with high affinity, having a $K_d$ for the target of about 100 μM or less (e.g. less than about 50 μM, less than about 10 μM, less than about 1 μM, less than about 100 nM, less than about 10 nM, less than about 1 nM, less than about 100 pM, less than about 10 pM). The first and second binding agents can be respectively chosen from an antibody (monoclonal or polyclonal), antibody fragment (e.g. scFV fragment), antibody binding domain or aptamer. The first and second binding agents can be different, e.g. an antibody and an aptamer.

In an exemplary embodiment, the analyte for detection in a blood sample contained in the first channel portion is NT-proBNP (e.g. human NT-proBNP). The first and second binding agents are anti-NT-proBNP antibodies that bind different epitopes on NT-proBNP. The first binding agent is:
    a monoclonal mouse anti-human NT-proBNP antibody 15C4 (HyTest Ltd., Intelligate 6th floor, Joukahaisenkatu 6, 20520, Turku Finland; Catalogue #:4NT1)

and the second binding agent is chosen from:
    monoclonal mouse anti-human NT-proBNP antibody 15F11 (HyTest Ltd., Intelligate 6th floor, Joukahaisenkatu 6, 20520, Turku Finland; Catalogue #:4NT1);
    monoclonal mouse anti-human NT-proBNP antibody 29D12 (HyTest Ltd., Intelligate 6th floor, Joukahaisenkatu 6, 20520, Turku Finland; Catalogue #:4NT1).

The first binding agent can be biotinylated to facilitate conjugation to streptavidin coated magnetically susceptible particles. The second binding agents can be conjugated to horse radish peroxidise and 20 nm or 40 nm diameter colloidal gold sol particles.

Other antibodies to NT-proBNP are publicly available, e.g. those available from HyTest Ltd., Intelligate 6th floor, Joukahaisenkatu 6, 20520, Turku Finland, e.g. monoclonal mouse anti-human NT-proBNP antibodies 5B6, 7B5, 13G12, 11D1, 16E6, 15D7, 24E11, 28F8, 18H5, 16F3 (Catalogue #:4NT1).

Figure 30:
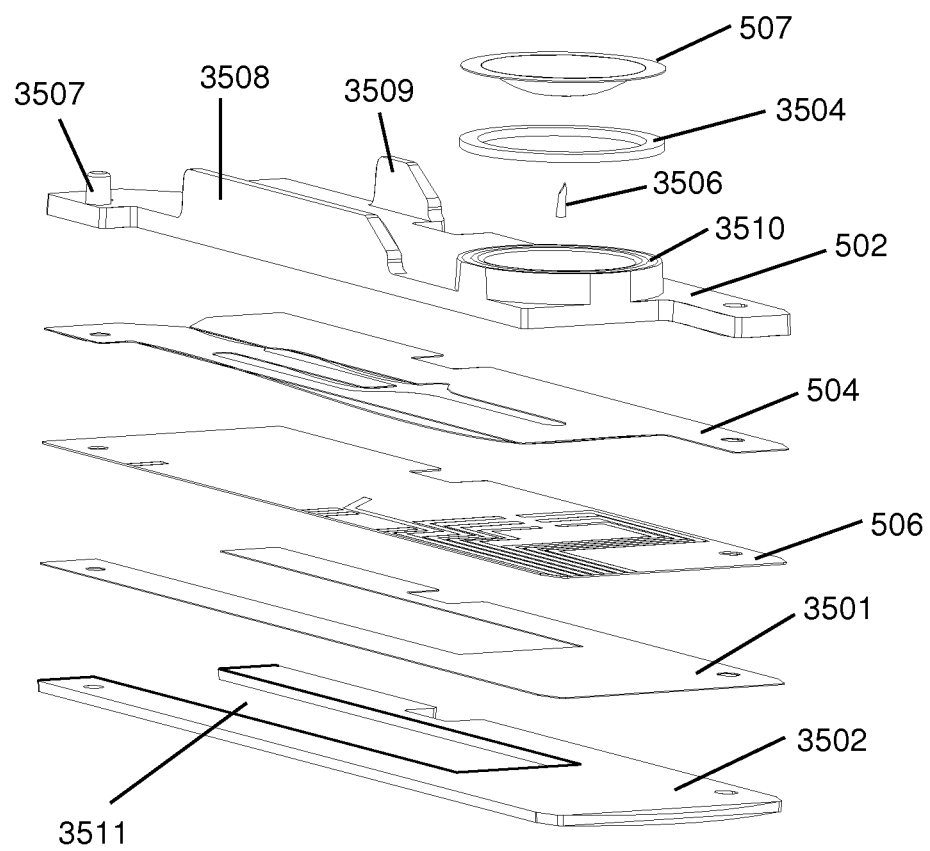
FIG. 30 shows a perspective side view of the components of an assay device.

Referring to FIGS. 30 and 31 the third substrate layer 506 has sensors in the form of electrodes 3601, 516w, 516c, 516r configured to contact liquid in the second channel portion 4304. The electrodes are formed by a conductive network defining a series of one or more electrodes and terminals, as described above. The conductive network can include one or more independent conductive traces that connect an electrode that is intended to make contact with a fluid in microfluidic network 508 with a detector and/or processor in meter 400. An electrode might be used to measure a substance or parameter of interest within a sample applied to assay device 500.

The conductive network includes electrodes 516w, 516c and 516r, as described above, connected to terminals 518w, 518c, 518r. The conductive network further includes electrode 3601 positioned in the device in the overflow channel 524. In use, electrode 3601 can detect the flow of liquid into the overflow, contact of liquid with the electrode producing a detectable electrical signal that is communicated with the meter 400 via terminal 3602. This signal provides an indicator of formation of the liquid sample:liquid interface and can be used to prevent further application of pressure to the actuator 408 via the actuator mechanism in meter 400, thereby preventing further agitation of the liquid in the second channel portion 4304 once the liquid sample:liquid interface has been formed. Electrode 3601 can be a silver/silver chloride (Ag/AgCl) electrode.

In exemplary embodiments the meter can, therefore, detect if the liquid sample:liquid interface has been formed. If electrode 3601 is not wetted the meter can display an error message and instruct the user to test again. The same principle of electrode wetting can be used to check for filling of the second channel portion. Thus, in some exemplary embodiments the meter 400 can monitor rupture of the buffer pouch 507 via wetting of one or more of electrodes 516w, 516c, 516r. If wetting is not detected the meter can display an error message and ask the user to test again. Electrode wetting can be detected by a potentiometric measurement.

In some exemplary embodiments electrodes 516w, 516c, 516r can also be used to check for arrival of magnetically susceptible particles at the working electrode and trigger the start of measurement of the electrochemical signal. For example, a potentiometeric measurement at the working electrode 516w can be used to demonstrate that magnetically susceptible particles have arrived at the working electrode 516w. Meter 400 can start the measurement before the movement of the magnetically susceptible particles across the interface to establish a baseline measurement and detect a change from the baseline when the magnetically susceptible particles arrive. For example, if no voltage change is measured when the magnet 2803 arrives at the working electrode 516w the magnetically susceptible particles have failed to transfer across the interface or subsequently reach the working electrode 516w and the meter can display an error message. The same voltage change can also be used to inform the meter when to start the measurement, e.g. after an incubation time of about 1 minute after the voltage change is detected (e.g. at least about 5 seconds, at least about 10 seconds, at least about 20 seconds, at least about 30 seconds, at least about 40 seconds, at least about 50 seconds, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, less than about 11 minutes, less than about 12 minutes, less than about 13 minutes, less than about 14 minutes, less than about 15 minutes). The voltage trace may also be used to indicate if the particles are on the working electrode 516w or have gone past the working electrode 516w.

Referring to FIG. 31, the conductive network can include traces 3603, which form electrodes (e.g. a pair of electrodes) positioned in the first channel portion 4302. These electrodes can detect electrical conduction or an electrochemical signal in the first channel portion. Where the liquid sample is a blood sample they may be used to determine the hematocrit of the blood sample. The detected hematocrit can be used to correct for and/or normalize the determination made by the assay device 500 and meter 400 to produce an assay result.

Electrodes 516w, 516c and 516r form an electrode set that can detect an electrochemical signal in the second liquid. The signal can be an electrochemical change. In an exemplary embodiment the electrochemical change is oxidation or reduction of a substrate by an enzyme. The enzyme can be an enzyme label conjugated to a binding agent wherein the enzyme label is part of a magnetically susceptible particle:analyte:enzyme label complex. The enzyme substrate can be present in the liquid contained in the second channel portion.

In an exemplary embodiment in the electrode set 516w, 516c, 516r positioned in the second channel portion 4304 the working electrode 516w is positioned closest the junction 4305 at a distance of at least about 15 mm to the centre line of the electrode from the junction (e.g. at least about 1.5 mm, at least about 3 mm, at least about 5 mm, at least about 7 mm, at least about 10 mm, at least about 13 mm, less than about 20 mm, less than about 25 mm) Electrode 516w has a width of about 1.6 mm (e.g. at least about 1.0 mm, at least about 1.3 mm, less than about 2.0 mm, less than about 1.8 mm) Between the working electrode and reference electrode 516r is a counter electrode 516c. The working and counter electrodes are made from carbon paste and the reference electrode from silver paste. The reference electrode is an Ag/AgCl reference electrode and is about 1 mm wide (e.g. at least about 0.6 mm, at least about 0.8 mm, less than about 1.4 mm, less than about 1.2 mm) and about 22.5 mm to the centre line of the electrode from the junction 4305 (e.g. at least about 15 mm, at least about 18 mm, less than about 26 mm, less than about 30 mm).

In one exemplary embodiment the enzyme label is horse radish peroxidase and the liquid in the second channel portion 4304 is a reaction buffer containing sodium acetate buffer, hydrogen peroxide substrate, and the redox mediator 2,2'-azino-bis-(3-ethylbenzo-thiazoline-sulfonic acid) (ABTS), as described above. In one exemplary embodiment the buffer liquid is 10 mM ABTS, 10 mM $H_2O_2$, 150 mM KCl, 125 mM sodium acetate; 0.1% v/v Tween-20™, made to a final pH 4.2.

In other embodiments where detection of analyte in the second channel portion is other than by electrochemical detection—e.g. detection of fluorescence or colour—the sensor may comprise a region of the second channel portion at which a signal, e.g. fluorescence or colour, can be detected. In such embodiments the sensor can comprise a transparent portion of the device permitting interaction with a detector, e.g. a photodetector or scintillation counter, in meter 400.

The device can have one or more "on-board controls" to serve as checkpoints for the proper operation of the device. For example, a first on-board control can be the use of one of the electrodes 516w, 516c, 516r to detect flow of liquid from the liquid inlet 520 towards the junction 4305. Flow of liquid through the second channel portion 4304 will form a conductive bridge between two of the electrodes 516w, 516c, 516r. By operating meter 400 during liquid flow through the second channel portion 4304 towards the junction 4305 to detect current flow through two electrodes, e.g. the working and counter electrodes 516w and 516r, the meter can detect progress of the liquid towards the junction 4305. Referring to FIG. 50A, a second on-board control can be the use of an electrode or electrode pair 3601 positioned in overflow channel 524 to detect flow of liquid into the overflow channel and provide an indication of liquid sample: liquid interface formation at junction 4305 (as described above).

Further on-board controls can act as controls for the assay being performed. For example, because substrates or reagents can decompose or lose activity over time, one may wish to test for activity of these substrates or reagents, e.g. of a substrate contained in liquid introduced into the second channel portion 4304. In one exemplary arrangement the enzyme label can be horse radish peroxidase, which catalyses conversion of hydrogen peroxide and ABTS to water and oxidised-ABTS. Hydrogen peroxide and ABTS are provided in the buffer liquid introduced to the second channel portion 4304. Referring to FIG. 50B, the presence and/or activity of the hydrogen peroxide and ABTS can be verified by immobilizing a pre-determined quantity of the horse radish peroxidase enzyme label 5501 at electrode(s) 3601 in the overflow channel 524. Active buffer liquid components reaching the overflow will be catalysed and produce oxidized ABTS and an electrochemical signal that can be detected by electrode(s) 3601. Detection of a signal is indicative of active buffer components and serves to verify the validity of the determination made at working electrode 516w. Referring to FIG. 50C, in an alternative arrangement the immobilized horse radish peroxidase can be substituted for an immobilized complex of magnetically susceptible particle:first binding agent:analyte:second binding agent, wherein the horse radish peroxidase is conjugated to the second binding agent. Such an arrangement may more accurately reflect the form of ternary complex formed at the working electrode 516w and provide an improved control.

Figure 49A:
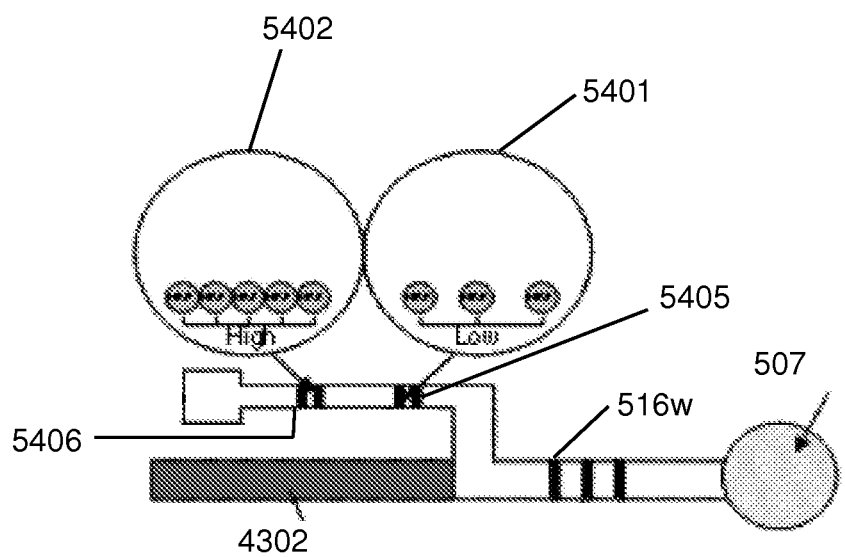
FIGS. 49A-B show on-board control configurations.
Figure 49B:
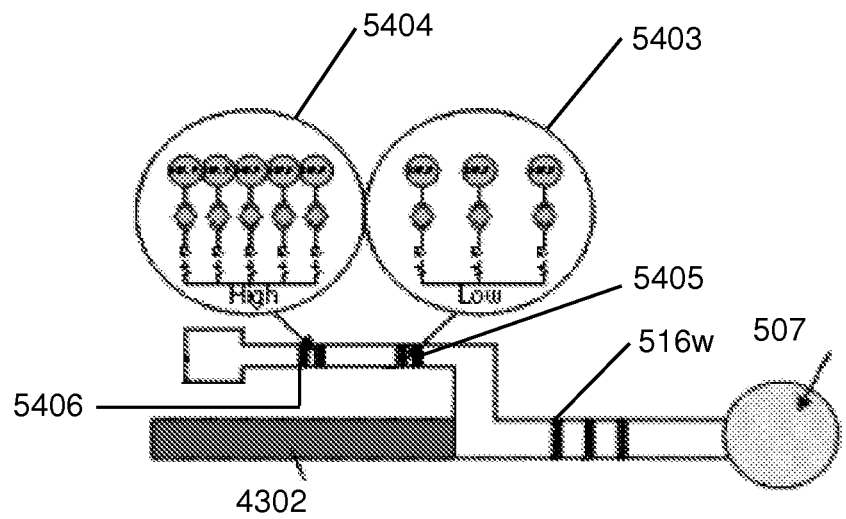
Figure 51:
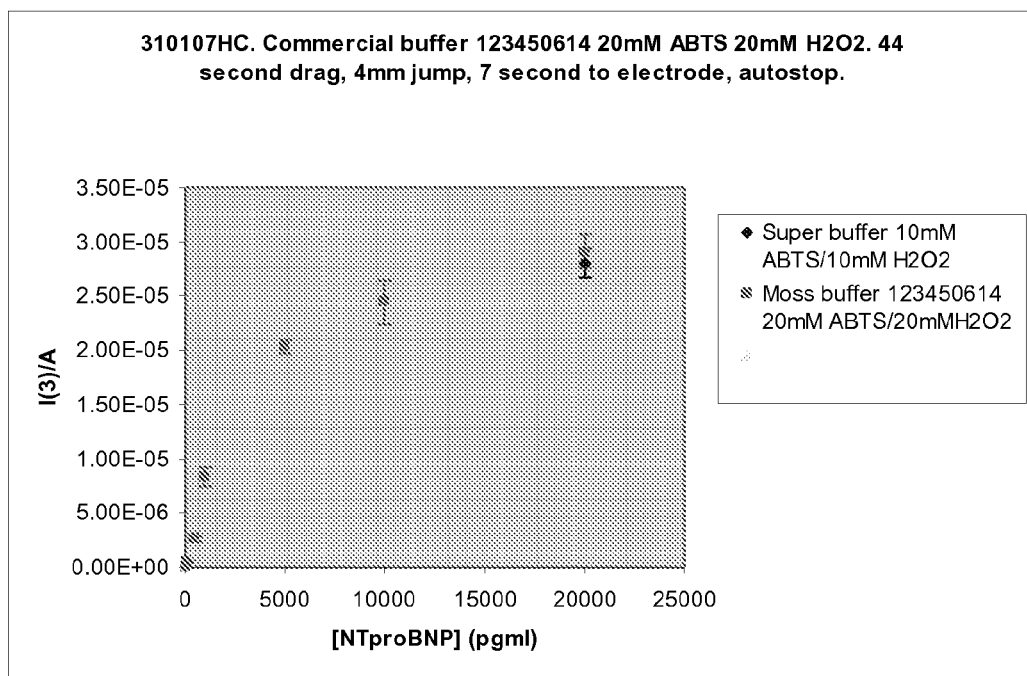
FIG. 51 shows a typical dose response curve for NT-proBNP (concentrations) 0-20,000 pg/ml.

Variations of the controls illustrated in FIGS. 50B and 50C are illustrated in FIGS. 49A and 49B respectively. Referring to FIG. 49A, first and second electrodes (or pairs of electrodes) 5405, 5406 are provided in the overflow channel 524. A predetermined amount of horse radish peroxidase is immobilized 5401 at the first electrode pair 5405 and will produce a first electrochemical signal $R_1$ when buffer liquid containing hydrogen peroxide and ABTS is present. A second predetermined amount of horse radish peroxidase is immobilized 5402 at electrode pair 5406, wherein the second amount is larger than the first amount at electrode 5401. The second amount of horse radish peroxidase will produce an electrochemical signal $R_2$ when buffer liquid containing hydrogen peroxide and ABTS is present, where $R_2 > R_1$. $R_2$ and $R_1$ can be configured to provide high and low control electrochemical signals, with respect to the selected assay and provide verification of the operable range of the assay. Referring to FIG. 49B, in an alternative arrangement the immobilized horse radish peroxidase can be substituted for an immobilized complex of magnetically susceptible particle:first binding agent:analyte:second binding agent, wherein the horse radish peroxidase is conjugated to the second binding agent. Such an arrangement may more accurately reflect the form of ternary complex formed at the working electrode 516w and provide an improved control.

Inadequate transfer of magnetically susceptible particles across the liquid sample:liquid interface ("bead loss") is a possible source of a low signal detected at the working electrode 516w. Referring to FIG. 50D, in one exemplary embodiment a control for this problem is provided by including a quantity of enzyme label substrate (e.g. hydrogen peroxide and ABTS, when the enzyme label is horse radish peroxidase) and control electrodes 5502 in the first channel portion 4302. Detection of an electrochemical signal at control electrodes 5502 indicates that ternary complexes of magnetically susceptible particle:first binding agent:analyte:second binding agent:horse radish peroxidase have been formed.

In some exemplary embodiments the assay can be performed such that one or more of the electrodes is positioned on an upper surface of the channel network 508, i.e. the electrode is uppermost in the channel with respect to the prevailing local gravitation field which acts to draw particles away from the electrode. Such an embodiment can assist in preventing reagents or other particles collecting on the electrode which may reduce the ability of the electrode to detect an electrochemical signal. One or more (or all) of the electrodes in the assay device 500 could be configured in this way. For example, in some embodiments one or more electrodes are positioned in the first channel portion 4302 for determination of hematocrit in a blood sample contained in the first channel portion 4302. Red blood cells in the blood sample may collect on a lower surface of the first channel portion 4302 and, therefore, could collect on electrodes positioned on that lower surface for determination of hematocrit. In one exemplary embodiment these electrodes are positioned on an upper surface, e.g. the ceiling, of the first channel portion 4302.

In general, the assay device can be made by depositing reagents on a base and sealing a lid over the base. The base can be a micro-molded platform or a laminate platform.

Micro-Molded Platform

For an assay device prepared for optical detection, the base, the lid, or both base and lid can be transparent to a desired wavelength of light. Typically both base and lid are transparent to visible wavelengths of light, e.g., 400-700 nm. The base and lid can be transparent to near UV and near IR wavelengths, for example, to provide a range of wavelengths that can be used for detection, such as 200 nm to 1000 nm, or 300 nm to 900 nm.

For an assay device that will use electrochemical detection, electrodes are deposited on a surface of the base. The electrodes can be deposited by screen printing on the base with a carbon or silver ink, followed by an insulation ink; by evaporation or sputtering of a conductive material (such as, for example, gold, silver or aluminum) on the base, followed by laser ablation; or evaporation or sputtering of a conductive material (such as, for example, gold, silver or aluminum) on the base, followed by photolithographic masking and a wet or dry etch.

An electrode can be formed on the lid in one of two ways. A rigid lid can be prepared with one or more through holes, mounted to a vacuum base, and screen-printing used to deposit carbon or silver ink. Drawing a vacuum on the underside of the rigid lid while screen printing draws the conductive ink into the through holes, creating electrical contact between the topside and underside of the lid, and sealing the hole to ensure that no liquid can leak out.

Alternatively, the lid can be manufactured without any through holes and placed, inverted, on a screen-printing platform, where carbon or silver ink is printed. Once the electrodes have been prepared, the micro-molded bases are loaded and registered to a known location for reagent deposition. Deposition of reagents can be accomplished by dispensing or aspirating from a nozzle, using an electromagnetic valve and servo- or stepper-driven syringe. These methods can deposit droplets or lines of reagents in a contact or non-contact mode. Other methods for depositing reagents include pad printing, screen printing, piezoelectric print head (e.g., ink-jet printing), or depositing from a pouch which is compressed to release reagent (a "cake icer"). Deposition can preferably be performed in a humidity- and temperature-controlled environment. Different reagents can be dispensed at the same or at a different station. Fluorescent or colored additives can optionally be added to the reagents to allow detection of cross contamination or overspill of the reagents outside the desired deposition zone. Product performance can be impaired by cross-contamination. Deposition zones can be in close proximity or a distance apart. The fluorescent or colored additives are selected so as not to interfere with the operation of the assay device, particularly with detection of the analyte.

After deposition, the reagents are dried. Drying can be achieved by ambient air-drying, infrared drying, infrared drying assisted by forced air, ultraviolet light drying, forced warm, controlled relative humidity drying, or a combination of these. Micro-molded bases can then be lidded by bonding a flexible or rigid lid on top. Registration of the base and lid occurs before the two are bonded together. The base and lid can be bonded by heat sealing (using a heat activated adhesive previously applied to lid or base, by ultrasonic welding to join two similar materials, by laser welding (mask or line laser to join two similar materials), by cyanoacrylate adhesive, by epoxy adhesive previously applied to the lid or base, or by a pressure sensitive adhesive previously applied to the lid or base. After lidding, some or all of the assembled assay devices can be inspected for critical dimensions, to ensure that the assay device will perform as designed. Inspection can include visual inspection, laser inspection, contact measurement, or a combination of these.

The assay device can include a buffer pouch. The buffer pouch can be a molded well having a bottom and a top opening. The lower opening can be sealed with a rupturable foil or plastic, and the well filled with buffer. A stronger foil or laminate is then sealed over the top opening. Alternatively, a preformed blister pouch filled with buffer is placed in and bonded in the well. The blister pouch can include 50 to 200 µL of buffer and is formed, filled, and sealed using standard blister methods. The blister material can be foil or plastic. The blister can be bonded to the well with pressure sensitive adhesive or a cyanoacrylate adhesive.

Laminate Platform

Three or more laminates, fed on a roll form at a specified width, can be used to construct an assay device. The base laminate is a plastic material and is coated on one surface with a hydrophilic material. This laminate is fed into a printing station for deposition of conductive electrodes and insulation inks. The base laminate is registered (cross web) and the conductive electrodes deposited on the hydrophilic surface, by the techniques described previously. The base laminate is then fed to a deposition station and one or more reagents applied to the laminate. Registration, both cross web and down web, occurs before reagents are deposited by the methods described above. The reagents are dried following deposition by the methods described above. A middle laminate is fed in roll form at a specified width. There can be more than one middle laminate in an assay device. The term middle serves to indicate that it is not a base laminate or lid laminate. A middle laminate can be a plastic spacer with either a pressure sensitive adhesive or a heat seal adhesive on either face of the laminate. A pressure sensitive adhesive is provided with a protective liner on either side to protect the adhesive. Variations in the thickness of the middle laminate and its adhesives are less than 15%, or less than 10%.

Channels and features are cut into the middle laminate using a laser source (e.g., a $CO_2$ laser, a YAG laser, an excimer laser, or other). Channels and features can be cut all the way through the thickness of the middle laminate, or the features and channels can be ablated to a controlled depth from one face of the laminate. The middle and base laminates are registered in both the cross web and down web directions, and bonded together. If a pressure sensitive adhesive is used, the lower liner is removed from the middle laminate and pressure is applied to bond the base to the middle laminate. If a heat seal adhesive is used, the base and middle laminate are bonded using heat and pressure.

The top laminate, which forms the lid of the assay device, is fed in roll form at a specified width. The top laminate can be a plastic material. Features can be cut into the top laminate using a laser source as described above. The top laminate is registered (cross web and down web) to the base and middle laminates, and bonded by pressure lamination or by heat and pressure lamination, depending on the adhesive used. After the laminate is registered in cross and down web directions, discrete assay devices or test strips are cut from the laminate using a high powered laser (such as, for example, a $CO_2$ laser, a YAG laser, an excimer laser, or other).

Some, or all, of the assembled assay devices can be inspected for critical dimensions, to ensure that the assay device will perform as designed. Inspection can include visual inspection, laser inspection, contact measurement, or a combination of these.

An example of one application that employs the use of assays to detect analytes is the analysis of physiological fluid samples, such as blood samples. In particular, it has become increasingly common to analyse blood samples for analytes that may be indicative of disease or illness. Such analyses can be performed using an assay that directly or indirectly detects an analyte.

Interaction of Assay Device and Meter

Figure 2:
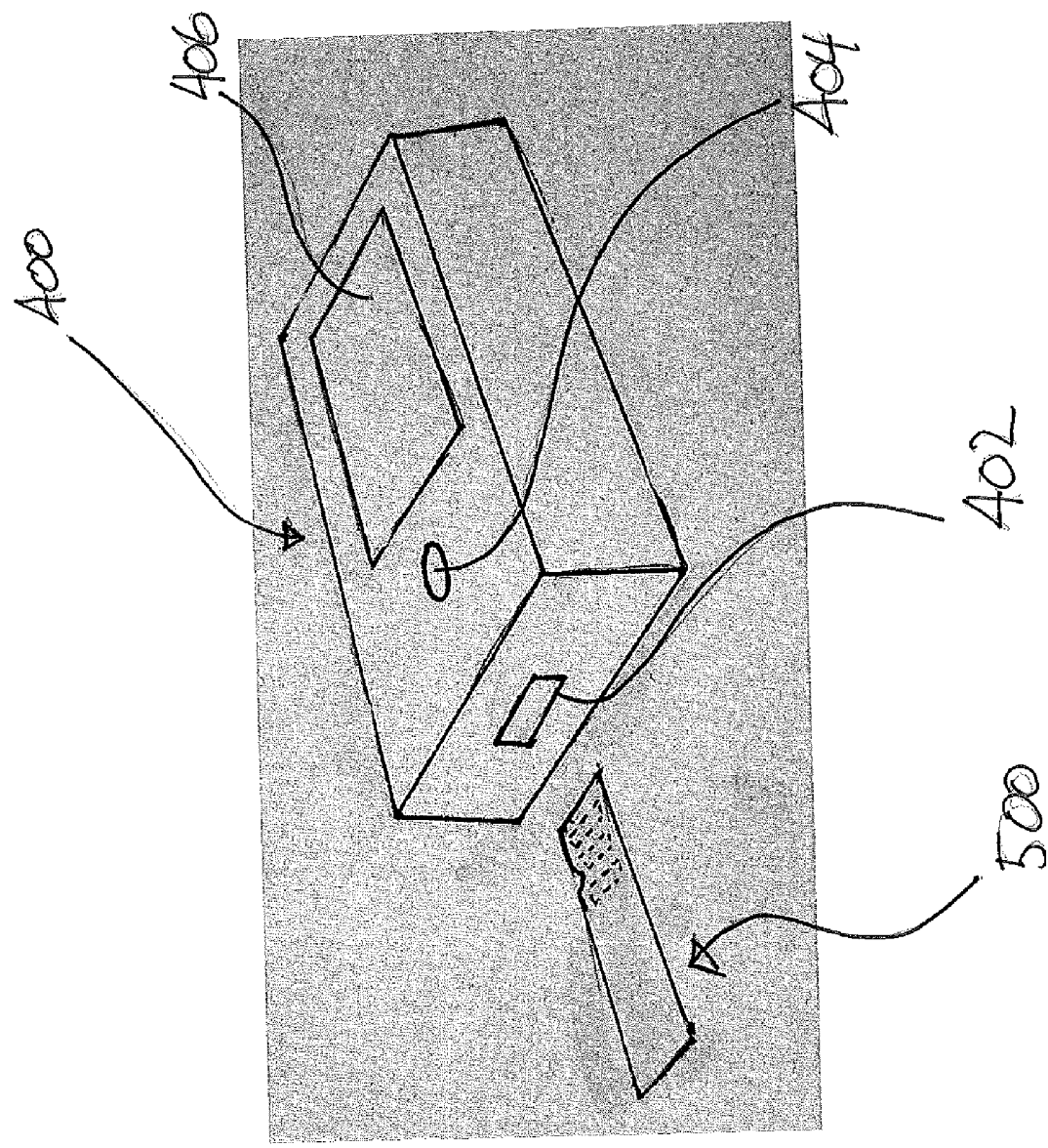
FIG. 2 is perspective view of an assay device and meter suitable for performing the assay method.
Figure 19:
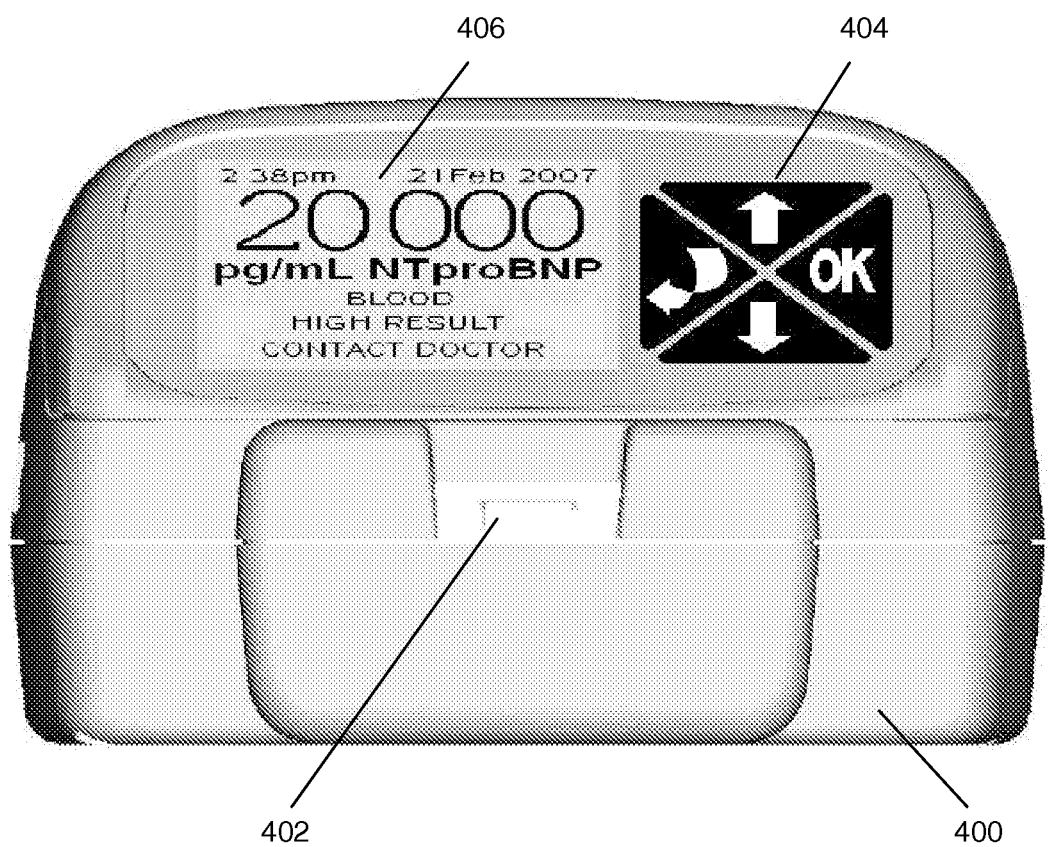
FIG. 19 is a front view of a meter.
Figure 20:
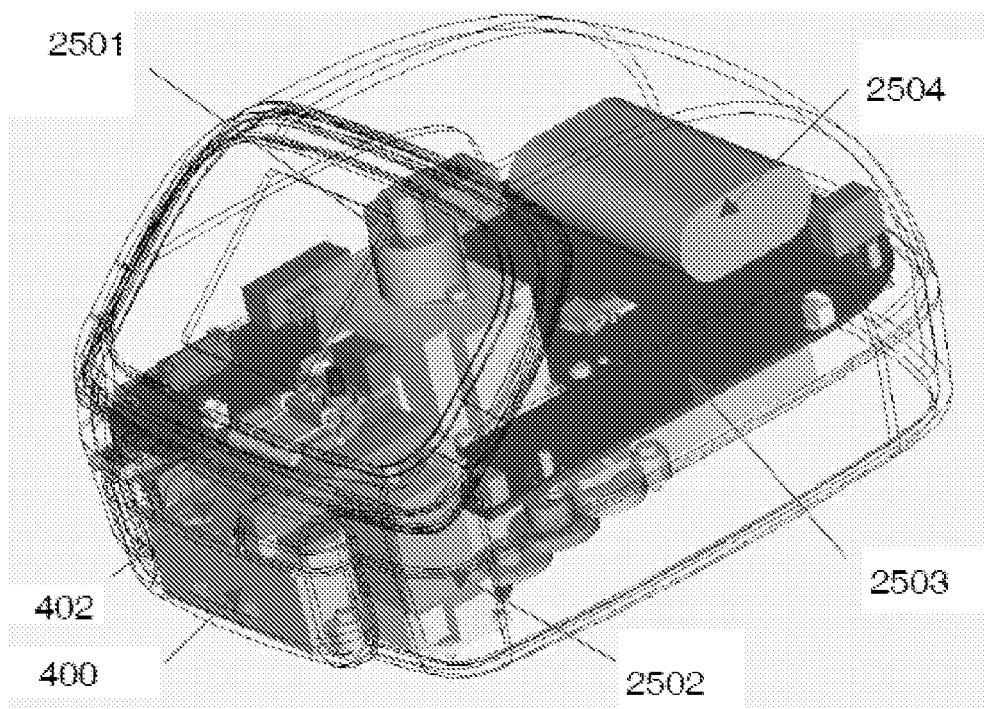
FIG. 20 shows the positioning of the meter internal mechanism.

Referring to FIGS. 2 and 19-20, meter 400 accepts test assay device 500 and includes display 406. The display 406 may be used to display images in various formats, for example, text, joint photographic experts group (JPEG) format, tagged image file format (TIFF), graphics interchange format (GIF), or bitmap. Display 406 can also be used to display text messages, help messages, instructions, queries, test results, and various information to patients. Display 406 can provide a user with an input region 404. Input region 404 can include keys. In one embodiment, input region 404 can be implemented as symbols displayed on the display 406, for example when display 406 is a touch-sensitive screen. User instructions and queries are presented to the user on display 406. The user can respond to the queries via the input region.

Meter 400 also includes an assay device reader, which accepts diagnostic test assay devices 500 for reading. The assay device reader can measure the level of an analyte based on, for example, the magnitude of an optical change, an electrical change, or other detectable change that occurs on a test assay device 500. For reading assay devices that produce an optical change in response to analyte, the assay device reader can include optical systems for measuring the detectable change, for example, a light source, filter, and photon detector, e.g., a photodiode, photomultiplier, or Avalance photo diode. For reading assay devices that produce an electrical change in response to analyte, the assay device reader can include electrical systems for measuring the detectable change, including, for example, a voltameter or amperometer.

Meter 400 further can include a communication port (not pictured). The communication port can be, for example, a connection to a telephone line or computer network. Meter 400 can communicate the results of a measurement to an output device, remote computer, or to a health care provider from a remote location. A patient, health care provider, or other user can use meter 400 for testing and recording the levels of various analytes, such as, for example, a biomarker, a metabolite, or a drug of abuse.

Various implementations of diagnostic meter 400 may access programs and/or data stored on a storage medium (e.g., a hard disk drive (HDD), flash memory, video cassette recorder (VCR) tape or digital video disc (DVD); compact disc (CD); or floppy disk). Additionally, various implementations may access programs and/or data accessed stored on another computer system through a communication medium including a direct cable connection, a computer network, a wireless network, a satellite network, or the like.

Meter 400 may include hardware and software access to a remote computer network, e.g. WAN, and permit integration with a remote computer host, proxy or server. Access may be wireless access, and may be via the internet. The meter may include Bluetooth® compatible hardware and software to facilitate wireless access.

The software controlling the meter can be in the form of a software application running on any processing device, such as, a general-purpose computing device, a personal digital assistant (PDA), a special-purpose computing device, a laptop computer, a handheld computer, or a network appliance. The meter may be implemented using a hardware configuration including a processor, one or more input devices, one or more output devices, a computer-readable medium, and a computer memory device. The processor may be implemented using any computer processing device, such as, a general-purpose microprocessor or an application specific integrated circuit (ASIC).

The processor can be integrated with input/output (I/O) devices to provide a mechanism to receive sensor data and/or input data and to provide a mechanism to display or otherwise output queries and results to a service technician. Input device may include, for example, one or more of the following: a mouse, a keyboard, a touch-screen display, a button, a sensor, and a counter. The display 406 may be implemented using any output technology, including a liquid crystal display (LCD), a television, a printer, and a light emitting diode (LED).

The computer-readable medium provides a mechanism for storing programs and data either on a fixed or removable medium. The computer-readable medium may be implemented using a conventional computer hard drive, or other removable medium. Finally, the system uses a computer memory device, such as a random access memory (RAM), to assist in operating the reader. Implementations of the reader can include software that directs the user in using the device, stores the results of measurements. The meter 400 can provide access to applications such as a medical records database or other systems used in the care of patients. In one example, the device connects to a medical records database via the communication port. Meter 400 may also have the ability to go online, integrating existing databases and linking other websites.

Referring to FIG. 2 meter 400 is shown along with assay device 500. Meter 400 has a port 402 that receives assay device 500. A user of meter 400 inserts an assay device 500 through port 402 prior to performing an analysis of a sample. Meter 400 has an interface 406 that is used to convey appropriate information to a user during the course of performing a measurement. When a user inserts assay device 500 into meter 400 through port 402, interface 406 presents the user with information. For example information that describes (i) how to apply a sample, (ii) the value of a measurement result, (iii) what to do if a certain measurement result is obtained, may be presented.

Meter 400 is configured to operate assay device 500 when assay device 500 has been inserted through port 402. Meter 400 includes a liquid reservoir actuator 408, a magnetic actuator, electrochemical detector, and a processor. Reservoir actuator 408 is configured to actuate reservoir 507 of device 500, as discussed with reference to FIG. 8. The magnetic actuator is configured to manipulate (e.g., move and/or position) magnetically susceptible particles within microfluidic network 508 of assay device 500. The electrochemical detector is configured to determine the presence of analyte transported to electrodes 516w, 516r, 516c by the magnetically susceptible particles. The electrochemical detector includes electrical contacts which respectively communicate with electrical contacts 518w, 518r, 518c of device 500 when received within meter 400. The processor is in operable communication with reservoir actuator 408, the magnetic actuator, electrochemical detector, electrical contacts, and interface 406. Interface 406 is configured to display information (e.g., device status and/or assay result) to a user.

In use, assay device 500 is inserted into meter 400 via port 402. A sample, e.g. a blood sample, is applied to inlet 510 of assay device 500. An amount of the sample (e.g., at least about 5 µl or 10 µl) moves into microfluidic network 508 (e.g. by capillary action). The sample interacts with reagents in reagent zone 512. Target analyte is then transported to detection zone 514 where an electrochemical signal is recorded. Target analyte interacts with electrodes 516w, 516r, 516c and a signal is detected by the electrochemical detector. The processor interprets the signal detected by the electrochemical detector and displays information to a user on interface 406.

A user of meter 400 can review the results of historical measurements by activating meter 400 using switch 404. Display 406 will display various data. For example, the date and time of measurement, the level of analyte measured, what the user had been doing prior to making the measurement, what medication the user had taken, could be stored in the meter when a user conducts a test. Thus a user of meter 400 can use the historical data to facilitate improved management of their condition.

Referring to FIG. 19 an exemplary embodiment of meter 400 having display 406 and port 402 is shown. The display 406 shows exemplary information, including an assay result in the form of information regarding the amount of analyte detected (in this example the analyte is NT-proBNP), the sample type (e.g. blood), a message to the user generated in connection with the assay result (in this example "High result, contact doctor") as well as time and date information. Switch 400 is provided as a button panel providing a control means for the user to operate the meter and optionally navigate around the display 406. The illustrated meter 400 has width ~156 mm, height ~97 mm and length ~185 mm.

Referring now to FIG. 20, the internal mechanism of meter 400 is shown to include buffer actuator 2501, port 402 configured to receive an assay device, motor 2502, a main circuit board 2503 and a rechargeable battery 2504. In operation, an assay device 500 is inserted in meter 400 and a sample is deposited at the assay device inlet 510. The meter 400 is operated to move a magnet located adjacent the underside of the assay device from a first position adjacent the reagent zone 512 of the assay device 500 to a second position adjacent the electrodes 516w, 516r, 516c in the detection zone, thereby moving magnetically susceptible particles and bound analyte from the detection zone 512 of the assay device 500 to electrodes 516w, 516r, 516c in the detection zone of the assay device where an assay signal may be detected and processed to provide an assay result for display on the meter display 406. The operation of the meter will now be described with respect to the various component parts and with reference to FIGS. 21-29.

Figures 21A, 21B:
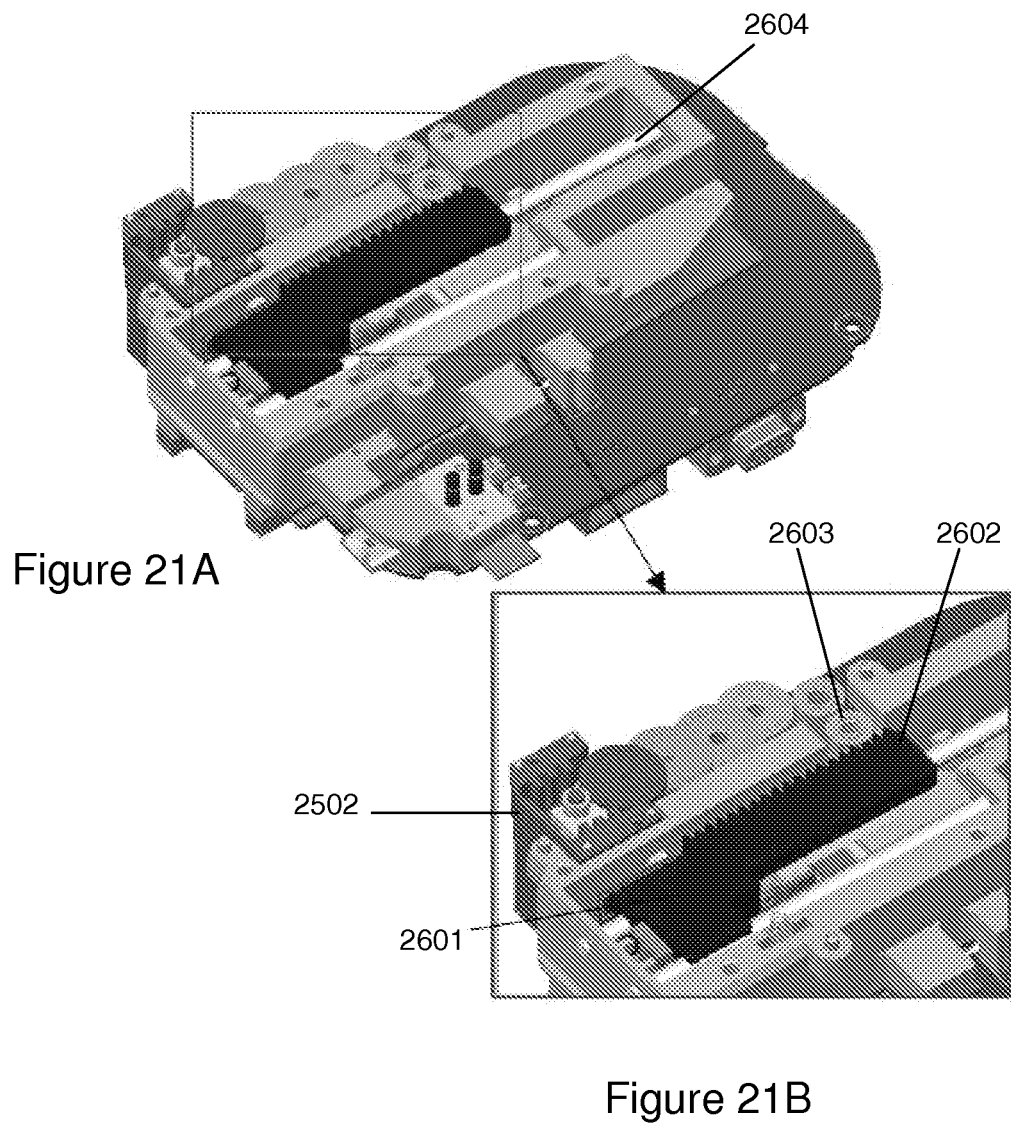
FIG. 21A shows the underside of the internal meter mechanism.

Referring to FIG. 21A, meter 400 includes a rack and pinion transmission system (shown in enlarged view from the underside in FIG. 21B) for mounting and movement of the magnet between the first and second position. Rack 2601 includes a set of teeth 2602 mechanically connected to a gear train 2603 which is mechanically connected to a stepper motor 2502. The rack 2602 is mounted on guide rods 2604 defining a path of movement between a first and second position.

Figure 22A:
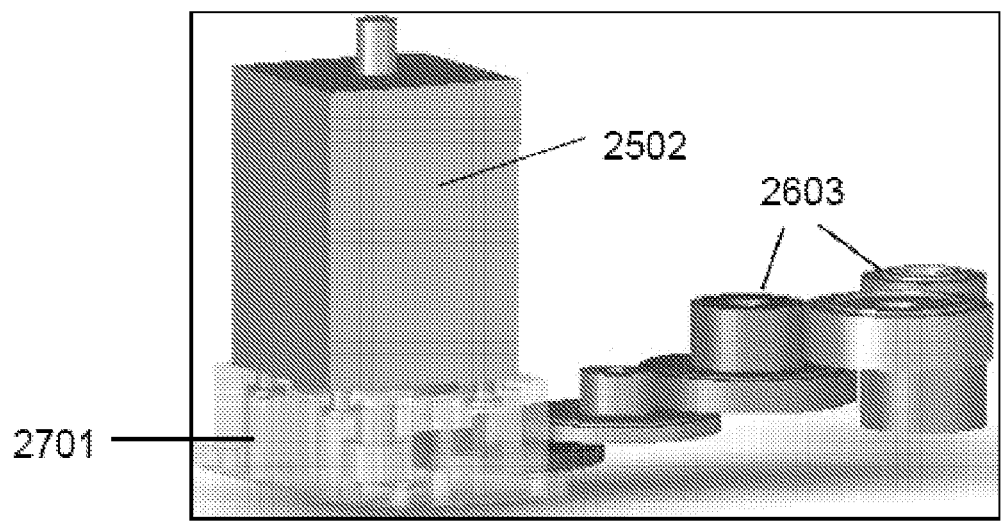
FIGS. 22A-B shows the meter configuration of motor 2502 and drive gears 2603.
Figure 22B:
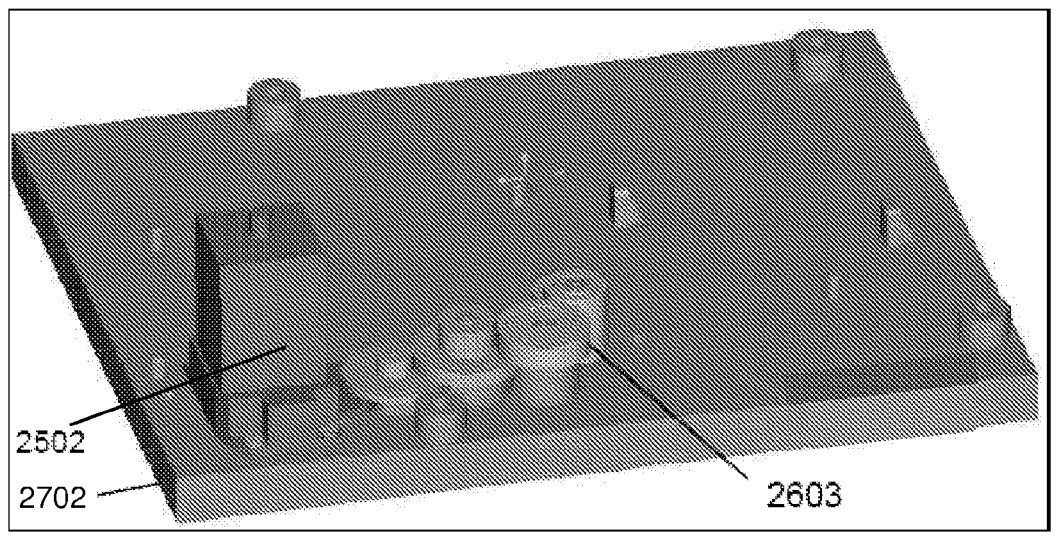

Referring to FIG. 22A, motor 2502 is mounted on bracket 2701 at which gear train 2603 is arranged to mechanically interact with the motor drive shaft. Referring to FIG. 22B, motor 2502 is mounted on base part 2702 of meter 400 by attachment to bracket 2701. Base part 2702 is further configured to mount gear train 2603 in mechanical communication with motor 2502.

Figures 23B, 23C:
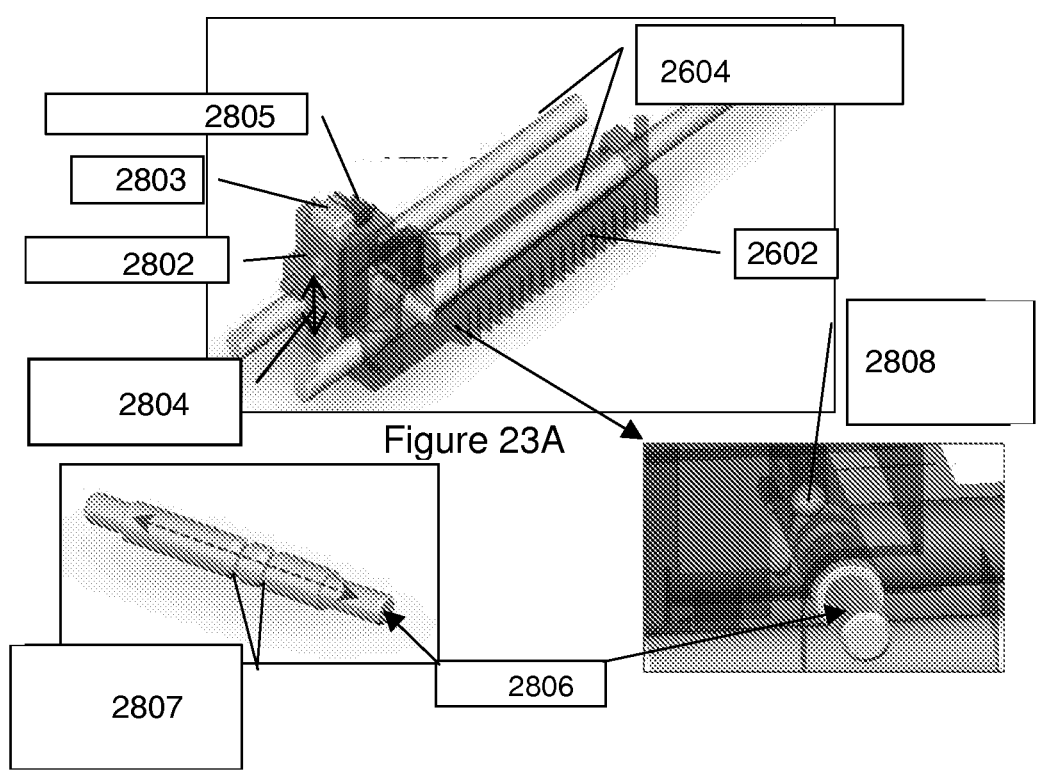
FIG. 23B shows an enlarged view of the rack 2602.
FIG. 23C shows the position of the locking bar in the magnet transmission system.

Referring to FIGS. 23A-C, rack 2602 is slideably mounted on two guide rods 2604. A carriage 2802 forms a holder at one end of rack 2602 for magnet 2803 which is positioned adjacent the underside of the base of assay device 500 (not shown) when inserted in meter 400. An optical sensor 2805 is positioned adjacent magnet 2803 in carriage 2802, the optical sensor 2805 is configured to detect sample filling of the detection zone 512 of the assay device 500. Carriage 2802 is resiliently mounted to permit vertical adjustment of the position of carriage 2802, as indicated by arrow 2804, and biasing of the magnet 2803 towards the underside of the assay device 500 in order to minimize the distance between the magnet 2803 and the underside of assay device 500 and ensure an effective magnetic field strength is directed toward the adjacent region of assay device 500. Carriage 2802 further comprises a locking bar 2806 having a main longitudinal axis orthogonal to the main longitudinal axis of guide rails 2604, the locking bar having two detents 2807 for interaction with a spring loaded ball bearing 2808 mounted in carriage 2802. Interaction of ball bearing 2808 and detents 2807 enables the locking bar to toggle between a first position and second position in which ejection of the inserted assay device is respectively prevented and permitted.

Figure 24A:
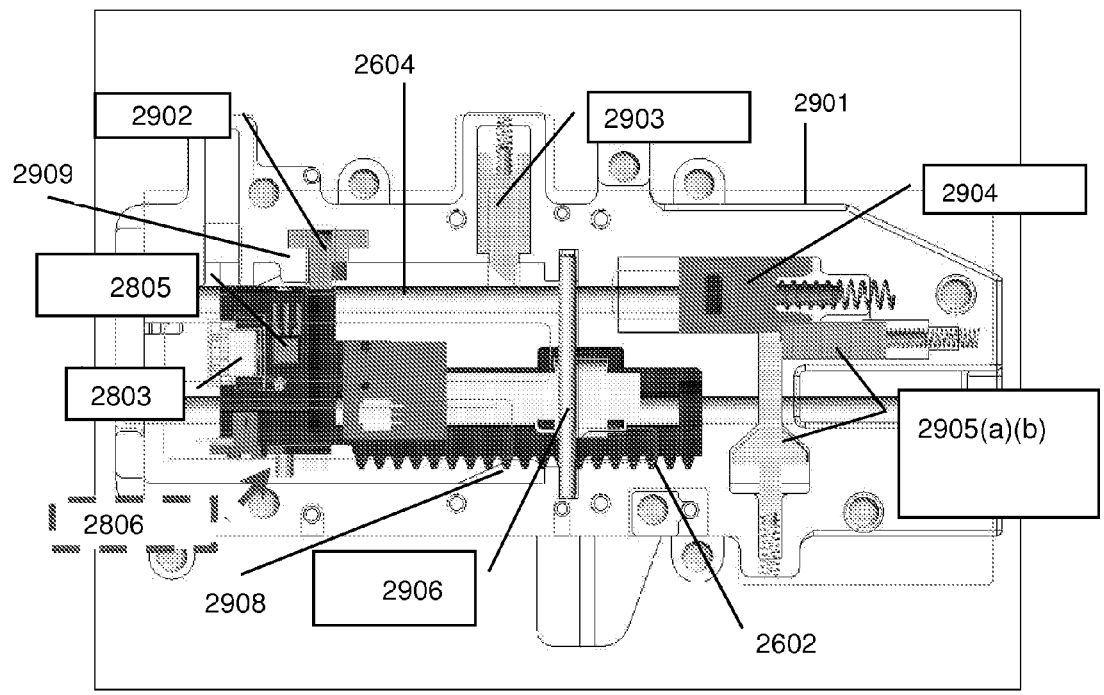
Figure 24B:
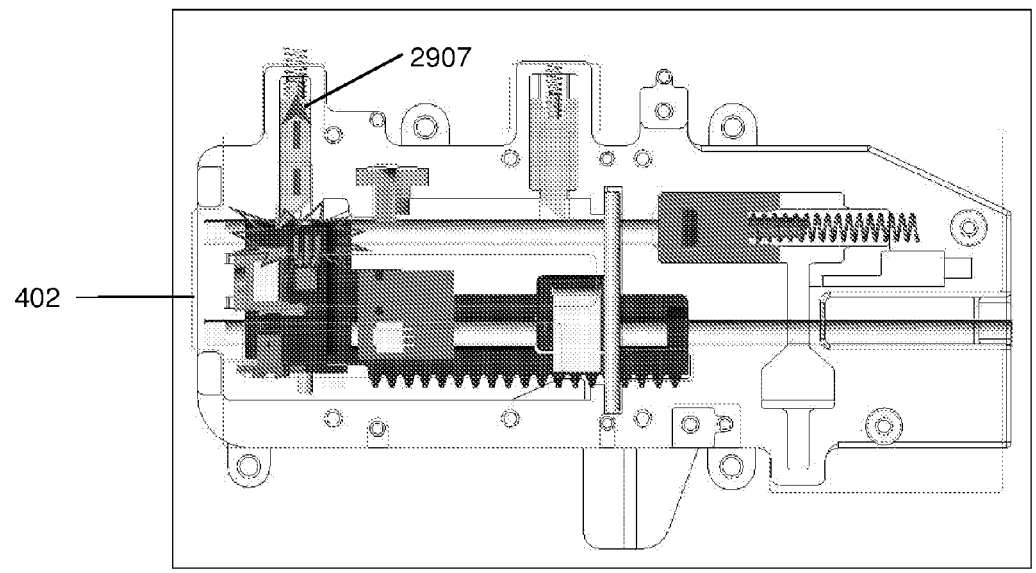

Referring to FIG. 24A, meter 400 has a main chassis 2901 on which guide rails 2604 and rack 2602 are mounted. Chassis 2901 provides ramps 2909 and 2908 for interaction with the assay device insertion and ejection mechanism. Chassis 2901 further provides recesses and mountings for a locking member 2902, resiliently mounted chamfer 2903, resiliently mounted ejector member 2904, and resiliently mounted first and second rear lock members 2905(a)(b) and 30N counter balance rod 2906. In FIG. 24A the meter 400 is in a resting configuration. Referring to FIG. 24B, chassis 2901 further provides mounting for a front lock chamfer 2907.

Insertion and ejection of an assay device 500 in meter 400 will now be described with reference to FIGS. 24B-J (in which the assay device is not shown) and FIGS. 25A-I (in which the assay device is shown in FIGS. 25A and 25G-I).

Referring to FIG. 24B, prior to insertion of assay device 500 through port 402 rear lock members 2905 are disengaged from ejector member 2904 which is thereby permitted to bias rack 2602 towards port 402 and against front lock chamfer 2907 thereby biasing the front lock chamfer 2907 away from rack 2602. Assay device 500 may then be inserted through port 402 and be received in meter 400 such that the planar underside of the assay device is positioned adjacent magnet 2803 and generally parallel to rack 2602.

Figure 24C:
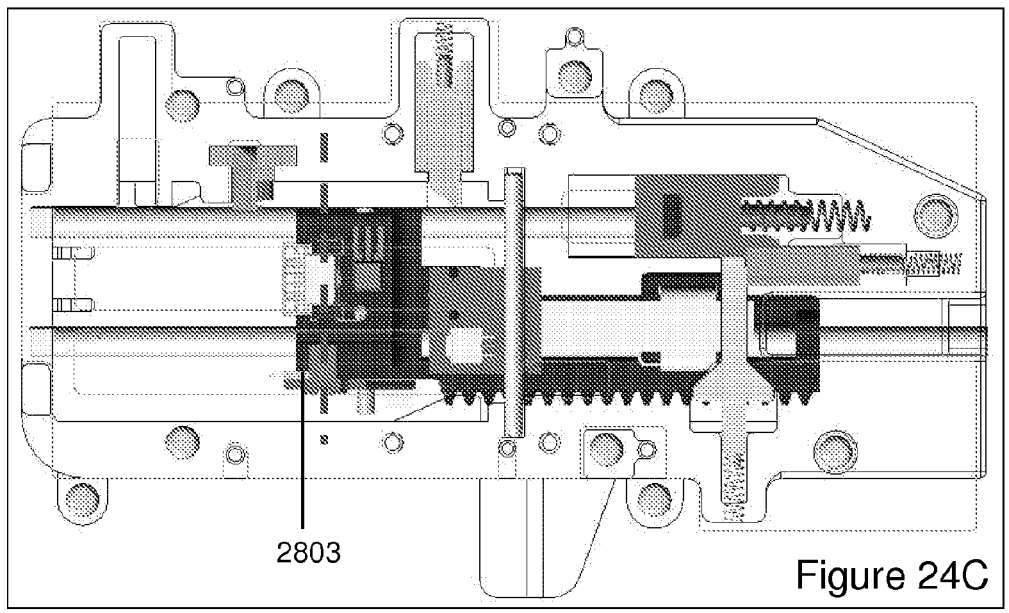

During operation of meter 400 motor 2502 is activated to drive gears 2603 and rack 2602 to move magnet 2803 through a plane that is adjacent to the base of assay device 500 and substantially parallel to the base of assay device 500 from a first position adjacent the reagent zone 512 of the inserted assay device to a second position in the detection zone 514 of the inserted assay device adjacent electrodes 516w, 516c, 516r. The path of movement of the magnet 2803 between these first and second positions is such as to bring the magnet to an intermediate position where the magnet is adjacent the interface zone 522 and junction 4305 of first and second channel portions of the assay device 500. In one exemplary embodiment meter 400 is configured to pause movement of the magnet at the intermediate position for a predetermined amount of time (as will be described below). Referring to FIG. 24C, magnet 2803 is located at the intermediate position.

The magnet 2803 applies a magnetic field to the adjacent region of the assay device 500 and movement of the magnet from the first position to the second position causes the magnetic field to be moved along the path of the first and then second channel portions 4302 and 4304 of the assay device between the reagent zone 512 and detection zone 514. Movement of the magnetic field between the first and second positions draws magnetically susceptible particles in the reagent zone through the liquid sample contained in the reagent zone 512 to the junction 4305 of the first and second channel portions of the assay device 500, and then across the junction 4305 to the electrodes 516w, 516c, 516r. In one exemplary embodiment the magnet is moved from the first position to the second position continuously, without pause. The speed of movement of the magnet (and the magnetic field) can be constant. However, in an exemplary embodiment the speed of movement of the magnet is varied by controlling the speed of motor 2502. Movement of the magnet (and the magnetic field) through the detection zone 512 is carried out at a speed $S^1$ of about 36 mm/min (±5%) (e.g. at least about 20 mm/min, at least about 25 mm/min, at least about 35 mm/min, less than about 40 mm/min, less than about 45 mm/min, less than about 50 mm/min, less than about 60 mm/min, less than about 80 mm/min). Speed $S^1$ is a "collection speed" at which magnetically susceptible particles are clustered and brought to junction 4305. As the magnetic field is moved past the junction 4305 the speed of movement of the magnet 2803 is increased to speed $S^2$ of about 144 mm/min (±5%) (e.g. at least about 120 mm/min, at least about 125 mm/min, at least about 130 mm/min, at least about 135 mm/min, at least about 140 mm/min, less than about 145 mm/min, less than about 150 mm/min, less than about 155 mm/min, less than about 160 mm/min). The speed of movement of the magnet 2803 at the junction is called the "jump speed". In one exemplary embodiment the jump speed is maintained or increased as the magnet moves the magnetically susceptible particles to the second position in the detection zone 514. In another exemplary embodiment the jump speed is decreased to about 108 mm/min (±5%) (e.g. at least about 70 mm/min, at least about 90 mm/min, at least about 95 mm/min, at least about 100 mm/min, at least about 105 mm/min, less than about 110 mm/min, less than about 115 mm/min, less than about 120 mm/min, less than about 125 mm/min) during movement of the magnetic field from the junction to the electrodes 516w, 516c, 516r. This slower speed is called the "electrode drag speed".

In one exemplary embodiment, prior to initiating movement of the magnet 2803 towards the junction 4305 and detection zone 514, the magnet is moved adjacent the detection zone, e.g. by oscillating or rotating the magnet, to agitate the liquid sample and cause mixing of the liquid sample with the magnetically susceptible particles and other reagents contained in the reagent zone 512. The speed of back and forth movement of the magnet 2803 is called the "mixing speed" and is about 144 mm/min (±5%) (e.g. at least about 120 mm/min, at least about 125 mm/min, at least about 130 mm/min, at least about 135 mm/min, at least about 140 mm/min, less than about 145 mm/min, less than about 150 mm/min, less than about 155 mm/min, less than about 160 mm/min).

Figure 48A:
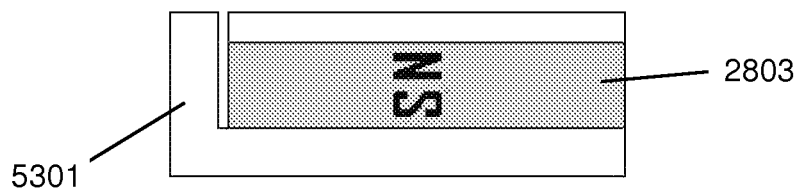
FIGS. 48A-C illustrate magnet configurations.
Figure 48B:
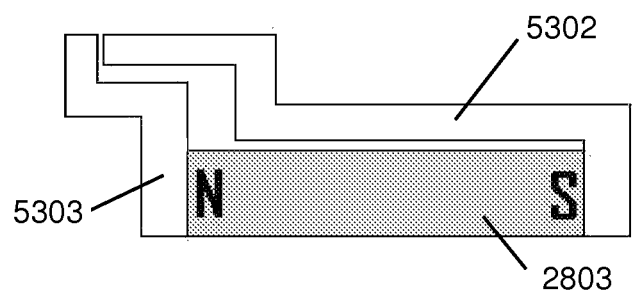
Figure 48C:
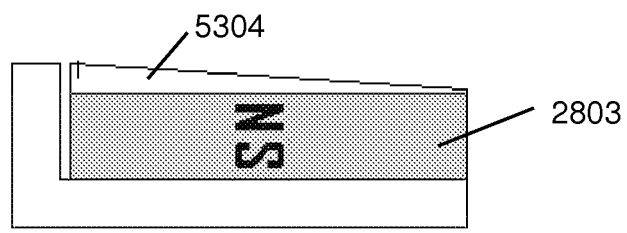

In exemplary embodiments the design of magnet 2803 is configured to focus the lines of magnetic flux at a localized position in the adjacent assay device 500. Referring to FIG. 48A-C, three exemplary arrangements are shown. Referring to FIG. 48A, the magnet 2803 is wide and shallow, having an L-shaped pole piece 5301 which focuses the lines of magnetic flux between the back edge of the north pole face and the pole piece. Referring to FIG. 48B the magnet 2803 is long and thin, and the pole pieces 5302, 5303 are shaped to form a channel directing the lines of magnetic flux to a desirable position which may be distal to the magnet 2803.

Referring to FIG. 48C, a variation in thickness of a pole piece 5304 is used to vary the magnetic field along the length of the magnet.

The magnetic field source can be configured to provide a shaped magnetic field. A shaped magnetic field can have magnetic field lines designed to direct magnetically susceptible particles toward a detection zone in the device 500. Such a shaped magnetic field can be useful to control the diffusion or migration of magnetically susceptible particles and label particles. More than one magnetic field source can be provided, particularly when a shaped magnetic field is desired. For example, magnetic field sources can be provided at either end of an assay device, where one is configured to attract magnetically susceptible particles and the other to repel magnetically susceptible particles. Such a configuration can favor the location of all magnetically susceptible particles at one end of the assay device.

In the embodiment described above, movement of the magnetic field applied to the assay device is achieved by movement of magnet 2803 positioned adjacent the underside of the channel network of the assay device 500. Movement of a magnetic field along the channel can be achieved without movement of a single magnet along a path adjacent the assay device.

For example, referring to FIG. 47A-E, in another exemplary embodiment multiple magnets are used to apply a magnetic field to different parts of the channel network of the assay device 500. Motor 2502 is replaced by three magnets 5201, 5202, 5203. Two magnets 5201, 5202 are moveable, either about a pivot 5204, or as part of a respective solenoid such that as one of magnets 5201, 5202 is moved proximal the underside of assay device 500 the other is moved distal. The first magnet 5201 is positioned towards the inlet 510 and the second magnet proximal the junction 4305. A third magnet 5203 is moveable on a solenoid proximal and distal the assay device 500 and is positioned underneath the working electrode 516w.

Figure 47:
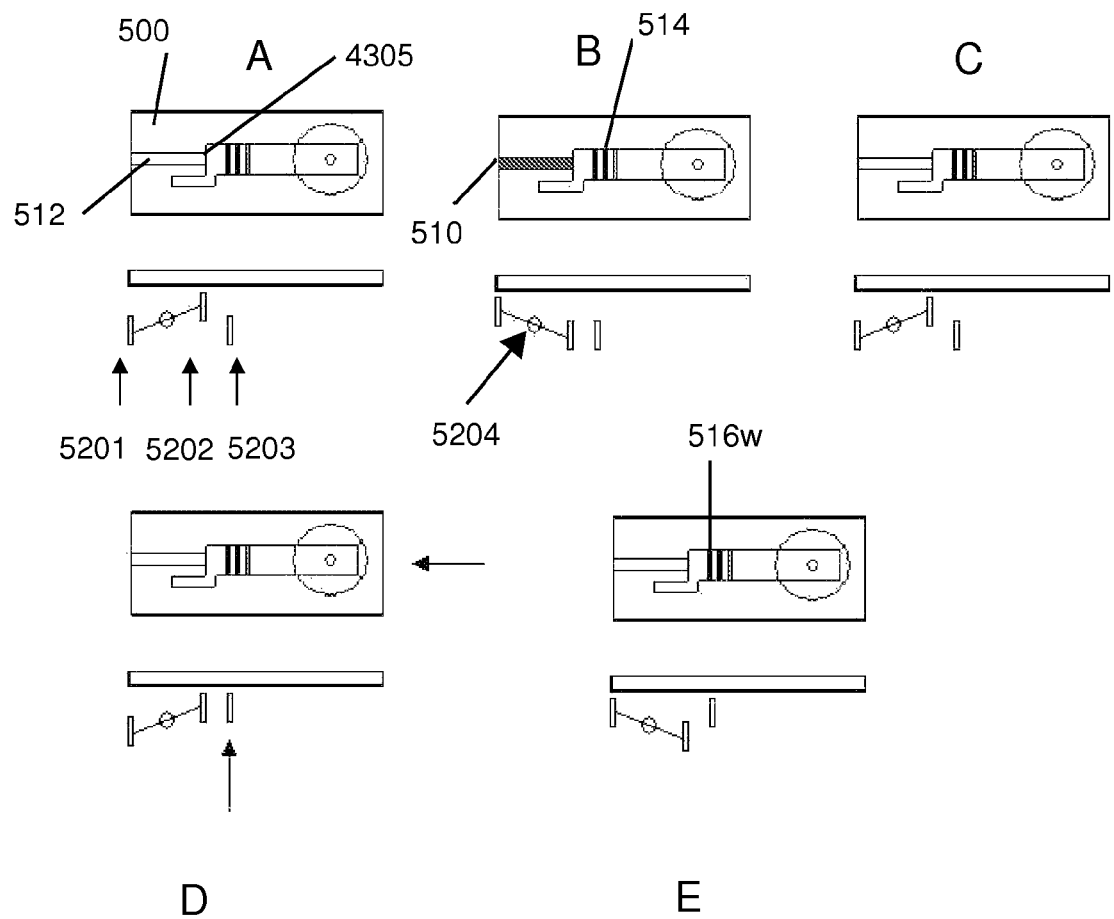
FIG. 47A-E illustrate an exemplary arrangements of magnets in relation to an assay device.

Mixing in the reagent zone 512 is achieved by alternately bringing the first and second magnets 5201, 5202 proximal to the underside of the reagent zone 512 (FIGS. 47A-B). Magnetically susceptible particles are moved to the junction 4305 by moving the second magnet 5202 towards the assay device 500 (FIG. 47C). The third magnet 5203 is then moved proximal to working electrode 516w as buffer reaches the junction 4305 and forms the liquid sample:buffer interface (FIG. 47D). By moving the second magnet 5202 away from the assay device 500 magnetically susceptible particles 'jump' across the interface and are drawn into the detection zone 514 and to the working electrode 516w (FIG. 47E).

In yet a further exemplary embodiment, the working electrode 516w is magnetised, e.g. by loading the carbon ink used to print the electrode, with material that can be magnetised, e.g. neodymium. This arrangement can be used to eliminate the need for a magnet in the meter to be positioned, or moved, adjacent the working electrode. Magnetically susceptible particles that are magnetically positioned in the second channel part 4304 are attracted to the magnetised working electrode.

Figure 24D:
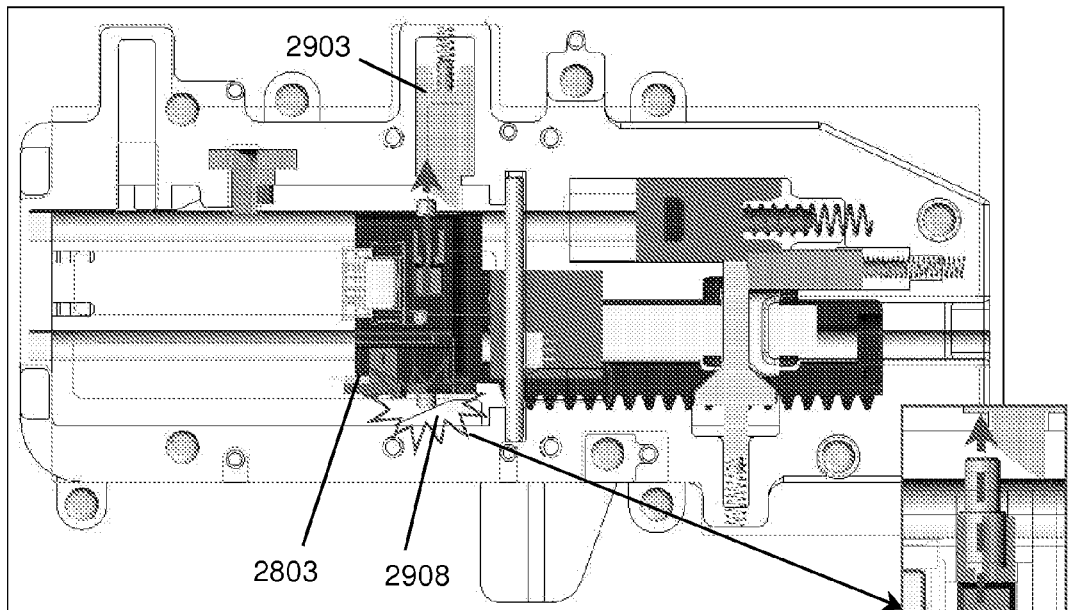
Figure 24E:
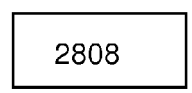
Figure 24E:
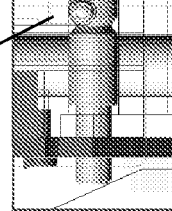

Referring to FIG. 24D, movement of magnet 2803 towards the second position brings locking bar 2806 in contact with ramp 2908 formed on chassis 2901 thereby deflecting the locking bar 2806 towards chamfer 2903 to bias chamfer 2903 away from rack 2602 and the inserted assay device 500. Referring to FIG. 24E, translational displacement of locking bar 2908 and detents 2807 by contact with ramp 2908 towards chamfer 2903 results in ball bearing 2808 being displaced from a first detent 2807 and relocated in a second detent 2807 distal from chamfer 2903. Rack 2602 is then prevented from returning towards port 402 by action of locking bar 2806 against detent 2903. The magnet is now located in the second position adjacent electrodes 516w, 516c, 516r in the detection zone of the assay device and an electrochemical signal can be detected from the assay device via electrodes 516w, 516r, 516c and electrical contacts.

Figure 24I:
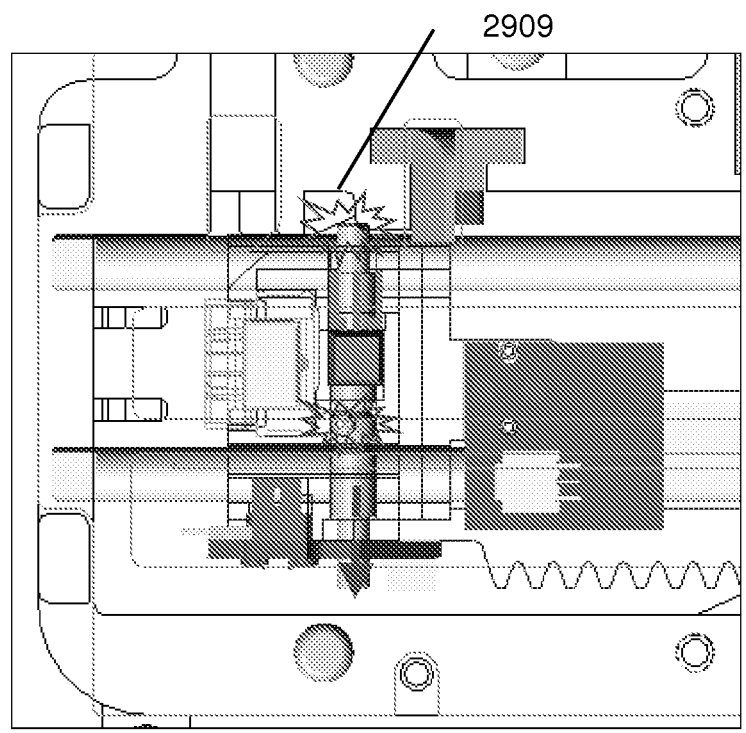
Figure 24J:
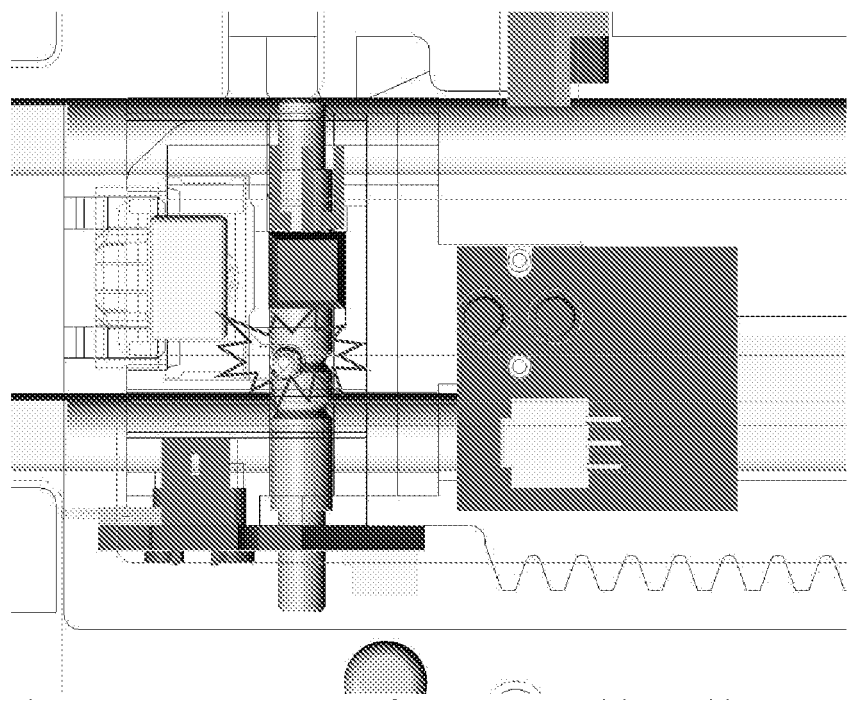

Referring to FIG. 24G, on return movement of the rack 2602 towards port 402, locking bar 2806 encounters locking member 2902 and abuts a ramp profile therein (not shown) to deflect locking member 2902 (FIG. 24H) and allow the rack 2602 and assay device to pass. Referring to FIG. 24I, on further return movement of the rack 2602 and assay device 500 locking bar 2806 interacts with ramp 2909 on chassis 2901 moving the locking bar 2806 back across rack 2602 such that ball bearing 2808 is re-positioned in the first detent 2807 (FIG. 24J) and the locking bar position is re-set to the starting position described above with reference to FIG. 24A.

Figure 25A:
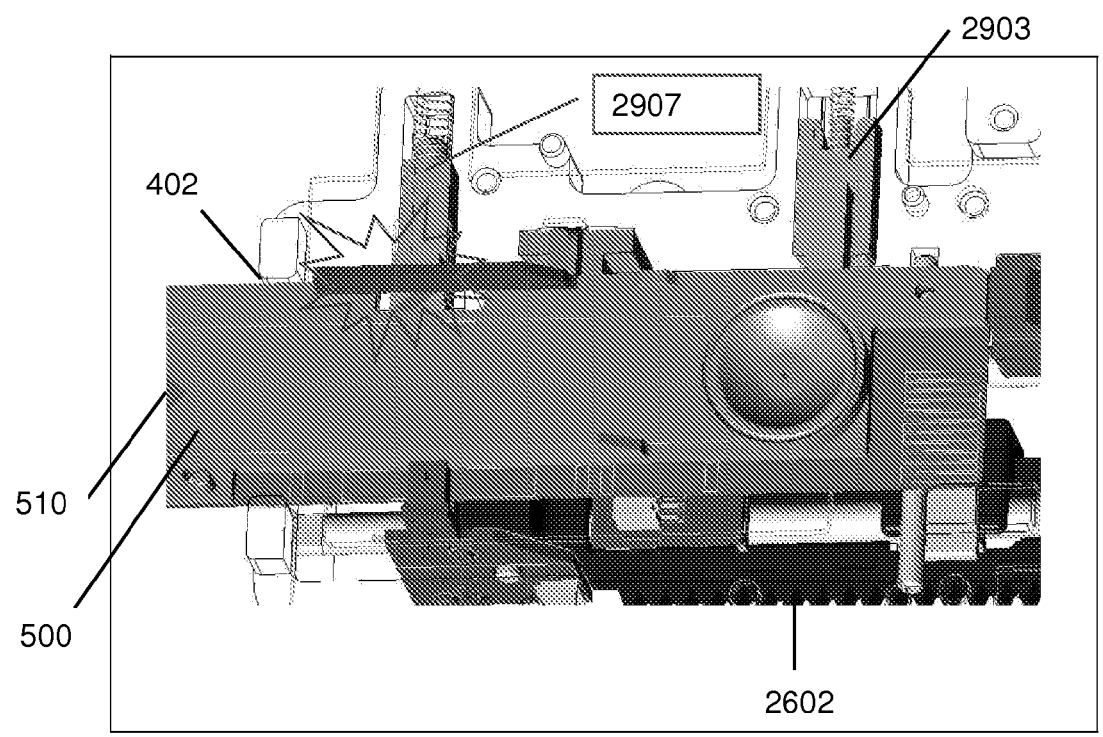
Figure 25D:
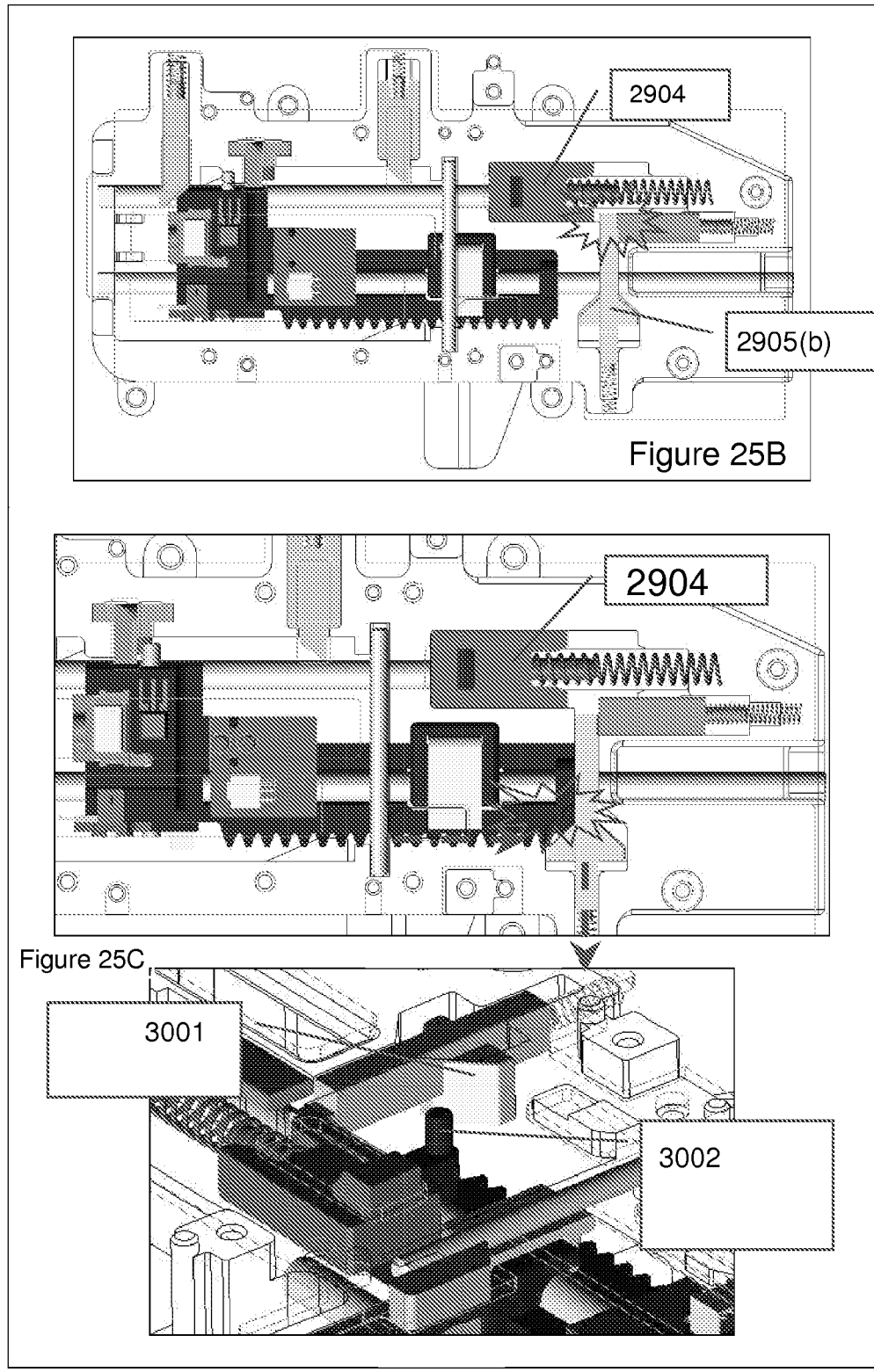
Figure 25E:
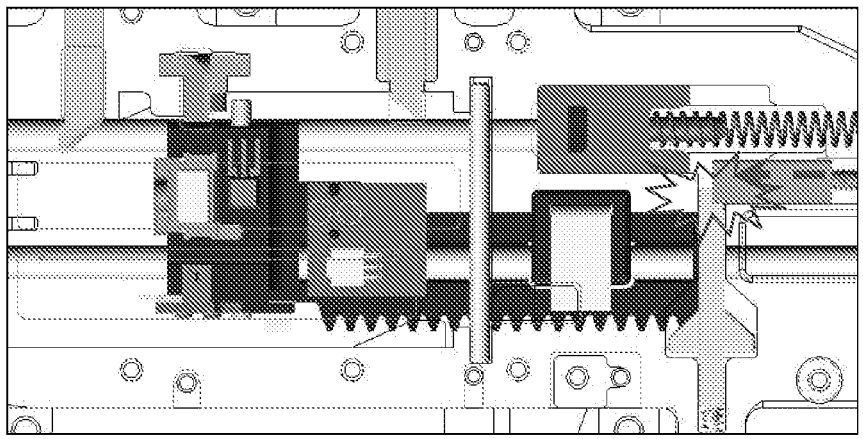
Figure 25F:
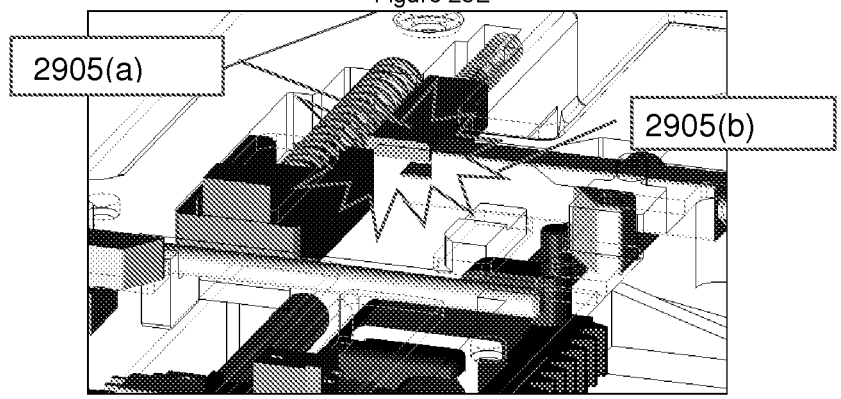
Figure 25G:
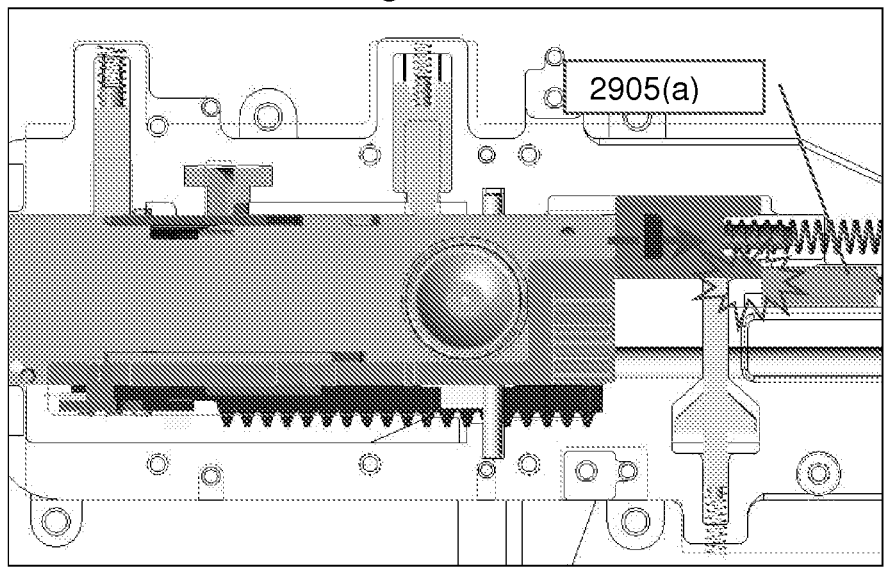

Referring to FIG. 25A, an assay strip 500 is shown inserted in meter 400 through port 402 with inlet 510 projecting out of the meter housing thereby allowing a user to deposit a sample at inlet 510. Front lock chamfer 2907 is engaged with a recess portion 4002 on assay device 500. Following insertion of assay device 500 and movement of rack 2602 away from port 402, front lock chamfer 2907 enters recess 4002 preventing ejection of the assay device 500 during performance of the assay and signal detection.

Referring to FIG. 25B, a rear lock is formed by first and second rear lock members 2905(a)(b) in co-operation with ejector member 2904. In a starting position second rear lock member 2905(b) is positioned to prevent movement of ejector member 2904 away from port 402. Referring to FIGS. 25C-G, movement of rack 2602 away from port 402 results in contact of projection 3002, formed on rack 2602, with chamfer 3001, formed on second rear lock member 2905(b), as the rack 2602 moves past second rear lock member 2905(b), thereby displacing the second rear lock member 2905(b) away from ejector member 2904 allowing first rear lock member 2905(a) to move across an end of second reinsertion member 2905(b) thereby permitting movement of ejector member 2904 away from port 2904 in response to insertion of an assay device 500.

Figure 25H:
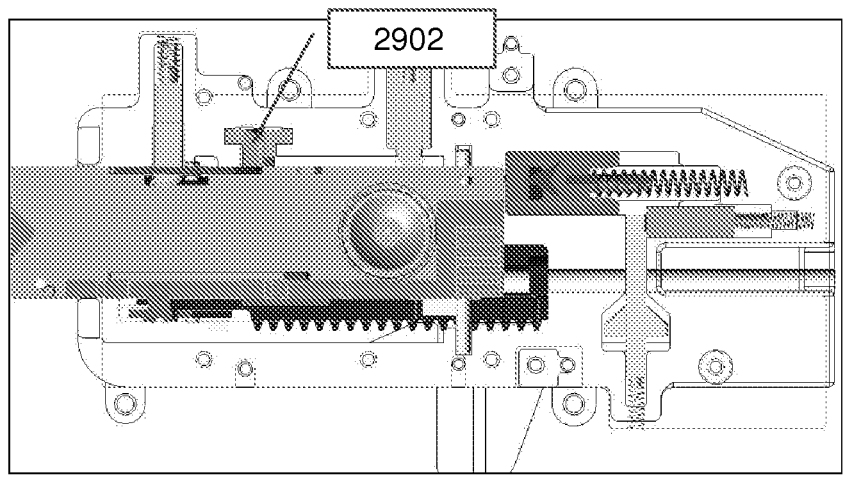
Figure 25I:
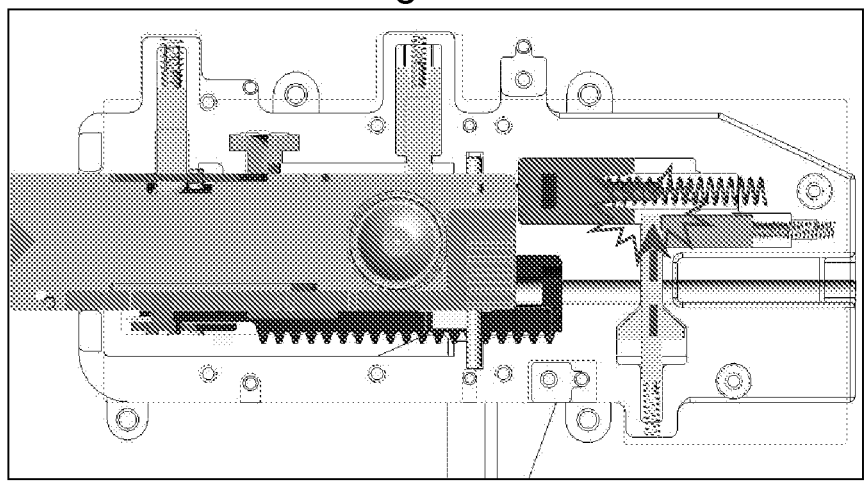
Figure 26:
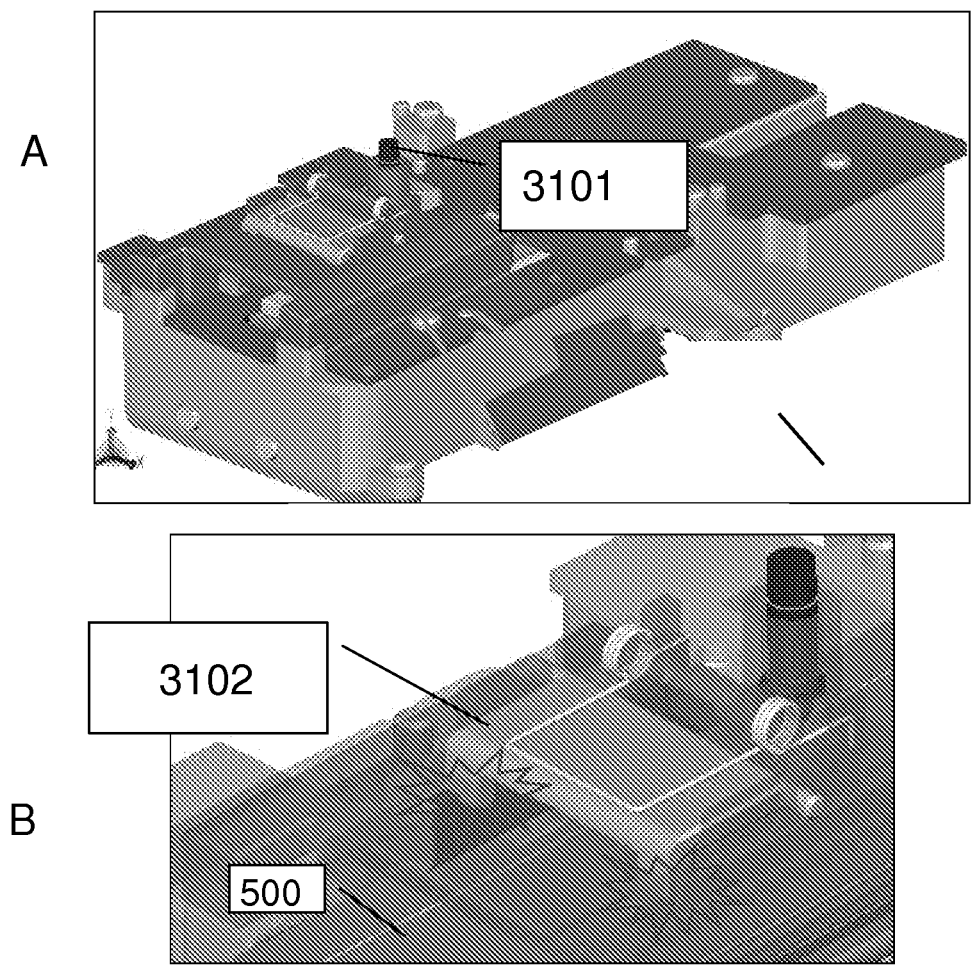
FIGS. 26A-B show interaction of the meter bias member and device.

Referring to FIGS. 25H-I, on return movement of rack 2602 towards port 402 ejector member 2904 resiliently biases assay device 500 through port 402 to effect ejection of the assay device 500. Second rear lock 2905(b) is biased towards ejector member 2904 to block first rear lock member 2905(a) and return the ejector-rear lock mechanism to a starting position.

Referring to FIG. 29B, assay device 500 is inserted in meter 400 such that inlet 510 protrudes out of port 402 enabling a liquid sample to be deposited at inlet 510. The assay device 500 is locked in position by the front lock chamfer 2907 and locking member 2902 and is biased horizontally by bias member 3401. Insertion of the assay device 500 against ejector member 2904 biases the ejector member away from port 402 and into a compressed state.

Referring to FIG. 29A-B, meter 400 comprises an optical sensor 3402 mounted on a moveable carriage. In some embodiments, upon insertion of assay device 500, optical sensor 3402 is positioned to move along one edge of the assay device 500 and read a code (e.g. bar code) printed on the upper or lower surface 4001 of assay device 500.

Referring to FIG. 26A, meter 400 comprises an optical sensor for detecting sample liquid in the reagent zone 512 of assay device 500. The optical sensor comprises a light-emitting diode (LED) 3101 configured to direct light towards the reagent zone. Transmission of light through an optically transparent portion of the assay device 500 forming reagent zone 512 is reduced in the presence of a liquid sample such as blood. Detection of a reduction in light transmission at an optical sensor 2805 arranged on carriage 2802 to detect light from LED 3101 passing through the assay device 500 provides an indication of filling of the reagent zone 512 with liquid sample and formation of the liquid sample:gas interface.

Referring to FIG. 26B, meter 400 comprises positioning member 3102 biased towards an inserted assay device 500, acting to apply pressure to an upper surface of the assay device 500 and bias the device 500 towards magnet 2803. The bias applied by the positioning member 3102 to assay device 500 minimizes the gap between magnet 2803 and the channel network formed in the assay device 500.

Figure 27:
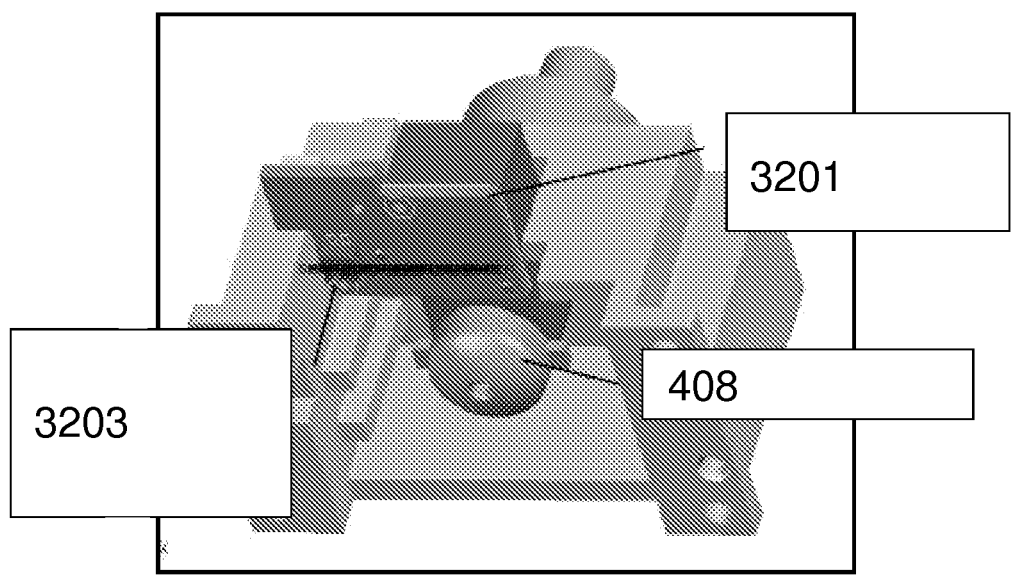
FIG. 27 shows a perspective view of the actuator assembly.
Figure 28:
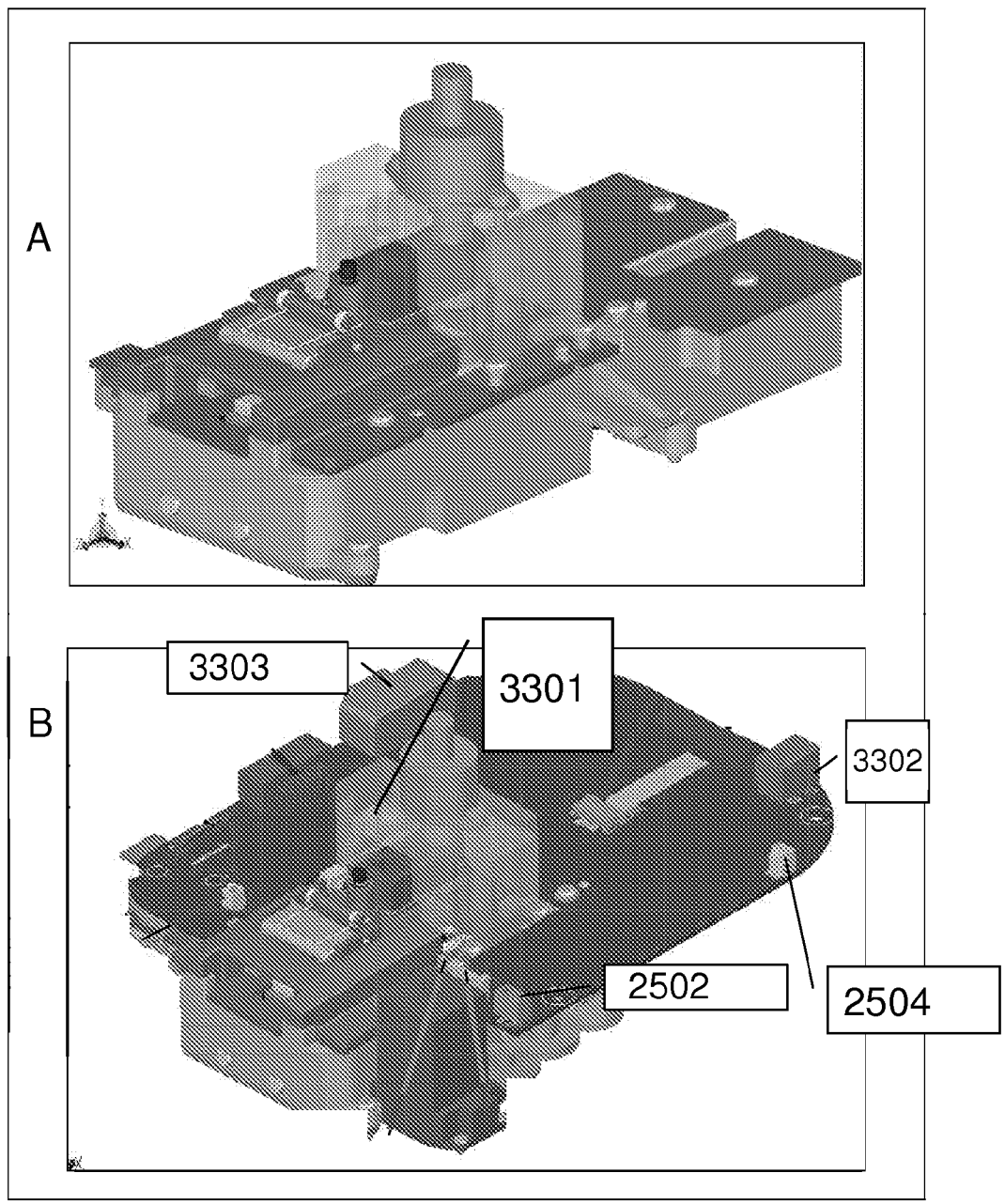
FIG. 28A-B shows the configuration of the actuator assembly in the meter.
Figure 29:
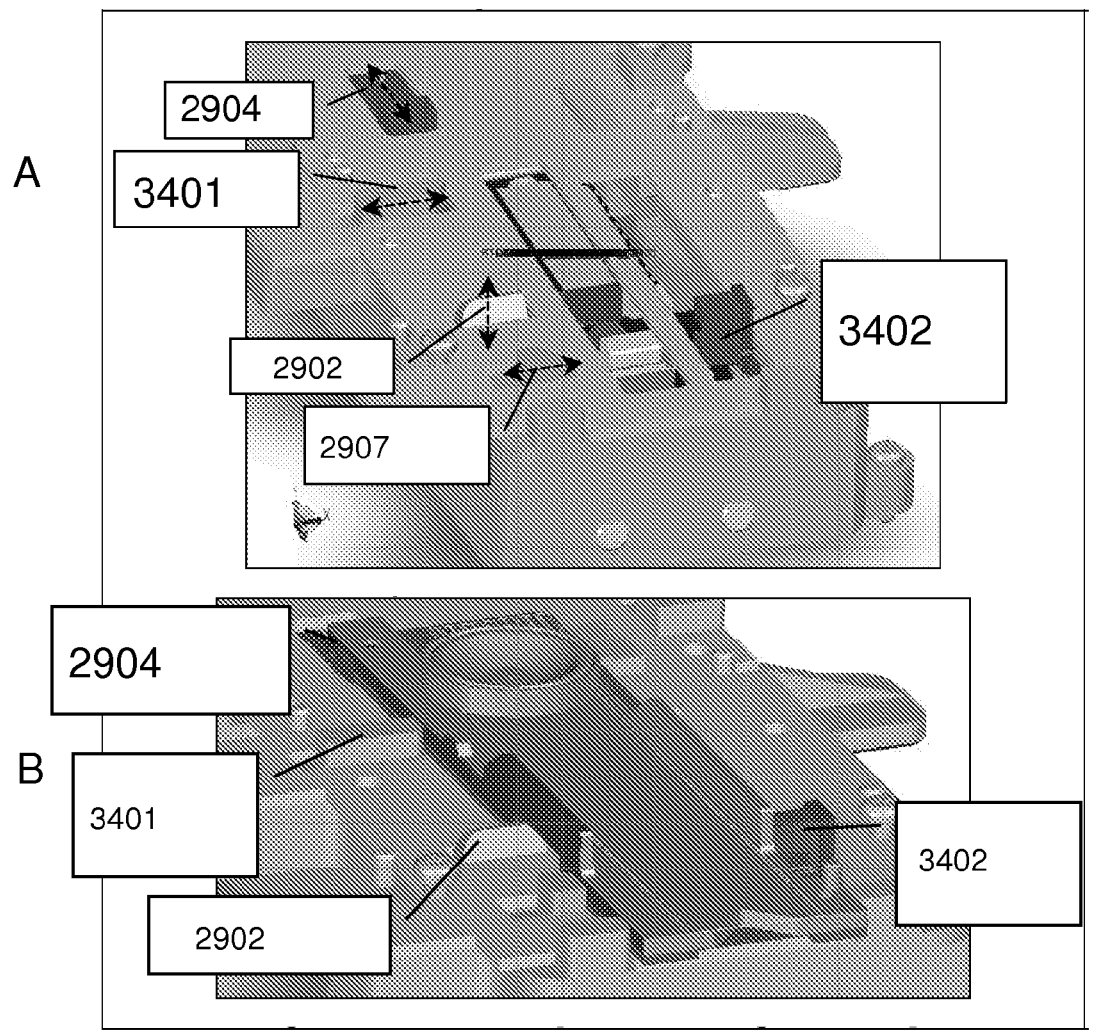
FIG. 29 shows the internal meter configuration (A) in the absence of an assay device and (B) in the presence of an assay device.

Referring to FIG. 27, meter 400 comprises an actuator 2501 configured to interact with a reservoir 507 on assay device 500 and apply pressure to the reservoir to release and/or force buffer liquid from the reservoir into the second channel portion 4304 of the assay device 500. The actuator mechanism has a linear actuator motor controlled by a circuit 3201. An actuator/plunger 408 is connected to the motor and is moveable by the motor toward and away from an assay device inserted in meter 400. A switch 3203 registers the end of a stroke movement of the plunger 408 towards the reservoir.

Referring to FIG. 28A-B, the actuator mechanism 3301 is mounted on meter 400 above a slot in which an assay device 500 is received. Meter 400 also has an input port 3302 for a dc power supply and serial communications output port 3303.

Use of the Assay Device

The methodology of use of the device 500 will now be described with reference to an exemplary embodiment.

The method comprises the steps of introducing a liquid sample to a first channel portion 4302 of a channel network 508; contacting the liquid sample with magnetically susceptible particles configured to bind an analyte in the liquid sample; forming, proximal to a junction 4305 between the first portion of the channel 4302 and a second portion of the channel 4304, a liquid sample:gas interface; forming a liquid sample:second liquid interface by displacing gas of the liquid sample:gas interface with a second liquid, and; magnetically moving the magnetically susceptible particles across the liquid sample:second liquid interface into the second liquid.

In an exemplary embodiment this method is achieved by interaction of the device 500 in a meter 400, wherein the liquid sample:gas and liquid sample:liquid interfaces are formed in the device and the magnetically susceptible particles are magnetically moved by applying a magnetic field to the device from a meter 400 with which the device 500 is interacting.

A user of the device, e.g. a human, inserts a device 500 into meter 400 such that the device 500 is received in meter 400 and the inlet 510 is accessible for deposit of a liquid sample. The user deposits the liquid sample (e.g. an amount of human blood obtained via a finger stick) at inlet 510 from which the liquid sample enters the first channel portion, e.g. by capillary action. Entry of the liquid sample may be facilitated by an optional inlet channel 4303 connecting the inlet 510 and first channel portion 4303. The inlet channel 4303 can act as a volume buffer to assist in complete filling of the first channel portion 4303.

Entry of the liquid sample into the first channel portion 4302 and filling of the first channel portion 4302 up to the capillary stop provided at junction 4305 results in formation of a liquid:gas (e.g. liquid:air) interface proximal the junction. The interface is substantially static with little or no bulk movement of the interface along the length of the first channel portion 4302.

Accordingly, in use, a liquid sample (e.g. an amount of mammalian blood obtained from a finger stick or a venous draw) is applied to assay device 500 at sample inlet 510. The sample contains an amount of analyte (e.g. NT-proBNP). In some cases, the amount of analyte present in the sample may be so small as to be undetectable; in other cases, the amount of analyte present in the sample may be zero (i.e., NT-proBNP is absent from the sample).

If desired, small adjustments in the position of the liquid sample:gas interface can be made by moving the liquid sample:gas interface by a distance $D^C$ or less along the channel between forming the liquid sample:gas interface and forming the liquid sample:second liquid interface, wherein $D^C$ is 3 mm (e.g. at least about 2.5 mm, at least about 2.0 mm, at least about 1.5 mm, at least about 1.0 mm, at least about 0.5 mm). This movement may be achieved by changing the capillary pressure applied to the channels or by magnetically moving the magnetically susceptible particles along the first channel portion in a direction towards the liquid sample:gas interface thereby drawing the interface along the first channel portion.

Liquid sample entering the first channel portion 4302 contacts the reagents deposited in the first channel portion. The reagents and liquid sample are allowed to mix to form a sample-reagent mixture in which the first and second binding agents are allowed to bind the analyte and form complexes of magnetically susceptible particles:first binding agent:analyte (and optionally the second binding agent). Mixing of the reagents and liquid samples is allowed to occur for an amount of time $T^A$ which is at least about 1 minute (e.g. at least about 10 seconds, at least about 30 seconds, at least about 45 seconds, less than about 15 minutes, less than about 10 minutes, less than about 5 minutes, less than about 3 minutes, less than about 2 minutes). Mixing of the reagents and liquid sample can be assisted by agitation of the mixture. This agitation can be effected by applying a magnetic field to the first channel portion and moving the magnetic field thereby moving the magnetically susceptible particles within the first channel portion 4302 and mixing the magnetically susceptible particles with the reagents. The magnetic field can be applied by a magnet 2803 in meter 400, which can be moved to effect movement of the magnetic field. This movement of the magnetic field is confined to moving the magnetically susceptible particles within the first channel portion 4302. The mixing can be achieved by moving the magnetic field the mixing speed described above.

Accordingly, the liquid sample is drawn into reagent zone 512 (e.g. by capillary action), where it makes initial contact with and subsequently mixes with reagents 513r1, 513r2, 513r3, 513r4. In an exemplary embodiment the reagents include magnetically susceptible particles linked to streptavidin, anti-analyte antibody (e.g. anti-NT-proBNP antibody 15F11) linked to biotin, and a detectable label (e.g. horseradish peroxidase (HRP)) conjugated to an anti-analyte antibody (e.g. anti-NT-proBNP antibody 24E11) linked to colloidal gold sol with average particle diameter of at least about 40 nm (the antibody-linked enzyme). The reagents are resuspended in solution with the liquid sample, and form an inhomogeneous mixture. The streptavidin (which is linked to magnetically susceptible particles) binds to biotin (which is linked to the an anti-analyte antibody), thus forming an antibody:magnetically susceptible particle complex. The analyte is bound by the antibody:magnetically susceptible particle complex and the antibody-linked enzyme, thereby forming a ternary complex. If desired, a magnetic field can be applied such that the magnetically susceptible particles undergo an induced motion (e.g., a periodic or oscillatory motion) to promote or enhance resuspension and mixing of the reagents with the sample (as described above). In an exemplary embodiment a magnetic field is oscillated beneath reagent zone 512 to mix reagents at the mixing speed. Antibody complexes are then collected into a common location at the collection speed. Complexes are then moved from reagent zone 512 to detection zone 514 by a combination of the jump and electrode drag speeds (described above).

The time between forming the liquid sample:gas interface and the liquid sample:second liquid interface (described below) is less than time $T^K$, wherein $T^K$ is about 1 minute but may be less (e.g. about 5 seconds or less, about 10 seconds or less, about 20 seconds or less, about 30 seconds or less, about 40 seconds or less, about 50 seconds or less), or more (e.g. less than about 2 minutes, less than about 5 minutes, less than about 10 minutes, less than about 15 minutes).

At a predetermined time after deposit of the liquid sample at the inlet 510, meter 400 operates to activate actuator motor to move plunger 3203 towards reservoir 507, the plunger 3203 contacts the reservoir 507 and moves it to contact sharp projection 3506 which punctures a wall of the reservoir 507. Buffer liquid is released from the punctured reservoir 507 and enters the second channel portion 4304 through inlet 520 and flows towards junction 4305. Flow of buffer liquid through the second channel portion 4304 towards the junction 4305 can be detected by one of electrodes 516w, 516c, 516r providing an electrical signal to the processor in meter 400 to indicate successful puncture of reservoir 507 and delivery of the buffer liquid into the second channel portion.

As buffer liquid advances towards the junction 4305 it encounters capillary stop 532 on one wall of the second channel portion 4304. This retards the flow of buffer liquid along that wall of the second channel portion. Buffer liquid flow continues at the opposing wall such that the flow of buffer liquid advances around the bend portion 4308 past corner 536 and down the slope 534. This causes the buffer liquid to flow across the liquid sample:gas interface displacing the gas and replacing it with buffer liquid and decreasing the area of the liquid sample:gas interface until a liquid sample:buffer liquid interface is formed.

Buffer liquid continues to flow into overflow channel 524 expelling air from the second channel portion 4304 through vent 526. Flow of buffer liquid into overflow channel 524 can be detected by electrode 3601 generating an electrical signal which is sent to the processor in meter 400 via terminal 3602 indicating that the liquid sample:buffer liquid interface has been formed.

Figure 9A:
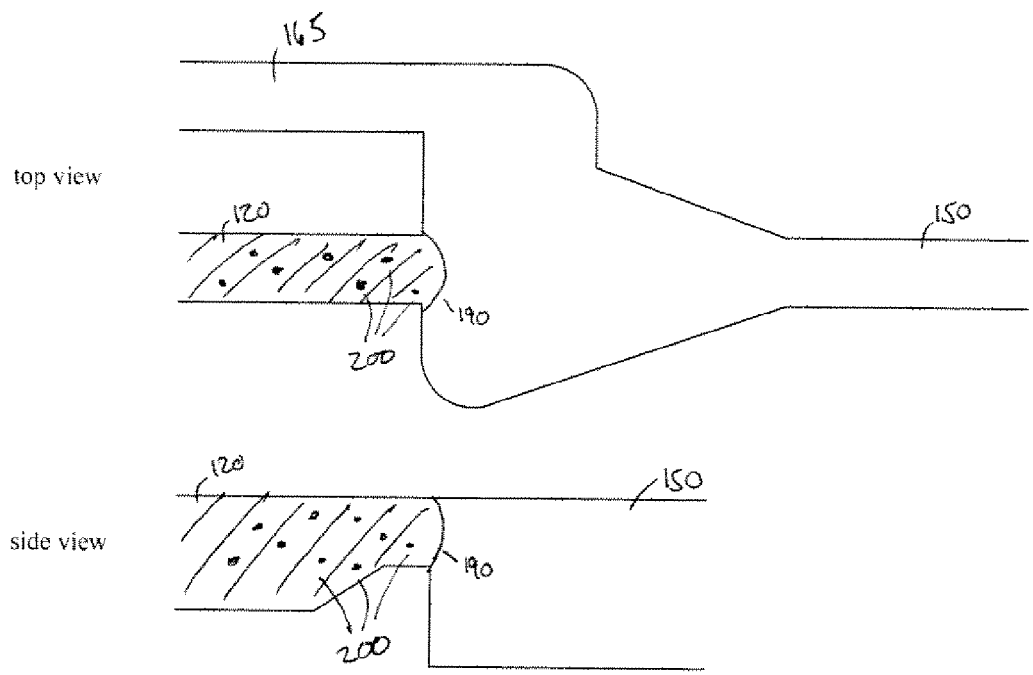
FIGS. 9A-D show the movement of reagents through the interface formation feature of FIG. 6.

Formation of the interface is now described with reference to FIGS. 9A-D and 10A-B. FIG. 9A shows top and side views of the assay device 500 in the region of interface zone 522 after a sample liquid has been added to sample inlet 510. The sample liquid (e.g., blood) is drawn (e.g. by capillary action) to fill reagent zone 512. Upon reaching capillary stop 530, the liquid forms a meniscus 590. As the sample liquid approaches capillary stop 530 from reagent zone 520, it experiences a sudden increase in the cross-sectional area of the channel at capillary stop 530, where interface zone 522 has a greater depth and width than reagent zone 520. This sudden change in dimensional profile prevents the sample liquid from entering interface zone 522. Any surface tension forces at meniscus 590 exceed any capillary forces that would tend to draw the sample liquid into interface zone 512. At this stage, a liquid sample:gas interface (e.g., blood: air interface) is formed at meniscus 590. FIG. 9A also illustrates magnetically susceptible particles 200 dispersed in the blood.

A magnetic field is applied to reagent zone 512. The applied field can be manipulated (e.g., by moving a permanent magnet relative to the test strip, or by actuating an electromagnetic solenoid) so as to move the magnetically susceptible particles 200, and therefore the analyte that has been captured by the antibodies on the magnetically susceptible particles. The magnetically susceptible particles 200 are moved along reagent zone 512 toward capillary stop 530.

The magnetic field source can be configured to provide a shaped magnetic field. A shaped magnetic field can have magnetic field lines designed to direct magnetically susceptible particles toward the detection zone 514. Such a shaped magnetic field can be useful to control the diffusion or migration of magnetically susceptible particle complexes. More than one magnetic field source can be provided, particularly when a shaped magnetic field is desired. For example, magnetic field sources can be provided at either end of an assay device, where one is configured to attract magnetically susceptible particles and the other to repel magnetically susceptible particles. Such a configuration can favour the location of all magnetically susceptible particles at one end of the assay device.

Figure 9B:
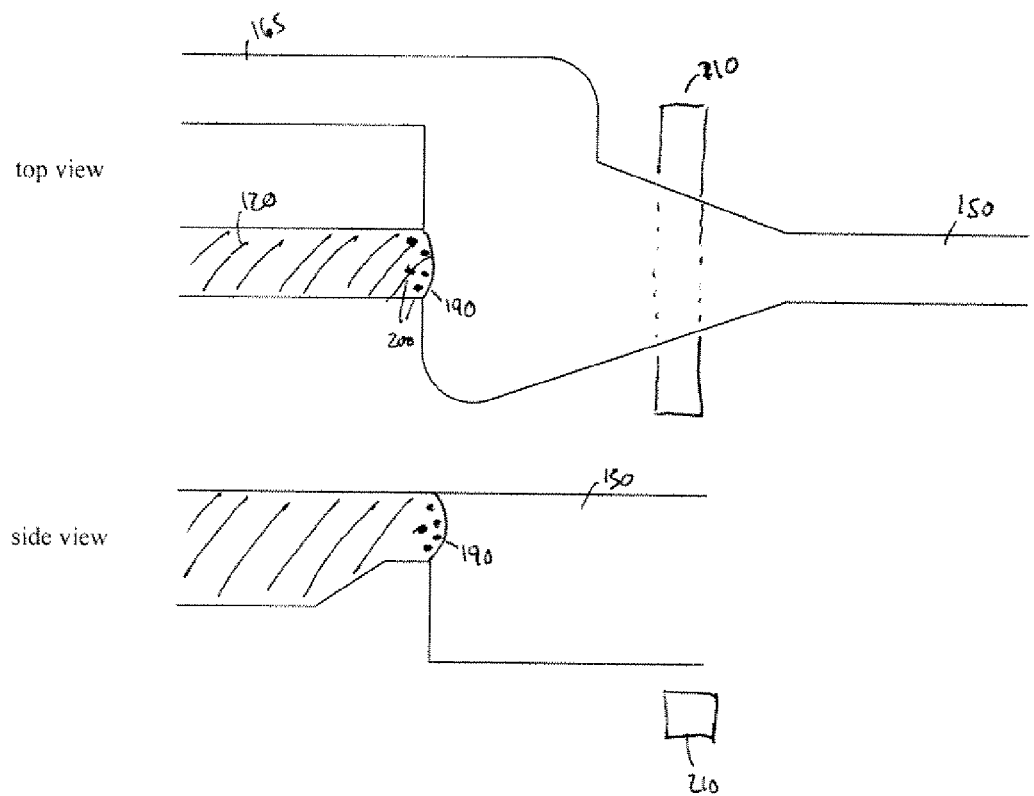

FIG. 9B shows top and side views of the device after an applied magnetic field (applied by magnetic field source 210) has drawn magnetically susceptible particles 200 toward meniscus 590. The magnetic field source 210 can be configured (e.g., with regard to location, magnetic field intensity and magnetic field shape) so as to retain magnetically susceptible particles 200 in proximity to meniscus 590. Magnetic field source 210 can be manipulated such that particles 200 are subject to a magnetic force at meniscus 190 sufficient to resist diffusion away from the magnetic field source.

When the sample has been in contact with reagents 513$r$1, 513$r$2, 513$r$3, 513$r$4 for a predefined interval of time sufficient to permit formation of complex between the analyte, (e.g. NT-proBNP), and the respective anti-analyte antibodies, a second liquid is introduced to assay device 500 via buffer inlet 520. Where horse radish peroxidase is used as a detectable enzyme label, the second liquid contains sodium acetate buffer, hydrogen peroxide substrate, and the redox mediator 2,2'-azino-bis-(3-ethylbenzo-thiazoline-sulfonic acid) (ABTS). The second liquid flows along detection zone 514 under positive pressure applied by reservoir activator 408. The second fluid contacts the blood sample at meniscus 190 to form a liquid:liquid interface. The formation of the liquid:liquid interface facilitates the movement of the magnetically susceptible particle conjugate complex from the liquid sample to the second liquid under the influence of magnetic field source 210. The movement of analyte from the liquid sample to the second liquid as part of the magnetically susceptible particle conjugate complex minimises the likelihood that potentially interfering sample components and analytes that are of no interest get transferred to the second liquid. The magnetically susceptible particles and all that is bound to them, including the analyte (in the form of a ternary complex of analyte with antibody-magnetically susceptible particle complex and antibody-linked enzyme) are transferred to the second liquid in the detection zone 514.

Figure 9C:
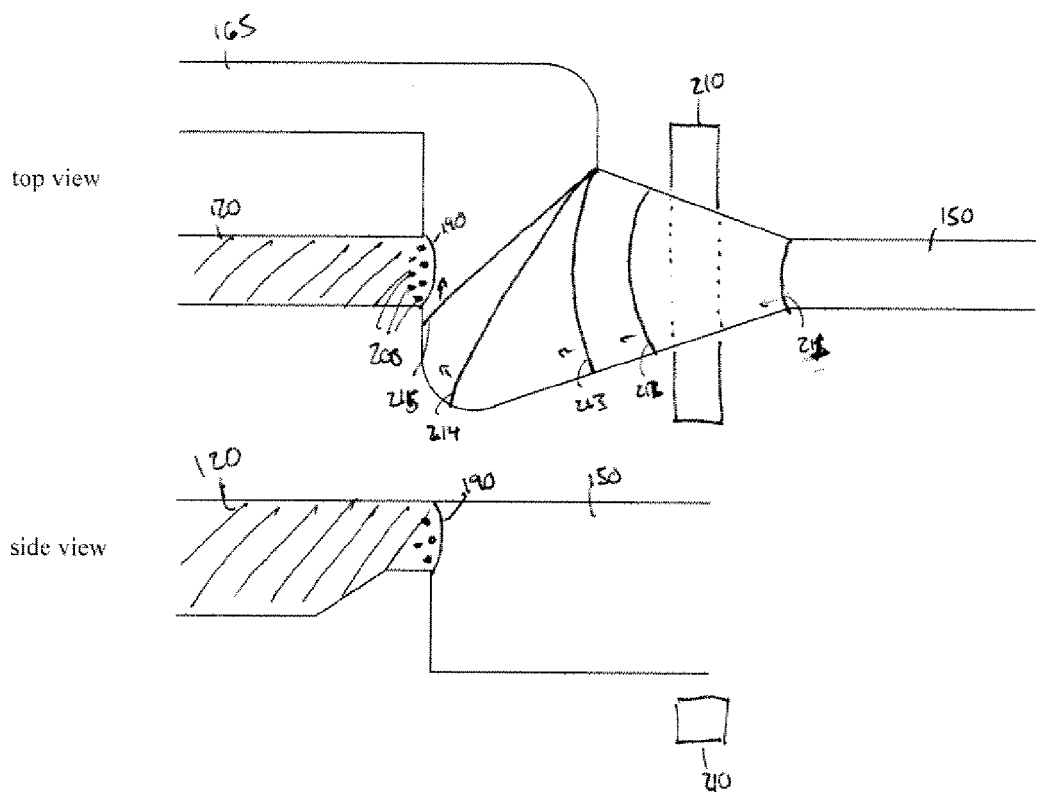

Interface zone 522 can be shaped such that a liquid front of the second liquid flows laterally across meniscus 590, rather than meeting meniscus 590 head-on. FIG. 9C illustrates a plan view from above of assay device 500 in the region of interface zone 522. FIG. 9C represents a time series of profiles indicating the moving liquid front as the second liquid flows from detection zone 514 towards capillary stop 530. In particular, sequential positions of liquid front 211, 212, 213, 214, 215 illustrate how interface zone 512 can be shaped to guide the liquid front of the second liquid so that it flows laterally across meniscus 590 held at capillary stop 530. The lateral movement of the second liquid meniscus 215 across the liquid sample meniscus 590 reduces the likelihood that air bubbles become trapped between the first liquid and second liquid. The presence of air bubbles at the liquid:liquid interface may reduce the efficiency with which magnetically susceptible particles are transferred from the blood sample into the second liquid. Therefore it may be desirable to have a bubble free interface to reduce possible reduction in the efficiency of sample transfer.

Figure 9D:
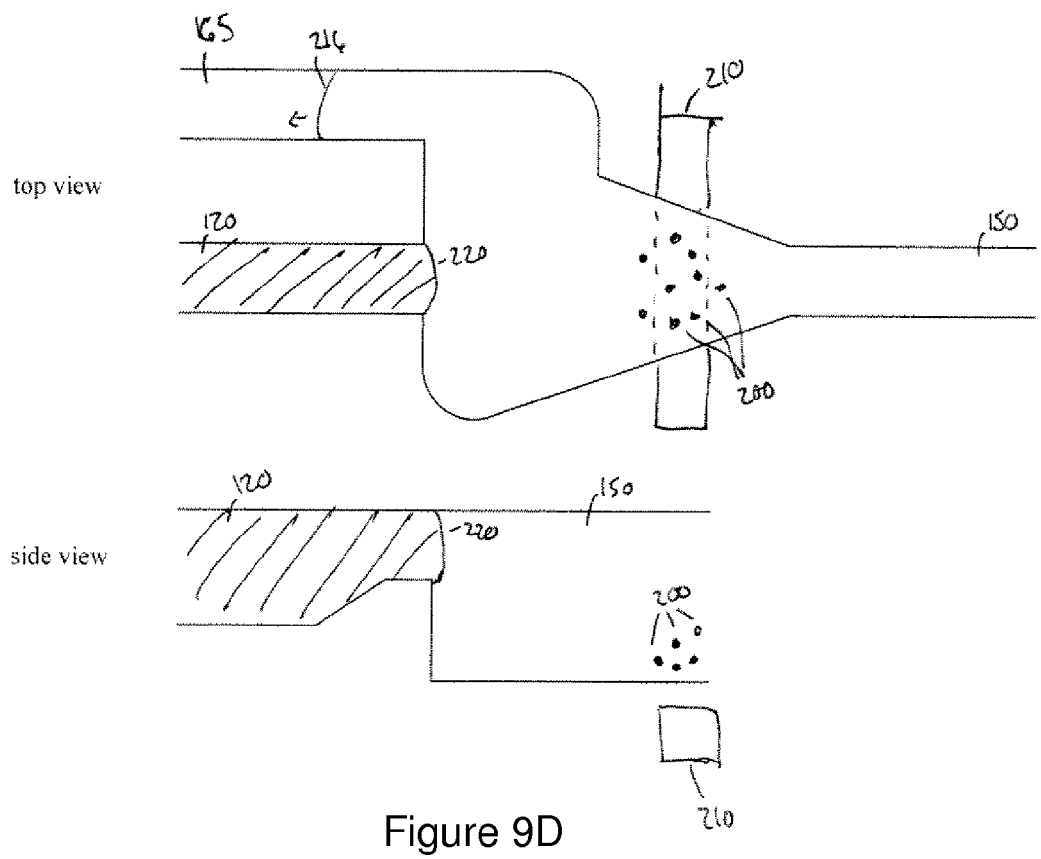

FIG. 9D shows top and side views of assay device 500 after the second liquid has filled interface zone 512, and formed liquid:liquid interface 220. Liquid front 216 of the second liquid continues to flow through overflow channel 524 towards vent 526. Magnetically susceptible particle: analyte complex 200 is transferred across liquid:liquid interface 220 by virtue of the attractive magnetic field applied by source 210. The magnetically susceptible particle:analyte complex 200 is progressively moved along detection zone 514 under the influence of magnetic field source 210. The continued flow of the second liquid from buffer inlet 520 through detection zone 514, interface zone 522 and overflow channel 524 after the liquid:liquid interface 220 has been formed can help to wash non-magnetic material away from magnetically susceptible particle:analyte complex 200. Such washing can help ensure that only material associated with the magnetically susceptible particles is detected by electrodes 516$w$, 516$c$, 516$r$ in detection zone 514.

A fluid reservoir 507 incorporated into the assay device can deliver a reaction buffer, and the composition of the buffer can be varied (e.g., sodium acetate, phosphate-citrate, sodium citrate or any other buffer at any suitable concentration or pH). Any suitable liquid can be used instead of a buffer (see, for example, U.S. Patent Application No. 60/736,302, filed Nov. 15, 2005, which is incorporated by reference in its entirety). In some embodiments reservoir 507 may be provided as a non-integral part of assay device 500, in which case an interface port may be provided that integrates the reservoir 507 with buffer inlet 520.

Figure 10A:
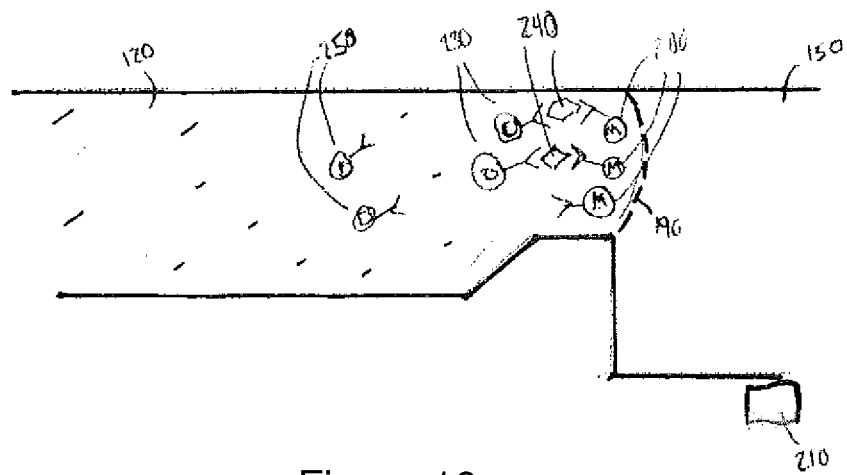
FIGS. 10A-B show detailed description of reagent separation in assay device.
Figure 10B:
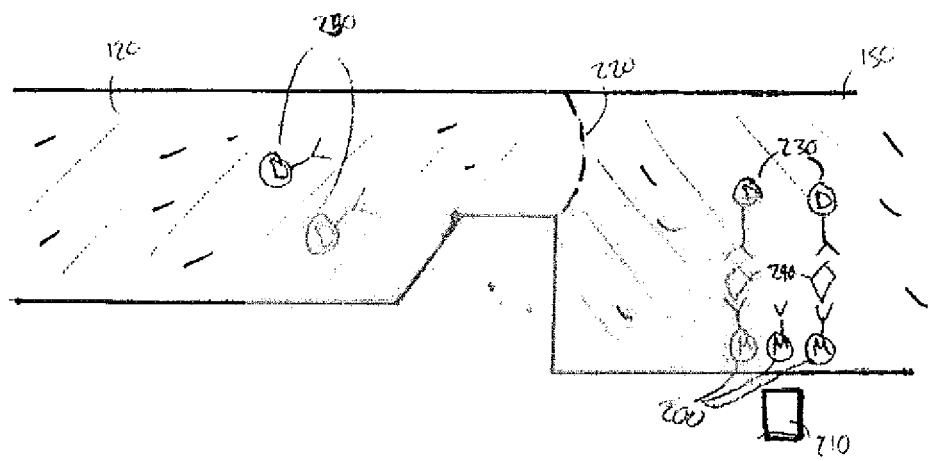

FIGS. 10A and 10B illustrate the separation of the magnetically susceptible particle:analyte complex from the non-magnetically susceptible particle associated antibodies across the liquid:liquid interface in greater detail. In FIG. 10A (as in FIG. 9B), magnetically susceptible particles 200 are located near meniscus 590 by virtue of the magnetic field applied by magnetic field source 210. Some of magnetically susceptible particles 200 are bound to second analyte 240 in an antibody:magnetically susceptible particle complex, which in turn is bound to antibody-linked enzyme 230. Because the antibody-linked enzyme in reagent zone 512 is present in excess compared to second analyte 240, some antibody-linked enzyme 250 can remain unbound to target analyte. Magnetic separation helps ensure that unbound antibody-linked enzyme 250 does not reach detection zone 514; in other words, it is only magnetically susceptible particle:analyte complex linked enzyme 230 that should arrive at electrodes 516w, 516c, 516r under influence of magnetic field source 210 that contributes to the detectable signal. Thus the detectable signal can be reproducibly related to the amount or concentration of analyte (e.g. NT-proBNP) 240 in the sample.

When the flow of buffer liquid ends, a stable liquid sample:liquid interface is formed. The liquid sample:liquid liquid interface is substantially static and remains essentially static with respect to movement along the channel between forming the liquid sample:gas interface and forming the liquid sample:liquid interface, i.e. diffusion may occur across the sample liquid:liquid interface but bulk movement of either liquid across the interface does not occur. Substantially no bulk movement of liquid occurs across the interface between the liquid sample and buffer liquid. The liquid sample:liquid interface remains essentially static for a time $T^M$, wherein $T^M$ is at least 1 second (e.g. at least 2 seconds, at least 3 seconds, at least 5 seconds, at least 10 seconds, at least 30 seconds, at least 1 minute).

The liquid sample:gas and liquid sample:buffer liquid interfaces are both formed substantially vertically with respect to the assay device. The assay device is formed as an elongate strip, held during measurement in a substantially horizontal plane, the interfaces are formed substantially perpendicular to this plane. The interfaces can also be described as being formed substantially parallel to the field lines of the earth's local gravitational field, i.e. the gravitational field lines predominating in the space immediately proximal to and including the device 500 and surrounding meter 400.

Having received a signal from electrode 3601 indicating that the liquid sample:buffer liquid interface has been formed, meter 400 operates to apply a magnetic field to the first channel portion and magnetically move magnetically susceptible particles across the liquid sample:liquid interface. This movement separates magnetically susceptible particles (whether or not bound to first and/or second binding agents and analyte) from the liquid sample into the buffer liquid. Reagents not bound to the magnetically susceptible particles remain in the liquid sample.

To magnetically move magnetically susceptible particles into the buffer liquid the particles are first clustered by relatively slow movement of the magnetic field through the first channel portion 4302 to collect the magnetically susceptible particles into a cluster. The particles are drawn slowly towards the junction 4305 at a "collection speed" ($S^1$) of about 36 mm/min (as described above) until the magnetically susceptible particles are adjacent the junction 4305 and retained in the liquid sample.

This movement of the magnetically susceptible particles towards the junction can occur prior to formation of the liquid sample:buffer liquid interface such that the magnetically susceptible particles are initially clustered adjacent the liquid:gas interface. Alternatively, the clustering can occur after the liquid sample:buffer liquid interface is formed. In one exemplary embodiment, the movement of the magnetic field through the first channel portion is timed so as to cluster the magnetically susceptible particles adjacent the liquid sample:buffer liquid interface as it formed.

All, or substantially all, of the magnetically susceptible particles contained in the first channel portion 4302 are clustered adjacent the liquid sample:gas or liquid sample:liquid interface (e.g. at least about 70%, at least about 80%, at least about 85%, at least about 90%, at least about 95%, at least about 98% of the magnetically susceptible particles).

Where the magnetically susceptible particles are clustered adjacent the junction in the liquid sample prior to formation of the liquid sample:liquid interface movement of the magnetic field can be paused such that the clustered magnetically susceptible particles are held in the liquid sample adjacent the liquid sample:gas interface. Following formation of the liquid sample:liquid interface the magnetic field can be moved towards the second channel portion causing the magnetically susceptible particles to be drawn across the liquid sample:buffer liquid interface into the buffer liquid.

In an exemplary embodiment, clustering of the magnetically susceptible particles adjacent the junction in the liquid sample occurs either when the liquid sample:buffer liquid interface has already been formed or at the same time as it is formed. In such an arrangement the magnetic field can be moved continuously, without the need for a pause, towards the second channel portion causing the magnetically susceptible particles to be drawn across the liquid sample:buffer liquid interface into the buffer liquid. The step of magnetically moving the magnetically susceptible particles across the liquid sample:second liquid interface into the second liquid can be a predetermined period of time $D^K$ (after forming the liquid sample:second liquid interface, wherein $D^K$ (is in the range 1-60 seconds (e.g. about 1 second or more, less than about 2 seconds, less than about 5 seconds, less than about 10 seconds, less than about 20 seconds, less than about 30 seconds, less than about 40 seconds, less than about 50 seconds, less than about 60 seconds) and in exemplary embodiments is at least about less than 10 seconds (e.g. at least about less than 8 seconds, at least about less than 6 seconds, at least about 5 seconds, at least about 3 seconds, at least about 2 seconds, at least about 1 second, at least about 0.5 seconds).

When drawing the clustered magnetically susceptible particles across the liquid sample:buffer liquid interface the speed of movement of the magnetic field can be increased to a "jump speed" for a short period of time, e.g. at least about 2 seconds (at least about 0.5 s, at least about 1 s, less than about 3 s less than about 4 s). This temporary acceleration in speed of movement of the magnetic field assists in successfully transferring substantially all of the magnetically susceptible particles clustered in the liquid sample adjacent the liquid sample:buffer liquid interface into the buffer liquid. Of a total N magnetically susceptible particles contained in the liquid sample, at least 70% (e.g. at least 80%, at least 90%, at least 95%, at least 98%, at least 99% or 100%) are transferred across the liquid sample:buffer liquid interface into the buffer liquid. The magnetically susceptible particles are moved across the liquid sample:buffer liquid interface within a time $T^N$ of one another, where $T^N$ is 3 seconds (e.g. where $T^N$ is 2.5 seconds, where $T^N$ is 2.0 seconds, where $T^N$ is 1.5 seconds, where $T^N$ is 1.0 seconds, where $T^N$ is 0.5 seconds). In exemplary embodiments the direction of movement of magnetically susceptible particles across the liquid sample:liquid interface is substantially orthogonal to the direction of flow of second liquid when forming the interface. The direction of movement can be parallel to the major longitudinal axis of the first and/or second channel portions.

Once the magnetically susceptible particles have transferred into the buffer liquid, the applied magnetic field is moved towards electrodes 516w, 516c and 516r at the "electrode drag speed" $S^2$.

The applied magnetic field can then be positioned, and optionally focused, to localize the magnetically susceptible particles at the working electrode 516w in the second channel portion 4304.

On reaching the working electrode 516w, measurement of an electrochemical signal is delayed for an incubation period (or turnover time), described below, in which the magnetically susceptible particle:first binding agent:analyte:second binding agent:detectable label complexes can react with substrates and cofactors in the buffer liquid to produce a detectable signal. This incubation period starts on arrival of the complexes at the working electrode. At the end of the incubation period the electrochemical measurement is performed over a measurement period of about 3 seconds (e.g. about 0.5 seconds, about 1 second, about 2 seconds, about 4 seconds, about 5 seconds, about 7 seconds, about 9 seconds, about 10 seconds).

In an exemplary embodiment magnetically susceptible particles transferred into the buffer liquid will include complexes of magnetically susceptible particles:first binding agent:analyte:second binding agent and enzyme label, wherein the enzyme label is capable of reducing or oxidizing one or more enzyme substrates and/or cofactors. This oxidation or reduction provides a detectable signal which can be amperometrically or voltametrically detected at the working electrode. The detected signal is communicated with the meter 400 and its processor by terminals 518w, 518c and 518r.

This detection provides the determination of a characteristic of the buffer liquid, e.g. whether analyte is present in the buffer liquid and/or the amount of analyte present in the buffer liquid and/or an indication of the amount of analyte present in the buffer liquid. The meter 400 can process this information provided by the detected signal to provide an assay result. The processing can involve the step of comparing the amount of analyte determined against a reference amount to produce an assay result. The assay result can take the form of a determination that analyte is present in the sample, the determination of a qualitative or quantitative amount of analyte present in the sample and/or the communication or display of information based on the determination. The assay result can be displayed on the meter. Alternatively, or in addition, information based on the assay result can be displayed, for example a message to the user such as "Seek medical assistance", or "Call 911" or "Take dose [y] of medicament [α]".

Detection of low and high amounts of analyte by a single assay system requires the system to have sensitivity across the detectable range. It is useful for the system to be able to detect a doubling in amount of analyte. This may require detection of a change in sample analyte concentration from, e.g., 50 pM to 100 pM analyte to, e.g., 10,000 pM to 20,000 pM analyte. In one exemplary embodiment determining an amount of analyte detected in the buffer liquid comprises comparing a detected electrochemical current (or potential) against a standard calibration curve. A dataset for the calibration curve can be stored on a memory device (e.g. RAM or ROM) in meter 400 and the detected current signal from the working electrodes 516w can be compared against the calibration dataset to provide a determination of an amount of analyte in the buffer liquid. This amount can be displayed on the meter 400 on display 406. The meter 400 can store information describing more than one calibration curve or line. For example, to provide accurate results a linear or log linear calibration curve is preferred (such as that described by Equation 1 above). Calibration data may be linear or have a substantially constant curve over a given range of parameters. When detecting low amounts of analyte (e.g. 1-10 pM NT-proBNP) calibration data may be linear when the electrochemical signal is measured a short time after the magnetically susceptible particles have reached the working electrode (e.g. 1-10 seconds) but may become non-linear when the measurement is made after a longer time period (e.g. 5-10 minutes). For detection of large amounts of analyte (e.g. 10,000 pM NT-proBNP) the calibration data may be linear when the electrochemical signal is detected at a longer time point after the magnetically susceptible particles have reached the working electrode (e.g. 5-10 minutes). Thus, two or more calibration datasets may be provided (e.g. stored in a memory device on meter 400) A dataset may be selected for use in determination of an assay result in accordance with the time point from the beginning of a measurement step at which a signal is detected.

Accordingly, detection of analyte in the buffer liquid may comprise:

(i) measuring at time $T_1$ the electrochemical signal $Q_1$ at the working electrode, (ii) comparing $Q_1$ against a $T_1$ calibration dataset and, where $Q_1$ is within the $T_1$ dataset, using the $T_1$ dataset to determine an amount of analyte in the buffer liquid, (iii) where $Q_1$ does not exist in the $T_1$ calibration dataset, measuring at time $T_2$ the electrochemical signal $Q_2$ at the working electrode, wherein $T_2 > T_1$, (iv) comparing $Q_2$ against a $T_2$ calibration dataset and where a valid comparison of $Q_2$ and $T_2$ is made, determining an amount of analyte in the buffer liquid.

$T_1$, $T_2$, $T_3$, $T_4$ are time points or ranges corresponding the measurement period and starting at T=0 when the magnetically susceptible particles are brought adjacent the working electrode 516w such that determination of analyte in the buffer liquid by detection of an electrochemical signal may commence.

One can repeat one or more of steps (i)-(iv) for times $T_3$, $T_4$ onwards using datasets for each time point ($Q_3$, $Q_4$ ... ) until the measured electrochemical signal fits within the corresponding calibration dataset and a determination of the amount of analyte can be made. The electrochemical signal can be the measured current or potential at the working electrode (as compared with the reference electrode) in accordance with standard electrochemical amperometric or voltametric measurement techniques. The datasets can provide information on amount of analyte in the sample for a given electrochemical current (or potential) detected at the working electrode.

The amount of analyte determined can be a qualitative amount (e.g. the comparison can lead to a qualitative indication—e.g. high, low or medium), or a quantitative amount (e.g. 50 pM analyte).

Meter 400 can be programmed to take electrochemical measurements $Q_1$, $Q_2$, $Q_3$, $Q_4$, . . . from the working electrode 516w (and other electrodes 516r and 516c as necessary) at predetermined time intervals $T_1$, $T_2$, $T_3$, $T_4$ etc and use the processor in meter 400 to compare the detected electrochemical signals against the respective calibration datasets stored on a memory device in the meter 400.

To measure the electrochemical signal at the working electrode 516w the magnetically susceptible particles can be magnetically held at the working electrode for a period of time sufficient to take the measurement. This amount of time should be at least long enough to measure an electrochemical signal $Q_x$ that fits calibration dataset $T_x$ and permits a qualitative or quantitative indication of the amount of analyte in the buffer liquid to be obtained. In an exemplary embodiment movement of magnetically susceptible particles from the junction 4305 to the working electrode 516w is conducted rapidly to minimize the extent of reaction occurring between enzyme label and buffer substrates prior to reaching the working electrode 516w where the reaction can be determined through detection of an electrochemical signal.

The time $T_x$ starts either when the magnetically susceptible particles reach the working electrode, or when measurement at the working electrode 516w is commenced. In an exemplary embodiment measurement at the working electrode commences on arrival of magnetically susceptible particles at the working electrode. In an exemplary embodiment $T_x$ is chosen from one of: at least about 2 seconds, at least about 5 seconds, at least about 10 seconds, at least about 20 seconds, at least about 30 seconds, at least about 45 seconds, at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 12 minutes, at least about 15 minutes or less than about 10 seconds, less than about 20 seconds, less than about 30 seconds, less than about 45 seconds, less than about 1 minute, less than about 2 minutes, less than about 3 minutes, less than about 4 minutes, less than about 5 minutes, less than about 6 minutes, less than about 7 minutes, less than about 8 minutes, less than about 9 minutes, less than about 10 minutes, less than about 12 minutes, less than about 15 minutes, at least about 2-30 seconds, at least about 30-60 seconds, at least about 1-3 minutes, at least about 3-5 minutes, at least about 5-8 minutes, at least about 8-10 minutes, at least about 10-12 minutes, at least about 13-15 minutes, at least about 15-20 minutes.

In an exemplary embodiment, The time taken from the point at which magnetically susceptible particles first cross the liquid sample:buffer interface and enter the buffer to the point at which magnetically susceptible particles reach the working electrode 516w is less than about 60 seconds (e.g. less than about 45 seconds, less than about 30 seconds, less than about 20 seconds, less than about 15 seconds, less than about 10 seconds, less than about 5 seconds, less than about 3 seconds, less than about 2 seconds, less than about 1 second).

DESCRIPTION OF FURTHER EXEMPLARY EMBODIMENT

Detection of NT-proBNP

In an exemplary embodiment, the analyte is N terminal pro-brain natriuretic peptide (NT-proBNP) and the sample material is whole blood from a human. The presence of NT-proBNP is indicative of a cardiac condition (i.e., a physiological condition related to the heart (e.g., a cardiac dysfunction such as heart failure)). Based at least in part on the result of the NT-proBNP determination, the presence of the cardiac condition can be determined. For example, it can be determined whether the human has experienced, is experiencing, or has a tendency to develop heart failure.

Referring to FIG. 1 an assay method 1000 includes a mixture formation step 1010, a reagent/analyte capture step 1020, a complex transport/wash step 1030, a complex determination step 1040 and determining cardiac condition step 1050. In mixture formation step 1010 a mixture including blood from a human and antibody reagents capable of binding to NT-proBNP is formed. In reagent/analyte capture step 1020 antibody reagents form complexes with any NT-proBNP that is present in the sample of blood. In complex transport/wash step 1030 antibody reagent-NT-proBNP complexes formed during the previous step are washed to remove non-complex material and transported to a detection zone. In complex determination step 1040, the presence of antibody reagent-NT-proBNP complexes that have been transported to the detection zone is determined (e.g. qualitatively or quantitatively). In determining cardiac condition step 1050, the cardiac condition of the subject human is determined at least in part on the result of the complex determination step 1040

Assay method 1000 will now be discussed in greater detail.

Figure 65:
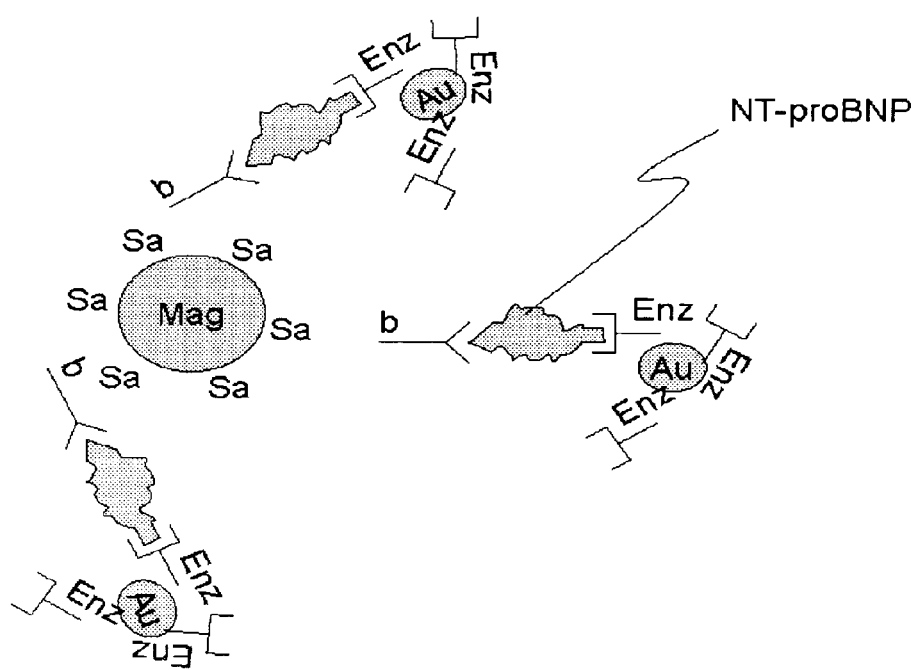
FIG. 65 illustrates a conjugate complex is formed with NT-proBNP.

In mixture formation step 1010 a mixture is formed between reagent materials that are disposed within a reagent zone of an assay device and a sample of human blood sufficient to fill the assay device. A sample of blood can be obtained from a finger stick or a venous puncture. Several reagents are present within the reagent zone of the assay device. The reagents include the following species; a first antibody capable of binding to NT-proBNP, a second antibody capable of binding to NT-proBNP concurrently with the first antibody, an anti-coagulant to prevent clotting of the blood sample within the reagent zone, at least one magnetic particle, an enzyme label that can be used to produce a detectable species, buffer salts, and at least one colloidal particle. The first antibody can be modified with biotin, the second antibody can be conjugated with the enzyme label. The second antibody-enzyme conjugate can be adsorbed onto a colloidal gold sol particle to increase the number of antibody-enzyme conjugates. The magnetic particle can be coated with streptavidin, which can be used to capture the biotin modified first antibody. When the reagents interact with NT-proBNP a conjugate complex is formed, which can be represented stylistically in FIG. 65.

The streptavidin coated magnetic particle can accommodate a number of biotin modified antibodies. The biotin modified first antibody binds to a first unique region of NT-proBNP. The second antibody-enzyme conjugate binds to a second unique region of NT-proBNP. Second antibody-enzyme conjugate is provided pre-associated with gold sol particles thus increasing the number of enzyme labels that become part of the NT-proBNP antibody complex. In an exemplary embodiment a first monoclonal antibody, clone 15F11 was biotin modified, and a second antibody, clone 24E11 was conjugated with HRP.

Buffer salts present in the reagent zone control the pH of the mixture to give a pH value that favours the formation of complexes. An anticoagulant that does not interfere with the formation of NT-proBNP antibody complexes is also included to prevent the sample of blood from coagulating within the reagent zone and therefore reducing the likelihood that complexes could be transported from the reagent zone to the detection zone.

In some embodiments the volume of blood required to fill the reagent zone can be obtained from a small number of (e.g. three or less, two or less, one) finger sticks. For example in some embodiments the volume of blood required to fill reagent zone can be obtained from a single finger stick. The volume of blood is typically about 10 µl (e.g. at least about 0.5 at least about 1 µl, at least about 5 µl, at least about 15 µl, at least about 25 µl, at least about 50 µl). In Some embodiments the volume of blood required to fill the reagent zone is about 50 µl or less (e.g. about 40 µl or less, about 25 µl or less, about 15 µl or less, about 10 µl or less, about 5 µl or less). In an exemplary embodiment the volume of blood required to fill the device is 10 µl.

The reagents can be deposited into the reagent zone using a number of known techniques, including for example, dispensing or aspirating from a nozzle, using an electromagnetic valve and servo- or stepper-driven syringe. These methods can deposit droplets or lines of reagents in a contact or non-contact mode. Other methods for depositing reagents include pad printing, screen printing, piezoelectric print head (e.g., ink-jet printing), or depositing from a pouch which is compressed to release reagent (a "cake icer"). Deposition can preferably be performed in a humidity- and temperature-controlled environment. Different reagents can be dispensed at the same or at a different station.

Fluorescent or coloured additives can optionally be added to the reagents to allow detection of cross contamination or overspill of the reagents outside the desired deposition zone. Product performance can be impaired by cross-contamination. Deposition zones can be in close proximity or a distance apart. The fluorescent or coloured additives are selected so as not to interfere with the operation of the assay device, particularly with detection of the analyte.

After deposition, the reagents are dried. Drying can be achieved by ambient air drying, infrared drying, infrared drying assisted by forced air, ultraviolet light drying, forced warm air, controlled relative humidity drying, or a combination of these.

Reagent/analyte capture step 1020 includes forming complexes between the reagents and NT-proBNP contained within the sample of blood. When a sample of blood is applied to the assay device, the dried reagents initially form an inhomogeneous mixture with the blood. Within a short interval of time, e.g. at least about 1 second, at least about 5 seconds, at least about 20 seconds, at least about 60 seconds, the reagents become sufficiently hydrated that they begin to interact with the sample. The anticoagulant disperses through the sample to prevent clot formation and therefore maintain the sample in a fluid state. The buffer salts disperse through the sample to maintain the pH of the sample to a desirable value that favours formation of antibody-analyte complexes. The pH value is maintained at the pH of blood, which is about 7.4, for example the pH may be maintained within a range of between about pH 7.2 and about pH 7.6 (e.g. about 6.9 or more, about 7.0 or more, about 7.1 or more, about 7.2 or more, about 7.3 or more, about 7.4 or more, about 7.5 or more) (e.g. about 8.0 or less, about 7.9 or less, about 7.8 or less, about 7.7 or less, about 7.6 or less, about 7.5 or less, about 7.4 or less). The first and second antibodies bind to NT-proBNP and form complexes. The biotin labelled first antibody binds to the streptavidin coated magnetic particle(s). The enzyme labelled second antibody is pre-mixed with gold sol prior to deposition within the reagent zone. The sample is allowed to mix with the reagents for a defined interval of time that is sufficient to ensure that adequate complex formation occurs to permit detection of analyte, in this case NT-proBNP. The reagent/analyte capture step 1020 can take at least about 5 minutes (e.g. at least about seconds, at least about 60 seconds, at least about 2 minutes, at least about 4 minutes, at least about 7 minutes, at least about 10 minutes, at least about 15 minutes, at least about 30 minutes). In an exemplary embodiment reagent/analyte capture step 1020 takes 10 minutes.

In some embodiments a magnetic field can be applied to reagent zone. The magnetic field can be used to manipulate the magnetic particle(s) within the reagent zone. The magnetic particle(s) can be oscillated/moved within the reagent zone to cause agitation of the blood sample. The magnetic particle(s) can thus be used to mix the reagents with the sample and increase the likelihood that target analyte, NT-proBNP, forms complexes with the first and second antibodies.

Complex transport/wash step 1030 includes moving the NT-proBNP antibody complexes from the reagent zone to the detection zone. The assay device includes reagent zone, in which the sample reacts with the reagents, an interface zone, which provides an interface between the reagent zone and the detection zone, and a detection zone in which the analyte (NT-proBNP) present in the sample is measured (either qualitatively or quantitatively). The detection zone is actively filled with a buffer solution during the course of a sample assay. Buffer is released from a reservoir at a predefined time after sample has been applied to the assay device. Buffer solution fills the detection zone and the interface zone. When buffer solution is delivered into the interface zone, the buffer forms a liquid-liquid interface with the sample in the reagent zone (as will be described in more detail below). Excess buffer solution moves in to an overflow channel. When buffer has made contact with and formed an interface with the sample there is a continuous liquid path through the microfluidic network of the assay device. The reagent/analyte complex can thus be moved along the length of the assay device supported in a continuous liquid stream.

A magnetic field can be used to manipulate the reagent/analyte complex within the assay device. The reagent/analyte complex can be drawn along the reagent zone, through the interface zone to the detection zone by a moving magnetic field. In some embodiments the magnetic field can be a permanent magnet on a drive mechanism that tracks a path parallel to and beneath the microfluidic network in the assay device. The path of the magnet moves in a direction that transfers magnetically susceptible complexes from the reagent zone to the detection zone. In other embodiments the magnetic field can be an electromagnetic field, which can produce a magnetic field gradient that will cause the magnetically susceptible complexes to move within the assay device from the reagent zone to the detection zone.

When reagent/analyte complexes form within reagent zone during reagent/analyte capture step 1020 it is possible for other sample components to become trapped or associated with the so formed complexes. Such extraneous material could interfere with the detection of target analyte, NT-proBNP, and it is therefore desirable to minimise the amount of extraneous material associated with complexes prior to complex determination step 1040. At this stage enzyme labelled second antibody that is not associated with NT-proBNP and first antibody magnetic particle(s) is considered extraneous material. It is desirable to reduce to a minimum any extraneous material prior to complex determination step 1040. When reagent/analyte complexes are transported across the sample-buffer interface into the interface zone under the influence of a magnetic field, buffer may be flowing in a direction opposite the direction of movement of the reagent/analyte complexes. Buffer can be continually delivered through detection zone, across interface zone, and into an overflow while complexes are transferred from reagent zone into detection zone. The counterflow of buffer over the reagent/analyte complexes effectively separates extraneous material from the magnetically susceptible complexes. Extraneous material is thus transported away from the detection zone towards the overflow. Magnetically susceptible complexes can thus be transported to detection zone with minimal extraneous material associated therewith.

During complex determination step 1040 any magnetically susceptible reagent/analyte complexes that have been transferred to the detection zone can be measured. In an exemplary embodiment the detection zone includes electrodes that can be used to perform an electrochemical analysis of the sample. The enzyme labelled antibody that is part of reagent/analyte complex can convert a substrate present in the buffer used to fill the detection zone. The substrate can be converted from a first form that is not detectable to a second form that is detectable. A measurement electrode within the detection zone can be used to measure the detectable form of the substrate. For example, an amperometric measurement can be made, in which a working electrode is polarised at a certain potential versus a reference electrode e.g. a sliver/silver chloride (Ag/AgCl) reference electrode. For example, potassium ferricyanide can be converted (reduced) to potassium ferrocyanide by glucose oxidase during the conversion of glucose to gluconic acid. Any potassium ferrocyanide formed can be measured at about +400 mV vs Ag/AgCl as a positive current. The ferrocyanide is re-oxidised back to ferricyanide by the working electrode. An electroactive species can be oxidised, in which case it loses electrons to the electrode, or reduced, in which case it receives electrons from the electrode. The transfer of electrons between the electrode and the electroactive substance results in a measurable current, which may be a positive or negative current.

An amperometric measurement of an electroactive substance can be used to construct a calibration line. A known amount of substance yields a unique current, which can be described by the equation (Eq. 1) $y=mx+c$, where y represents the measured current, x represents the concentration of substance, m is the gradient of the line and c is the intercept of the line on the y-axis. Thus the measured current can be used to determine the concentration of an unknown amount of substance in solution following rearrangement of Eq. 1 to give (Eq. 2) $x=(y-c)/m$.

The buffer contained within the reservoir of the assay device includes a buffer salt and a substrate for the enzyme. The buffer salt buffers the pH to provide an environment suitable for the enzyme to convert the substrate to a product which can be detected. For example, the buffer salt is an acetate buffer (e.g., sodium acetate). In embodiments, the buffer can include at least about 100 mM sodium acetate (e.g., at least about 110 mM sodium acetate). In embodiments, the buffer can include about 150 mM sodium acetate (e.g., about 135 mM sodium acetate). In an exemplary embodiment, the buffer salt includes about 125 mM sodium acetate (e.g., made to pH4.0 by addition of 125 mM sodium acetate with 125 mM acetic acid). The buffer solution can also contain a chloride salt to stabilise the electrochemistry of the reference electrode during analysis (e.g. potassium chloride (KCl)). In some embodiments the chloride salt can include at least about 100 mM KCl (e.g. at least about 125 mM KCl). In some embodiments the chloride salt can be at least about 200 mM KCl (e.g. at least about 175 mM KCl). In an exemplary embodiment the chloride salt include 150 mM KCl. The buffer solution can also include a detergent to reduce the likelihood of antibody complexes from adhering to the internal surfaces of microfluidic network 508. In some embodiments the buffer can contain at least about 0.05% (v/v) Tween-20™, (e.g. at least about 0.075% (v/v) Tween-20™). In some embodiments the buffer can contain at least about 0.25% (v/v) Tween-20™, (e.g. at least about 0.15% (v/v) Tween-20™). In an exemplary embodiment the buffer solution includes 0.1% (v/v) Tween-20™. The buffer also includes substrate for the enzyme label, which in the case of horse radish peroxidase is 2,2'-azino-bis(3-ethylbenzthiazoline-6-sulphonic acid) (ABTS) and hydrogen peroxide ($H_2O_2$). In some embodiments the buffer contains at least about 5 mM ABTS and at least about 5 mM $H_2O_2$ (e.g. at least about 7.5 mM ABTS and at least about 7.5 mM $H_2O_2$). In some embodiments the buffer contains at least about 15 mM ABTS and at least about 15 mM $H_2O_2$. (e.g. at least about 12.5 mM ABTS and at least about 12.5 mM $H_2O_2$). In an exemplary embodiment the buffer includes 10 mM ABTS and 10 mM $H_2O_2$. The buffer solution has a final pH equal 4.2 (e.g. a pH at least about 3.8, a pH at least about 4.0) (e.g. a pH of 4.6 or less, a pH of 4.4 or less).

The enzyme label that is conjugated to second antibody can be horse raddish peroxidase (HRP), for example. HRP catalyses the conversion of hydrogen peroxide and ABTS to water and oxidised-ABTS. Any oxidised-ABTS that is produced can be measured electrochemically at a working electrode. Therefore during complex determination step 1040 any NT-proBNP antibody complexes that have been transported through the microfluidic network of assay device can be measured according to the amount of oxidised-ABTS that is produced in the proximity of a measurement electrode. The measured current is proportional to the amount of oxidised-ABTS according to Eq. 2 and hence the measured current is proportional to the amount of NT-proBNP in the complexes that have been transported to the electrode.

In determining cardiac condition step 1050, the measurement result obtained during complex determination step 1040 is used to determine the status of the patient. An elevated measurement result can indicate that a patient is experiencing or has recently experienced heart failure. An elevated result is one that is greater than a level that would be measured in a cross section of a population known not to be experiencing heart failure.

In determining a cardiac condition step 1050 a user of assay device can be presented with information. If the user is qualified to make a clinical judgment (such as a medical doctor) the information might be different compared with a non qualified person, such as a patient performing a self-test measurement. The information produced following a test can be classified into groups according to the qualification of the user. In a first group information might be a positive or negative indicator, e.g. the measurement result is or is not indicative of heart failure. In a second group information might be a numerical value indicative of the amount of analyte present in the sample. In a third group information might be presented as one or more "textual prompts", for example "contact your health care professional", "take an additional tablet", "take a nap". Thus in determining a cardiac condition step 1050 the application of measurement data obtained during complex determination step 1040 will differ according to the end user of the information. A health care professional will typically want numerical data that will facilitate a prognosis. An end user will typically want reassurance that "the way the feel" is a consequence of (i) an unrelated issue, e.g. indigestion or (ii) occurrence or re-occurrence of heart failure, in which case they will be prompted to dial 911, for example.

The assay device used in assay method 1000 will now be described in more detail with reference to FIGS. 2-11.

Referring to FIG. 2 meter 400 is shown along with assay device 500. Meter 400 has a port 402 that receives assay device 500. A user of meter 400 inserts an assay device 500 through port 402 prior to performing an analysis of a sample. Meter 400 has an interface 406 that is used to convey appropriate information to a user during the course of performing a measurement. When a user inserts assay device 500 into meter 400 through port 402, interface 406 presents the user with information. For example information that describes (i) how to apply a sample, (ii) the value of a measurement result, (iii) what to do if a certain measurement result is obtained, may be presented.

Meter 400 is configured to operate assay device 500 when assay device 500 has been inserted through port 402. Meter 400 includes a liquid reservoir actuator 408, a magnetic actuator 410, electrochemical detector 412, and a processor 414. Reservoir actuator 408 is configured to actuate reservoir 507 of device 500, as will be discussed with reference to FIG. 8. Magnetic actuator 410 is configured to manipulate (e.g., move and/or position) magnetic reagent 513a within microfluidic network 508 of assay device 500. Electrochemical detector 412 is configured to determine the presence of analyte transported to electrodes 516w, 516r, 516c by magnetic reagent 513a. Electrochemical detector 412 includes electrical contacts 416w, 416c, 416r, which respectively communicate with electrical contacts 518w, 518r, 518c of device 500 when received within meter 400. Processor 414 is in operable communication with reservoir actuator 408, magnetic actuator 410, electrochemical detector 412, electrical contacts 416w, 416c, 416r, and interface 406. Interface 406 is configured to display information (e.g., device status and/or assay result) to a user.

In use, assay device 500 is inserted into meter 400 via port 402. A sample, e.g. a blood sample, is applied to inlet 510 of assay device 500. An amount of the sample (e.g., at least about 10 µl) moves into microfluidic network 508 by capillary action. The blood sample interacts with reagents in reagent zone 512. Target analyte is then transported to detection zone 516 where an electrochemical signal is recorded. Target analyte interacts with electrodes 516w, 516r, 516c and a signal is detected by electrochemical detector 412. Processor 414 interprets the signal detected by electrochemical detector 412 and displays information to a user on interface 406.

A user of meter 400 can review the results of historical measurements by activating meter 400 using switch 404. Display 406 will display various data. For example, the date and time of measurement, the level of analyte measured, what the user had been doing prior to making the measurement, what medication the user had taken, could be stored in the meter when a user conducts a test. Thus a user of meter 400 can use the historical data to facilitate improved management of their condition.

Referring now to FIGS. 3 and 4, assay device 500 includes composite 501 that defines a microfluidic network 508. In one exemplary embodiment composite 501 includes first, second and third substrates 502, 504, 506 respectively. Microfluidic network 508 includes one or more zones, including reagent zone 512 which is in communication with detection zone 514 at interface zone 522. Microfluidic network 508 also includes sample inlet 510 in communication with a reagent zone 512 and a buffer inlet 520 in communication with a detection zone 514. Detection zone 514 is in communication with a reservoir 507 via buffer inlet 520. Interface zone 522 contains a capillary stop 530, which acts to contain a sample within reagent zone 512. Microfluidic network 508 has an overflow channel 524 in communication with interface zone 522. Overflow channel 524 has a vent 526 through first substrate 502. Overflow channel 524 receives buffer from reservoir 507 that has moved through detection zone 514 and interface zone 522.

Sample inlet 510 defines a region that receives a sample, for example a blood sample, and transfers the sample into reagent zone 512. Reagent zone 512 has a width of at least about 2.5 mm (e.g. at least about 0.5 mm; at least about 2 mm; at least about 4 mm; at least about 8 mm), a height of at least about 0.15 mm (e.g. at least about 0.04 mm; at least about 0.08 mm; at least about 0.1 mm; at least about 0.2 mm; at least about 0.4 mm) and a length of at least about 26.7 mm, (e.g. at least about 10 mm; at least about 15 mm; at least about 20 mm; at least about 30 mm; at least about 50 mm) which defines a volume of at least about 10 µl (e.g. at least about 2 ul; at least about 5 ul; at least about 7.5 ul; at least about 15 µl; at least about 20 µl). A sample is drawn in to reagent zone 512 by capillary forces and the sample moves into reagent zone 512 until the sample reaches capillary stop 530. Once a sample has reached capillary stop 530, the changes in capillary force between the sample zone and the buffer zone are sufficient that no further sample is drawn into reagent zone 512. Typically a pressure difference of at least about 4 millibars (e.g. at least about 2 millibars; at least about 6 millibars) will cause the sample to stop flowing when it reaches the capillary stop. A capillary stop can be achieved by introducing a change in channel dimensions, or by introducing a hydrophobic patch (altering the contact angle of the surface), for example, such that flow of fluid along the channel is impeded. The pressure difference required to stop flow at the junction can be defined as the pressure that would need to be applied to the advancing liquid front to cause it to stop advancing.

Reagent zone 512 contains first, second, third, and fourth reagents 513r1, 513r2, 513r3, 513r4. Reagent 513r1 is susceptible to a magnetic field. As sample is drawn in to reagent zone 512 by capillary forces, reagents 513r1, 513r2, 513r3, 513r4 initially mix with the sample to form an inhomogeneous mixture. A magnetic field can be used to agitate reagent 513r1 and cause reagent 513r1 to move within the sample. Thus reagent 513r1 may be used to disperse and mix the reagents 513r1, 513r2, 513r3, 513r4 within the enclosed sample volume to enhance the distribution of each reagent throughout the sample and thereby increase the likelihood that a specific component of the sample is contacted by one or more of reagents 513r1, 513r2, 513r3, 513r4. Reagents 513r1, 513r2, 513r3, 513r4 will interact with the sample for a defined interval of time (e.g. at least about 5 s; at least about 30 s; at least about 2 min; at least about 5 min; at least about 10 min) to form a complex with a component of interest within the sample.

FIG. 4 depicts the respective layers used to form composite 501. First substrate 502 has a first major surface and a second major surface with a width w1, length l1 and thickness t1. One major surface of first substrate 502 includes microfluidic network 508. Another major surface of first substrate 502 includes reservoir 507 and buffer inlet 520. First substrate 502 can be formed from a hydrophobic material such as polystyrene or polycarbonate. First substrate 502 can also be formed from a hydrophilic material such as polyester. First substrate can be formed by injection moulding, hot embossing, laser ablation, etching, milling. The width w1 can be at least about 25 mm (e.g. at least about 15 mm; at least about 20 mm; at least about 30 mm; at least about 50 mm). The length l1 can be at least about 100 mm (e.g. at least about 50 mm; at least about 75 mm; at least about 125 mm; at least about 150 mm; at least about 200 mm) The thickness t1 can be at least about 2 mm (e.g. at least about 0.5 mm; at least about 0.75 mm; at least about 1.5 mm; at least about 2.5 mm; at least about 5 mm).

Reagent zone 512 includes reagents 513r1, 513r2, 513r3, 513r4, which can be applied to the major surface of first substrate 502 that includes microfluidic network 508. Each respective reagent 513r1, 513r2, 513r3, 513r4 can be applied to the surface of first substrate 502 within the confines of the region that represents reagent zone 512.

When substrate 502 has hydrophobic characteristics the likelihood that reagents will migrate away from the location to which they were applied is negligible. When substrate 502 has hydrophilic characteristics there is increased likelihood that reagents might migrate from the location to which they were applied. Reagents can be applied by a process of microspotting, inkjet printing, pipetting, slot dye printing, or the like, which methods of deposition allow accurate and controlled dosing of each respective reagent. Reagents 513r1, 513r2, 513r3, 513r4 can be applied in discrete areas such that they are physically distant or they can be applied as a laminate or as interspersed dots. Reagents can be formulated to facilitate rapid solubilisation upon contact with a sample.

Second substrate 504 has a first major surface and a second major surface which includes an opening with the profile of microfluidic network 508. Substrate 504 has a width w1, a length l1 and a thickness t2. Thickness t2 can be at least about 50 microns (e.g. at least about 20 microns; at least about 40 microns; at least about 60 microns; at least about 100 microns). Second substrate 504 has adhesive characteristics and can be used to physically attach first substrate 502 to third substrate 506. Second substrate 504 can be a single material or a composite material. For example second substrate can be a double sided adhesive layer which includes a carrier layer onto which is disposed one each major surface an adhesive layer. An adhesive layer can be a pressure sensitive adhesive, which will adhere to another substrate when pressure is applied to the compress the adhesive layer against the substrate. Adhesive layer can be a heat sensitive adhesive, in which case elevated temperature and pressure are required to bond the adhesive to a substrate. Second substrate 504 can have a hydrophobic or a hydrophilic characteristic. When second substrate 504 is a composite material on a carrier layer one major surface can be a pressure sensitive adhesive and the other major surface can be a heat sensitive adhesive. When second substrate 504 is a composite with an inner carrier layer each major surface can be a pressure sensitive adhesive or heat sensitive adhesive as required. The profile of microfluidic network 508 is provided in second substrate 504. When second substrate 504 is applied to first substrate 502 the profile of microfluidic network 508 is registered over first substrate 502.

In some embodiments first substrate 502 does not include microfluidic network 508. In which case second substrate 504, which includes the profile of microfluidic network 508, defines the outline of microfluidic network 508 when it is bonded between first substrate 502 and third substrate 506.

Third substrate 506 has a first major surface and a second major surface, with a width w1, a length l1 and a thickness t3. On one major surface is disposed a conductive network 509 that defines a series of one or more electrodes and terminals. Conductive network 509 can be formed by a process of screen printing of a conductive paste, for example a carbon paste, a gold paste, a silver paste, a platinised carbon paste. Conductive network 509 can also be formed by a process of photolithography, photogravure, laser ablation, laser etching to define a pattern in a metallic or metallised film. Metallic or metallised films can be formed by sputtering, electroplating, or rolling.

Conductive network 509 can include one or more independent conductive traces that connect an electrode that is intended to make contact with a fluid in microfluidic network 508 with a detector and/or processor in meter 400. An electrode might be used to measure a substance or parameter of interest within a sample applied to assay device 500. A substance of interest can include a biomarker indicative of a cardiac condition, such as for example NT-proBNP. A parameter of interest could be a haematocrit value, the percentage of red blood cells within the sample.

Lamination of first, second and third substrates 502, 504, 506, to yield composite 501 involves registration of each respective layer with respect to the other. For example, first substrate 502 and second substrate 504 are placed together such that the profile of microfluidic network formed in first substrate 502 is aligned with the profile of microfluidic network 508 in second substrate 504. Third substrate 506 is then placed onto second substrate 504 such that conductive network 509 and in particular first, second and third electrodes 516w, 516r, 516c are correctly aligned over detection zone 516. FIG. 5 represents a plan view from above of assay device 500 and indicates the spatial location of the various features of the device. Microfluidic network 508 is defined by a series of dimensional parameters; length l2, length l3, length l4, length l5, length l6, width w2, width w3, width w4, width w5, width w6, area a1, distance d1.

Sample inlet 510 has an area a1 of at least about 1.57 mm$^2$ (e.g. at least about 1 mm$^2$, at least about 1.25 mm$^2$, at least about 1.75 mm$^2$, at least about 2 mm$^2$), which is defined by distance d1 and width w4. Width w4 is at least about 2.5 mm (e.g. at least about 1 mm, at least about 1.5 mm, at least about 2 mm, at least about 3 mm, at least about 5 mm) and distance d1 is at least about 1.24 mm (e.g. at least about 1 mm; at least about 1.15 mm, at least about 1.5 mm, at least about 2 mm).

Reagent zone 512 has a minor portion with a length l3 and width w3, and a major portion with a length l2 and a width w2 that terminates at capillary stop 530. Length l3 is at least about 2 mm (e.g. at least about 1 mm, at least about 1.5 mm, at least about 2 mm, at least about 3 mm, at least about 5 mm) and width w3 is at least about 0.45 mm (e.g. at least about 0.1 mm, at least about 0.3 mm, at least about 0.3 mm, at least about 0.5 mm, at least about 0.6 mm). Length l2 is at least about 25 mm (e.g. at least about 10 mm, at least about 15 mm, at least about 20 mm, at least about 30 mm, at least about 50 mm) and width w2 is at least about 2.5 mm (e.g. at least about 1 mm, at least about 1.5 mm, at least about 2 mm, at least about 3 mm, at least about 5 mm).

Interface zone 522 has a length l7 and a width w5, and includes chamfer 532 and capillary stop 534. Length l7 is at least about 4.9 mm (e.g. at least about 2.5 mm, at least about 4 mm, at least about 6 mm) and width w5 is at least about 11 mm (e.g. at least about 6 mm, at least about 8 mm, at least about 10 mm, at least about 12 mm, at least about 15 mm). Interface zone 522 will be described in more detail with reference to FIG. 6.

Detection zone 514 has a length l4, length l5 and width w6. Length l4 is at least about 53 mm (e.g. at least about 35 mm, at least about 40 mm, at least about 45 mm, at least about 55 mm, at least about 65 mm), length l5 is at least about 14.6 mm (e.g. at least about 10 mm, at least about 20 mm, at least about 25 mm, at least about 30 mm) and width w6 is at least about 2.5 mm (e.g. at least about 1 mm, at least about 1.5 mm, at least about 2 mm, at least about 3 mm, at least about 5 mm) Length l5 represents the distance from capillary stop 530 to measurement electrode 516w. Length l6 represents the distance between buffer inlet 520 and capillary stop 530.

Prior to addition of a sample to assay device 500, microfluidic network 508 is filled with a gas, for example air. When a sample is applied to application zone 510, the sample is drawn in to reagent zone 512 by capillary forces. The gas within reagent zone 512 is expelled via interface zone 522 as liquid moves into and through reagent zone 512.

The back pressure experienced by the advancing liquid front is negligible compared with the capillary force that causes the meniscus (the liquid-gas interface) to advance along the capillary channel. Thus as the meniscus moves further along the reagent zone, driving the gas ahead of it, additional fluid is drawn in from sample zone 510. As the fluid within reagent zone 512 reaches capillary stop 530, the difference in pressure on either side of the capillary stop is sufficient to halt the flow of liquid. A pressure difference of at least about 4 millibars is sufficient to prevent liquid crossing capillary stop 530 into moving interface zone 522. The liquid expels no further air from the channel.

Capillary stop 530 is configured such that the effective back pressure applied to the liquid front is greater on the detection zone 514 side of the capillary stop than reagent zone 512 side. The driving force on the reagent zone 512 side of the capillary stop is lower than the backpressure exerted by the detection zone 514 side of the capillary stop. When fluid approaches capillary stop from detection zone 514, capillary stop 530 would not impede the flow of fluid into reagent zone 512, since the capillary pressure is greatest on the side of the capillary stop from which the fluid is approaching. Whereas when fluid approaches capillary stop 530 from the reagent zone 512, a sample gas interface forms at the capillary stop.

Detection zone 514 includes first, second and third electrodes 516w, 516r, 516c respectively. First, second and third electrodes 516w, 516r, 516c are in communication with terminals 518w, 518c, 518r. Terminals 518w, 518c, 518r interface with reader 600 as described above with reference to FIG. 2. When a sample has been applied to assay device 500 and sufficient time has passed to allow reagents 513r1, 513r2, 513r3, 513r4 to interact with the sample and form a complex between the reagents and the analyte (NT-proBNP), a buffer solution is introduced into detection zone 514 from reservoir 507. Reservoir 507 is pressurised by reservoir actuator 408 under control of processor 414 (as will be described in greater detail with reference to FIG. 8). Buffer is driven from reservoir 507 at a rate that reduces the likelihood of air bubbles being trapped within microfluidic network 508 (e.g. at a flow rate of at least 1uls; at least 5 ul/s; at least 10 ul/s). In an exemplary embodiment buffer initially fills detection zone 514 from the opposite end of assay device 500 to which sample is applied. An advancing buffer gas (e.g. air) interface moves uniformly along the edge walls of detection zone 514 towards capillary stop 530. The gas contained within detection zone 514 is expelled from assay device 500 through vent 526 within overflow channel 524.

Interface zone 522 includes capillary stop 530 which controls the movement of sample into microfluidic network 508. Interface zone 522 also includes chamfer 532 and capillary stop 534. Chamfer 532 and capillary stop 534 permit controlled movement of buffer through interface zone 522. When the advancing buffer gas interface reaches interface zone 522, capillary stop 534 retards the movement of the advancing buffer front along one edge wall of microfluidic network 508. Capillary stop 534 thus acts to steer the buffer gas interface around the corner in which capillary stop 534 is located. The advancing buffer gas interface thus moves down chamfer 532 and along the edge of microfluidic network 508 in which capillary stop 530 is formed. Buffer moves transversely across the sample gas interface held at capillary stop 530 to form a sample-buffer (e.g. liquid-liquid) interface. The sample-buffer interface is formed in such a way that retention of air bubbles at the interface is minimised. Once a sample buffer interface has been formed, excess buffer moves in to overflow 524 until it reaches vent 526.

The formation of a bubble free liquid-liquid interface between the sample of blood in reagent zone 512 and the buffer in interface zone 522 is achieved by the design of the interface as will be described with reference to FIG. 6, which shows an expanded perspective view of interface zone 522. FIG. 6 depicts the various aspects of interface zone 522 that enable formation of a stable junction between blood and buffer.

Referring to FIG. 6, on the left hand side as drawn, reagent zone 512 has a width w2 and a height h1 of at least about 0.15 mm (e.g. at least about 0.075 mm, at least about 0.9 mm, at least about 0.125 mm, at least about 0.175 mm, at least about 0.2 mm), which terminates at capillary stop 530. Reagent zone 512 has an edge 528 that represents an opening that forms the transition from reagent zone 512 into interface zone 522. Edge 528 has a square profile with a negligible radius of curvature (e.g. the angle between the two edges is as close to 90 degrees as is possible). Edge 528 is sufficiently well defined that the likelihood of blood breaching capillary stop 530 is negligible. Blood is thus prevented from crossing the interface and entering the gas filled interface zone 522.

Interface zone 522 includes capillary stop 530, capillary stop 532, chamfer 534, corner 536. Interface zone 522 has a height h2 of at least about 0.45 mm (e.g. at least about 0.2 mm, at least about 0.3 mm, at least about 0.5 mm, at least about 0.75 mm) and a width w5. Corner 536 is at least about 3 mm (e.g. at least about 1.5 mm, at least about 4.5 mm) from the longitudinal centre line of reagent zone 512, such that there is a clear and distinct separation between heights h1 and h2 to reduce the likelihood of liquid in reagent zone 512 breaching edge 528 to enter interface zone 522. Chamfer 534 provides a smooth transition between h3 of detection zone 516 and h2 of interface zone 522 which leads into overflow channel 524. Detection zone 516 has a height h3 of at least about 0.25 mm (e.g. at least about 0.1 mm, at least about 0.2 mm, at least about 0.4 mm, at least about 0.5 mm) When buffer approaches interface zone 522 from detection zone 516 (flowing right to left as drawn) the meniscus (buffer-gas interface) contacts capillary stop 532. The moving buffer meniscus is retarded by capillary stop 532 on one wall of the capillary channel at the transition between detection zone 516 and interface zone 522. However, the meniscus continues to move along the wall opposite capillary stop 532 towards corner 536. As buffer approaches corner 536, capillary stop 532 continues to retard the flow of buffer into interface zone 522. The advancing buffer meniscus flows down chamfer 534 and around corner 536 and along the capillary wall that includes edge 528 and capillary stop 530. Thus the buffer meniscus moves across the end of reagent zone 512 and in so doing contacts the liquid (e.g. blood) that is within reagent zone 512. When the buffer meniscus has moved across the end of reagent zone 512 the effect of capillary stop 532 is overcome because buffer in interface zone 522 with height h2 contacts the buffer held at capillary stop 532 (with height h3) from the opposite side of capillary stop 532, thereby neutralising the pressure differential. Buffer then flows into overflow channel 526.

Referring now to FIG. 7 which shows a cross sectional view through line A-A' of FIG. 6, represents the profile of interface zone 522. FIG. 7 shows the respective heights h1, h2, h3 of microfluidic network 508 through the transition from reagent zone 512, interface zone 522 and detection zone 514. When liquid moves into microfluidic network 508 in direction X along reagent zone 512, it approaches edge 528 of capillary stop 530. The difference in height h1 compared with height h2 is such that the capillary force in reagent zone 512 is different to the capillary force in interface zone 522. The capillary pressure exerted by interface zone 522 in direction Y is greater than the capillary force exerted by reagent zone 512 in direction X. Therefore when sample liquid approaches and reaches edge 528 of capillary stop 530 sample flow stops and a liquid gas interface forms. The liquid gas meniscus thus defines one end wall of the volume of liquid that is contained within reagent zone 512. The effect of capillary stop 530 is thus to contain liquid within reagent zone 512. As has been described herein above, other means of controlling the flow of liquid within a channel also exist. One such example is the use of a hydrophobic patch, which may be provided as a ring around the walls of the capillary channel. The characteristics of the hydrophobic material are such that when a liquid approaches the ring of hydrophobic patch it is retarded in much the same way as capillary stop 530. The hydrophobic ring exerts a force in direction Y equivalent to that exerted by capillary stop 530.

Referring now to FIG. 8 which shows a longitudinal cross section through assay device 500, and includes the cross sectional view of FIG. 7. FIG. 8 includes fluid reservoir 507, buffer inlet 520, detection zone 514, interface zone 522, reagent zone 512 and sample inlet 510. FIG. 8 also shows reservoir activator 408. Reservoir activator 408 is urged towards fluid reservoir 507 under control of processor 414 of meter 400 at a defined rate which causes fluid to be released from fluid reservoir 507 via buffer inlet 520, wherein the buffer enters detection zone 514.

When a user correctly inserts assay device 500 into meter 400, processor 414 is actuated to conduct a measurement cycle. Processor 414 causes information relevant to the measurement to be made to be displayed on interface 406. The information includes prompts to apply a sample to assay device 500. When a sample has been applied to assay device 500, detector 412 senses the presence of sample in reagent zone 512 and provides feedback to processor 414. Processor 414 then actuates reservoir actuator 408. After a predefined interval of time from the presence of sample being detected in reagent zone 512, reservoir activator 408 is urged towards and makes contact with reservoir 507. After initial contact is made with reservoir 507, reservoir activator 408 continues to be urged into reservoir 507. Reservoir activator 408 applies pressure to reservoir 507, which is in turn pressed against buffer inlet 520. Buffer inlet 520 has a sharpened element that protrudes towards reservoir 507. Prior to insertion into meter 400, reservoir 507 can be protected by a removable cover that prevents premature rupture and therefore accidental release of fluid from the reservoir. In which case a user would first remove the protective cover before inserting assay device 500 into meter 400. In some instances protective cover may not be provided with assay device 500, and in other instances the protective cover may not require removal prior to insertion of assay device 500 into meter 400.

The movement of reservoir activator 408 towards reservoir 507 under control of processor 414 occurs at such a rate that following initial rupture of reservoir 507 and therefore release of fluid contained therein that fluid is delivered through buffer inlet 520 into detection zone at a controlled and defined flow rate. In an exemplary embodiment buffer is moved through microfluidic network at a flow rate of about 0.5 mL/min (e.g. at least about 0.1 mL/min, a1 least about 0.3 mL/min, about 0.7 ml/min or less, about 0.9 mL/min or less). Fluid is pumped towards interface zone 522 until the meniscus reaches capillary stop 532. The fluid front is then caused to turn about capillary stop 532. The meniscus continues to be pushed around the opposite edge wall of interface zone 522 to capillary stop 532 as reservoir activator is further urged into reservoir 507 under control of processor 414. Once the progressing fluid front has moved across the end of reagent zone 512, thereby forming an interface between the liquid in reagent zone 512 and the fluid that has been pushed from reservoir 507, the fluid is further driven into overflow channel 524 towards vent 526.

In use, a sample (e.g., an amount of mammalian blood obtained from a finger stick or a venous draw) is applied to assay device 500 at sample inlet 510. The blood contains an amount of N-terminal pro-brain natriuretic peptide (NT-proBNP), the analyte. In some cases, the amount of NT-proBNP present in the sample may be so small as to be undetectable; in other cases, the amount of NT-proBNP present in the sample may be zero (i.e., NT-proBNP is absent from the sample).

The sample of blood is drawn into reagent zone 512 by capillary action, where it makes initial contact with and subsequently mixes with reagents 513$r$1, 513$r$2, 513$r$3, 513$r$4. The reagents include, magnetic particles linked to streptavidin, anti-NT-proBNP antibody 15F11 linked to biotin, and horseradish peroxidase (HRP) conjugated to anti-NT-proBNP antibody 24E11 linked to colloidal gold sol with average particle diameter of at least about 40 nm (the antibody-linked enzyme). The reagents are resuspended in solution with the blood, and form a homogeneous mixture. The streptavidin (which is linked to magnetic particles) binds to biotin (which is linked to the anti-NT-proBNP antibody 15F11), thus forming an antibody-magnetic particle complex. The analyte is bound by the antibody-magnetic particle complex and the antibody-linked enzyme, thereby forming a ternary complex. If desired, a magnetic field can be applied such that the magnetic particles undergo an induced motion (e.g., a periodic or oscillatory motion) to promote or enhance resuspension and mixing of the reagents with the sample. In an exemplary embodiment a magnetic field is oscillated beneath reagent zone 512 to mix reagents at a first speed. Antibody complexes are then collected into a common location at a second speed. Complexes are then moved from reagent zone 512 to detection zone 514 at a third speed. First speed can be at least about 100 mm/min, (e.g. at least about 120 mm/min, at least about 140 mm/min). First speed can be about 180 mm/min or less (e.g. about 160 mm/min or less, about 140 mm/min or less). In an exemplary embodiment first speed could be 144 mm/min. Second speed can be at least about 10 mm/min, (e.g. at least about 20 mm/min, at least about 35 mm/min). Second speed can be about 80 mm/min or less (e.g. about 60 mm/min or less, about 40 mm/min or less). In an exemplary embodiment second speed could be 36 mm/min. Third speed can be at least about 70 mm/min, (e.g. at least about 90 mm/min, at least about 110 mm/min). Third speed can be about 150 mm/min or less (e.g. about 130 mm/min or less, about 110 mm/min or less). In an exemplary embodiment third speed could be 108 mm/min.

FIG. 9A shows top and side views of the assay device 500 in the region of interface zone 522 after a sample liquid has been added to sample inlet 510. The sample liquid (e.g., blood) is drawn by capillary action to fill reagent zone 512. Upon reaching capillary stop 530, the liquid forms a meniscus 590. As the sample liquid approaches capillary stop 530 from reagent zone 520, it experiences a sudden increase in the cross-sectional area of the channel at capillary stop 530, where interface zone 522 has a greater depth and width than reagent zone 520. This sudden change in dimensional profile prevents the sample liquid from entering interface zone 522. Any surface tension forces at meniscus 590 exceed any capillary forces that would tend to draw the sample liquid into interface zone 512. At this stage, a liquid-gas interface (i.e., blood-air interface) is formed at meniscus 590. FIG. 9A also illustrates magnetic particles 200 dispersed in the blood.

A magnetic field is applied to reagent zone 512. The applied field can be manipulated (e.g., by moving a permanent magnet relative to the test strip, or by actuating an electromagnetic solenoid) so as to move the magnetic particles 200, and therefore the analyte that has been captured by the antibodies on the magnetic particles. The magnetic particles 200 are moved along reagent zone 512 toward capillary stop 530.

The magnetic field source can be configured to provide a shaped magnetic field. A shaped magnetic field can have magnetic field lines designed to direct magnetic particles toward the detection zone 514. Such a shaped magnetic field can be useful to control the diffusion or migration of magnetic particle complexes. More than one magnetic field source can be provided, particularly when a shaped magnetic field is desired. For example, magnetic field sources can be provided at either end of an assay device, where one is configured to attract magnetic particles and the other to repel magnetic particles. Such a configuration can favour the location of all magnetic particles at one end of the assay device.

FIG. 9B shows top and side views of the device after an applied magnetic field (applied by magnetic field source 210) has drawn magnetic particles 200 toward meniscus 590. The magnetic field source 210 can be configured (e.g., with regard to location, magnetic field intensity and magnetic field shape) so as to retain magnetic particles 200 in proximity to meniscus 590. Magnetic field source 210 can be manipulated such that particles 200 are subject to a magnetic force at meniscus 190 sufficient to resist diffusion away from the magnetic field source.

When the sample has been in contact with reagents 513r1, 513r2, 513r3, 513r4 for a predefined interval of time sufficient to permit formation of complex between the analyte, NT-proBNP, and the respective anti-NT-proBNP antibodies, a second liquid is introduced to assay device 500 via buffer inlet 520. The second liquid contains sodium acetate buffer, hydrogen peroxide substrate, and the redox mediator 2,2'-azino-bis-(3-ethylbenzo-thiazoline-sulfonic acid) (ABTS). The second liquid flows along detection zone 514 under positive pressure applied by reservoir activator 408. The second fluid contacts the blood sample at meniscus 190 to form a liquid-liquid interface. The formation of the liquid-liquid interface facilitates the movement of the magnetic particles conjugate complex from the blood to the second liquid under the influence of magnetic field source 210. The movement of analyte from the blood to the second liquid as part of the magnetic particle conjugate complex, minimises the likelihood that potentially interfering sample components and analytes that are of no interest into get transferred to the second liquid. The magnetic particles and all that is bound to them, including the NT-proBNP (in the form of a ternary complex of NT-proBNP with antibody-magnetic particle complex and antibody-linked enzyme) are transferred to the second liquid in the detection zone 514.

Interface zone 522 can be shaped such that a liquid front of the second liquid flows laterally across meniscus 590, rather than meeting meniscus 590 head-on. FIG. 9C illustrates a plan view from above of assay device 500 in the region of interface zone 522. FIG. 9C represents a time series of profiles indicating the moving liquid front as the second liquid flows from detection zone 514 towards capillary stop 530. In particular, sequential positions of liquid front 211, 212, 213, 214, 215 illustrate how interface zone 512 can be shaped to guide the liquid front of the second liquid so that it flows laterally across meniscus 590 held at capillary stop 530. The lateral movement of the second liquid meniscus 215 across the blood meniscus 590 reduces the likelihood that air bubbles become trapped between the first liquid and second liquid. The presence of air bubbles at the liquid-liquid interface may reduce the efficiency with which magnetic particles are transferred from the blood sample into the second liquid. Therefore it may be desirable to have a bubble free interface to reduce possible reduction in the efficiency of sample transfer.

FIG. 9D shows top and side views of assay device 500 after the second liquid has filled interface zone 512, and formed liquid-liquid interface 220. Liquid front 216 of the second liquid continues to flow through overflow channel 524 towards vent 526. Magnetic particle-analyte complex 200 is transferred across liquid-liquid interface 220 by virtue of the attractive magnetic field applied by source 210. The magnetic particle-analyte complex 200 is progressively moved along detection zone 514 under the influence of magnetic field source 210. The continued flow of the second liquid from buffer inlet 520 through detection zone 514, interface zone 522 and overflow channel 524 after the liquid-liquid interface 220 has been formed can help to wash non-magnetic material away from magnetic particle-analyte complex 200. Such washing can help ensure that only material associated with the magnetic particles is detected by electrodes 516w, 516c, 516r in detection zone 514.

A fluid reservoir 507 incorporated into the test strip can deliver a reaction buffer, and the composition of the buffer can be varied (e.g., sodium acetate, phosphate-citrate, sodium citrate or any other buffer at any suitable concentration or pH). Any suitable liquid can be used instead of a buffer (see, for example, U.S. Patent Application No. 60/736,302, filed Nov. 15, 2005, which is incorporated by reference in its entirety.). In some embodiments reservoir 507 may be provided as a non-integral part of assay device 500, in which case an interface port may be provided that integrates the reservoir 507 with buffer inlet 520.

FIGS. 10A and 10B illustrate the separation of the magnetic particle-analyte complex from the non-magnetic particle associated antibodies across the liquid-liquid interface in greater detail. In FIG. 10A (as in FIG. 9B), magnetic particles 200 are located near meniscus 590 by virtue of the magnetic field applied by magnetic field source 210. Some of magnetic particles 200 are bound to second analyte 240 in an antibody-magnetic particle complex, which in turn is bound to antibody-linked enzyme 230. Because the antibody-linked enzyme in reagent zone 512 is present in excess compared to second analyte 240, some antibody-linked enzyme 250 can remain unbound to target analyte. Magnetic separation helps ensure that unbound antibody-linked enzyme 250 does not reach detection zone 514; in other words, it is only magnetic particle-analyte complex linked enzyme 230 that should arrive at electrodes 516w, 516c, 516r under influence of magnetic field source 210 that contributes to the detectable signal. Thus the detectable signal can be reproducibly related to the amount or concentration of analyte (e.g. NT-proBNP) 240 in the sample.

The analyte can be a biomarker for a condition that afflicts the mammalian body. The term "biomarker" refers to a biochemical in the body that has a particular molecular trait to make it useful for diagnosing a condition, disorder, or disease and for measuring or indicating the effects or progress of a condition, disorder, or disease. For example, common biomarkers found in a person's bodily fluids (i.e., breath or blood), and the respective diagnostic conditions of the person providing such biomarkers include, but are not limited to, ischemia modified albumin "IMA" (source: lack of oxygen to the blood; diagnosis: coronary artery disease), N-terminal truncated pro-brain natriuretic peptide "NT proBNP" (source: stretching of myocytes; diagnosis: congestive heart failure), acetaldehyde (source: ethanol; diagnosis: intoxication), acetone (source: acetoacetate; diagnosis: diet; ketogenic/diabetes), ammonia (source: deamination of amino acids; diagnosis: uremia and liver disease), CO (carbon monoxide) (source: CH2Cl2, elevated % COH; diagnosis: indoor air pollution), chloroform (source: halogenated compounds), dichlorobenzene (source: halogenated compounds), diethylamine (source: choline; diagnosis: intestinal bacterial overgrowth), H2 (hydrogen) (source: intestines; diagnosis: lactose intolerance), isoprene (source: fatty acid; diagnosis: metabolic stress), methanethiol (source: methionine; diagnosis: intestinal bacterial overgrowth), methylethylketone (source: fatty acid; diagnosis: indoor air pollution/diet), O-toluidine (source: carcinoma metabolite; diagnosis: bronchogenic carcinoma), pentane sulfides and sulfides (source: lipid peroxidation; diagnosis: myocardial infarction), H2S (source: metabolism; diagnosis: periodontal disease/ovulation), MeS (source: metabolism; diagnosis: cirrhosis), and Me2S (source: infection; diagnosis: trench mouth).

A reagent zone can also include a second reagent capable of recognizing a desired analyte. The second reagent can recognize the same or a different analyte. The first and second recognition reagents can be selected to recognize the same analyte simultaneously. For example the first and second recognition reagents can each be an antibody that recognizes distinct epitopes of the analyte. In this way, a ternary (i.e., three-component) complex of analyte, first recognition reagent and second recognition reagent can be formed. In general, the first and second recognition reagents do not associate with one another in the absence of analyte. The presence of analyte, however, can associate the first and second recognition reagents together, in a ternary complex. The reagent zones can include further reagents such as redox mediators, substrates for particular enzymes and salts suitable for forming buffer solutions.

The second recognition reagent can be linked to a particle that can induce mobility on the so-formed ternary complex. The particle can be, for example, a polymer microsphere, a metal nanoparticle, or a magnetic particle.

Generally, the detection zones collect the analytes and are the sites of detectable changes. The extent of the detectable changes can be measured at the detection zones. Usually, greater amounts of analytes will result in greater detectable changes; however, the assays can also be configured to produce smaller changes when the analytes are present in greater quantities. The detection zones can collect the analytes by immobilizing them (for example, with a reagent immobilized in the detection zone, where the immobilized reagent binds to the analyte). Alternatively, the detection zone can attract or immobilize a component associated with the analyte. For example, a recognition reagent that binds an analyte and is linked, directly or indirectly, to a magnetic particle can be attracted to a particular detection zone by a magnetic field provided in one or more detection zones.

In some embodiments, one or more of the detection zones include one or more electrodes. The electrodes can be formed of a material selected for electrical conductivity and low reactivity with sample components, for example, silver, gold, aluminum, palladium, platinum, iridium, a conductive carbon, a doped tin oxide, stainless steel, or a conductive polymer. The electrodes in the detection zones (the working electrodes), in conjunction with second electrodes in the reference zones (the reference electrodes) can measure an electrical property of the sample, such as a voltage or a current. Alternatively, the detection zones and the reference zones can each have at least one working electrode and counter electrode. That is, the detection and reference zones can make independent measurements. Optionally, counter electrodes are also included in the assay device. Assay devices including electrodes for measuring electrical properties of a sample are described in, for example, U.S. Pat. Nos. 5,708,247, 6,241,862, and 6,733,655, each of which is incorporated by reference in its entirety.

In some embodiments, the assay device base, assay device lid, or both have a translucent or transparent window aligned with the detection zone. An optical change that occurs in the detection zone can be detected through the window. Detection can be done visually (i.e., the change is measured by the user's eye) or measured by an instrument (e.g., a photodiode, photomultiplier, or the like). In general, the reference zone is similar in nature to the detection zone. In other words, when the detection zone includes an electrode, the reference can likewise include an electrode. When the detection zone is aligned with a window for optical measurement, the reference zone can similarly be aligned with a window for optical measurement. In some embodiments, the reference zone is not adapted to collect analyte. Alternatively, the reference zone is adapted to collect analyte, but performs a different analysis on said analyte. Thus, the detectable change measured in the reference zone can be considered a background measurement to be accounted for when determining the amount of analyte present in the sample.

The sample can be any biological fluid, such as, for example, blood, blood plasma, serum, urine, saliva, mucous, tears, or other bodily fluid. The analyte can be any component that is found (or may potentially be found) in the sample, such as, for example, a protein, a peptide, a nucleic acid, a metabolite, a saccharide or polysaccharide, a lipid, a drug or drug metabolite, or other component. The assay device can optionally be supplied with a blood separation membrane arranged between a sample inlet and the detection zone, such that when whole blood is available as a sample, only blood plasma reaches the detection zone.

The assay device and included reagents are typically provided in a dry state. Addition of a liquid sample to the assay device (i.e., to the capillary channel) can resuspend dry reagents (as described above with reference to assay method 1000).

Referring to FIG. 11A, device 100 includes base 102. Base 102 includes first inlet 110. Inlet 110 is fluidly connected to first fluid flow channel 120. Flow channel 120 extends from inlet 110 to junction 130.

Base 102 also includes second inlet 140. Inlet 140 is fluidly connected to second fluid flow channel 150. Second channel 150 extends from inlet 140 to junction 130. Channels 120 and 150 are fluidly connected to each other at junction 130. Second channel 150 is also fluidly connected to vent 160. Vent 160 is located so that a liquid introduced at inlet 140 fill channel 150 completely. In other words, as the liquid advances from inlet 140 toward junction 130 (e.g., via capillary action), gas in channel 150 escapes via vent 160, so that liquid fills channel 150 without trapping any gas bubbles in channel 150.

First detection zone 170 is located in first channel 120. Detection zone 170 includes electrodes 172, which are electrically connected to leads 174. Similarly, second detection zone 180 is located in second channel 150. Detection zone 180 includes electrodes 182, which are electrically connected to leads 184.

The electrodes can be formed of a material selected for electrical conductivity and low reactivity with sample components, for example, silver, gold, aluminum, palladium, platinum, iridium, a conductive carbon, a doped tin oxide, stainless steel, or a conductive polymer. The electrodes can measure an electrical property of the sample, such as a voltage or a current. Assay devices including electrodes for measuring electrical properties of a sample are described in, for example, U.S. Pat. Nos. 5,708,247, 6,241,862, and 6,733,655, each of which is incorporated by reference in its entirety.

First channel 120 can include one or more reagent zones. A reagent zone includes one or more reagents in a dry state on a surface of channel 120. The reagent zone can be located anywhere along channel 120, such as between inlet 110 and detection zone 170; between detection zone 170 and junction 130; or in the vicinity of detection zone 170. The reagents may be deposited on one or more electrode and on one or more electrode set. The reagents can be deposited on any part of the channels that facilitates interaction with analytes in the sample before detection takes place. When a sample, or other fluid, is introduced to the channels, (for example, by contacting the sample with a sample inlet), liquid can fill the channels and contact the surface of the base, resuspending the reagents deposited on the surface.

Base 102 is covered by lid 104, which seals against a surface of base 102. The seal between base 102 and lid 104 ensures that fluid channels 120 and 150 are liquid-tight. Lid 104 can include through holes at appropriate locations, e.g., at inlet 140 and at vent 160.

FIG. 11B shows a side view of junction 130. First channel 120 includes a region having a first depth 122. The depth of channel 120 at a particular location can be described as the vertical distance from surface of base 102 internal to channel 122 to surface of lid 104 internal to channel 120. Closer to junction 130, channel 120 has a region of decreased depth 132. As can be seen in FIG. 11B, first channel 120 and second channel 150 define a continuous space between base 102 and lid 104. The location of junction 130 (which marks the location where first channel 120 is conceptually distinguished from second channel 150) can therefore be described as the location where region of decreased depth 132 abuts the larger depth of channel 150.

The junction 130 is characterized by the intersection of a small cross-sectional area defined by region of reduced depth 132 in first channel 120 abutting a substantially greater cross-sectional area defined by channel 150. At junction 130, channel 120 has a smaller depth and width than does channel 150. The meeting of channels with substantially different cross-sectional areas can have useful properties in the operation of the device, as will be described below.

The reagent zone in channel 120 can include a reagent for detecting a first analyte and a reagent for detecting a second analyte. For example, when the first analyte is albumin, the first reagent can include a metal ion capable of binding to albumin and capable of electrochemical detection. One such metal ion is cobalt(II), which can be present in the first reagent as a cobalt salt, such as $CoCl_2$.

The reagent for detecting a second analyte can include a magnetic particle and a first recognition reagent that is capable of binding specifically to a desired analyte (such as an antibody to the analyte). The magnetic particle can be linked to the first recognition reagent. The reagent for detecting a second analyte can further include a second recognition reagent that is capable of binding specifically to the same analyte. The first and second recognition reagents can bind to the analyte simultaneously. This second recognition reagent is labeled so as to facilitate detection of the analyte, for example, by being linked to an enzyme that can produce an electrochemical change. For example, if the second analyte is NTproBNP, a reagent zone in first channel 120 can include magnetic particles that are linked to anti-NTproBNP antibodies. The reagent zone can also include a second anti-NTproBNP antibody linked to a redox enzyme, such as glucose oxidase (GOD) or horserasdish peroxidase (HRP). The recognition reagents can be present in excess with respect to the second analyte, for example, there can be a sufficient amount of recognition reagents to bind substantially all of the second analyte, while a portion of each recognition reagent remains unbound.

A magnetic particle is a particle that is influenced by a magnetic field. The magnetic particle can be, for example, a magnetic particle described, in U.S. Patent Application Publication Nos. 20050147963 or 20050100930, or U.S. Pat. No. 5,348,876, each of which is incorporated by reference in its entirety, or commercially available beads, for example, those produced by Dynal AS under the trade name DYNABEADS™. In particular, antibodies linked to magnetic particles are described in, for example, United States Patent Application Nos. 20050149169, 20050148096, 20050142549, 20050074748, 20050148096, 20050106652, and 20050100930, and U.S. Pat. No. 5,348,876, each of which is incorporated by reference in its entirety.

Second channel 150 can also include one or more reagent zones including one or more reagents in a dry state on a surface of channel 150, for example between inlet 140 and detection zone 180, between detection zone 180 and junction 130, or in the vicinity of detection zone 180. The dry reagents can be resuspended upon contact with a liquid, e.g., a buffer. The buffer can be introduced to channel 150 via inlet 140. For example, a reagent zone in channel 150 can include a substrate for the redox enzyme and a redox mediator.

Operation of the Device

A sample (e.g., an amount of mammalian blood obtained via a finger stick) is added to the test strip at inlet 110. The blood contains albumin, the first analyte, some of which may be present as ischemia modified albumin (IMA). The blood also contains an amount of N-terminal truncated pro-brain natriuretic peptide (NTproBNP), the second analyte. In some cases, the amount of NTproBNP present in the sample may be so small as to be undetectable; in some cases, NTproBNP is absent from the sample.

The sample of blood enters channel 120 via capillary action, where it mixes with reagents in the first reagent zone. The reagents in the first reagent zone include cobalt, magnetic particles bound to anti-NTproBNP antibody 7206 (the antibody-linked magnetic particle), and horseradish peroxidase "HRP" conjugated to anti-NTproBNP antibody 15F11 (the antibody-linked enzyme). The reagents are resuspended in solution with the blood, and forming a mixture. In the mixture, a portion of the cobalt can be bound by albumin, while some of the cobalt remains free in solution. The amount of cobalt in the first reagent zone is greater than the cobalt-binding capacity of the sample, such that some cobalt remains free in solution. At the same time, the second analyte is bound by the antibody-linked magnetic particle and the antibody-linked enzyme, thereby forming a ternary complex. If desired, a magnetic field can be applied such that the magnetic particles undergo an induced motion (e.g., a periodic or oscillatory motion) to promote resuspension and mixing of the reagents with the sample.

FIG. 9A shows top and side views of the device after a sample liquid has been added to inlet 110. The sample liquid (e.g., blood) is drawn by capillary action to fill channel 120. Upon reaching junction 130, the liquid forms a meniscus 190. The change in cross-sectional area of the channel at junction 130 does not allow the sample liquid to fill channel 150. Rather, surface tension forces at meniscus 190 exceed any capillary forces that would tend to draw the sample liquid farther into channel 150. Junction 130 thus acts a capillary stop, prevent substantial fluid flow beyond that point. At this stage, a gas-liquid interface (i.e., blood-air interface) is formed at meniscus 190. FIG. 9A also illustrates magnetic particles 200 dispersed in the blood.

An electrochemical analysis is then performed on the first mixture to determine the concentration of cobalt that remains unbound. The presence of IMA in the sample will reduce the cobalt binding capacity of the sample; accordingly, greater concentrations of unbound cobalt can be indicative of the presence of IMA. The assay for IMA may be optimized in accordance with application no. GB 0603049.8, which is incorporated herein by reference.

After the first assay is complete, a magnet field is applied to the channel 120. The applied field can be manipulated (e.g., by moving a permanent magnet relative to the test strip) so as to move the magnetic particles 200, and all components bound to them. The magnetic particles 200 are moved along channel 120 toward junction 130.

The magnetic field source can be configured to provide a shaped magnetic field. A shaped magnetic field can have magnetic field lines designed to direct magnetic particles toward the first or second detection zones. Such a shaped magnetic field can be useful to control the diffusion or migration of magnetic particles and label particles. More than one magnetic field source can be provided, particularly when a shaped magnetic field is desired. For example, magnetic field sources can be provided at either end of an assay device, where one is configured to attract magnetic particles and the other to repel magnetic particles. Such a configuration can favor the location of all magnetic particles at one end of the assay device.

FIG. 9B shows top and side views of the device after an applied magnetic field (applied by magnetic field source 210) has drawn magnetic particles 200 toward meniscus 190. The magnetic field source 210 can be configured (e.g., with regard to location, magnetic field intensity and magnetic field shape) so as to retain magnetic particles 200 in proximity to meniscus 190. Magnetic field source 210 can be manipulated such that particles 200 are subject to a magnetic force at meniscus 190 sufficient to resist diffusion away from the magnetic field source.

A second liquid is then added to the test strip at the second inlet. The second liquid contains sodium acetate buffer, hydrogen peroxide substrate, and the redox mediator 2,2'-azino-bis-(3-ethylbenzo-thiazoline-sulfonic acid) (ABTS). The second liquid flows along the second channel 150 via capillary action to junction 130, where the second fluid contacts the blood sample at meniscus 190 to form a liquid-liquid interface. The formation of the liquid-liquid interface facilitates the movement of the magnetic particles (and all that is bound to them) from the blood to the second liquid, leaving interfering sample components and analytes that are not of interest in the blood in the first channel. Only the magnetic particles and all that is bound to them, including the NTproBNP (in the form of a ternary complex of NTproBNP with antibody-linked magnetic particle and antibody-linked enzyme) are transferred to the second liquid in the second channel 150.

FIG. 9C shows top and side views of the device after the second liquid has been added to second channel 150. Particles 200 have traveled across liquid-liquid interface 220 by virtue of the magnetic field applied by source 210. Particles 200 are located in the vicinity of magnetic field source 210.

A buffer pouch incorporated into the test strip can deliver the reaction buffer, and the composition of the buffer can be varied (e.g., sodium acetate, phosphate-citrate, sodium citrate or any other buffer at any suitable concentration or pH). Any suitable liquid can be used instead of a buffer (see, for example, U.S. Patent Application No. 60/736,302, filed Nov. 15, 2005, which is incorporated by reference in its entirety.).

FIGS. 10A and 10B illustrate magnetic separation across the liquid-liquid interface in greater detail. In FIG. 10A (as in FIG. 9B), magnetic particles 200 are located near meniscus 190 by virtue of the magnetic field applied by source 210. Some of magnetic particles 200 are bound to second analyte 240, which in turn is bound to detectable particles 230. Because the detectable particles in channel 120 are present in excess to second analyte 240, some detectable particles 250 remain unbound. Magnetic separation helps ensure that unbound particles 250 do not reach second detection zone 180; in other words, that only bound particles 230 contribute to the detectable signal so that the detectable signal can be reproducibly related to the amount or concentration of second analyte 240 in the sample.

The magnetic particles are next moved to second detection zone 180 by manipulation of the applied magnetic field (e.g., by moving a permanent magnet). The magnetic particles are held at the second detection zone, where the second analyte is detected electrochemically.

The analyte can be a biomarker for a condition that afflicts the mammalian body. The term "biomarker" refers to a biochemical in the body that has a particular molecular trait to make it useful for diagnosing a condition, disorder, or disease and for measuring or indicating the effects or progress of a condition, disorder, or disease. For example, common biomarkers found in a person's bodily fluids (i.e., breath or blood), and the respective diagnostic conditions of the person providing such biomarkers include, but are not limited to, ischemia modified albumin "IMA" (source: lack of oxygen to the blood; diagnosis: coronary artery disease), N-terminal truncated pro-brain natriuretic peptide "NT proBNP" (source: stretching of myocytes; diagnosis: congestive heart failure), acetaldehyde (source: ethanol; diagnosis: intoxication), acetone (source: acetoacetate; diagnosis: diet; ketogenic/diabetes), ammonia (source: deamination of amino acids; diagnosis: uremia and liver disease), CO (carbon monoxide) (source: $CH_2Cl_2$, elevated % COH; diagnosis: indoor air pollution), chloroform (source: halogenated compounds), dichlorobenzene (source: halogenated compounds), diethylamine (source: choline; diagnosis: intestinal bacterial overgrowth), H (hydrogen) (source: intestines; diagnosis: lactose intolerance), isoprene (source: fatty acid; diagnosis: metabolic stress), methanethiol (source: methionine; diagnosis: intestinal bacterial overgrowth), methylethylketone (source: fatty acid; diagnosis: indoor air pollution/diet), O-toluidine (source: carcinoma metabolite; diagnosis:

bronchogenic carcinoma), pentane sulfides and sulfides (source: lipid peroxidation; diagnosis: myocardial infarction), $H_2S$ (source: metabolism; diagnosis: periodontal disease/ovulation), MeS (source: metabolism; diagnosis: cirrhosis), and $Me_2S$ (source: infection; diagnosis: trench mouth). A reagent zone can also include a second reagent capable of recognizing a desired analyte. The second reagent can recognize the same or a different analyte. The first and second recognition reagents can be selected to recognize the same analyte simultaneously. For example the first and second recognition reagents can each be an antibody that recognizes distinct epitopes of the analyte. In this way, a ternary (i.e., three-component) complex of analyte, first recognition reagent and second recognition reagent can be formed. In general, the first and second recognition reagents do not associate with one another in the absence of analyte. The presence of analyte, however, can associate the first and second recognition reagents together, in a ternary complex. The reagent zones can include further reagents such as redox mediators, substrates for particular enzymes and salts suitable for forming buffer solutions.

The second recognition reagent can be linked to a particle that can induce mobility on the so-formed ternary complex. The particle can be, for example, a polymer microsphere, a metal nanoparticle, or a magnetic particle. A magnetic particle is a particle that is influenced by a magnetic field. The magnetic particle can be, for example, a magnetic particle described, in U.S. Patent Application Publication Nos. 20050147963 or 20050100930, or U.S. Pat. No. 5,348,876, each of which is incorporated by reference in its entirety, or commercially available beads, for example, those produced by Dynal AS under the trade name DYNABEADS™. In particular, antibodies linked to magnetic particles are described in, for example, United States Patent Application Nos. 20050149169, 20050148096, 20050142549, 20050074748, 20050148096, 20050106652, and 20050100930, and U.S. Pat. No. 5,348,876, the teachings of each of which is incorporated by reference in its entirety.

Generally, the detection zones collect the analytes and are the sites of detectable changes. The extent of the detectable changes can be measured at the detection zones. Usually, greater amounts of analytes will result in greater detectable changes; however, the assays can also be configured to produce smaller changes when the analytes are present in greater quantities. The detection zones can collect the analytes by immobilizing them (for example, with a reagent immobilized in the detection zone, where the immobilized reagent binds to the analyte). Alternatively, the detection zone can attract or immobilize a component associated with the analyte. For example, a recognition reagent that binds an analyte and is linked to a magnetic particle can be attracted to a particular detection zone by a magnetic field provided in one or more detection zones.

In some embodiments, one or more of the detection zones include one or more electrodes. The electrodes can be formed of a material selected for electrical conductivity and low reactivity with sample components, for example, silver, gold, aluminum, palladium, platinum, iridium, a conductive carbon, a doped tin oxide, stainless steel, or a conductive polymer. The electrodes in the detection zones (the working electrodes), in conjunction with second electrodes in the reference zones (the reference electrodes) can measure an electrical property of the sample, such as a voltage or a current. Alternatively, the detection zones and the reference zones can each have at least one working electrode and counter electrode. That is, the detection and reference zones can make independent measurements. Optionally, counter electrodes are also included in the assay device. Assay devices including electrodes for measuring electrical properties of a sample are described in, for example, U.S. Pat. Nos. 5,708,247, 6,241,862, and 6,733,655, each of which is incorporated by reference in its entirety.

In some embodiments, the assay device base, assay device lid, or both have a translucent or transparent window aligned with the detection zone. An optical change that occurs in the detection zone can be detected through the window. Detection can be done visually (i.e., the change is measured by the user's eye) or measured by an instrument (e.g., a photodiode, photomultiplier, or the like). In general, the reference zone is similar in nature to the detection zone. In other words, when the detection zone includes an electrode, the reference can likewise include an electrode. When the detection zone is aligned with a window for optical measurement, the reference zone can similarly be aligned with a window for optical measurement. In some embodiments, the reference zone is not adapted to collect analyte. Alternatively, the reference zone is adapted to collect analyte, but performs a different analysis on said analyte. Thus, the detectable change measured in the reference zone can be considered a background measurement to be accounted for when determining the amount of analyte present in the sample.

The sample can be any biological fluid, such as, for example, blood, blood plasma, serum, urine, saliva, mucous, tears, or other bodily fluid. The analyte can be any component that is found (or may potentially be found) in the sample, such as, for example, a protein, a peptide, a nucleic acid, a metabolite, a saccharide or polysaccharide, a lipid, a drug or drug metabolite, or other component. The assay device can optionally be supplied with a blood separation membrane arranged between a sample inlet and the detection zone, such that when whole blood is available as a sample, only blood plasma reaches the detection zone.

The assay device and included reagents are typically provided in a dry state. Addition of a liquid sample to the assay device (i.e., to the capillary channel) can resuspend dry reagents.

Figure 17:
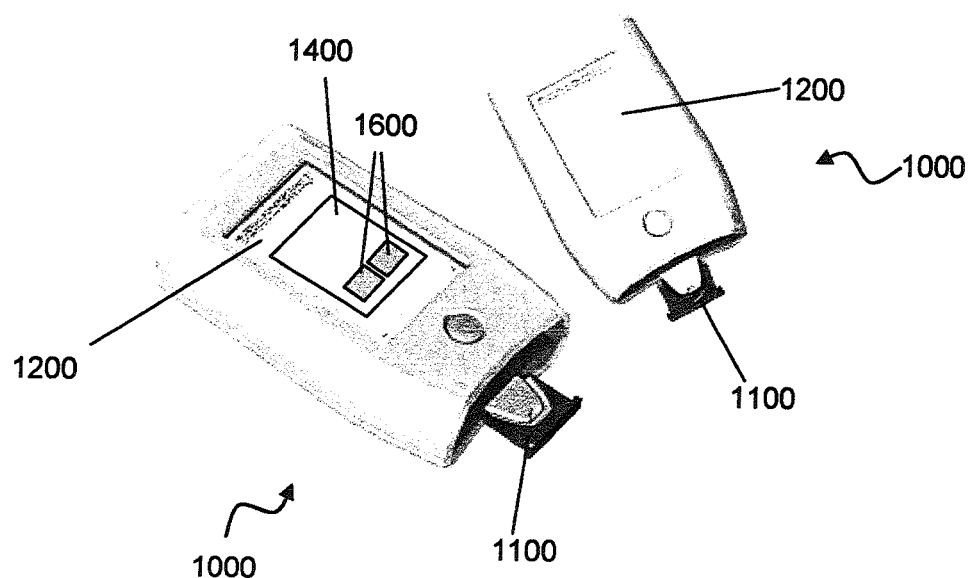
FIG. 17 is an illustration of a hand-held assay device reader.

Referring to FIG. 17, reader instrument 1000 accepts test assay device 1100 and includes display 1200. The display 1200 may be used to display images in various formats, for example, text, joint photographic experts group (JPEG) format, tagged image file format (TIFF), graphics interchange format (GIF), or bitmap. Display 1200 can also be used to display text messages, help messages, instructions, queries, test results, and various information to patients. Display 1200 can provide a user with an input region 1400. Input region 1400 can include keys 1600. In one embodiment, input region 1400 can be implemented as symbols displayed on the display 1200, for example when display 1200 is a touch-sensitive screen. User instructions and queries are presented to the user on display 1200. The user can respond to the queries via the input region.

Reader 1000 also includes an assay device reader, which accepts diagnostic test assay devices 1100 for reading. The assay device reader can measure the level of an analyte based on, for example, the magnitude of an optical change, an electrical change, or other detectable change that occurs on a test assay device 1100. For reading assay devices that produce an optical change in response to analyte, the assay device reader can include optical systems for measuring the detectable change, for example, a light source, filter, and photon detector, e.g., a photodiode, photomultiplier, or Avalance photo diode. For reading assay devices that produce an electrical change in response to analyte, the assay device reader can include electrical systems for measuring the detectable change, including, for example, a voltameter or amperometer.

Device 1000 further can include a communication port (not pictured). The communication port can be, for example, a connection to a telephone line or computer network. Device 1000 can communicate the results of a measurement to an output device, remote computer, or to a health care provider from a remote location. A patient, health care provider, or other user can use reader 1000 for testing and recording the levels of various analytes, such as, for example, a biomarker, a metabolite, or a drug of abuse.

Various implementations of diagnostic device 1000 may access programs and/or data stored on a storage medium (e.g., a hard disk drive (HDD), flash memory, video cassette recorder (VCR) tape or digital video disc (DVD); compact disc (CD); or floppy disk). Additionally, various implementations may access programs and/or data accessed stored on another computer system through a communication medium including a direct cable connection, a computer network, a wireless network, a satellite network, or the like.

The software controlling the reader can be in the form of a software application running on any processing device, such as, a general-purpose computing device, a personal digital assistant (PDA), a special-purpose computing device, a laptop computer, a handheld computer, or a network appliance. The reader may be implemented using a hardware configuration including a processor, one or more input devices, one or more output devices, a computer-readable medium, and a computer memory device. The processor may be implemented using any computer processing device, such as, a general-purpose microprocessor or an application specific integrated circuit (ASIC).

The processor can be integrated with input/output (I/O) devices to provide a mechanism to receive sensor data and/or input data and to provide a mechanism to display or otherwise output queries and results to a service technician. Input device may include, for example, one or more of the following: a mouse, a keyboard, a touch-screen display, a button, a sensor, and a counter. The display 1200 may be implemented using any output technology, including a liquid crystal display (LCD), a television, a printer, and a light emitting diode (LED).

The computer-readable medium provides a mechanism for storing programs and data either on a fixed or removable medium. The computer-readable medium may be implemented using a conventional computer hard drive, or other removable medium. Finally, the system uses a computer memory device, such as a random access memory (RAM), to assist in operating the reader. Implementations of the reader can include software that directs the user in using the device, stores the results of measurements. The reader 1000 can provide access to applications such as a medical records database or other systems used in the care of patients. In one example, the device connects to a medical records database via the communication port. Device 1000 may also have the ability to go online, integrating existing databases and linking other websites.

In general, the assay device can be made by depositing reagents on a base and sealing a lid over the base. The base can be a micro-molded platform or a laminate platform.

Micro-Molded Platform

For an assay device prepared for optical detection, the base, the lid, or both base and lid can be transparent to a desired wavelength of light. Typically both base and lid are transparent to visible wavelengths of light, e.g., 400-700 nm. The base and lid can be transparent to near UV and near IR wavelengths, for example, to provide a range of wavelengths that can be used for detection, such as 200 nm to 1000 nm, or 300 nm to 900 nm.

For an assay device that will use electrochemical detection, electrodes are deposited on a surface of the base. The electrodes can be deposited by screen printing on the base with a carbon or silver ink, followed by an insulation ink; by evaporation or sputtering of a conductive material (such as, for example, gold, silver or aluminum) on the base, followed by laser ablation; or evaporation or sputtering of a conductive material (such as, for example, gold, silver or aluminum) on the base, followed by photolithographic masking and a wet or dry etch.

An electrode can be formed on the lid in one of two ways. A rigid lid can be prepared with one or more through holes, mounted to a vacuum base, and screen-printing used to deposit carbon or silver ink. Drawing a vacuum on the underside of the rigid lid while screen printing draws the conductive ink into the through holes, creating electrical contact between the topside and underside of the lid, and sealing the hole to ensure that no liquid can leak out.

Alternatively, the lid can be manufactured without any through holes and placed, inverted, on a screen-printing platform, where carbon or silver ink is printed. Once the electrodes have been prepared, the micro-molded bases are loaded and registered to a known location for reagent deposition. Deposition of reagents can be accomplished by dispensing or aspirating from a nozzle, using an electromagnetic valve and servo- or stepper-driven syringe. These methods can deposit droplets or lines of reagents in a contact or non-contact mode. Other methods for depositing reagents include pad printing, screen printing, piezoelectric print head (e.g., ink-jet printing), or depositing from a pouch which is compressed to release reagent (a "cake icer"). Deposition can preferably be performed in a humidity- and temperature-controlled environment. Different reagents can be dispensed at the same or at a different station. Fluorescent or colored additives can optionally be added to the reagents to allow detection of cross contamination or overspill of the reagents outside the desired deposition zone. Product performance can be impaired by cross-contamination. Deposition zones can be in close proximity or a distance apart. The fluorescent or colored additives are selected so as not to interfere with the operation of the assay device, particularly with detection of the analyte.

After deposition, the reagents are dried. Drying can be achieved by ambient air-drying, infrared drying, infrared drying assisted by forced air, ultraviolet light drying, forced warm, controlled relative humidity drying, or a combination of these. Micro-molded bases can then be lidded by bonding a flexible or rigid lid on top. Registration of the base and lid occurs before the two are bonded together. The base and lid can be bonded by heat sealing (using a heat activated adhesive previously applied to lid or base, by ultrasonic welding to join two similar materials, by laser welding (mask or line laser to join two similar materials), by cyanoacrylate adhesive, by epoxy adhesive previously applied to the lid or base, or by a pressure sensitive adhesive previously applied to the lid or base. After lidding, some or all of the assembled assay devices can be inspected for critical dimensions, to ensure that the assay device will perform as designed. Inspection can include visual inspection, laser inspection, contact measurement, or a combination of these.

The assay device can include a buffer pouch. The buffer pouch can be a molded well having a bottom and a top opening. The lower opening can be sealed with a rupturable foil or plastic, and the well filled with buffer. A stronger foil or laminate is then sealed over the top opening. Alternatively, a preformed blister pouch filled with buffer is placed in and bonded in the well. The blister pouch can include 50 to 200 μL of buffer and is formed, filled, and sealed using standard blister methods. The blister material can be foil or plastic. The blister can be bonded to the well with pressure sensitive adhesive or a cyanoacrylate adhesive.

Laminate Platform

Three or more laminates, fed on a roll form at a specified width, can be used to construct an assay device. The base laminate is a plastic material and is coated on one surface with a hydrophilic material. This laminate is fed into a printing station for deposition of conductive electrodes and insulation inks. The base laminate is registered (cross web) and the conductive electrodes deposited on the hydrophilic surface, by the techniques described previously. The base laminate is then fed to a deposition station and one or more reagents applied to the laminate. Registration, both cross web and down web, occurs before reagents are deposited by the methods described above. The reagents are dried following deposition by the methods described above. A middle laminate is fed in roll form at a specified width. There can be more than one middle laminate in an assay device. The term middle serves to indicate that it is not a base laminate or lid laminate. A middle laminate can be a plastic spacer with either a pressure sensitive adhesive or a heat seal adhesive on either face of the laminate. A pressure sensitive adhesive is provided with a protective liner on either side to protect the adhesive. Variations in the thickness of the middle laminate and its adhesives are less than 15%, or less than 10%.

Channels and features are cut into the middle laminate using a laser source (e.g., a $CO_2$ laser, a YAG laser, an excimer laser, or other). Channels and features can be cut all the way through the thickness of the middle laminate, or the features and channels can be ablated to a controlled depth from one face of the laminate. The middle and base laminates are registered in both the cross web and down web directions, and bonded together. If a pressure sensitive adhesive is used, the lower liner is removed from the middle laminate and pressure is applied to bond the base to the middle laminate. If a heat seal adhesive is used, the base and middle laminate are bonded using heat and pressure.

The top laminate, which forms the lid of the assay device, is fed in roll form at a specified width. The top laminate can be a plastic material. Features can be cut into the top laminate using a laser source as described above. The top laminate is registered (cross web and down web) to the base and middle laminates, and bonded by pressure lamination or by heat and pressure lamination, depending on the adhesive used. After the laminate is registered in cross and down web directions, discrete assay devices or test strips are cut from the laminate using a high powered laser (such as, for example, a $CO_2$ laser, a YAG laser, an excimer laser, or other).

Some, or all, of the assembled assay devices can be inspected for critical dimensions, to ensure that the assay device will fit perform as designed. Inspection can include visual inspection, laser inspection, contact measurement, or a combination of these.

An example of one application that employs the use of assays to detect analytes is the analysis of physiological fluid samples, such as blood samples. In particular, it has become increasingly common to analyse blood samples for analytes that may be indicative of disease or illness. Such analyses can be performed using an assay that directly or indirectly detects an analyte.

Embodiments provide a device and method for performing more than one assay on a single small volume blood sample, or other biological materials or complex mixtures. Also, the device and method can provide the detection of at least a second analyte without contamination of assay reagents with non-specific reactions, and physical occlusions of target molecules with cellular debris.

DESCRIPTION OF OTHER EXEMPLARY EMBODIMENTS

Figure 12:
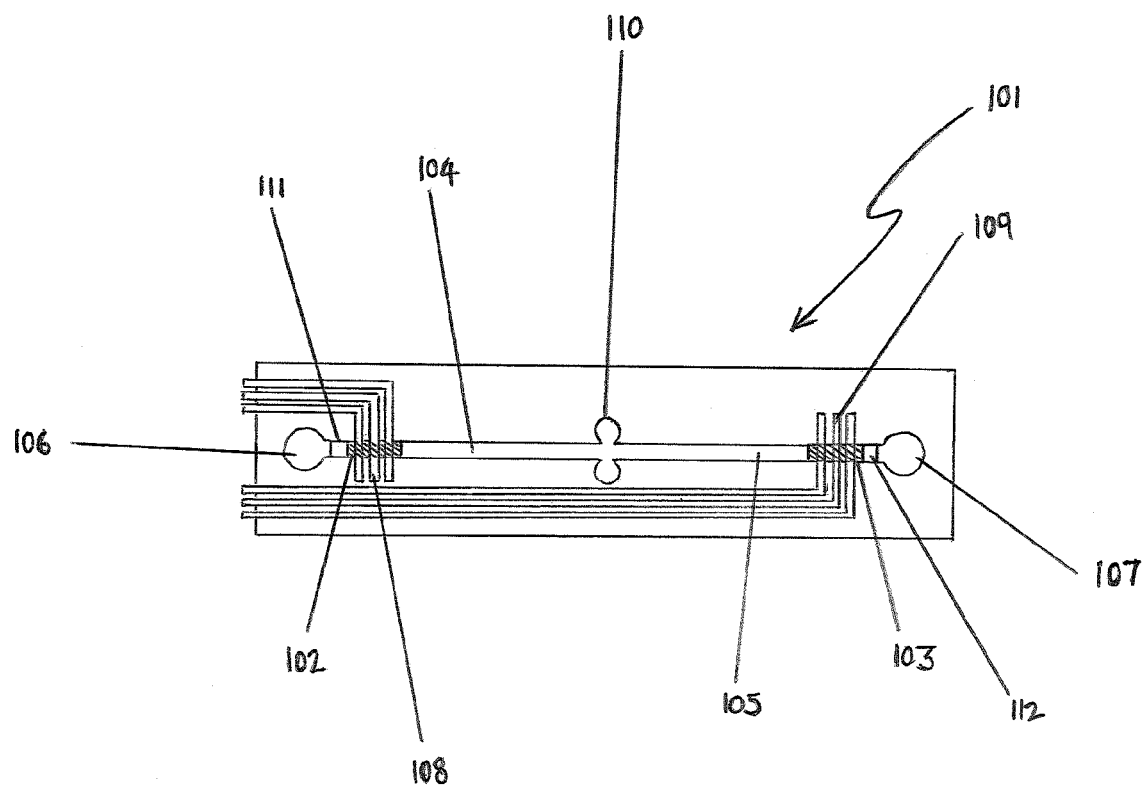
FIG. 12 is a perspective view of a schematic representation of a test strip for use with a hand-held electrochemical analysis apparatus.

Referring now to FIG. 12, a test strip suitable for use with the assay device is generally depicted at 101. The test strip has a first detection zone 102 and a second detection zone 103 fluidly connected by a first linear channel 104 and a second linear channel 105. The first linear channel 104 is fluidly connected to a first application zone 106 and the second linear channel 105 is fluidly connected to a second application zone 107. The first and second detection zones, 102 and 103, are equipped with a first set of electrodes 108 and a second set of electrodes 109 respectively. The electrodes are suitable for directly or indirectly detecting a component of the sample. At a point substantially equidistant from the two detection zones, 102 and 103, there is provided a fusable vent 110 fluidly connected to, and forming a coupling between, the first channel 104 and the second channel 105. The vent 110 acts to prevent or promote the flow of fluids in the first and second channels, 104 and 105.

Fluidly connected to the first channel 104, situated between the first application zone 106 and the first detection zone 102, there is provided a first reagent zone 111. Similarly, fluidly connected to the second channel 105, situated between the second application zone 107 and the second detection zone 103, there is provided a second reagent zone 112. The first reagent zone 111 includes a substrate (for example, cobalt) for binding to an analyte (for example, IMA). The first reagent zone 111 also includes a first recognition reagent linked to an enzyme capable of oxidizing or reducing a redox active enzyme substrate. For example, when the redox active enzyme substrate is glucose, the enzyme can be a glucose oxidase (GOD). The first reagent zone 111 further comprises a second recognition reagent selected to bind the desired analyte. In particular, the second recognition reagent is selected to bind the desired analyte simultaneously with the first recognition reagent to form a ternary complex. The second recognition reagent is linked to a magnetic particle. The second reagent zone 112 includes a redox active enzyme substrate (e.g., glucose) and a redox mediator (e.g., potassium ferricyanide, $K_3Fe(CN)_6$). Reagents are dried onto the reagent zones and may be resuspended on the addition of a fluid such as blood or buffer.

The assay device is further provided with a magnet (not shown), which acts on the magnetic particles in the channel. The magnet is used to move the magnetic particles, and anything bound to them, from one area of the test strip to another. The test strip is suitable for insertion into a reader, which presents to the user the results of any assays performed.

In a detailed embodiment of the method, there is first provided an assay device comprising a test strip, suitable for reading by an electronic reader. To the test strip is added a sample of mammalian blood suspected of containing ischemia modified albumin "IMA" (the first analyte) and N-terminal truncated pro-brain natriuretic peptide "NTproBNP" (the second analyte). The sample of blood mixes with cobalt which has been dried onto the test strip, resuspending the cobalt in solution, and forming a mixture under conditions suitable for interaction of the first analyte with cobalt. In this mixture, some cobalt binds to IMA in the blood to form a complex, whilst some cobalt remains unbound. The sample of blood also mixes with magnetic particles bound to anti-NTproBNP antibody 7206 (the antibody bound magnetic particle) and horse radish peroxidase "HRP" conjugated to anti-NTproBNP antibody 15F11 (the antibody bound enzyme), which have been dried onto the test strip, resuspending these components in solution, and forming a mixture under conditions suitable for interaction of the second analyte with the antibody bound magnetic particle and the antibody bound enzyme, thereby forming a ternary complex.

An electrochemical analysis is then performed on the first mixture. This analysis provides an indication of the amount of unbound cobalt present in the first mixture. In turn, the amount of IMA present in the sample can be determined. This test procedure for detecting IMA may be optimized in accordance with our co-pending Application GB 0603049.8, which is incorporated herein by reference.

This step of the method as described generally allows the indirect detection of any analyte in a complex mixture, although it will be appreciated that the method is also suitable for the indirect detection of an analyte in simple mixtures. The method has applications in any assay where the interaction between a detectable material and an analyte modifies the detectability of said detectable material.

After the first assay is complete, a magnet is moved along the test strip, moving the magnetic particles, and all components bound to them (as the ternary complex or otherwise) along a first channel to an air vent. The magnet is moved approximately 5 mm beyond the air vent, towards a second channel where it is held. This holds the magnetic particles at the fluid-air interface, as they cannot pass through the so-formed meniscus.

A second fluid is added to the test strip at the second application zone. The second fluid contains sodium acetate buffer, hydrogen peroxide substrate, and ABTS redox mediator. The second fluid flows along the second channel to the vent where the second fluid contacts the blood sample to form a liquid-liquid interface. The formation of the fluid-fluid interface facilitates the movement of the magnetic particles (and all that is bound to them) from the blood to the second fluid, leaving interferents and analytes that are not of interest in the blood in the first channel. Only the magnetic particles and all that is bound to them, including the NTproBNP (in the form of a ternary complex of NTproBNP with antibody bound magnetic particle and antibody bound enzyme) are transferred to the second fluid in the second channel. The magnetic particles are moved to a second detection zone using the magnet. The magnetic particles are held at the second detection zone, where the second analyte is indirectly detected electrochemically.

In this embodiment the first, second and any further assays are optionally performed sequentially. In an alternative embodiment, at least two assays are performed simultaneously.

Figure 13:
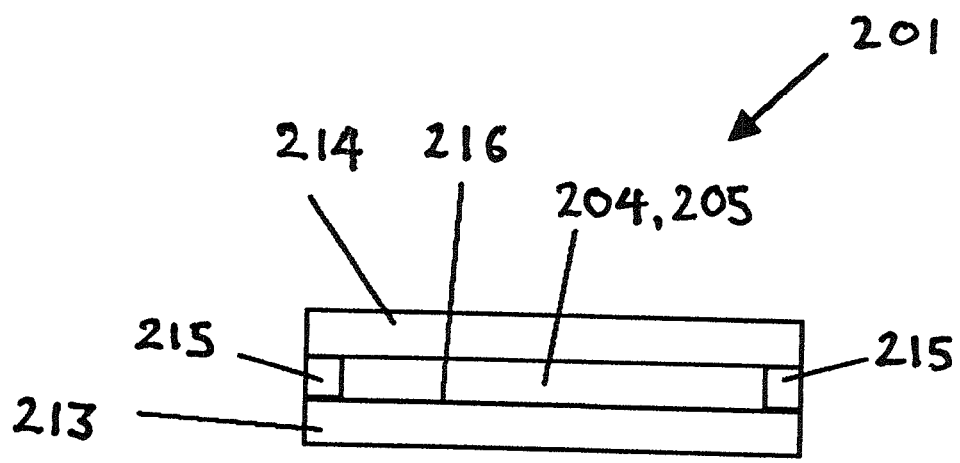
FIG. 13 is a schematic end view of an assembled test strip.

Referring now to FIG. 13, assembled test strip 201 includes base 213 separated from lid 214 by spacers 215. Spacers 215 can be formed as an integral part of base 213 or lid 214. Alternatively, base 213, lid 214 and spacers 215 can be formed separately and assembled together. When assembled, together, connections between base 213, lid 214 and spacers 215 can be sealed, for example with an adhesive or by welding. Base 213, lid 214 and spacers 215 can define liquid-tight channels 204, 205 where a liquid sample is allowed to contact interior surfaces that define the channels 204, 205, such as surface 216 of base 213. Between the liquid tight channels there is located a vent (not shown) that can promote or prevent capillary flow. The dimensions of spacer 215 can be selected such that surfaces of base 213 and lid 214 facing the interior the channels 204, 205 form a capillary, i.e., the base and lid provide capillary action to a liquid inside channels 204, 205. Alternatively, base 213 or lid 214 can provide capillary action independently of each other. Channels 204, 205 can have a volume of less than 100 microliters, less than 20 microliters, less than 10 microliters, or 5 microliters or less.

Figure 14A:
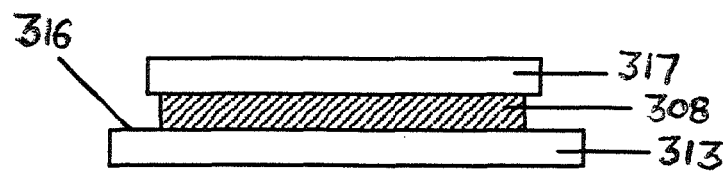
FIGS. 14A-14C are schematic views of a cross-section parallel to the shortest side of an assembled test strip.

Referring now to FIG. 14 there is illustrated alternate configurations of reagent deposition on base 313, as a cross-section parallel to the short side of the test strip. In FIG. 14A, first electrode set 308 is arranged on surface 316 of base 313. First reagent mixture 317 is deposited over at least one electrode in first electrode set 308. First reagent mixture 317 includes first reagent, second reagent and third reagent, second reagent and third reagent are illustrated in FIG. 15A. The first reagent includes cobalt and can interact with a first analyte. Referring to FIG. 15A, second reagent 419 includes magnetic particle 421 linked to a first antibody 422. Third reagent 420 includes detectable component 423 linked to a second antibody 424.

Figure 14B:
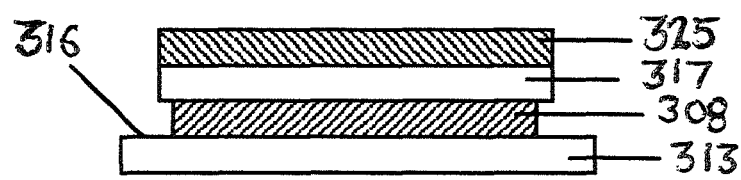
Figure 15A:
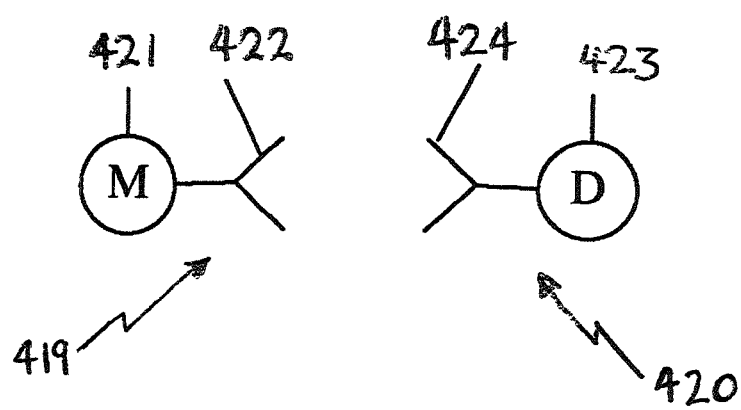
FIGS. 15A-15B are schematic depictions of reagents and analytes.

An alternate configuration is shown in FIG. 14B, in which at least one electrode from electrode set 308 is arranged on surface 316 of base 313, overlayed with first reagent mixture 317, which in turn is overlayed with second reagent mixture 325. First reagent mixture 317 includes first reagent. Second reagent mixture 325 includes second reagent and third reagent. It will be apparent that alternative combinations of different reagents can be incorporated into one or more layers. Selecting the order in which reagents are deposited can allow selective or timed release of the reagent upon contact with a sample, in order to suit assay kinetics and improve sensitivity.

The reagents may be deposited on one or more electrode and on one or more electrode set. The reagents can be deposited on any part of the channels that facilitates interaction with analytes in the sample before detection takes place.

Figure 14C:
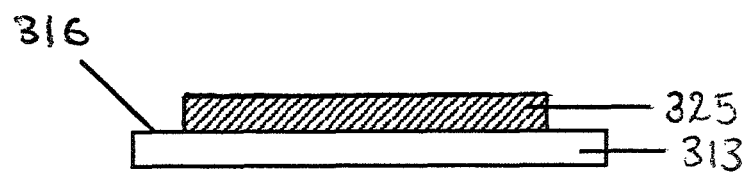

Alternatively, referring now to FIG. 14C, second reagent mixture 325 is deposited on surface 316 of base 313.

When a sample, or other fluid, is introduced to the channels, (for example, by contacting the sample with a sample inlet), liquid can fill the channels and contact the surface of the base, resuspending the reagents deposited on the surface.

If the sample contains the first analyte to which the first reagent binds, the first reagent will bind to the first analyte. The first reagent is chosen to include cobalt, which binds to albumin and IMA. The binding of cobalt can be assayed electrochemically or photochemically, among other techniques.

Figure 15B:
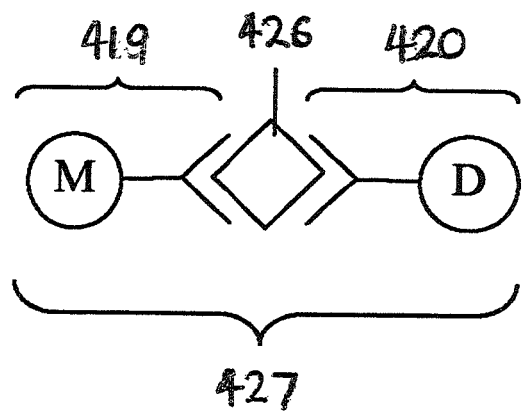

Referring again to FIG. 15, if the sample contains the second analyte 426 recognized by the first and second antibodies 422 and 424, then the antibodies 422, 424 will bind to the second analyte. The antibodies 422, 424 are chosen to bind to different epitopes of the analyte 426, allowing the formation of a ternary complex 427 of reagent 419, analyte 426, and reagent 420, as illustrated in FIG. 15B.

Figure 16A:
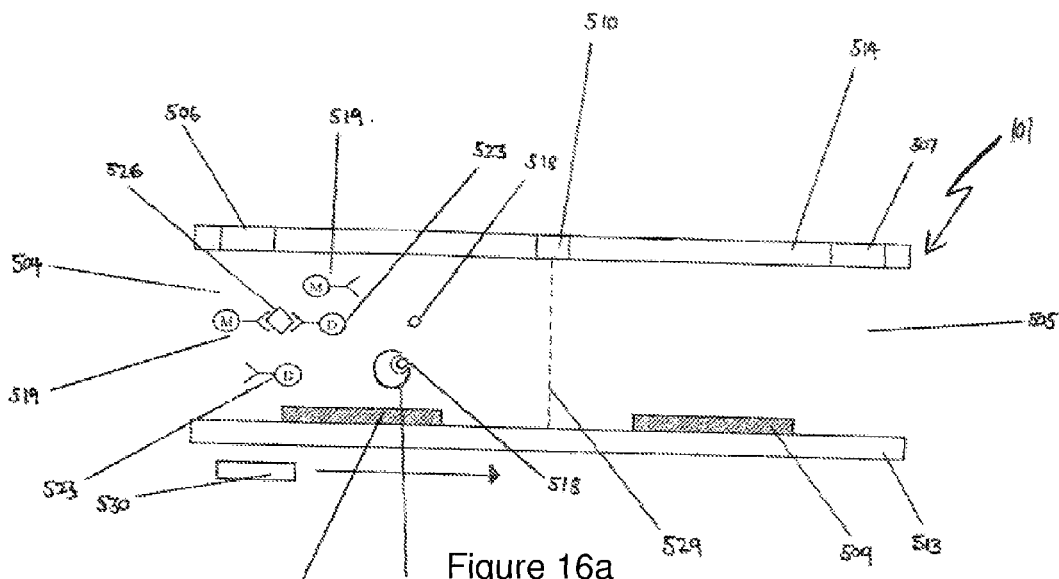
FIGS. 16A-16B are schematic views of a cross-section parallel to the longest side of an assembled test strip.
Figure 16B:
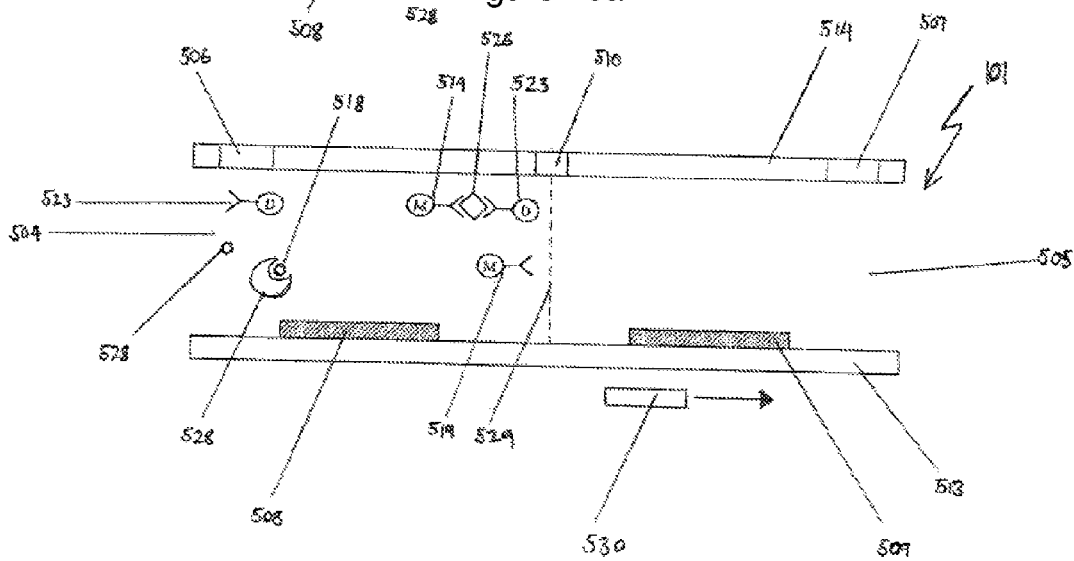

FIGS. 16A and 16B illustrate the assay device, for example, cartridge or test strip 101, during operation. In FIG. 16A, there is a side view into the first channel 504 and the second channel 505. The base 513 and lid 514 confine a liquid sample which includes dissolved first reagent 518, second reagent 519 and third reagent 520 and a first analyte 528 and second analyte 526. The reagents 518, 519, 520 can be supplied in excess relative to the amount of analytes 528, 526 present in the sample, such that all analytes 528, 526 are bound, while a portion of the reagents 518, 519, 520 can remain unbound. On the lid 514 there is located a first application zone 506 and a second application zone 507, and a vent 510. A blood sample is introduced to the assay device 101, and the reagents are resuspended by the sample. The sample flows along the first channel 504 to the vent 510 where capillary flow stops, forming a meniscus 529 with air. Reagents, analytes, and complexes can be distributed by diffusion near the location in channel 504 or 505 where the reagents originated. An analysis of the first reagent 518 is performed at a first set of electrodes 508 to give an indication of the presence of the first analyte 528.

After the first assay is complete a magnetic field source 530, located underneath the base 513 and proximate to the first application zone 506, is configured to move the antibody bound magnetic particles 519 and also the second analyte 526 and detectable component 523 where they form a ternary complex with the antibody bound magnetic particles 519, toward the meniscus 529. The magnetic field source 530 is held proximate to the second channel 505. A buffer solution (not shown) containing a substrate (not shown) for the detectable component 523, and a redox mediator (not shown), is added to the second channel 505 via the second application zone 507. The buffer solution travels along the second channel 505 to the meniscus 529 where it forms a liquid-liquid interface with the sample fluid. On formation of the liquid-liquid interface, the magnetic particle bound antibodies 519, and all that is bound to them, moves rapidly from the sample fluid to the buffer solution; the magnetic particles being attracted to the magnetic field source 530 situated proximate to the second channel 505. The rapid movement of the magnetic particles across the liquid-liquid interface prevents impurities from being dragged into the second channel 505. This allows an accurate second assay to be performed at the second electrode set 509 in the second channel 505. The magnetic field source 530 is moved towards the second electrode set 509 to localize the second analyte 526 over said electrodes 509.

The magnetic field source can be configured to provide a shaped magnetic field. A shaped magnetic field can have magnetic field lines designed to direct magnetic particles toward the first or second detection zones. Such a shaped magnetic field can be useful to control the diffusion or migration of magnetic particles and label particles. More than one magnetic field source can be provided, particularly when a shaped magnetic field is desired. For example, magnetic field sources can be provided at either end of an assay device, where one is configured to attract magnetic particles and the other to repel magnetic particles. Such a configuration can favour the location of all magnetic particles at one end of the assay device.

Referring once more to FIG. 15, detectable component 423 can be directly detectable (e.g., a colored particle detected by observation of a colour change, or component 423 can be detected indirectly. Component 423 can produce a product that is directly detected, such that detection of the product is an indirect detection of component 423. For example, component 423 can be an enzyme whose product is detected directly (e.g., optically or electrochemically). The amount of product formed, or rate of product formation, can be related to the amount of detectable component 423.

Glucose oxidase (GOD) is one enzyme that can be used as the detectable component 423. In the presence of glucose and mediator, the GOD (whether or not the associated particle is bound to a magnetic particle 421 via the analyte 426) converts glucose to gluconic acid and converts the mediator (e.g., ferricyanide) from an oxidized form to a reduced from.

Referring again to FIG. 16, after a predetermined period of time has elapsed, a working electrode 509 in the second detection zone (not shown) can be turned on. The amount of reduced mediator in the bulk fluid is measured as a current at the working electrode or electrodes 509. This current, produced when the GOD is distributed homogeneously in the sample, is the background signal. When magnetic field source 530 applies a magnetic field in the vicinity of second detection zone (not shown), antibody bound magnetic particles 519, and all reagents bound to them, become localized near the second detection zone. The magnetic field localizes particles whether the particles are bound to reagent or not. The application of a magnetic field by source 530 causes an increase in the concentration of enzyme 523 near the second detection zone. Enzyme 523 in turn produces a change detectable in the second detection zone.

When enzyme 523 is GOD, the increased concentration of reduced mediator at the surface of working electrode 509 is reflected as a higher current at that electrode when the magnetic field is applied. The higher the analyte 526 concentration, the larger the current will be.

The magnetic field can be applied and removed a number of times, and a series of magnetized and non-magnetized working electrode currents can be measured. The data collected allow the concentration of analyte in the sample to be measured. In some embodiments, two working electrodes can be used, one with a magnet and one without, each on opposite internal faces of the channel. In this case, one electrode is magnetized while the other is not, and both electrodes are activated simultaneously. The currents at the two working electrodes are then compared. The detectable components can be selected to produce an optical change. For example, a detectable change in chemiluminescent signal can be produced when an analyte molecule in a sample brings two particles (or beads) together in close proximity. A first particle, called a donor particle, is linked to a first antibody, and a second particle (an acceptor particle) is linked to a second antibody. The first and second antibodies bind to different epitopes of the same antigen, such that a ternary complex of donor particle antigen acceptor particle can be formed. A cascade of chemical reactions that depends on the proximity of the beads (and therefore on the presence of the analyte) can produce greatly amplified signal. Detection of an analyte at attomolar (i.e., on the order of $10^{-18}$ molar) concentrations is possible.

Photosensitizer particles (donor particles) including a phthalocyanine can generate singlet oxygen when irradiated with light having a wavelength of 680 nm. The singlet oxygen produced has a very short half-life—about 4 microseconds—and hence it decays rapidly to a ground state. Because of the short half-life, singlet oxygen can only diffuse to a distance of a few hundred microns from the surface of the particles before it decays to ground state. The singlet state survives long enough, however, to enter a second particle held in close proximity. The second particles (acceptor particles) include a dye that is activated by singlet oxygen to produce chemiluminescent emission. This chemiluminescent emission can activate further fluorophores contained in the same particle, subsequently causing emission of light at 520-620 nm. See, for example, *Proc. Natl. Acad. Sci.* 91:5426-5430 1994; and U.S. Pat. No. 6,143,514, each of which is incorporated by reference in its entirety. An optical change can also be produced by a bead linked to an antibody. The bead can include a polymeric material, for example, latex or polystyrene. To produce the optical change, the bead can include a light-absorbing or light-emitting compound. For example, a latex bead can include a dye or a fluorescent compound. The reagent can include a plurality of beads. The beads in the plurality can be linked to one or more distinct antibodies. A single bead can be linked to two or more distinct antibodies, or each bead can have only one distinct antibody linked to it. The reagent can have more than one distinct antibody each capable of binding to the same analyte, or antibodies that recognizes different analytes. When the bead includes a light absorbing compound, the optical measurement can be a measurement of transmittance, absorbance or reflectance. With a fluorescent compound, the intensity of emitted light can be measured. The extent of the measured optical change can be correlated to the concentration of analyte in the sample.

A detectable change can be produced by the enzyme multiplied immunoassay technique (EMIT). In an EMIT assay format, an enzyme-analyte conjugate is used. A first reagent can include an antibody specific for the analyte, an enzyme substrate, and (optionally) a coenzyme. A second reagent can include a labeled analyte: a modified analyte that is linked to an enzyme. For example, the enzyme can be a glucose-6-phosphate dehydrogenase (G-6-PDH). G-6-PDH can catalyze the reaction of glucose-6-phosphate with NAD (P) to yield 6-phosphoglucono-D-lactone and NAD(P)H. NAD(P)H absorbs light with a wavelength of 340 nm, whereas NAD(P) does not. Thus, a change in absorption of 340 nm light as a result of the G-6-PDH catalyzed reaction can be a detectable change. When the first reagent is mixed with a sample, the analyte is bound by the antibody in the first reagent.

The second reagent is added, and any free antibody binding sites are occupied by the enzyme-linked analyte of the second reagent. Any remaining free antibodies bind the labeled analyte, inactivating the linked enzyme. Labeled analyte bound by the antibody is inactive, i.e., it does not contribute to the detectable change. Labeled analyte that is not bound by antibody (a quantity proportional to amount of analyte in sample) reacts with the substrate to form a detectable product (e.g., NAD(P)H).

Another assay format is the cloned enzyme donor immunoassay (CEDIA). CEDIA is a homogeneous immunoassay based on the bacterial enzyme E-galactosidase of *E. coli* which has been genetically engineered into two inactive fragments. These two inactive fragments can recombine to form an active enzyme. One fragment consists of an analyte-fragment conjugate, and the other consists of an antibody-fragment 5 conjugate. The amount of active enzyme that generates the signal is proportional to the analyte concentration. See, for example, Khanna, P. L. and Coty, W. A. (1993) In: *Methods of Immunological Analysis, volume 1* (Masseyeff, R. F., Albert, W. H., and Staines, N. A., eds.) Weinheim, FRG: VCH Verlagsgesellschaft MbH, 1993: 416-426; Coty, W. A., Loor, R., Powell, M., and Khanna, P. L. (1994) *J. Clin. Immunoassay* 17(3): 144-150; and Coty, W. A., Shindelman, J., Rouhani, R. and Powell, M. J. (1999) *Genetic Engineering News* 19(7), each of which is incorporated by reference in its entirety.

The assay device can be used in combination with a reader configured to measure the detectable change. The reader can include an optical system to detect light from the analysis region. The light to be detected can be, for example, emitted, transmitted, reflected, or scattered from the detection zone. Emitted light can result from, for example, chemiluminescent or fluorescent emission. The optical system can include an illumination source, for example, to be used in the detection of a change in fluorescence, absorbance, or reflection of light. For an assay device configured for an electrochemical measurement, the reader can be in electrical contact with the working electrode and reference electrode. The assay device electrodes can have electrical leads connecting the electrodes to contacts outside the assay void. The contacts register with and contact corresponding contacts of the assay device to provide electrical contact. The reader can also include an output display configured to display the results of the measurement to a user.

The assay device reader can include magnetic field source. The assay device reader can be configured to apply a magnetic field via source at predetermined times, such as after a predetermined period of time has elapsed after a sample has been applied to the assay device. Magnetic field source can be, for example, an electromagnet or a permanent magnet. An electromagnet can selectively apply a field when a current is supplied to the electromagnet. A permanent magnet can be moved toward or away from the detection zone in order to control the strength of the field at that site.

Referring to FIG. 17, reader instrument 1000 accepts test assay device 1100 and includes display 1200. The display 1200 may be used to display images in various formats, for example, text, joint photographic experts group (JPEG) format, tagged image file format (TIFF), graphics interchange format (GIF), or bitmap. Display 1200 can also be used to display text messages, help messages, instructions, queries, test results, and various information to patients. Display 1200 can provide a user with an input region 1400. Input region 1400 can include keys 1600. In one embodiment, input region 1400 can be implemented as symbols displayed on the display 1200, for example when display 1200 is a touch-sensitive screen. User instructions and queries are presented to the user on display 1200. The user can respond to the queries via the input region.

Reader 1000 also includes an assay device reader, which accepts diagnostic test assay devices 1100 for reading. The assay device reader can measure the level of an analyte based on, for example, the magnitude of an optical change, an electrical change, or other detectable change that occurs on a test assay device 1100. For reading assay devices that produce an optical change in response to analyte, the assay device reader can include optical systems for measuring the detectable change, for example, a light source, filter, and photon detector, e.g., a photodiode, photomultiplier, or Avalance photo diode. For reading assay devices that produce an electrical change in response to analyte, the assay device reader can include electrical systems for measuring the detectable change, including, for example, a voltameter or amperometer.

Device 1000 further can include a communication port (not pictured). The communication port can be, for example, a connection to a telephone line or computer network. Device 1000 can communicate the results of a measurement to an output device, remote computer, or to a health care provider from a remote location. A patient, health care provider, or other user can use reader 1000 for testing and recording the levels of various analytes, such as, for example, a biomarker, a metabolite, or a drug of abuse.

Various implementations of diagnostic device 1000 may access programs and/or data stored on a storage medium (e.g., a hard disk drive (HDD), flash memory, video cassette recorder (VCR) tape or digital video disc (DVD); compact disc (CD); or floppy disk). Additionally, various implementations may access programs and/or data accessed stored on another computer system through a communication medium including a direct cable connection, a computer network, a wireless network, a satellite network, or the like.

The software controlling the reader can be in the form of a software application running on any processing device, such as, a general-purpose computing device, a personal digital assistant (PDA), a special-purpose computing device, a laptop computer, a handheld computer, or a network appliance. The reader may be implemented using a hardware configuration including a processor, one or more input devices, one or more output devices, a computer-readable medium, and a computer memory device. The processor may be implemented using any computer processing device, such as, a general-purpose microprocessor or an application specific integrated circuit (ASIC).

The processor can be integrated with input/output (I/O) devices to provide a mechanism to receive sensor data and/or input data and to provide a mechanism to display or otherwise output queries and results to a service technician. Input device may include, for example, one or more of the following: a mouse, a keyboard, a touch-screen display, a button, a sensor, and a counter. The display 1200 may be implemented using any output technology, including a liquid crystal display (LCD), a television, a printer, and a light emitting diode (LED).

The computer-readable medium provides a mechanism for storing programs and data either on a fixed or removable medium. The computer-readable medium may be implemented using a conventional computer hard drive, or other removable medium. Finally, the system uses a computer memory device, such as a random access memory (RAM), to assist in operating the reader. Implementations of the reader can include software that directs the user in using the device, stores the results of measurements. The reader 1000 can provide access to applications such as a medical records database or other systems used in the care of patients. In one example, the device connects to a medical records database via the communication port. Device 1000 may also have the ability to go online, integrating existing databases and linking other websites.

According to some embodiments the method is performed using wet assays. The instrumentation used includes an Eco Chemie™ Autolab™ with a six-way multistat and GPES™ software. The electrodes used were screen printed in-house. The working and counter electrodes were prepared using carbon D2 (GEM™ Ltd), silver/silver chloride electrodes were prepared using AgCl 70:30 (GEM™ Ltd or DuPont™), and dielectric electrodes were prepared using dielectric D1 (GEM™ Ltd)

The materials used for the test strip include a hydrophobic polyester base and a hydrophilic antifog lid, with a double-sided adhesive spacer (200 nm) forming channel therebetween. The antifog lid is preblocked with 40 mg/ml bovine serum albumin, 1.5% Tween™ in phosphate buffered saline, pH 7.3, before it is rinsed and dried. Alternatively the substrate comprises alumina ceramic or polyester cards.

In this embodiment the reagents used in the first assay include, cobalt chloride, 4-morpholinepropanesulfonic acid (MOPS), potassium chloride. A buffer of pH 7.4 is prepared using 100 mM MOPS and 150 mM potassium chloride and a cobalt chloride standard for 45 mM in 1.5 M potassium chloride is also prepared. The reagents used in the second assay include 200 mM glucose, 100 mM potassium ferri- cyanide in 5 M ammonium acetate buffer, pH 7.3, Glucose oxidase (GOD) conjugated to antibody 15F11 and 1 um magnetic particles (Chemicell with COOH on surface) bound to antibody 7206.

The samples used for analysis include frozen serums and whole blood samples from volunteers.

5 μL of the cobalt standard is added to 100 μL of the blood sample (serum, plasma or blood) in a tube. The so-formed mixture is mixed for 10 seconds using a vortexer, before being allowed to incubate for 2 minutes. Cobalt binds to albumin and, to a lesser extent, IMA in the blood. Magnetic particles (with anti-NTproBNP antibody 7206 bound) GOD conjugated to anti-NTproBNP antibody 15F11 are added to the sample and the sample is mixed for 30 min at 600 rpm. Between 7.5 μL and 15 μL of the mixture is then removed and applied to a first channel via the first application zone in a test strip.

The sample mixture travels along the first channel and is stopped at a specific point where air vents are positioned at either side of said first channel. These air vents remain open to a second channel.

A first measurement, to detect the amount of IMA present in the sample fluid, is performed at the first electrode set. The working electrode is poised at +1 Volt for 40 seconds before a linear sweep is applied from +1 Volt to −0.5 Volt at a scan rate of 0.7 V/second. The measurements made may be optimised in accordance with our co-pending Application GB 0603049.8, referred to herein previously.

The cobalt $2^+$ ions are oxidised and adsorbed as cobalt $3^+$ hydroxy species at the electrode surface at +1 Volt. During the scan the cobalt $3^+$ is reduced back to cobalt $2^+$ giving a cathodic signal peak at around +0.7 Volts. To calibrate the test, the performance of the electrodes is tested for a range of cobalt concentrations in buffer. To determine whether the amount of IMA in the sample, the value recorded is correlated with the Albumin Cobalt Binding (ACB™) test for IMA.

The magnetic particles (and everything bound to them) are dragged to the liquid/air interface at the air vents using a magnet. The magnet is pulled 5 mm past liquid-air interface and held is over the empty second channel. This holds the magnetic particles at the liquid-air interface as they cannot pass through the so-formed meniscus.

Around 11 ul of reaction buffer containing 5M ammonium acetate pH 7.3, 200 mM glucose and 100 mM ferricyanide is added to the second channel via the second application zone. This flows towards the liquid-air interface, the flow being facilitated by the presence of a vent positioned at said interface. The reaction buffer forms a liquid-liquid interface with the blood sample. At this point the magnetic particles 'jump' across the liquid-liquid interface, as they are attracted by the magnet which is located proximate to the second channel. This 'jump' minimises the loss of particles at the interface and minimises the carry over of blood into the reaction buffer zone.

The magnet is then moved at a controlled speed (minimising particle loss) to a position over the working electrode of the second electrode set. The magnet drags the particles along the underside of the blocked lid. This drags the magnetic particles over the working electrode of the second electrode set, whilst separating them from any remaining unbound GOD conjugate. Upon arrival over the second electrode set, the magnetic particles are held in place by the magnet, and a further 50 ul of reaction buffer (to further wash the magnetic particles) is added to the second channel via the second application zone. Once this is delivered, the magnet is removed and the reaction is allowed to proceed for 10 minutes with the magnetic particles on the working electrode of the second electrode set. In this setup, a three carbon electrode system is used.

After 10 minutes reaction, the device is attached to a potentiostat, and the potential stepped from open circuit to +0.4V. The current is measured after 10 seconds and compared to calibration curve to give NTproBNP concentration. The ferrocyanide ions produced by reaction between ferricyanide, GOD and glucose, are converted to ferricyanide species at the electrode surface at +0.4 Volts.

In some embodiments, both assays are carried out in whole blood. In this embodiment, IMA binding reagent, magnetic particles and enzyme conjugate are provided in dry form in the first channel, whilst reaction substrates and mediators are provided in dry form in the second channel. The dried reagents are resuspended by the addition of blood. The resuspended IMA binding reagent binds IMA in solution and an assay is performed at a first set of electrodes. The magnetic particles and the enzyme label are mixed with the NTproBNP in the blood. The magnetic particles, and its conjugates, are then moved by magnetic manipulation to the second set of electrodes, separating the magnetic from the unbound enzyme. The second reaction would then proceed over the second electrode set.

In a further alternative the magnetic particles are used as a 'filter'. Magnetic particles and enzyme conjugate are dried onto a test strip and are resuspended by the addition of blood. With antibody bound, they could be positioned above a centrally located electrode in the blood sample. The blood sample could then be pumped back and forward passed the magnetic particles, allowing maximal binding of NTproBNP to the magnetic particle antibody complex and enzyme conjugate, whilst they are held in position. The buffer pouch would then be used to wash the blood away from the beads, into a sink area. A second assay, for IMA, can be performed in the sink area, where there are further sets of electrodes. The reagents for the IMA assay can be dried onto the test strip, or may be present in the buffer fluid. The buffer in which the magnetic particles are left contains substrate and mediator for reaction with enzyme conjugate which occurs over the electrode and which can be measured electrochemically.

In a still further embodiment, the IMA assay can be carried out as described and the second assay uses magnetic particles coated with streptavidin, and a biotinylated antibody (eg 7206). The biotinylated antibody binds NTproBNP, which also binds the enzyme conjugate in whole blood. This has preferential binding kinetics in the absence of bound magnetic particles. The magnetic particles can then be mixed with the binding complexes and bound to the antibody through a streptavidin-biotin association. The magnetic particle complexes are then dragged to the electrodes as described. It is also possible to use a streptavidin-biotin association between the label and anti-NTproBNP antibody (e.g., 15F11) instead. Also, streptavidin, can be coupled to antibodies and biotin coupled to magnetic particles.

In another embodiment, there is planar capture of magnetic particles bound to NTproBNP on the electrode surface. Anti-NTproBNP antibody is attached either to the electrode, or to the lid above the electrode. Magnetic beads have another anti-NTproBNP antibody as well as an enzyme label bound to their surface. These beads are bound to NTproBNP in the blood sample as in the previous examples, and are dragged over the electrodes and allowed to bind the surface-bound antibodies. Unbound magnetic beads (without NTproBNP bound) are washed away by a wash with a reaction buffer. A signal is then produced by reaction of the enzyme label bound to the beads, proportional to the NTproBNP concentration.

This planar capture can also involve biotin-streptavidin associations to bind the magnetic particle to the antibody (e.g., 7206) where the magnetic particle, as well as having enzyme label bound to its surface, has streptavidin bound also. The anti NTproBNP antibody (e.g. 7206) is biotinylated. The NTproBNP binding to biotinylated antibody and surface-bound antibody occurs prior to attachment of streptavidin-coated magnetic particle to the biotinylated antibody. In a variation of this system, the surface bound antibody can be biotinylated and the surface to which it is attached can be streptavidin coated. In this way, after the magnetic particles with antibody and attached enzyme bind NTproBNP, and NTproBNP binds biotinylated antibody, this complex can be attached to the surface via the streptavidin-biotin association. Also, the streptavidin and biotin coupling can be reversed, for example the streptavidin can be coupled to antibodies and biotin coupled to magnetic particles or surfaces.

In a still further embodiment, the first assay is performed as described in the examples given. In the second assay, the working electrode is positioned at the point where the magnetic particles jump to after the liquid-liquid interface is formed. This allows a stationary magnet to be used that positions the beads over the working electrode. This requires the reaction buffer to wash past the beads, washing the blood sample into a 'sink' area, whilst the beads are held in position against this flow. This can also be performed using two or three magnets set up in a see-saw arrangement, collecting the beads at specific regions along the channel. As one magnet is lowered towards the device to manipulate the particles, a connected magnet is simultaneously removed, removing its effect on the particles. Electromagnets can also be used instead of permanent magnets. Multiple stationary electromagnets can be switched on/off in sequence to control to positioning of the magnetic particles.

It will be apparent that any suitable antibody pairings can be used including, but not limited to, 15F11-24E11, 15C4-29D12, 15C4-13G12, 15C4-18H5, 7206-15F11. Also, various sizes, makes and surface coatings of magnetic particle can be used including, but not limited to, 0.1-1 um diameter particles from Chemicell™, Bangs™ Spherotech™, Ademtech™, Polymicrospheres™, Chemagen™, Dynal™, Coprtex™, Micromod™, Polysciences™, Estapor™, Seradyn™ or Bioclone™, with surface coatings of carboxyl, amine, aldehyde, epoxide, N-hydroxysuccinimide, choromethyl, polyglutaraldehyde, thiol, cyanuric, tosyl, hydrazide, hydroxyl, protein, protein G, streptavidin or biotin).

The method can be performed using different labels such as other enzymes including, but not limited to, glucose oxidase, alkaline phosphatase, glucose dehydrogenase, glucose-6-phosphate dehydrogenase, and acetylcholine esterase. Other labels that can be used include fluorescent molecules/particles (e.g., TRF™ latex beads), absorbance labels (e.g., Goldsol™), and radiolabels. To amplify the signal multiple labels such as poly HRP dextran conjugates, or beads coated in glucose oxidase and anti-NTproBNP antibody, can be used.

The fluid stopping point can be controlled by other suitable mechanisms such as introducing a step change in channel height/depth or using fusable vents. Also, mixing can be performed within the assay device using magnetic, thermal and (ultra)sonic mixing techniques. A blood separator can be introduced to separate the red blood cells and allow only plasma into the device channel.

A buffer pouch incorporated into the test strip can deliver the reaction buffer, and the composition of the buffer can be varied (e.g., sodium acetate, phosphate-citrate, sodium citrate or any other buffer at any suitable concentration or pH). Any suitable liquid can be used instead of a buffer.

The concentrations of the redox mediator and the enzyme substrate can be varied. Other mediators such as TMB (tetramethyl benzene), ferrocene and its derivatives, or Ru(phenylimidazole)(phenanthroline) $PF_6$, or indophane blue could be used for HRP, and other substrates such as sodium perborate or urea peroxide. Depending on the enzyme labels being used, reaction buffers containing relevant substrate/mediator/solution conditions are used. Other labels, such as fluorescent particles, only require solutions that are compatible with, for example, fluorescent measurement (such as water, buffer, salt solution, oil or other organic or aqueous solvents). When a non-electrochemical detection method is used the magnetic particles do not require to be deposited over an electrode. Other methods of detection include absorbance, fluorescence, surface plasmon resonance, scintillation counting, radiography, and luminescence.

The test strip can be equipped with a longer channel, mitigating the use of the extra 50 μL wash. A simple drag of the magnetic particles over the electrode is sufficient to remove interferents.

The magnet used can be located less than or greater than 5 mm away from the interface, as long as the magnetic particles are still influenced by the magnetic field. The magnetic particles can be positioned within the blood sample (not at interface) until after the liquid-liquid interface has been formed. Also, the magnetic particles can be dragged through the liquid-liquid interface, after it is formed, by moving the magnet from the first channel to the second channel, across the liquid-liquid interface.

The magnet can hold the magnetic particles in place over the electrode during the reaction and/or measurement. Also, the magnet can drag the magnetic particles along the base of the channel, or in mid-channel. The magnet can be moved in non-linear directions (e.g., the beads can be moved in any shaped channel, such as linear, circular or spiral by, for example, a rotating magnet) and/or in sweeping movements before dragging the particles to the electrode.

The label used can be allowed to react over the electrode for a longer or shorter period of time. If another label was used (such as fluorescence or absorbance), detection of the signal can be performed without an incubation period.

A three or two electrode system can be used, with either gold or carbon electrodes. The electrodes can be positioned in a pit or depression or side channel in order to allow easy positioning of magnetic particles upon it. When deposited in a pit or depression, the lid of the device can be pushed down enclosing the beads in the pit/depression to reduce reaction volume, increasing relative reaction concentrations. Electrodes can also be positioned on either side of the liquid-liquid interface and can act as fill indicators so that the formation of the interface can be monitored.

The magnetic particles can position the beads on the lid above the electrode, or anywhere in the vicinity of the electrode. The magnetic particles can be mixed during the reaction to increase access of substrate/mediator to the enzyme.

The geometry of the channel and interface dimensions can be varied to increase mixing of reagents, decrease interfacial mixing, and maximise the signal produced over the electrodes, for example, a narrowing of the channel at the interface reduces diffusion mixing of the two separate fluids in the separate channels.

In the electrochemical assay step, any voltage that reduces oxidised species, or that oxidises reduced species, can be used. For example, other potentials are be used for measurement of other species. When other labels are used, such as fluorescence or absorbance, appropriate optical measurements are made.

Although in the examples given the sample is derived from blood it will be appreciated that the method is suitable for detecting other analytes contained in other mediums. For example the first analyte may be, although is not limited to, a protein, a blood protein, albumin, ischemia modified albumin, a mixture of albumin and ischemia modified albumin, and any other chemical or biological species suitable for analysis and/or detection. In some embodiments the first analyte may comprise ischemia modified albumin.

In the example above the reagent in the first assay is cobalt. The reagent used can be any reagent suitable for interacting with the analyte. For example the reagent may be, although is not limited to, a metal, a divalent cation, a transition metal, cobalt, and any other reagent that is suitable for interacting with the analyte. In some embodiments the reagent may comprise cobalt.

In the electrochemical examples given the electrochemical analysis may involve a voltammetric sweep (single or multiple) during which the detectable components are quantified by the magnitude of their oxidation and/or reduction currents. In addition, the assay period may involve a preliminary period of electrochemical oxidation or reduction, as described previously. However, it will be appreciated that there are many electrochemical amperometric and voltammetric techniques that can be used.

The assay device may comprise more than two assay areas in series, in parallel or a combination of both. Such devices can have a plurality of channels, which can diverge and recombine such that a single sample may run in separate channels. Other embodiments of the device can comprise a corkscrew, spiral or zig-zag channel along which assays can be performed.

In a further embodiment of the device there is provided a central sample application area from which flow channels radiate. The radiating flow channels can have assay detection zones and further sample application zones, as well as other additional features.

All of the devices, test strips and flow channels described can have any the features of the devices, test strips and flow channels described in more detail previously.

In general, the assay device can be made by depositing reagents on a base and sealing a lid over the base. The base can be a micro-molded platform or a laminate platform.

Micro-Molded Platform

For an assay device prepared for optical detection, the base, the lid, or both base and lid can be transparent to a desired wavelength of light. Typically both base and lid are transparent to visible wavelengths of light, e.g., 400-700 nm. The base and lid can be transparent to near UV and near IR wavelengths, for example, to provide a range of wavelengths that can be used for detection, such as 200 nm to 1000 nm, or 300 nm to 900 nm.

For an assay device that will use electrochemical detection, electrodes are deposited on a surface of the base. The electrodes can be deposited by screen printing on the base with a carbon or silver ink, followed by an insulation ink; by evaporation or sputtering of a conductive material (such as, for example, gold, silver or aluminum) on the base, followed by laser ablation; or evaporation or sputtering of a conductive material (such as, for example, gold, silver or aluminum) on the base, followed by photolithographic masking and a wet or dry etch.

An electrode can be formed on the lid in one of two ways. A rigid lid can be prepared with one or more through holes, mounted to a vacuum base, and screen-printing used to deposit carbon or silver ink. Drawing a vacuum on the underside of the rigid lid while screen printing draws the conductive ink into the through holes, creating electrical contact between the topside and underside of the lid, and sealing the hole to ensure that no liquid can leak out.

Alternatively, the lid can be manufactured without any through holes and placed, inverted, on a screen-printing platform, where carbon or silver ink is printed. Once the electrodes have been prepared, the micro-molded bases are loaded and registered to a known location for reagent deposition. Deposition of reagents can be accomplished by dispensing or aspirating from a nozzle, using an electromagnetic valve and servo- or stepper-driven syringe. These methods can deposit droplets or lines of reagents in a contact or non-contact mode. Other methods for depositing reagents include pad printing, screen printing, piezoelectric print head (e.g., ink-jet printing), or depositing from a pouch which is compressed to release reagent (a "cake icer"). Deposition can preferably be performed in a humidity- and temperature-controlled environment. Different reagents can be dispensed at the same or at a different station. Fluorescent or colored additives can optionally be added to the reagents to allow detection of cross contamination or overspill of the reagents outside the desired deposition zone. Product performance can be impaired by cross-contamination. Deposition zones can be in close proximity or a distance apart. The fluorescent or colored additives are selected so as not to interfere with the operation of the assay device, particularly with detection of the analyte.

After deposition, the reagents are dried. Drying can be achieved by ambient air-drying, infrared drying, infrared drying assisted by forced air, ultraviolet light drying, forced warm, controlled relative humidity drying, or a combination of these. Micro-molded bases can then be lidded by bonding a flexible or rigid lid on top. Registration of the base and lid occurs before the two are bonded together. The base and lid can be bonded by heat sealing (using a heat activated adhesive previously applied to lid or base, by ultrasonic welding to join two similar materials, by laser welding (mask or line laser to join two similar materials), by cyanoacrylate adhesive, by epoxy adhesive previously applied to the lid or base, or by a pressure sensitive adhesive previously applied to the lid or base. After lidding, some or all of the assembled assay devices can be inspected for critical dimensions, to ensure that the assay device will perform as designed. Inspection can include visual inspection, laser inspection, contact measurement, or a combination of these.

The assay device can include a buffer pouch. The buffer pouch can be a molded well having a bottom and a top opening. The lower opening can be sealed with a rupturable foil or plastic, and the well filled with buffer. A stronger foil or laminate is then sealed over the top opening. Alternatively, a preformed blister pouch filled with buffer is placed in and bonded in the well. The blister pouch can include 50 to 200 µL of buffer and is formed, filled, and sealed using standard blister methods. The blister material can be foil or plastic. The blister can be bonded to the well with pressure sensitive adhesive or a cyanoacrylate adhesive.

Laminate Platform

Three or more laminates, fed on a roll form at a specified width, can be used to construct an assay device. The base laminate is a plastic material and is coated on one surface with a hydrophilic material. This laminate is fed into a printing station for deposition of conductive electrodes and insulation inks. The base laminate is registered (cross web) and the conductive electrodes deposited on the hydrophilic surface, by the techniques described previously. The base laminate is then fed to a deposition station and one or more reagents applied to the laminate. Registration, both cross web and down web, occurs before reagents are deposited by the methods described above. The reagents are dried following deposition by the methods described above. A middle laminate is fed in roll form at a specified width. There can be more than one middle laminate in an assay device. The term middle serves to indicate that it is not a base laminate or lid laminate. A middle laminate can be a plastic spacer with either a pressure sensitive adhesive or a heat seal adhesive on either face of the laminate. A pressure sensitive adhesive is provided with a protective liner on either side to protect the adhesive. Variations in the thickness of the middle laminate and its adhesives are less than 15%, or less than 10%.

Channels and features are cut into the middle laminate using a laser source (e.g., a $CO_2$ laser, a YAG laser, an excimer laser, or other). Channels and features can be cut all the way through the thickness of the middle laminate, or the features and channels can be ablated to a controlled depth from one face of the laminate. The middle and base laminates are registered in both the cross web and down web directions, and bonded together. If a pressure sensitive adhesive is used, the lower liner is removed from the middle laminate and pressure is applied to bond the base to the middle laminate. If a heat seal adhesive is used, the base and middle laminate are bonded using heat and pressure.

The top laminate, which forms the lid of the assay device, is fed in roll form at a specified width. The top laminate can be a plastic material. Features can be cut into the top laminate using a laser source as described above. The top laminate is registered (cross web and down web) to the base and middle laminates, and bonded by pressure lamination or by heat and pressure lamination, depending on the adhesive used. After the laminate is registered in cross and down web directions, discrete assay devices or test strips are cut from the laminate using a high powered laser (such as, for example, a $CO_2$ laser, a YAG laser, an excimer laser, or other).

Some, or all, of the assembled assay devices can be inspected for critical dimensions, to ensure that the assay device will fit perform as designed. Inspection can include visual inspection, laser inspection, contact measurement, or a combination of these.

An example of one application that employs the use of assays to detect analytes is the analysis of physiological fluid samples, such as blood samples. In particular, it has become increasingly common to analyse blood samples for analytes that may be indicative of disease or illness. Such analyses can be performed using an assay that directly or indirectly detects an analyte.

Embodiments provide a device and method for performing more than one assay on a single small volume blood sample, or other biological materials or complex mixtures. Also, the devices and methods can provide allows the detection of at least a second analyte without contamination of assay reagents with non-specific reactions, and physical occlusions of target molecules with cellular debris.

The assay methods and devices can be used in home testing kits for analysing species present in the blood. In particular, as embodiments facilitate the performance of more than one assay on a small sample volume, the assay device and method are suitable for use with home testing kits that utilise the "finger stick" or "finger prick" procedure.

Embodiments of the assay devices and methods may be capable of accepting small fluid samples in a simple step, and is able to present small fluid samples for immediate testing in a reliable and reproducible fashion. These can provide an efficient way to utilise obtained blood samples in a home testing kit by allowing the performance of a series of tests on the same sample.

Finally, the device and method of some embodiments facilitate the execution of more than one assay on the same blood sample by separating and isolating analytes of interest, within a complex mixture. This enables the visualisation of the analytes by a detection procedure. In particular, the present invention affords the use a specific reagent for visualising a marker related to an analyte and the reliable quantification of its presence to inform on a disease state in a subject. The analytes may be indicative of disease states in a subject.

EXAMPLES

The following are non-limiting examples of certain embodiments.

Example 1

Detection of NT-proBNP in a Human Blood Sample

A human blood sample is added to the assay device 500 at inlet 510. The blood contains an amount of an analyte: N-terminal truncated pro-brain natriuretic peptide (NT-proBNP).

The sample of blood enters the first channel portion 4302, e.g. via capillary action, where it mixes with reagents in the reagent zone. The reagents in the reagent zone include streptavidin coated magnetically susceptible particles and biotinylated first binding agent which is an anti-NT-proBNP antibody 15C4 (HyTest Ltd.; Catalogue #:4NT) and horseradish peroxidase ("HRP") conjugated to a second binding agent which is anti-NT-proBNP antibody 15F11 or 29D12 (HyTest Ltd.; Catalogue #:4NT) (the antibody-linked enzyme). The assay device and included reagents are provided in a dry state. Addition of a liquid sample to the assay device (i.e., to the inlet and first channel portion) re-suspends dry reagents.

The reagents are re-suspended in solution with the blood, and form a mixture. The streptavidin coated magnetically susceptible particles bind to the biotinylated first binding agent to form a conjugate (the antibody-linked magnetically susceptible particle). The NT-proBNP in the blood is also bound by the first binding agent and a ternary complex of NT-proBNP bound antibody-linked magnetically susceptible particle is formed. A magnetic field is applied such that the magnetically susceptible particles undergo an induced motion (e.g., a periodic or oscillatory motion) to promote resuspension and mixing of the reagents with the sample.

FIG. 38J shows a perspective view of the underside of device 500 after a sample liquid has been added to inlet 510. The blood sample fills the first channel portion 4302. Upon reaching junction 4305, the liquid forms a meniscus. The change in cross-sectional area of the channel at junction 4305 does not allow the blood sample to fill the second channel portion 4304. Rather, capillary pressure in the second channel portion exceeds any capillary forces that draw the sample liquid beyond junction 4305 into the second channel portion 4304. Junction 4305 thus acts as a capillary stop, preventing substantial liquid sample flow beyond that point. At this stage, a blood sample:air interface is formed by the blood meniscus at junction 4305.

After mixing of the reagents and blood sample, a magnetic field is applied to the first channel portion 4302. The applied field is manipulated so as to move the magnetically susceptible particles, and all components bound to them. The magnetically susceptible particles are magnetically moved along the first channel portion 4302 toward junction 4305.

A buffer liquid is added to the device at the second inlet 520. A buffer pouch 507 incorporated into the device delivers the reaction buffer. The buffer liquid contains 10 mM of the redox mediator 2,2'-azino-bis-(3-ethylbenzo-thiazoline-sulfonic acid) (ABTS), 10 mM $H_2O_2$, 150 mM KCl, 125 mM sodium acetate; 0.1% v/v Tween20, made to a final pH 4.2. The buffer does not contain analyte (NT-proBNP). The buffer liquid flows along the second channel portion 4304 to junction 4305, where the buffer liquid contacts the blood sample at the blood:air interface to form a blood:buffer interface.

The magnetically susceptible particles (and all that is bound to them) are moved across the blood:buffer interface by moving the applied magnetic field across the junction 4305 into the second channel portion 4304 and towards the working electrode 516w. The formation of the blood:buffer interface facilitates the magnetic movement of the magnetically susceptible particles (and all that is bound to them) from the blood to the buffer, leaving interfering sample components and analytes that are not of interest in the blood in the first channel portion 4302. The magnetically susceptible particles and all that is bound to them, including the NT-proBNP (in the form of a ternary complex of NT-proBNP with antibody-linked magnetically susceptible particle and antibody-linked enzyme) are transferred to the second liquid in the second channel portion 4304.

FIGS. 9A and 9B illustrate magnetic separation across the blood:buffer interface in greater detail. In FIG. 9A, magnetically susceptible particles 200 are located near blood meniscus 190 by virtue of the magnetic field applied by source 210. Some of the magnetically susceptible particles 200 are bound to NT-proBNP, which in turn is bound to the second binding agent and the detectable HRP enzyme label. Because the second binding agent:HRP conjugates in the first channel portion 4302 are present in excess to NT-proBNP, some of the second binding agent:HRP conjugates remain unbound. Magnetic separation helps ensure that unbound second binding agent:HRP conjugates do not reach second channel portion 4304 or electrodes 516w, 516c and 516r in the detection zone 514; in other words, only magnetically susceptible particles bound to NT-proBNP, via the first binding agent, contribute to the detectable signal so that the detectable signal can be reproducibly related to the amount or concentration of NT-proBNP in the sample.

The magnetically susceptible particles bound to NT-proBNP are next moved to the working electrode 516w by manipulation of the applied magnetic field. The magnetically susceptible particles are magnetically positioned and held at the detection zone for an incubation time of e.g. 1 minute. Magnetically susceptible particles bound to NT-proBNP and the second binding agent:HRP conjugates are detected electrochemically by HRP mediated catalysis of hydrogen peroxide and ABTS to water and oxidised-ABTS. At the end of the incubation time the electrochemical current produced by the reduction of oxidized ABTS at the electrodes is measured at the working electrode for a measurement period (e.g. 3 seconds).

The detected electrochemical current is received in meter 400 and compared against a corresponding calibration dataset to determine an amount and/or concentration of NT-proBNP. The meter displays or communicates an assay result to the user.

Example 2

Figure 52:
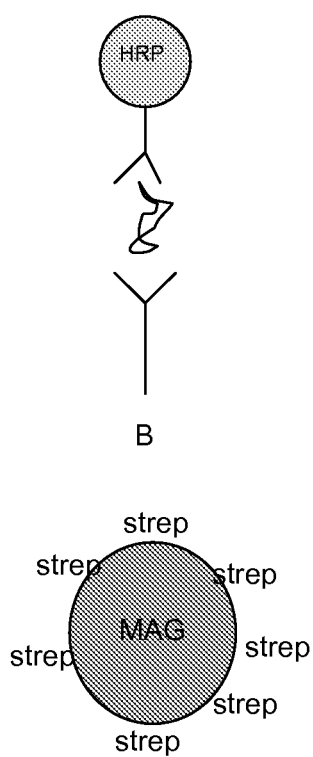
FIG. 52 illustrates the reagents used in the electrochemical NT-proBNP assay

Extension/Linearization of the Measurable NT-proBNP Range—Two Point Electrochemical Measurements to Extend the Dynamic Range Electrochemical measurements can be made using a single time point of HRP turnover time. A typical dose response curve for concentrations of 0-20,000 pg/ml NT-proBNP in the liquid sample is shown in FIG. 52. The performance of the electrochemical NT-proBNP assay may be optimised by extending the measurable range and linearising the response at the higher NT-proBNP concentrations. To achieve this we identified whether the plateau effect was a reagent, electrochemical or combined reagent and electrochemical limitation.

Figure 53:
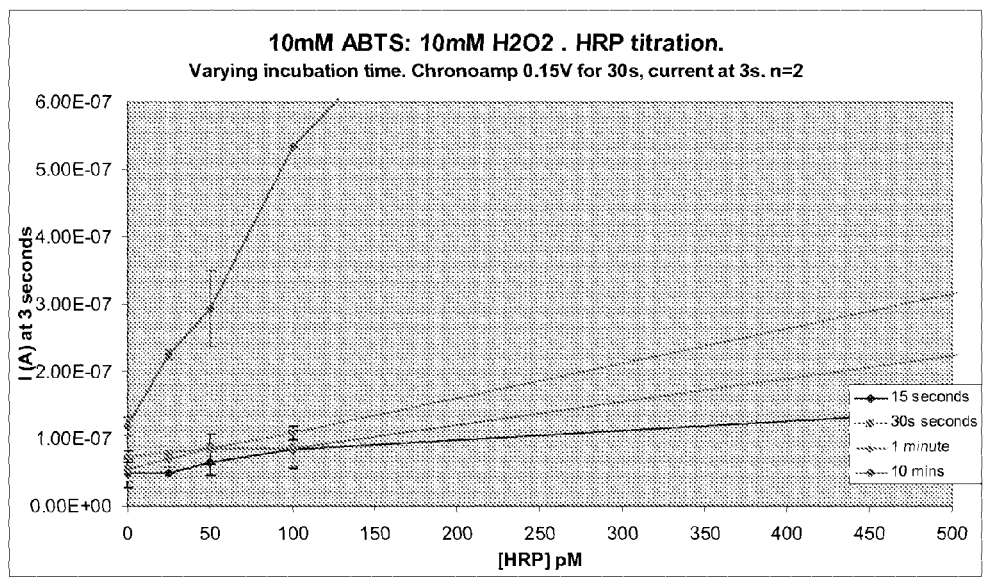
FIG. 53 illustrates summary HRP titration data at turnover times of 10 mins, 1 min, 30 sec and 15 seconds.
Figure 54:
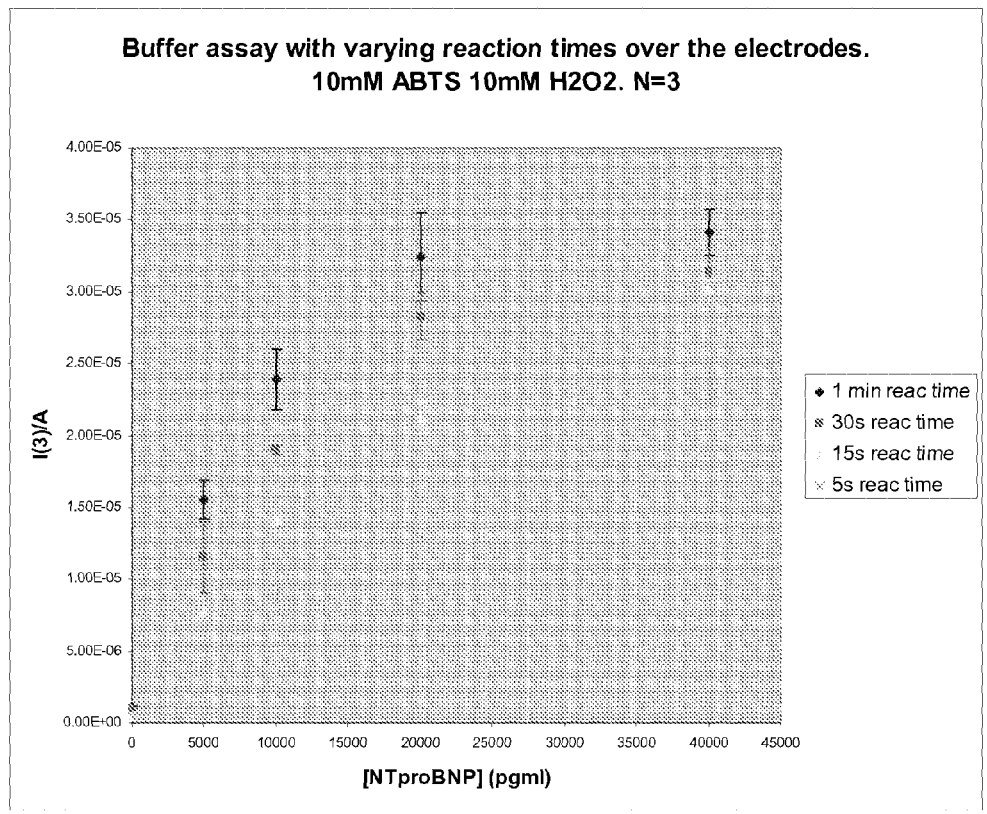
FIG. 54 illustrates NT-proBNP electrochemical assay results for 0, 5000, 10,000, 20,000 and 40,000 pg/ml NT-proBNP with HRP turnover times of, 1 min, 30, 15 and 5 seconds.

Within the current electrochemical measurement of NT-proBNP, effectively we are measuring the concentration of HRP; this is illustrated in FIG. 53. Therefore dose response curves of NT-proBNP are effectively current v.s HRP concentration as depicted in FIG. 54.

The ability to measure the HRP concentration electrochemically via the mediator ABTS provides the flexibility to tune the immunoassay response. Typically, once the particles were moved out of the blood and dragged to the electrode, captured HRP was allowed to react for a 1 minute turnover period (incubation time). No potential was applied to the electrode until after the 1 minute HRP turnover period, the subsequent potential applied was used to reduce the oxidised ABTS generated by the HRP.

To investigate the limitation of a 1 minute HRP turnover period, HRP titrations were performed to investigate the HRP turnover time on the sensitivity, linearity and range of the response. In these experiments the HRP was homogeneously distributed within the channel and not concentrated in the vicinity of the electrode when placed on the electrode via the magnetic particles.

The linear range of the HRP is seen to vary with turnover time. A 10 minute turnover time results in an approximately linear range up to 5000 pM HRP; a 1 minute turnover time results in an approximately linear range up to 20,000 pM HRP; a 30 second turnover time results in a approximately linear range of 50,000 pM HRP; a 15 second turnover time results in an approximately linear range of 80,000 pM HRP.

The effect of HRP turnover time is summarised in FIG. 53. There is a trade off between increased linearity of the HRP response and sensitivity, as the HRP range (pM) is increased the HRP measurement becomes less sensitive e.g. 10 minutes—limit of detection (LOD) at least 25 pM; 1 min—LOD 50-100 pM; 30 secs 100 pM; 15 secs LOD 100 pM.

From the titration data we conclude that we can significantly increase the measurable HRP concentration (pM) range and the linear component.

Experiments were performed to test this hypothesis, the summary results are shown in FIG. 54.

The application of reduced HRP turnover times has a significant effect upon extending and linearising the NT-proBNP response. This represents a significant optimisation for the electrochemical measurement of NT-proBNP.

It is desirable to be able to measure NT-proBNP concentrations over a 50-20,000 pg/ml range. This is a dynamic range for an immunoassay to measure. It would also be desirable to distinguish a doubling in NT-proBNP concentration. It would also be desirable to linearise the electrochemical response over the higher NT-proBNP concentrations.

Figure 55:
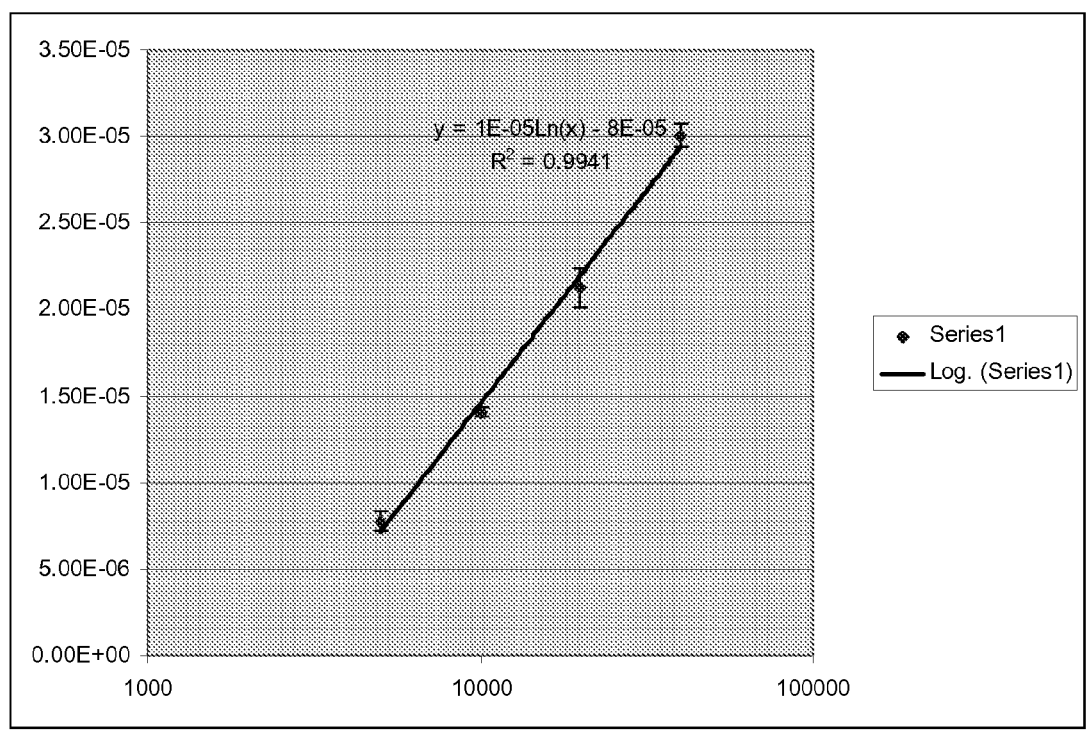
FIG. 55 illustrates a semi-log plot of NT-proBNP electrochemical assay results at a 15 sec turnover time.

For example, a 15 second turnover time allows the measurement of up 40,000 pg/ml NT-proBNP and easily allows the ability to measure the doubling of 5000 to 10000 to 20000 to 40000 pg/ml. This result demonstrates how the assay can be tuned for optimum performance. For example if the 15 sec measurement is plotted on a semi log curve a good linear response is observed as shown in FIG. 55 (x-axis shows NT-proBNP concentration).

This result provides a good model system to understand the complex interplay between many parameters. A two point electrochemical measurement can be made to measure the desired range with optimum performance, for example a 15 second measurement to capture the high NT-proBNP concentrations as shown and then a second measurement (e.g. 1, 2, 3 minutes) to measure the low NT-proBNP concentrations resulting in 2 calibrations curves for maximum sensitivity and performance.

Figure 56A:
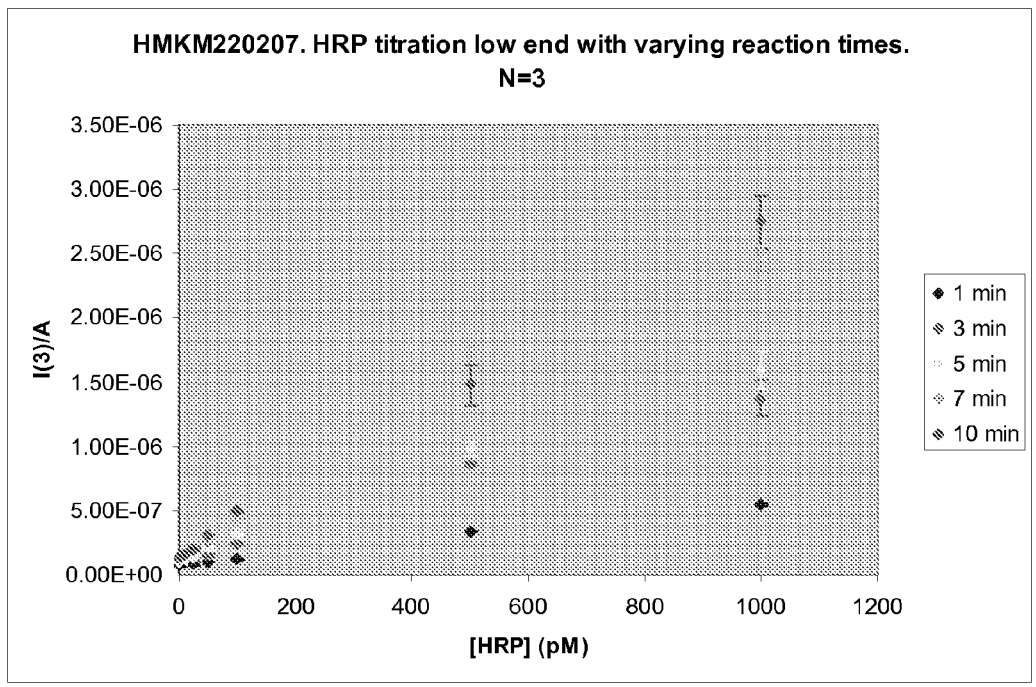
FIGS. 56A-B illustrate the results of HRP titration experiments showing the relationship between increased HRP turnover time and increased HRP LOD.
Figure 56B:
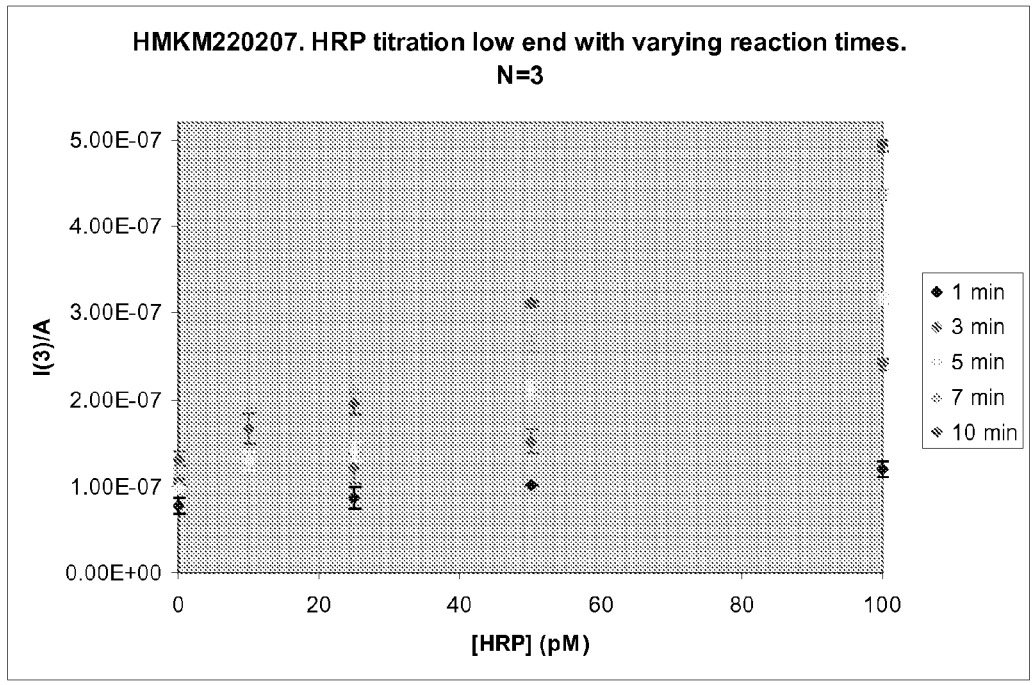

Further HRP titration experiments were performed to investigate the relationship between increased HRP turnover time and increased HRP LOD. A clear trend is observed as summarized in FIG. 56A-B.

The LOD and the associated slope of the response changes as a function of HRP turnover time. Specifically LOD of 10 pM are observed for the 10, 7 and 5 min HRP turnover time whilst 25 pM is observed for 3 mins and a 100 pM LOD for a 1 minute HRP turnover time. Significant increases in performance could be observed using a prolonged HRP time period for measurement of lower NT-proBNP concentrations compared with the previously used 1 minute turnover time. For example a secondary time point measurement after 5 minutes HRP turnover would result in changing the HRP LOD from 100 pM to 10 pM ($\times 10$ difference).

Two point HRP titrations experiments were performed. Identical titration responses were observed whether a single HRP concentration is measured in a single or dual time point manner, depletion of the generated oxidised ABTS over a 3 second period does not affect the signal obtained with the second time point measurement (300 sec). Shorter measurement times of the oxidised ABTS (<300 secs) may allow multiple time points to be measured.

Example 3

Blood to Blood Normalisation

Blood to blood variation between blood samples may be significant. The CV's (coefficient of variation) within a blood sample are generally good (10% or less).

Blood to blood and plasma to plasma variation was re-examined in a test assay device using a single NT-proBNP stock solution (elimination of stock to stock variation). Leakage of ABTS from the device around the electrodes was eliminated. Corresponding plasma measurements were made in plasma derived from the bloods used in the blood study.

Inter-blood sample CV's of 5.17% are seen for the mean of all repetitions at 20,000 pg/ml NT-proBNP concentration whilst an inter-blood sample CV of 1.53% is observed for 20,000 pg/ml NT-proBNP concentration when calculated from the mean of the means. The corresponding CV's in the plasma measurements are significantly higher than the blood based measurements.

Interestingly, the blood measurements were made in bloods with a hematocrit (HCT) range of 38-49. At the higher NT-proBNP concentrations there seems to be little or no effect of HCT on the current measured. The corresponding plasma measurements represent a zero HCT measurement for each NT-proBNP concentration in the blood measurement. However HCT may play a more important role at low concentrations of NT-proBNP; there is a greater spread in the 0 and 500 pg/ml data.

A relationship between current and HCT at a defined NT-proBNP concentration may exist at very low concentrations of NT-proBNP. The background appears to be influenced by the HCT, i.e. 0 pg/ml no HRP control, and gives an additive current to the low NT-proBNP concentrations. Normalisation of the data can be achieved in a number of ways The effect of increasing hematocrit is to increase the background signal. The effect of increasing hematocrit is to increase the current by the same amount in each case at the low end (at the high end this effect is insignificant to the larger signal).

The same slope of signal vs. hematocrit is seen for each set of data, this indicates that the effect is an additive current effect and means that it is possible to subtract the background signal from the specific signal. The slope is about 50 nA increase per % HCT increase, this compares with an approximate 2.2 nA per pg/ml of NT-proBNP seen in the linear part of the assay. This means that the magnitude of the effect of HCT is about 25 pg/ml increase in measured signal per 1% increase in hematocrit. This is clearly significant at the low end of the assay but less so at the higher end.

The data may be corrected by subtracting the background, this was done by calculating the theoretical zero HRP result for each hematocrit value based on the best fit line through the zero HRP data. This was then subtracted from the zero and 500 pg/ml NT-proBNP data sets and outliers were removed.

The correction was also applied by subtracting the calculated theoretical zero NT-proBNP result for each hematocrit value based on the best fit line through the zero NT-proBNP data. This was then subtracted from the zero and 500 pg/ml NT-proBNP data sets and the resulting data was plotted.

The data recorded indicates an effect of HCT of approximately 25 pg/ml increase per 1% HCT increase. This analysis shows that for a blood sample, if we have a predictable trend of assay response vs. HCT, and if the HCT is known, then applying a correction factor removes the effect of HCT on the signal. A HCT measurement on the device/meter allows a theoretical correction factor to be applied to low NT-proBNP concentrations to normalize the response. This measurement can be made electrochemically by electrodes positioned in the first channel portion. An alternative is to remove the no HRP contribution to the signal, e.g. through modification of the reagent chemistry, through the use of blockers of the electrochemical species or specific deactivation of the electrochemical species.

In addition, a range of HCT were artificially created in a single blood sample and the effect of HCT on current/signal at 20,000 pg/ml was studied. HCT does not skew the 20,000 pg/ml signal over a wide range of HCT.

Example 4

Transfer of Magnetically Susceptible Particles Across the Liquid Sample:Liquid Interface Although the blood to blood CV is very consistent an approximately 5 µA difference between a binding reaction carried out in buffer and blood or plasma at 20,000 pg/ml has been observed. There are a number of possible causes of this difference.
1. Reagents are limiting
    Previous experiments/data have shown the reagents are not a limiting factor in a buffer measurement; it would be highly improbable in a blood measurement.
2. Reduction in the capture efficiency in a viscous matrix such as blood or plasma
    Diffusion rates will be affected by the increased viscosity in blood vs. buffer; therefore a reduced efficiency of successful binding collisions could be expected.
3. Presence of an interferent that quenches the signal:
    A consistent level or reduction in signal because of an interferent (electrochemical) is unlikely because interferents generally vary between samples over a physiological range. Uric and ascorbic acid are known to react with the radical cation form of ABTS, reactions of this nature would suppress the signal generated by interfering with the HRP recycling of the ABTS (see FIG. 57).
4. Loss of more magnetically susceptible particles in blood samples than buffer samples
    Transfer of magnetically susceptible particles from the liquid sample to the electrode may be less efficient in blood samples than buffer samples ("bead loss").

We tested experimentally the hypothesis that the reduced 5 µA is due to capture efficiency (i.e. efficiency of magnetically susceptible particles binding to NT-proBNP) and not bead loss (failure of a magnetically susceptible particle to be transfer to the working electrode). Binding reactions (20,000 pg/ml) were set up in an eppendorf. After 10 minutes binding time 10 µl of binding reaction solution (buffer) was pipetted into the device (normal device separation and drag) or a wash step (removal of the HRP) was performed off the device, 10 µl of the washed binding reaction was then pipetted into the device and the normal transfer across the liquid sample:liquid interface and electrode drag was performed. The methodology was applied to blood reactions as well, i.e. the 10 µl of the blood binding reaction was pipetted into the device (followed by normal transfer across the blood sample:liquid interface and electrode drag) or the blood reaction was washed off device (removal of the HRP) and the magnetically susceptible particles re-suspended in buffer and 10 µl pipetted into the device and the normal transfer across the liquid sample:liquid interface and electrode drag performed. This allows any reduction in signal between buffer and blood measurements to be attributed to magnetically susceptible particles or capture efficiency in blood.

Results showed that there is always a reduction in signal in blood based measurements vs. buffer measurements. Statistically, there is little difference between measurements when washed off or on the assay device, either in blood or buffer. Importantly no difference between washed and unwashed blood indicates that reduced capture efficiency in blood is the most probable cause of reduced signal vs. buffer signal. In the washed blood measurements the capture event has been performed in blood, washed and then constituted in buffer and then the transfer across the blood sample:liquid interface and electrode drag to the electrode performed in the assay device (same as buffer measurement). In comparison the unwashed blood measurement involves conducting the capture event in blood contained in the assay device in addition to normal transfer across the blood sample:liquid interface and electrode drag in the assay device. Therefore any change in signal between the unwashed and washed bloods would be due to bead loss. However, the signals are very similar suggesting a reduced capture efficiency in blood.

In a further experiment this experiment was repeated to measure the capture efficiency and bead loss of the system in blood and buffer, using HRP immobilized at the working electrode.

If bead loss in blood is a problem, a higher concentration of magnetically susceptible particles can be added such that fewer magnetically susceptible particle complexes having bound HRP are lost and thereby increasing the number of HRP-gold sol labels reaching the working electrode thereby increasing the measured electrochemical signal. This approach is of benefit where a certain number of magnetically susceptible particles are lost rather than a proportion of them. If a proportion of the magnetically susceptible particles are lost then the signal would not be expected to change.

Additional magnetically susceptible particles do not increase the signal significantly in blood or buffer. In fact, adding 4× magnetically susceptible particles to blood results in a slight decrease in the signal. This is possibly due to the magnetically susceptible particles taking up space on the electrode surface and excluding ABTSox from reacting. More magnetically susceptible particles over the electrode would also change the measurement as the HRP labels will be dispersed over a greater volume (as more magnetically susceptible particles take up a greater volume over the electrode). Therefore, some HRP labels will be further away from the electrode surface, affecting the measurement due to diffusion of signal to the electrode.

It can be seen that when the concentration of magnetically susceptible particles is doubled, the background signal also doubles in buffer. This is due to an increase in the non-specific binding of HRP-gold sol to the magnetically susceptible particles. However, when the magnetically susceptible particle concentration is doubled in blood, the background only increases by about 15% (which is insignificant within the experimental error). This is, within error, the same background level as buffer. Therefore, if adding additional magnetically susceptible particles increases the sensitivity and precision of the assay (as has been demonstrated in other experiments) this may not have a significant effect on the background. It is possible that the blood is partially blocking the magnetically susceptible particles and thereby reducing the amount of HRP-gold sol that can bind.

If the capture efficiency of the assay is lower in blood than buffer then the lower signal seen in blood would be expected. In order to investigate this, reactions were carried out where binding reactions were performed in buffer and blood, but then the binding mixture removed (separating it from the magnetically susceptible particles using a magnetic separator) and replaced with buffer before running the sample in an assay. If the signal is limited by binding then the signal in blood does not increase when transferred to buffer.

However, it is possible that if a loss of magnetically susceptible particles occurs when collecting magnetically susceptible particles from blood in an assay device, then this may also occur using the magnetic separator. It is also possible that the HRP is inhibited by some blood agent that is not removed when magnetically susceptible particles are transferred to buffer. It is also possible that an electrochemical interferent could be magnetically susceptible particle bound and not removed when transferred to a buffer solution.

In order to investigate the first of these possibilities (magnetically susceptible particles lost during magnetic separation), after the 10 min binding reaction in blood, the reaction was diluted 10× with buffer to decrease the viscosity of the blood once added to the separator. The diluted reaction mix was then removed and replaced with the original volume of buffer. Results showed an increase in the blood signal and a decrease in the buffer electrochemical signal when these binding reactions are diluted and transferred to buffer before the assay is carried out.

The decrease in electrochemical signal shown by the buffer may be due to bead loss during the wash procedure or due to the effect of dilution of the sample affecting the binding equilibrium and causing dissociation of the sandwich complex. This would also be expected to occur in blood, so the fact that the blood signal goes up after dilution and wash may indicate it should be even higher, giving a similar signal to that of buffer. This would imply that the capture efficiency is not lower in blood.

In one experiment the binding reaction was carried out in buffer and blood, removing the binding mix and re-suspending the magnetically susceptible particles in blood before running the assay. In this experiment it was seen that re-suspending a blood binding reaction in blood has no effect on the signal magnitude, but re-suspending a buffer binding reaction in blood decreases the signal to that of the same magnitude of a blood binding reaction. This result argues against lower binding in blood and supports the suggestion of either bead loss in blood, electrochemical interference from blood agents, or inhibition of HRP from blood agents.

To further investigate the possibility of bead loss, an assay was set up whereby magnetically susceptible particles were dragged through either blood or buffer in an assay device in the usual manner of an NT-proBNP assay (with no NT-proBNP or HRP-goldsol). After transfer of the magnetically susceptible particles into the ABTS reaction buffer (without $H_2O_2$) they are removed from the device by means of pipetting them out through a 4 mm diameter hole placed in the moulded base of the device. The magnetically susceptible particles were then washed once with BSA (bovine serum albumin) before being diluted into 300 µl of PBS (phosphate buffered saline) and measured spectrophotometrically at 660 nm—the measurement was carried out as a scan from 400-800 nm to indicate any contamination from ABTS or blood. A calibration was carried out that showed a linear correlation of magnetically susceptible particle concentration with absorbance at 660 nm.

It should be noted that 10 µl of magnetically susceptible particles are added to an NT-proBNP assay. At this concentration, the assay at 20000 pg/ml NT-proBNP in blood gives roughly 78% of the signal seen in 20000 pg/ml in buffer. Although the signal in this bead loss assay appears to be slightly lower in blood (although insignificant within experimental error), this is not enough to account for the 22% difference seen in the NT-proBNP assay. However, this assay measures the magnetically susceptible particles after they have been transferred from the blood/buffer sample, but before they have been dragged to the position of the electrode. This extra drag could have additional effects of bead loss due to the potentially different dragging properties of the magnetically susceptible particles once they are removed from either blood or buffer. Also, in this assay there is no turn over of ABTS which may affect the properties of the magnetically susceptible particles when being transferred out of the blood/buffer sample into the buffer solution. It is possible there are multiple contributions from different factors to reduce the signal from blood.

The only significant difference between magnetically susceptible particle concentration dragged from blood compared to buffer is when using 5 µl of magnetically susceptible particles. In this case, only 65% of the magnetically susceptible particles that are removed from buffer can be removed from blood. At all other magnetically susceptible particle concentrations over 90% of magnetically susceptible particles removed from buffer are also removed from blood.

Bead loss in the assay device using buffer as the liquid sample is consistent at between 18-28% loss. Although this does not appear to be due to the removal of the magnetically susceptible particles from the device it could be contributed to by the wash step used to remove ABTS/blood from the magnetically susceptible particles before optical measurement. This can be measured and can be accounted for to determine the number of magnetically susceptible particles lost during the phases of transfer across the interface and drag to the working electrode.

Example 5

Wet and Dry Assays

Wet assays were performed by mixing reagents and liquid sample to form a solution that was introduced to the sample inlet of a test assay device. Magnetic transfer of the magnetically susceptible particles across the liquid sample:buffer interface and measurement of the electrochemical signal at the working electrode was performed.

Wet assays were conducted with blood samples to prove the feasibility of the assay device in detection of NT-proBNP. Wet assays were conducted to:
1. measure and distinguish a doubling of NT-proBNP concentration (e.g. 200 to 400 pg/ml) between and within liquid samples (including blood samples), including bursting of a buffer pouch to release buffer liquid into the second channel portion of the device, forming the liquid sample:buffer interface and magnetic transfer of magnetically susceptible particles across the liquid sample:buffer interface;
2. optimise the assay to detect a lower limit of NT-proBNP of 50 pg/ml;
3. optimise the assay to detect NT-proBNP over a range of 50-20,000 pg/ml;
4. optimise the assay to conduct detection of NT-proBNP over a total test time of about 11 minutes;
5. optimise the assay for use with a 5 µL blood sample.

Wet and dry assays can be performed on a large number of blood samples (e.g. 70-100) from human patients diagnosed with chronic heart failure. Wet and dry assays can be optimised to achieve intra-sample CV's (coefficient of variation) of <10% and $R^2$=0.9 ($R^2$=Square of the Correlation coefficient).

Dry assay experiments were conducted to prove successful drying down of wet assay reagents with effective re-suspension in the liquid sample and assay performance. Dry assays were performed using blood samples and an assay device having dry reagent deposits (e.g. in accordance with FIG. 41) to prove the feasibility of the assay device in detection of NT-proBNP. Dry assays were conducted to:
1. measure and distinguish a doubling of NT-proBNP concentration (e.g. 200 to 400 pg/ml) between and within liquid samples (including blood samples), including bursting of a buffer pouch to release buffer liquid into the second channel portion of the device, forming the liquid sample:buffer interface and magnetic transfer of magnetically susceptible particles across the liquid sample:buffer interface;
2. optimise the assay to detect a lower limit of NT-proBNP of 50 pg/ml;
3. optimise the assay to detect NT-proBNP over a range of 50-20,000 pg/ml;
4. optimise the assay to conduct detection of NT-proBNP over a total test time of about 10 minutes;
5. optimise the assay for use with a 5 µL blood sample;
6. demonstrate use of dried reagents including streptavidin coated magnetically susceptible particles, dried biotinylated antibody, dried HRP/antibody gold sol.

In dry assays the dry reagents were:
Streptavidin coated magnetically susceptible particles (1 µm diameter) (Dynal®, Invitrogen Corporation Carlsbad, Calif. USA) 6.6% solids (500 µl of 1% solids, remove 462.1 µl supernatant, add 37.9 µl of 10% Trehalose, 10% $PVP^{55K}$);
Biotinylated anti NT-proBNP antibody (e.g. 15C4 (Hytest Ltd)) 66 µg/mL (7.8 µl of 0.845 mg/mL in 92.2 µl 5% Trehalose, 5% $PVP^{55K}$);
Anti NT-proBNP antibody (e.g. 24E11, 15F11, 29D12 (Hytest Ltd)) HRP gold sol (4.3×) (400 µl stock, centrifuge 12,000 rcf, 10 min, 15° C., remove 353.5 µl supernatant, add 46.5 µl of 10% Trehalose, 10% $PVP^{55K}$)

Each reagent was deposited as three 100 nl droplets on a base plate which holds nine devices.

Drying and Assembly:

After deposition the base plate was transferred to the oven for 15 mins at 30° C. After the 15 min drying period, the devices were placed in a foil pouch (unsealed) with several desiccant sachets. The lid was then attached to the adhesive layer and the devices were laminated and placed back into the foil pouch (the pouch was sealed if the devices were not being used immediately) and used in the assay.

Dry Assay Procedure:

5 µl of 2% Tween, 26.5 µl PBS and 80 µl NT-proBNP is mixed (to account for the addition of Biotinylated anti NT-proBNP antibody, e.g. 15C4, magnetically susceptible particles and gold sol in the wet assay), and 10 µl of this solution added to the inlet of a device. This was then mixed for approx 10 mins on a jig (mixing times varied; usually 9 m 45 s), followed by magnetic transfer of magnetically susceptible particles across the interface and magnetic drag to the working electrode. Electrochemical signal was measured after one minute turnover time.

Stability of dried reagents (magnetically susceptible particle:anti-NT-proBNP antibody and anti-NT-proBNP antibody:gold sol:HRP) over one week was tested and optimized reagent conjugates selected.

Figure 58A:
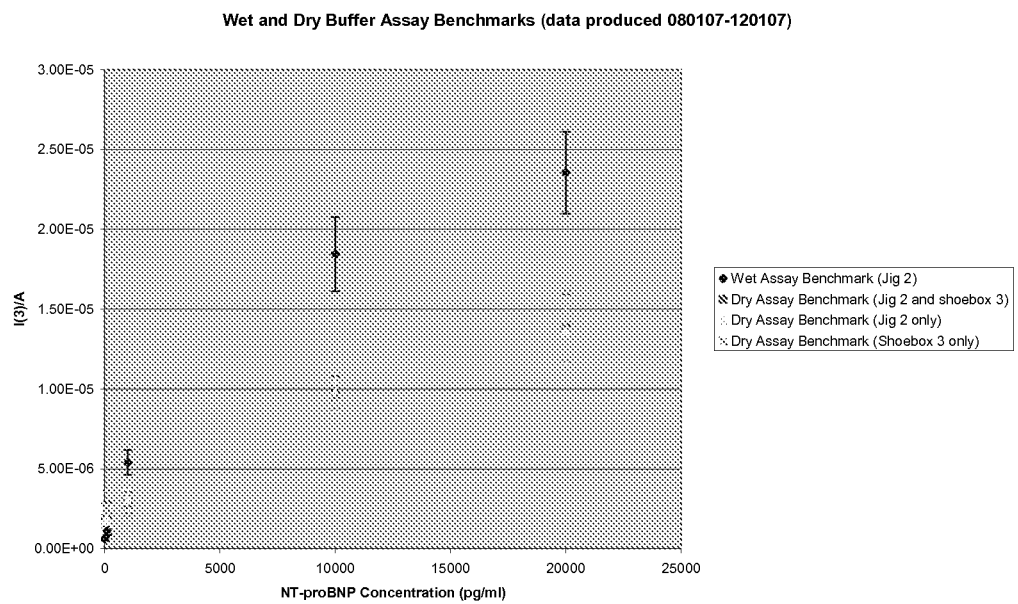
FIGS. 58A-B show the results of wet and dry assays.
Figure 58B:
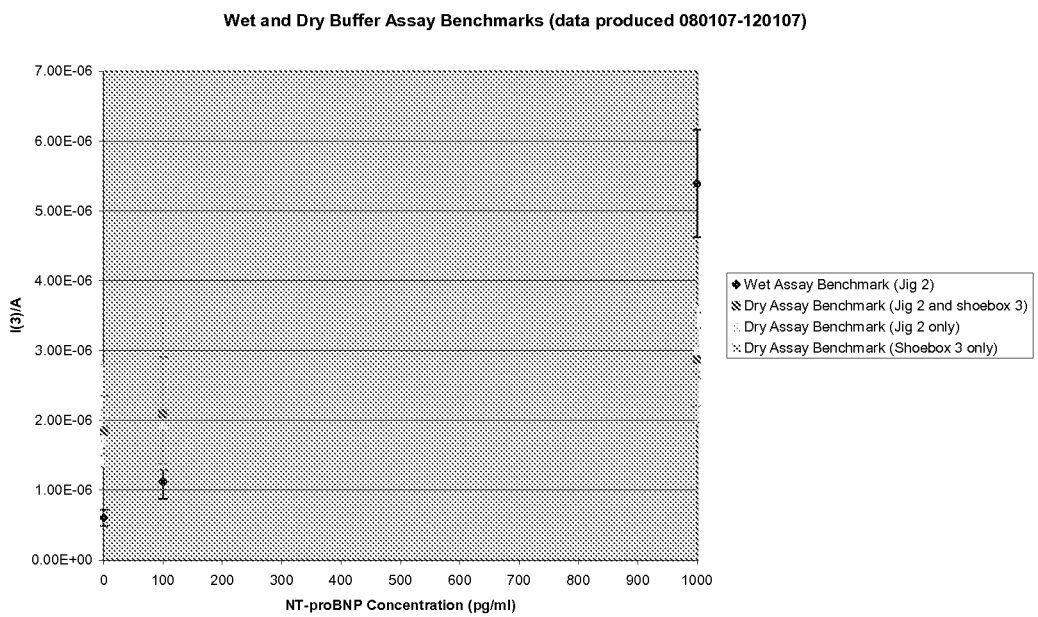

Electrochemical signal measurements for wet and dry assays are shown in FIGS. 58A-B.

Example 6

Incubation Time at Working Electrode

Experiments were conducted to investigate the effect of the incubation time (turnover period) at the working electrode.

In an assay for NT-proBNP, magnetically susceptible particle:anti-NT-proBNP antibody:NT-proBNP:anti-NT-proBNP:gold sol:HRP ternary complexes are magnetically moved to the working electrode where the oxidation of ABTS is measured as an electrochemical current. The time period from first contact of the ternary complexes with the working electrode to the detection of the electrochemical current is the incubation time (also called turnover period). The effect of varying this time on the measured electrochemical signal was investigated.

Figure 60:
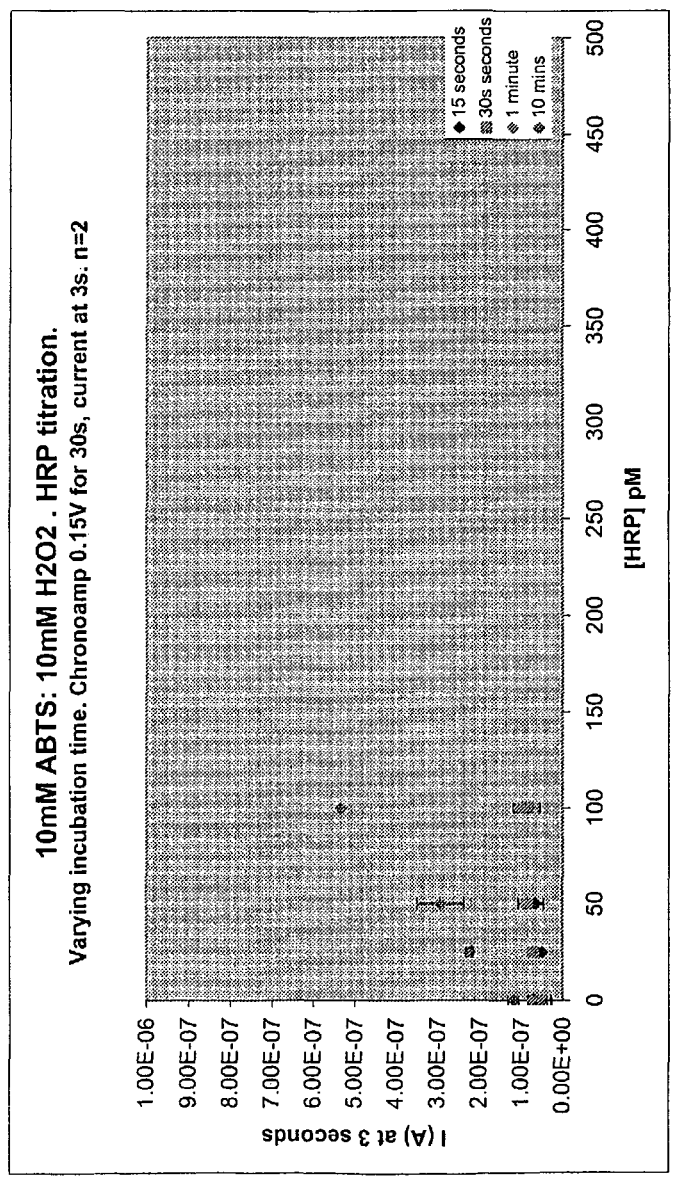
FIG. 60 illustrates a summary of the effect of varying the incubation time on the detected electrochemical current using 10 mM ABTS and 10 mM $H_2O_2$.
Figure 61:
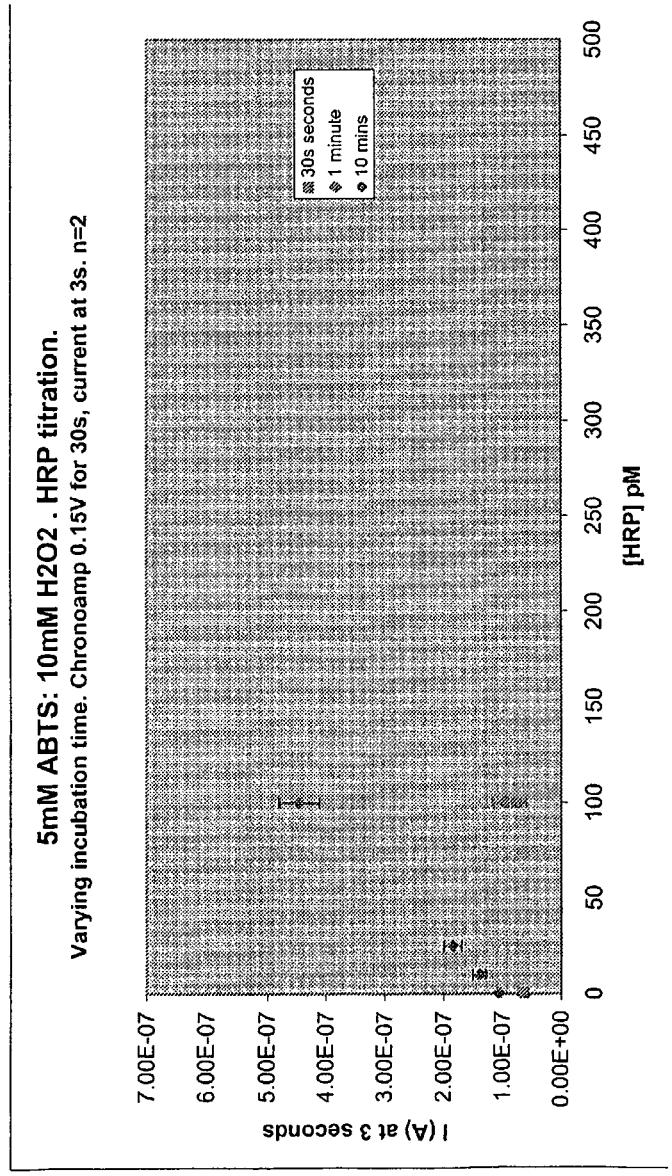
FIG. 61 illustrates a summary of the effect of varying the incubation time on the detected electrochemical current using 5 mM ABTS and 10 mM $H_2O_2$.
Figure 62:
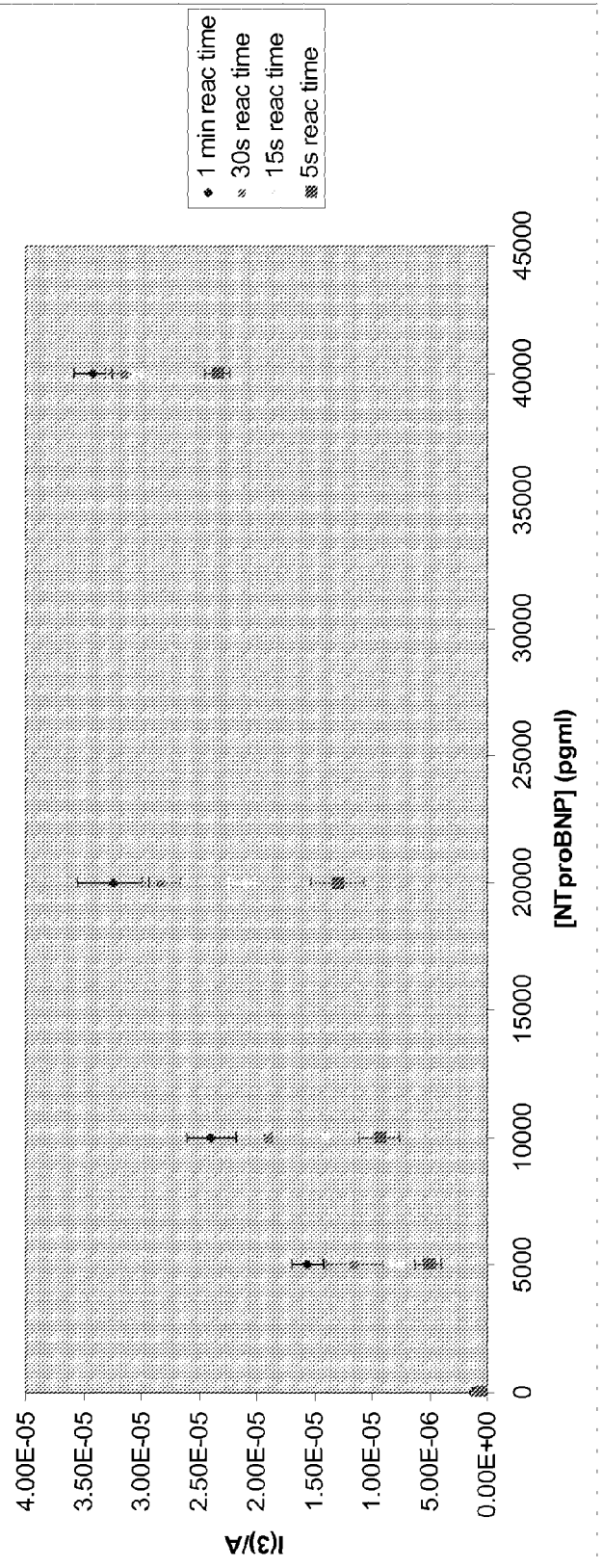
FIG. 62 illustrates the effect of varying the incubation time on the electrochemical current measured using 10 mM ABTS and 10 mM $H_2O_2$.

A summary of the results obtained when using buffer containing 10 mM ABTS, 10 mM $H_2O_2$, is shown in FIGS. 60 and 62. A summary of the results obtained when using buffer containing 5 mM ABTS, 10 mM $H_2O_2$, is shown in FIG. 61.

FIG. 62 shows a linear or near linear increase in electrochemical current with concentration of NT-proBNP for an incubation time of 5 seconds over an NT-proBNP concentration range of ~5000-40000 pM. This line provides the basis of a dataset of values for determination of NT-proBNP concentration at measured electrochemical currents for NT-proBNP concentrations in the range 5000-40000 pM.

Results showed a near linear increase in electrochemical current with concentration of HRP for an incubation time of 15 seconds over an HRP concentration range of ~250 pM to 10,000 pM. This line provides the basis of a dataset of values for determination of HRP (or NT-proBNP) concentration at measured electrochemical currents for HRP (or NT-proBNP) concentrations of ~250 pg/ml and above.

FIG. 60 shows a linear or near linear increase in electrochemical current with concentration of HRP for an incubation time of 10 minutes over an HRP concentration range of 0-100 pM. This line provides the basis of a dataset of values for determination of HRP (or NT-proBNP) concentration at measured electrochemical currents for HRP (or NT-proBNP) concentrations in the range 0-100 pM.

FIG. 61 shows a linear or near linear increase in electrochemical current with concentration of HRP for an incubation time of 10 minutes over an HRP concentration range of 0-100 pM. This line provides the basis of a dataset of values for determination of HRP (or NT-proBNP) concentration at measured electrochemical currents for HRP (or NT-proBNP) concentrations in the range 0-100 pM.

The results obtained from this experiment enable multiple datasets to be constructed for determination of a concentration of HRP or NT-proBNP at multiple incubation times. A single incubation can be conducted and continued until an electrochemical measurement having a valid corresponder in a dataset for that incubation time is identified. By providing multiple datasets, one can optimize the sensitivity of the assay, e.g. by improving the ability to detect a doubling of NT-proBNP concentration at both high (e.g. >10,000 pg/ml) and low (e.g. <100 pg/ml) NT-proBNP concentrations.

By programming the meter memory with multiple (e.g. two or more) calibration datasets providing information on NT-proBNP concentrations corresponding to measured electrochemical currents after an incubation time $T_x$, an electrochemical current $Q_x$ measured in an assay for NT-proBNP can be converted to a detected concentration of NT-proBNP.

For example, if at incubation time $T_x=15$ seconds ($T_{15\,s}$), $Q_{15\,s}$ is not present as a valid corresponder in the $T_{15\,s}$ dataset incubation can be continued and a second measurement can be made after a longer incubation time, e.g. $T_{1\,minute}$, and a check for $Q_{1\,minute}$ as a valid corresponder in the $T_{1\,minute}$ dataset can be made. This process can be repeated until a valid corresponder is identified in the corresponding data set.

Example 7

Proximity of Working Electrode and Liquid Sample:Liquid Interface

An investigation of the effect of a change in the position of the working electrode in the second channel portion was made.

An assay device ("direct transfer device") was provided in which the working electrode was positioned 3 mm from the junction of the first and second channel portions in which magnetic movement of the magnetically susceptible particles across the interface leads directly to positioning of the magnetically susceptible particles at the working electrode.

Another assay device ("indirect transfer device") was provided in which the working electrode was positioned 13.5 mm from the junction of the first and second channel portions. In this assay device an electrode drag step is required to magnetically move the magnetically susceptible particles across the interface and through the second channel portion towards the working electrode.

Figure 63:
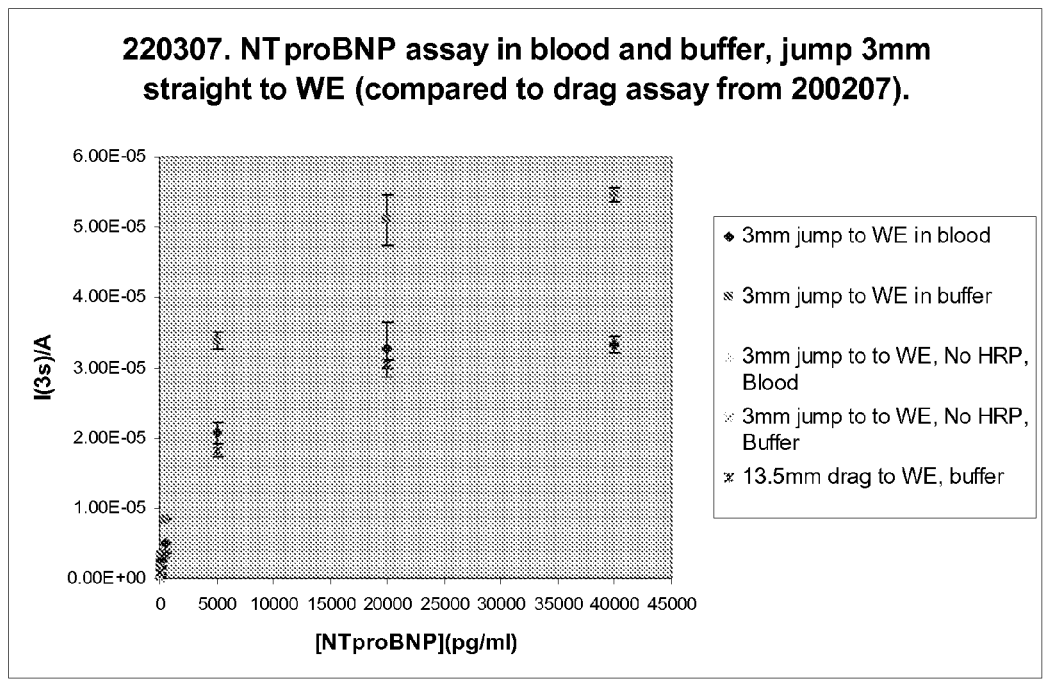
FIGS. 63 and 64 illustrate a comparison of the effect of direct transfer of magnetically susceptible particles through the interface to a working electrode with drag of the magnetically susceptible particles through a second channel portion to the working electrode.
Figure 64:
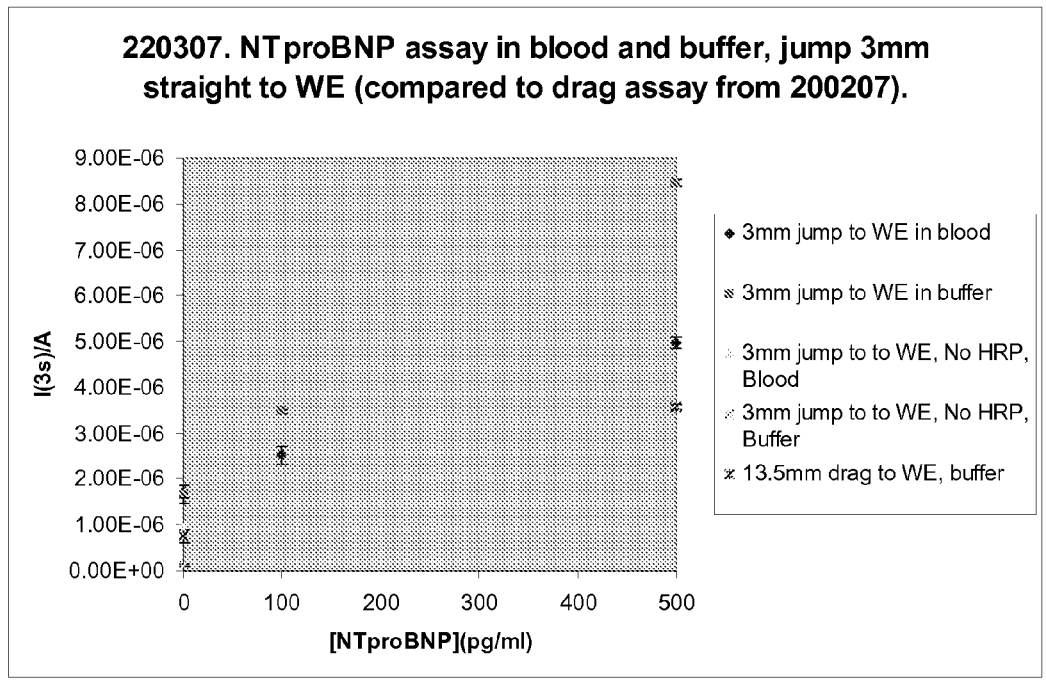

Dose response curves are shown in FIGS. 63 and 64.

An increase in sensitivity was observed when transfer of the magnetically susceptible particles was directly to the working electrode ("direct transfer device"). 100 pg/ml was readily observed in blood samples using the direct transfer device. It is hypothesized that particles are lost as they are dragged to the working electrode, resulting in a lower specific signal. This data suggests more sensitive measurements can be made using a direct transfer device.

Example 8

Software Configuration of NT-pro BNP Meter

In this Example, one exemplary example of operation of meter 400 in an assay to detect an electrochemical signal from an assay device 500 is described. The method steps may be implemented as software (e.g. a computer program product) implemented in the meter 400 to control operation of the meter during an assay. The software can be integrated in the meter on a memory device (e.g. ROM) for implementation in conjunction with the meter's processor.

For the purposes of this Example it is assumed that there is no voltage drop between the counter electrode and reference electrode (when the counter electrode is not switched out from the analogue front end circuitry). In an assay, when the counter electrode is connected to the analogue front end electronics, the voltage produced at the counter electrode is continuously changing to maintain the desired voltage at the reference electrode.

Blood application to the assay device is recognized through an optical sensor, the meter starts movement of the applied magnetic field and mixing of the sample throughout the first channel portion, followed by manipulation of the magnetic field to collect magnetically susceptible particles and cluster them in the blood sample adjacent the blood:buffer liquid interface. Once the magnetic field is in position at the interface and is configured to perform the transfer of magnetically susceptible particles into the buffer liquid, the buffer liquid is released using the vertically mounted plunger.

Figure 59:
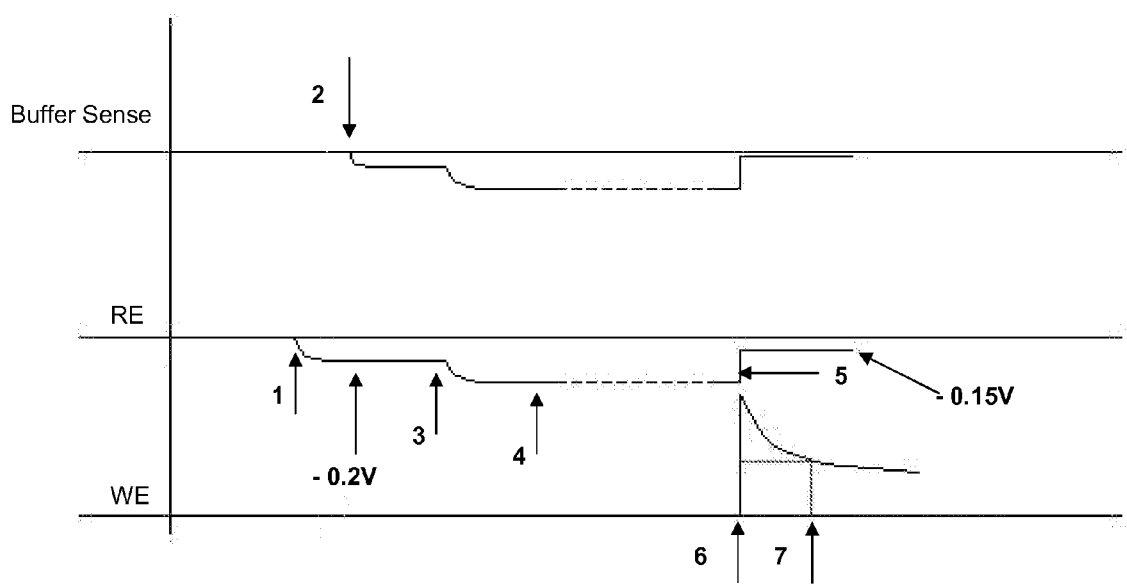
FIG. 59 illustrates a measurement algorithm for software implementation in a meter.

FIG. 59 illustrates a measurement algorithm for software implementation (e.g. as a computer program product) in a meter according to the present invention. Reference numerals 1 to 7 shown on FIG. 59 correspond with the following steps:

1. During this part of the assay the counter electrode is switched out from the analogue front end electronics so that the assay device/meter is in an effective open circuit state. As the buffer solution fills the buffer channel, firstly the working, counter and reference electrodes are wetted, this results in a potential of (e.g. −0.2V) measured at the reference electrode. This potential is produced solely by the assay device electrochemistry and is a potentiometric measurement, i.e. no current flow. At this time the buffer solution has yet to reach the buffer sense electrode positioned in the overflow channel, and so the potential at this electrode is still floating.
2. When the buffer reaches the buffer sense electrode, the potential measurement (e.g. −0.2V) will be present on the buffer sense electrode also. This potential is produced solely by the assay device electrochemistry and is a purely potentiometric measurement, i.e. no current flow. This allows the meter to know that the blood: buffer liquid interface has been formed. Note there may be a small voltage drop in the buffer sense electrode compared to the reference because of the distance from the working electrode of the buffer sense electrode, however this drop is expected to be minimal
3. With the magnetically susceptible particles having successfully transferred from the blood into the buffer, the particles are magnetically dragged through the buffer towards the working electrode. As the magnetically susceptible particles touch the front edge of the working electrode, the potential of the reference electrode drops again. The magnitude of the potential drop is dependent on the concentration of NT-proBNP contained in the sample under test.
4. Once the particles have been detected as arriving at the electrode, the magnet stops in its end position and the counter electrode is left switched out for the incubation period (e.g. a further 60 seconds).
5. At the end of the incubation period the counter electrode is switched back in and set to output a voltage of −0.15V.
6. This potential step results in a current transient being produced by the assay device, where current flows into the meter working electrode op amp from the assay device.
7. The value of the current transient at 3 seconds after the −0.15V is applied is the current value that correlates to the NT-proBNP concentration contained within the blood sample.

Example 9

The method can be performed using wet assays. The instrumentation used included an Eco Chemie™ Autolab™ with a six-way multistat and GPES™ software. The electrodes used were screen printed in-house. The working and counter electrodes were prepared using carbon D2 (GEM™ Ltd), silver/silver chloride electrodes were prepared using AgCl 70:30 (GEM™ Ltd or DuPont™), and dielectric electrodes were prepared using dielectric D1 (GEM™ Ltd).

The materials used for the test strip include a hydrophobic polyester base and a hydrophilic antifog lid, with a double-sided adhesive spacer (200 μm) forming a channel therebetween. The antifog lid was preblocked with 40 mg/mL bovine serum albumin, 1.5% Tween™ in phosphate buffered saline, pH7.3, before it was rinsed and dried. Alternatively the substrate comprises alumina ceramic or polyester cards.

The reagents used in the first assay included cobalt chloride, 4-morpholinepropanesulfonic acid (MOPS), potassium chloride. A buffer of pH 7.4 is prepared using 100 mM MOPS and 150 mM potassium chloride and a cobalt chloride standard for 45 mM in 1.5 M potassium chloride was also prepared. The reagents used in the second assay include 5 mM hydrogen peroxide, 5 mM 2,2'-azinobis-(3-ethylbenzthiazoline-6-sulfonate) (ABTS) in 125 mM sodium acetate buffer, pH 4.5. Other reagents included horseradish peroxidise (HRP) conjugated to antibody 15F11, and 1 μm magnetic particles (Chemicell™ with COOH on surface) bound to antibody 7206.

The samples used for analysis included frozen sera and whole blood samples from volunteers. 5 μL of the cobalt standard was added to 100 μL of the blood sample (serum, plasma or blood) in a tube. The so-formed mixture was mixed for 10 seconds using a vortexer, before being allowed to incubate for 2 minutes. Magnetic particles (with anti-NTproBNP antibody 7206 bound) and HRP conjugated to anti-NTproBNP antibody 15F11 are added to the sample and the sample is mixed for 30 min at 600 rpm. Between 7.5 μL and 15 μL of the mixture was then removed and applied to a first channel via the first application zone in a test strip.

The sample mixture traveled along a first channel and stopped at a junction with a second channel.

A first measurement, to detect the amount of IMA present in the sample fluid, was performed at the first electrode set. The working electrode was poised at +1 V for 40 seconds before a linear sweep was applied from +1 V to −0.5 V at a scan rate of 0.7 V/s. The measurements made may be optimized in accordance with co-pending Application GB 0603049.8, which is incorporated by reference in its entirety.

The cobalt $2^+$ ions were oxidized and adsorbed as cobalt $3^+$ hydroxy species at the electrode surface at +1 V. During the scan the cobalt $3^+$ was reduced back to cobalt $2^+$ giving a cathodic signal peak at around +0.7 V. To calibrate the test, the performance of the electrodes was tested for a range of cobalt concentrations in buffer. To determine whether the amount of IMA in the sample, the value recorded was correlated with the Albumin Cobalt Binding (ACB™) test for IMA.

The magnetic particles (and everything bound to them) are dragged to the liquid/air interface at the air vents using a magnet. The magnet is pulled 5 mm past liquid-air interface and held is over the empty second channel. This holds the magnetic particles at the liquid-air interface as they cannot pass through the so-formed meniscus.

Around 11 μL of reaction buffer containing 125 mM sodium acetate pH 4.5, 5 mM ABTS (2,2'-azino-bis(3-ethylbenzthiazoline-6-sulfonic acid)) and 5 mM hydrogen peroxide was added to the second channel via the second application zone. This flows towards the liquid-air interface, the flow being facilitated by the presence of a vent positioned at said interface. The reaction buffer formed a liquid-liquid interface with the blood sample. At this point the magnetic particles traveled across the liquid-liquid interface, being attracted by the magnet which was located proximate to the second channel.

The magnet was then moved at a controlled speed (minimising particle loss) to a position over the working electrode of the second electrode set. The magnet dragged the particles along the underside of the blocked lid. This dragged the magnetic particles over the working electrode of the second electrode set, while separating them from any remaining unbound HRP conjugate. Upon reaching the second electrode set, the magnetic particles were held in place by the magnet, and a further 50 μL of reaction buffer (to further wash the magnetic particles) is added to the second channel via the second application zone. Once this was delivered, the magnet was removed and the reaction is allowed to proceed for 10 minutes with the magnetic particles on the working electrode of the second electrode set. In this setup, a 3 carbon electrode system is used.

After 10 minutes reaction, the test strip was attached to a potentiostat, and the potential stepped from open circuit to +0.0V. The current is measured after 3 s and compared to calibration curve to give NTproBNP concentration. The oxidised ABTS ions produced by reaction between reduced ABTS, HRP and hydrogen peroxide, are converted to reduced ABTS species at the electrode surface at +0.0 Volts.

Example 10

According to one embodiment of the present invention the method is performed using wet assays. The instrumentation used includes an Eco Chemie™ Autolab™ with a six-way multistat and GPES™ software. The electrodes used were screen printed in-house. The working and counter electrodes were prepared using carbon D2 (GEM™ Ltd), silver/silver chloride electrodes were prepared using AgCl 70:30 (GEM™ Ltd or DuPont™), and dielectric electrodes were prepared using dielectric D1 (GEM™ Ltd)

The materials used for the test strip include a hydrophobic polyester base and a hydrophilic antifog lid, with a double-sided adhesive spacer (200 μm) forming channel therebetween. The antifog lid is preblocked with 40 mg/ml bovine serum albumin, 1.5% Tween™ in phosphate buffered saline, pH7.3, before it is rinsed and dried. Alternatively the substrate comprises alumina ceramic or polyester cards.

In this embodiment the reagents used in the first assay include, cobalt chloride, 4-morpholinepropanesulfonic acid (MOPS), potassium chloride. A buffer of pH 7.4 is prepared using 100 mM MOPS and 150 mM potassium chloride and a cobalt chloride standard for 45 mM in 1.5 M potassium chloride is also prepared. The reagents used in the second assay include 5 mM hydrogen peroxide, 5 mM 2,2'-azinobis-(3-ethylbenzthiazoline-6-sulfonate) (ABTS) in 125 mM sodium acetate buffer, pH4.5. Horse radish peroxidise (HRP) conjugated to antibody 15F11. 1 μm magnetic particles (Chemicell™ with COOH on surface) bound to antibody 7206.

The samples used for analysis include frozen serums and whole blood samples from volunteers.

5 μL of the cobalt standard is added to 100 μL of the blood sample (serum, plasma or blood) in a tube. The so-formed mixture is mixed for 10 seconds using a vortexer, before being allowed to incubate for 2 minutes. Cobalt binds to albumin and, to a lesser extent, IMA in the blood. Magnetic particles (with anti-NTproBNP antibody 7206 bound) and HRP conjugated to anti-NTproBNP antibody 15F11 are added to the sample and the sample is mixed for 30 min at 600 rpm. Between 7.5 μL and 15 μL of the mixture is then removed and applied to a first channel via the first application zone in a test strip.

The sample mixture travels along the first channel and is stopped at a specific point where air vents are positioned at either side of said first channel. These air vents remain open to a second channel.

A first measurement, to detect the amount of IMA present in the sample fluid, is performed at the first electrode set. The working electrode is poised at +1 Volt for 40 seconds before a linear sweep is applied from +1 Volt to −0.5 Volt at a scan rate of 0.7 V/second. The measurements made may be optimised in accordance with our co-pending Application GB 0603049.8, referred to herein previously.

The cobalt $2^+$ ions are oxidised and adsorbed as cobalt $3^+$ hydroxy species at the electrode surface at +1 Volt. During the scan the cobalt $3^+$ is reduced back to cobalt $2^+$ giving a cathodic signal peak at around +0.7 Volts. To calibrate the test, the performance of the electrodes is tested for a range of cobalt concentrations in buffer. To determine whether the amount of IMA in the sample, the value recorded is correlated with the Albumin Cobalt Binding (ACB™) test for IMA.

The magnetic particles (and everything bound to them) are dragged to the liquid/air interface at the air vents using a magnet. The magnet is pulled 5 mm past liquid-air interface and held is over the empty second channel. This holds the magnetic particles at the liquid-air interface as they cannot pass through the so-formed meniscus.

Around 11 ul of reaction buffer containing 125 mM sodium acetate pH4.5, 5 mM ABTS (2,2'-azino-bis(3-ethylbenzthiazoline-6-sulfonic acid)) and 5 mM hydrogen peroxide is added to the second channel via the second application zone. This flows towards the liquid-air interface, the flow being facilitated by the presence of a vent positioned at said interface. The reaction buffer forms a liquid-liquid interface with the blood sample. At this point the magnetic particles 'jump' across the liquid-liquid interface, as they are attracted by the magnet which is located proximate to the second channel. This 'jump' minimises the loss of particles at the interface and minimises the carry over of blood into the reaction buffer zone.

The magnet is then moved at a controlled speed (minimising particle loss) to a position over the working electrode of the second electrode set. The magnet drags the particles along the underside of the blocked lid. This drags the magnetic particles over the working electrode of the second electrode set, whilst separating them from any remaining unbound HRP conjugate. Upon arrival over the second electrode set, the magnetic particles are held in place by the magnet, and a further 50 ul of reaction buffer (to further wash the magnetic particles) is added to the second channel via the second application zone. Once this is delivered, the magnet is removed and the reaction is allowed to proceed for 10 minutes with the magnetic particles on the working electrode of the second electrode set. In this setup, a 3 carbon electrode system is used.

After 10 minutes reaction, the test strip is attached to a potentiostat, and the potential stepped from open circuit to +0.0V. The current is measured after 3 s and compared to calibration curve to give NTproBNP concentration. The oxidised ABTS ions produced by reaction between reduced ABTS, HRP and hydrogen peroxide, are converted to reduced ABTS species at the electrode surface at +0.0 Volts.

Example 11

Serial Monitoring of NT-proBNP

A patient that is in the early stages of heart failure will likely experience left ventricular systolic dysfunction (LVSD), in which the myocardium of the heart fails to contract normally and the left ventricle is dilated. The patient can become hypertensive, that is to say they experience elevated blood pressure as a consequence of the build up of fluid within the body due to reduced function of the heart. In order to control or reduce the effects of hypertension the body produces a molecule that has diuretic properties, that is one that causes increased excretion of fluid through the renal system. One such molecule that has diuretic effect is brain natriuretic peptide (BNP). BNP is secreted from the cardiac ventricles in response to pressure overload. It is produced as a pro-hormone that is cleaved to produce BNP and the amino-terminal portion, NT-proBNP. Both BNP and NT-proBNP have been shown to aid in the diagnosis of heart failure, correlating with functional status among patients with congestive heart failure. In patients presenting with acute myocardial infarction, levels of BNP and NT-proBNP correlate with left ventricular dilatation, remodeling, and dysfunction, as well as with the risk for the development of CHF or death.

Serial monitoring of NT-proBNP provides an indication of the status of a patient with respect to the progression of cardiac disease. A patient conducts a series of measurements as described, for example, in Example 1, in which the data acquired by a test device would be used to record an average baseline value over a period of time. A blood sample, for example a capillary finger stick sample, is analysed to determine the NT-proBNP levels on a regular basis on multiple occasions (e.g., over several days). Data values determined by the device are transmitted to a remote database, wherein they are analysed and in some instances are reviewed by medically qualified individuals who could, if appropriate, make contact with the patient. A baseline value is obtained from the multiple measurements and is subsequently used to determine whether a sample measurement performed at some time in the future yields a result that is significantly different from the baseline average stored by the test device. When a significant departure in the latest data value compared with the historical baseline occurs this indicates a significant worsening of the clinical condition. The data obtained from the serial monitoring of NT-proBNP is used to provide more timely intervention in administration of appropriate clinical care.

In a further example serial monitoring of NT-proBNP is used to provide an indication of the status of the renal system. NT-proBNP is eliminated from the body via the renal system alone, this part of the proBNP molecule has no biological activity, unlike BNP, which acts as a diuretic. NT-proBNP therefore does not participate in any biochemical interactions. Thus in cases where there is a significant elevation of the levels of NT-proBNP, this may provide an indication of impaired renal function. The additional monitoring of a marker of renal function, for example, serum creatinine or cystatin C, in conjunction with NT-proBNP can provide a more detailed clinical picture of the condition of the patient. In particular it is possible to determine both the renal status as well as the cardiac status. Furthermore, with serial tracking of such markers it is possible to follow the progression of the clinical condition as a function of time. Appropriate intervention can be taken to ensure patient welfare is maintained. Serial monitoring of BNP and NT-proBNP is described in U.S. application Ser. No. 11/013,353 filed Dec. 12, 2004, which is incorporated herein by reference.

Other embodiments are within the scope of the following claims.

What is claimed is:

1. A method of performing an assay to detect a presence of the natriuretic peptide in a first liquid sample comprising:
   (a) introducing the first liquid sample to a first channel portion of a microfluidic device;
   (b) contacting, within the microfluidic device, magnetically susceptible particles with the first liquid sample, the magnetically susceptible particles comprising a binding agent that specifically binds the natriuretic peptide in the first liquid sample;
   (c) contacting a second binding agent with the first liquid sample, wherein the second binding agent specifically binds the natriuretic peptide at a different epitope to the binding agent of the magnetically susceptible particle to form complexes comprising the magnetically susceptible particles, the natriuretic peptide and the second binding agent, wherein the second binding agent is conjugated to a detectable label;
   (d) forming, proximal to a junction between the first channel portion and a second channel portion of the microfluidic device, a first liquid sample:gas interface;
   (e) forming a first liquid sample:second liquid interface by displacing gas of the first liquid sample:gas interface with a second liquid;
   (f) magnetically moving the magnetically susceptible particles across the first liquid sample:second liquid interface into the second liquid in the second channel portion; and
   (g) detecting the complexes containing the natriuretic peptide in the second channel portion based on the activity of the detectable label.

2. The method of claim 1 wherein the first and second liquids are different, and wherein the first liquid sample is bodily fluid from a human or mammal.

3. The method of claim 1 wherein the detecting step (g) further comprises determining an amount of the natriuretic peptide based on the activity of the detectable label and displaying the determined amount of the natriuretic peptide.

4. The method of claim 3, further comprising comparing the amount of the natriuretic peptide determined against a reference amount to determine a result of the assay.

5. The method of claim 1 wherein the binding agent is a first antibody configured to bind the natriuretic peptide, and wherein the second binding agent is a second antibody configured to bind the natriuretic peptide at a different epitope to the first antibody.

6. The method of claim 1 wherein the step of magnetically moving the magnetically susceptible particles across the first liquid sample:second liquid interface into the second liquid comprises applying a magnetic field to a first position in the first channel portion, and moving the applied magnetic field along the channel through the junction to a second position in the second portion of the channel.

7. The method of claim 1 wherein during the forming step (e), the first-liquid sample:second liquid interface is formed by directing a flow of the second liquid across a face of the first liquid sample at the first liquid sample:gas interface to decrease an area of the first liquid sample:gas interface, the first liquid sample is held substantially static, and substantially no bulk movement of the first or second liquid occurs across the interface.

8. The method of claim 1 wherein the magnetically moving step (f) further comprises magnetically positioning the magnetically susceptible particles adjacent one or more electrodes configured in the second channel portion to contact the second liquid and wherein the detecting step (g) further comprises:
   a. measuring at time $T_1$ a first electrochemical signal $Q_1$ at a working electrode of the one or more electrodes;

b. comparing $Q_1$ against a $T_1$ calibration dataset and, where $Q_1$ is within the $T_1$ dataset, using the $T_1$ dataset to determine the amount of the natriuretic peptide in the first liquid sample;

c. where $Q_1$ does not exist in the $T_1$ calibration dataset, measuring at time $T_2$ a second electrochemical signal $Q_2$ at the working electrode, wherein $T_2>T_1$; and d. comparing $Q_2$ against a $T_2$ calibration dataset and where a comparison of $Q_2$ and $T_2$ is made, determining the amount of the natriuretic peptide in the first liquid sample.

9. The method of claim 1, wherein the first liquid sample:gas interface has a cross sectional area of about 1 mm2 or less and wherein the first liquid sample:gas interface has a first dimension H and a second dimension W and a ratio of W to H is 30 or less and wherein the first liquid sample:second liquid interface has a cross sectional area of about the same as the first liquid sample:gas interface or less.

10. The method of claim 9, wherein the first liquid sample:gas interface has a cross sectional area of about 0.15 mm2 or more.

11. The method of claim 1, wherein, upon forming the first liquid sample:gas interface, the first liquid sample occupies a total volume V of the channel upstream of the first liquid sample:gas interface and the method comprises mixing the first liquid sample by magnetically moving the magnetically susceptible particles within the total volume V after forming the first liquid sample:gas interface and prior to forming the first liquid sample:second liquid interface, wherein V is about 2 l to about 20 l.

12. The method of claim 11, wherein V is about 5 μl.

13. The method of claim 11, wherein V is about 7 μl.

14. The method of claim 11, wherein V is about 9 μl.

15. The method of claim 11, wherein V is about 15 μl.

16. The method of claim 11, wherein V is about 20 μl.

17. The method of claim 1 wherein the natriuretic peptide is a prohormone-brain natriuretic peptide (proBNP); N-terminal truncated prohormone-brain natriuretic peptide (NT-proBNP); or brain natriuretic peptide (BNP).

18. The method of claim 1, wherein the first channel portion has a main channel height h1, and a channel height h'1 at the junction, wherein h1>h'1, and wherein the second channel portion has height h2 at the junction, wherein h2>h1>h'1, and wherein the ratio of h1:h2 is at least 1:2.

19. The method of claim 1, wherein a ratio of a number of the magnetically susceptible particles that cross the first liquid sample:gas interface to a number of the magnetically susceptible particles that cross the first liquid sample:second liquid interface is less than 10%.

20. The method of claim 1 wherein the first liquid sample is blood.

21. The method of claim 1 wherein the first liquid sample is serum.

22. The method of claim 1 wherein the first liquid sample is plasma.

23. The method of claim 1 further comprising washing non-magnetic material away from the complexes to ensure that only material associated with the magnetically susceptible particles is detected.

24. The method of claim 1 further comprising verifying the activity of the detectable label by measuring activity of a predetermined quantity of immobilized detectable label at a control region in the microfluidic device.

25. A method of performing an assay to detect the presence of a natriuretic peptide in a first liquid sample comprising:

(a) introducing the first liquid sample to a first channel portion of a microfluidic device;

(b) contacting, within the microfluidic device, magnetically susceptible particles with the first liquid sample, the magnetically susceptible particles comprising a binding agent that specifically binds the natriuretic peptide in the first liquid sample, wherein the binding agent is conjugated to a detectable label;

(c) forming complexes comprising the magnetically susceptible particles, the natriuretic peptide and the binding agent conjugated to the detectable label;

(d) forming, proximal to a junction between the first channel portion and a second channel portion of the microfluidic device, a first liquid sample:gas interface;

(e) forming a first liquid sample:second liquid interface by displacing gas of the first liquid sample:gas interface with a second liquid, (f) magnetically moving the magnetically susceptible particles across the first liquid sample:second liquid interface into the second liquid;

(g) washing the complexes to remove non-complexed material so that only material associated with the complexes is detected; and (h) verifying the activity of the detectable label by measuring activity of a predetermined quantity of immobilized detectable label at a control region in the microfluidic device and detecting the complexes containing natriuretic peptide in the second channel portion based on the activity of the detectable label in the complexes.

* * * * *